US006927221B2

(12) United States Patent
Hibi et al.

(10) Patent No.: US 6,927,221 B2
(45) Date of Patent: Aug. 9, 2005

(54) TRICYCLIC FUSED HETEROCYCLIC COMPOUND, PROCESS FOR PREPARING IT AND MEDICAMENT COMPRISING IT

(75) Inventors: Shigeki Hibi, Ibaraki (JP); Yorihisa Hoshino, Ibaraki (JP); Tatsuya Yoshiuchi, Ibaraki (JP); Kogyoku Shin, Ibaraki (JP); Kouichi Kikuchi, Ibaraki (JP); Motohiro Soejima, Ibaraki (JP); Mutsuko Tabata, Ibaraki (JP); Yoshinori Takahashi, Ibaraki (JP); Hisashi Shibata, Ibaraki (JP); Tetsuya Hirakawa, Ibaraki (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 10/903,387

(22) Filed: Aug. 2, 2004

(65) Prior Publication Data

US 2005/0004159 A1 Jan. 6, 2005

Related U.S. Application Data

(62) Division of application No. 10/148,836, filed as application No. PCT/JP00/08811 on Dec. 13, 2000.

(30) Foreign Application Priority Data

Dec. 13, 1999 (JP) .......................................... 11-352553

(51) Int. Cl.[7] .................... C07D 471/04; A61K 31/437; A61P 25/24
(52) U.S. Cl. ......................................... 514/267; 546/84
(58) Field of Search ............................. 546/84; 514/292

(56) References Cited

U.S. PATENT DOCUMENTS

| | | | |
|---|---|---|---|
| 4,007,189 A | 2/1977 | Sato et al. | 260/256.4 |
| 5,942,515 A | 8/1999 | Namiki et al. | 514/267 |

FOREIGN PATENT DOCUMENTS

| | | |
|---|---|---|
| EP | 347252 A2 | 12/1989 |
| EP | 0 369 145 A2 | 5/1990 |
| EP | 0 611 766 A1 | 8/1994 |
| EP | 0 659 747 A1 | 6/1995 |
| JP | 46-31228 B1 | 9/1971 |
| JP | 2-275882 A | 11/1990 |
| JP | 5-255337 A | 10/1993 |
| JP | 11-43434 A | 2/1999 |
| WO | WO 94/13643 A1 | 6/1994 |
| WO | WO 94/13661 A1 | 6/1994 |
| WO | WO 94/13676 A1 | 6/1994 |
| WO | WO 94/13677 A1 | 6/1994 |
| WO | WO 94/18644 A1 | 8/1994 |
| WO | WO 95/10506 A1 | 4/1995 |
| WO | WO 95/34563 A1 | 12/1995 |
| WO | WO 97/29109 A1 | 8/1997 |
| WO | WO 97/29110 A1 | 8/1997 |
| WO | WO 97/44038 A1 | 11/1997 |
| WO | WO 98/08847 A1 | 3/1998 |
| WO | WO 98/33799 A1 | 8/1998 |
| WO | WO 98/45295 A1 | 10/1998 |

OTHER PUBLICATIONS

Sato et al., *J. Med. Chem.*, vol. 23, No. 8, (1980), pp. 927–937.
Chemical Abstracts, vol. 96, No. 17, p. 749, Abstract No. 142751b.
The Merck Index, Twelfth Edition, Merck & Co., p. 845, Monograph number 4957.
Wylie Vale et al., *Science* vol. 213, (Sep. 18, 1981), pp. 1394–1397.
Jean Rivier et al., Proc. Natl. Acad. Sci. USA, vol. 80, (Aug. 1983), pp. 4851–4855.
Shigeki Shibahara et al., The EMBO Journal, vol. 2, No. 5, (1983), pp. 775–779.
Atsushi Sasaki et al., Journal of Clinical Endocrinology and Metabolism, vol. 65, No. 1, (1987), pp. 176–182.
Atsushi Sasaki et al., Journal of Clinical Endocrinology and Metabolism, vol. 67, No. 4, (1988), pp. 768–773.
Wendell E. Nicholson et al., Regulatory Peptides, vol. 18, (1987), pp. 173–188.

(Continued)

*Primary Examiner*—Mark L. Berch
*Assistant Examiner*—Kahsay Habte
(74) *Attorney, Agent, or Firm*—Birch, Stewart, Kolasch & Birch, LLP

(57) ABSTRACT

The present invention provides a novel compound having an excellent corticotrophin-releasing-factor receptor antagonistic activity. That is, it provides a compound represented by the following formula, a pharmacologically acceptable salt thereof or hydrates thereof, (III)

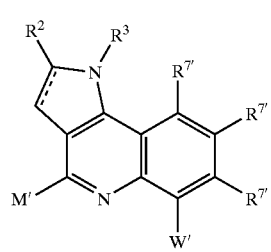

wherein
$R^2$ is a hydrogen atom, etc.; $R^3$ is a hydrogen atom, etc.; the partial structure - - - represents a single or double bond; M' represents a hydrogen atom, a halogen atom or a $C_{1-6}$ alkyl group; $R^{7'}$ represents a hydrogen atom or a $C_{1-6}$ alkyl group; and W' represents a phenyl group, pyridyl group, thienyl group, or furyl group, each being optionally substituted; and a pharmacologically acceptable salt thereof or hydrates thereof.

5 Claims, No Drawings

OTHER PUBLICATIONS

P. Petrusz et al., Peptides, vol. 5, Suppl. 1, (1984), pp. 71–78.
Derek T. Chalmers et al., The Journal of Neuroscience, vol. 15, No. 10, (Oct. 1995), pp. 6340–6350.
Chen W. Liaw et al., Endocrinology, vol. 137, No. 1, (1996), pp. 72–77.
Olivier Valdenaire et al., Biochimica et Biophysica Acta, vol. 1352, (1997), pp. 129–132.
Wylie Vale et al., Recent Progress In Hormone Research, vol. 39, (1983), pp. 245–270.
Adrian J. Dunn et al., Brain Research Reviews, vol. 15, (1990), pp. 71–100.
Michael J. Owens et al., Pharmacological Reviews, vol. 43, No. 4, (1991), pp. 425–473.
Csaba M. Banki et al., American Journal Psychiatry, vol. 144, No. 7, (Jul. 1987), pp. 873–877.
Frederik C. Raadsheer, PhD et al., American Journal Psychiatry, vol. 152, No. 9, (Sep. 1995), pp. 1372–1376.
Charles B Nemeroff, MD, PhD. et al., Arch. Gen. Psychiatry, vol. 45, (Jun. 1988), pp. 577–579.
Philip W. Gold, M.D. et al., The New England Journal of Medicine, vol. 314, No. 21, (May 22, 1986), pp. 1329–1335.
Margaret Altemus MD et al., Arch. Gen. Psychiatry, vol. 51, (Oct. 1994), pp. 794–803.
J. Douglas Bremner, MD et al., American Journal Psychiatry, vol. 154, No. 5, (May 1997), pp. 624–629.
Phillip Chappell et al., Biological Psychiatry, vol. 39, (1996), pp. 776–783.
Peter P. Roy–Byrne, MD et al., American Journal Psychiatry, vol. 143, No. 7, (Jul. 1986), pp. 896–899.
Hubert Monnikes et al., Brain Research, vol. 574, (1992), pp. 70–76.
Pamela D. Butler et al., The Journal of Neuroscience, vol. 10, No. 1, (Jan. 1990), pp. 176–183.
Mary P. Stenzel–Poore et al., The Journal of Neuroscience, vol. 14, No. 5, (May 1994), pp. 2579–2584.
Michael J. Owens et al., The Journal of Pharmacology and Experimental Therapeutics, vol. 258, No. 1, (1991), pp. 349–356.
Ned H. Kalin et al., Brain Research, vol. 509, (1990), pp. 80–84.
A. Tazi et al., Regulatory Peptides, vol. 18, (1987), pp. 37–42.
Helen A. Baldwin et al., Psychopharmacology, vol. 103, (1991), pp. 227–232.
Dalip J.S. Sirinathsinghji et al., Nature, vol. 305, (Sep. 15, 1983), pp. 232–287.
Jack E. Sherman et al., Pharmacology Biochemistry and Behavior, vol. 26, (1987), pp. 699–703.
Mark K. Lyons et al., Brain Research, vol. 545, (1991), pp. 339–342.
Paul J.L.M. Strijbos et al., Brain Research, vol. 656, (1994), pp. 405–408.
C.L. Ehlers et al., Brain Research, vol. 278, (1983), pp. 332–336.
Csaba M. Banki, MD et al., American Journal Psychiatry, vol. 144, No. 7, (Jul. 1987), pp. 873–877.
P.J. Whitehouse, MD, PhD. et al., Neurology, vol. 37, (Jun. 1987), pp. 905–909.
Errol B. DeSouza et al., Brain Research, vol. 437, (1987), pp. 355–359.
Randy J. Nelson et al., Letters to Nature, vol. 378, (Nov. 23, 1995), pp. 383–386.
Michaela Diamant et al., Neuroendocrinology, vol. 57, (1993), pp. 1071–1081.
M. P. Stenzel–Poore et al., Endocrinology, vol. 130, No. 6, (1992), pp. 3378–3386.
Mari Hotta et al, Journal of Clinical Endocrinology and Metabolism, vol. 62, No. 2, (1986), pp. 319–324.
A.S. Levine et al., Neuropharmacology, vol. 22, No. 3A, (1983), pp. 337–339.
Dean D. Krahn et al., Brain Research Bulletin, vol. 17, (1986), pp. 285–289.
K. Arase et al., Physiology and Behavior, vol. 45, (1989), pp. 565–570.
Paul M. Plotsky et al., Endocrinology, vol. 130, No. 4, (1992), pp. 1931–1941.
Thomas Garrick et al., Regulatory Peptides, vol. 21, (1988), pp. 173–181.
Y. Tache et al., American Journal Physiol., vol. 253, (1987), pp. G241–G245.
E. Barquist et al., American Journal Physiol., vol. 262, (1992), pp. G616–G620.
Mark W. Gunion et al., American Journal Physiol., vol. 258, (1990), pp. G152–G157.
Hans Kristian Bakke et al., Life Sciences, vol. 45, (1989), pp. 907–961.
H. Jurgen Lenz et al., Gastroenterology, vol. 95, (1988), pp. 1510–1517.
Michael J. Ford et al., Gastroenterology, vol. 109, (1995), pp. 1772–1780.
T. Lembo et al., Neurogastroenterol. Mot., vol. 8, (1996), pp. 9–18.
S. Fukudo et al., Gut., vol. 42, (1998), pp. 845–849.
Akio Morimoto et al., Journal of Physiology, vol. 460, (1993), pp. 221–229.
Katia Karalis et al., Science, vol. 254, (Oct. 18, 1991), pp. 421–423.
Leslie J. Crofford et al., The Journal of Clinical Investigation, Inc., vol. 90, (Dec. 1992), pp. 2555–2564.
Leslie J. Crofford et al, The Journal of Immunology, vol. 151, No. 3, (Aug. 1, 1993), pp. 1587–1596.
Theoharis C. Theoharides et al., Endocrinology, vol. 139, No. 1, (1998), pp. 403–413.
Leena K. Singh et al., The Journal of Pharmacology and Experimental Therapeutics, vol. 288, No. 3, (1999), pp. 1349–1356.
Chrisoula D. Scopa et al., American Journal of Pathology, vol. 145, No. 5, (Nov. 1994), pp. 1159–1167.
Sebastian Poliak et al., The Journal of Immunology, vol. 158, (1997), pp. 5751–5756.
Yoshio Murakami et al., Endocrine Journal, vol. 44, No. 4, (1997), pp. 627–629.
Vijendra K. Singh, Journal of Neuroimmunology, vol. 23, (1989), pp. 257–262.
Vijendra K. Singh, Neuroscience Letters, vol. 120, (1990), pp. 151–154.
Rajeev Jain et al., Endocrinology, vol. 128, No. 3, (1991), pp. 1329–1336.
Gerd Bohmer et al., European Journal of Pharmacology, vol. 182, (1990), pp. 405–411.
M. Nink et al., Acta Endocrinologica, vol. 127, (1992), pp. 200–204.
Jean Rivier et al., Science, vol. 224, (May 25, 1984), pp. 889–891.

Frederique Menzaghi et al., The Journal of Pharmacology and Experimental Therapeutics, vol. 269, No. 2, (1994), pp. 564–572.

Chen Chen et al., J. Med. Chem., vol. 39, (1996), pp. 4358–4360.

Jeffrey P. Whitten et al., J. Med. Chem., vol. 39, (1996), pp. 4345–4357.

J. Jones et al., *Gut 2000,* (Suppl. II), 47: ii1–ii19.

Derek T. Chalmers et al., *TiPS 17,* 166–172, (1996).

TRICYCLIC FUSED HETEROCYCLIC COMPOUND, PROCESS FOR PREPARING IT AND MEDICAMENT COMPRISING IT

This application is a Divisional of co-pending application Ser. No. 10/148,836 filed on Jun. 5, 2002 and for which priority is claimed under 35 U.S.C. § 120. Application Ser. No. 10/148,836 is the national phase of PCT International Application No. PCT/JP00/08811 filed on Dec. 13, 2000 under 35 U.S.C. § 371. The entire contents of each of the above-identified applications are hereby incorporated by reference. This application also claims priority of Application No. 11-352553 filed in JAPAN on Dec. 13, 1999 under 35 U.S.C. § 119.

FIELD OF THE INVENTION

The present invention relates to a tricyclic fused heterocyclic compound having corticotropin-releasing-factor receptor antagonistic activity, a pharmacologically acceptable salt thereof and hydrates thereof, and a process for preparing its and pharmaceutical use thereof.

PRIOR ART

Corticotropin-releasing-factor (hereinafter, referred to as 'CRF') is a neuropeptide comprising 41 amino acids, and isolated from sheep hypothalamus (Science, 213, 1394 (1981)) and, then, its presence was confirmed in a rat (Proc. Natl. Acad. Sci. USA, 80, 4851 (1983)) and a human being (EMBO J. 5, 775 (1983)). CRF is the most abundant in pituitary gland and hypothalamus and is widely distributed in a brain such as cerebral cortex, cerebellum and the like. In addition, in a peripheral tissue, CRF is confirmed to be present in placenta, adrenal gland, lung, lever, pancreas and digestive tract (J. Clin. Endocrinol. Metab., 65, 176 (1987), J. Clin. Endocrinol. Metab., 67, 768 (1988), Regul. Pept., 18, 173 (1987), peptides, 5 (Suppl. 1), 71 (1984)). Two subtypes CRF1 and CRF2 are present in a CRF receptor, and a CRF1 receptor is reported to be distributed at a large amount in cerebral cortex, cerebellum, olfactory bulb, pituitary gland, almond nucleus and the like. Recently, two subtypes CRF2α and CRF2β were confirmed to be present in a CRF2 receptor, and it was found that a CRF2α receptor is distributed in hypothalamus, septal area and choroid plexus at a large amount and a CRF2β is distributed in a peripheral tissue such as skeletal muscle and in a cerebrovascular part in central tissue (J. Neuroscience, 15 (10) 6340 (1995); Endocrinology, 137, 72 (1996); BBA, 1352, 129 (1997)). Since each receptor is distributed differently, it is suggested that its role is also different. CRF is produced in and secrete from hypothalamus and promotes the release of adrenocorticotropic hormone (ACTH) by stress (Recent Prog. Horm. Res., 39, 245 (1983)). CRF serves as a neurotransmitter or a neuromodulator also in a brain and integrates electrophysiology to stress, autonomic nerve and action, in addition to a role to incretion (Brain Res. Rev., 15, 71, (1990); Pharmacol. Rev., 43, 425 (1991)).

Currently, CRF is thought to be involved in a variety of diseases and there are reports as follows;

1) CRF in a cerebrospinal liquid in a depression patient is at a higher value as compared with a healthy man (Am. J. Psychiatry, 144 (7), 873 (1987)).
2) A CRF-mRNA level in hypothalamus in a depression patient is a higher value as compared with a healthy man (Am. J. Psychiatry, 152, 1372 (1995)).
3) A CRF receptor is decreased in a cerebral cortex of a person who commits suicide (Arch. Gen. Psychiatry, 45, 577 (1988)).
4) A rise of ACTH in a plasma is small in a depression patient upon administration of CRF (N. Engl. J. Med., 314, 1329 (1986)).
5) CRF in a cerebrospinal liquid of a certain anxiety patient such as compulsion disorder, posttraumatic stress disorder, teulett syndrome etc. is a higher value as compared with a healthy man (Arch. Gen. Psychiatry, mesityl, 51, 794 (1994); Am. J. Psychiatry, 154, 624 (1997); Biol. Psychiatry, 39, 776 (1996))
6) A rise of ACTH in a plasma is small in a panic disorder patient upon administration of a CRF (Am. J. Psychiatry, 143, 896 (1986)).
7) An anxiety behavior is recognized when CRF is administered in a brain of an experimental animal (Brain Res., 574, 70 (1992); J. Neurosci., 10 (1), 176 (1992)). In addition, many anxiety behavior are recognized in a CRF overexpressing mouse as compared with a normal animal (J. Neurosci., 14 (5), 2579 (1994)).
8) CRF blue spotted nucleus is decreased by administration of an anti-anxiety agent (J. Pharmaco. Exp. Ther., 258, 349 (1991)). In addition, α-helical CRF (9-41) of a peptidic CRF antagonist exerts an anti-anxiety behavior in an animal model (Brain Res., 509, 80 (1990); Regulatory Peptize, 18, 37 (1987); J. Neurosci., 14 (5), 2579 (1994)).
9) α-Helical CRF (9-41) of a peptidic CRF antagonist inhibits an abnormal behavior due to abstinence of dependency drug such as alcohol and cocaine (Psychopharmacology, 103, 227 (1991)).
10) CRF suppresses a sexual behavior of a rat (Nature, 305, 232 (1983)).
11) CRF is thought to be involved in sleep disorder because it reduces rat's sleep (Pharmacol. Biochem. Behav., 26, 699 (1987)).
12) α-Helical CRF (9-41) of a peptidic CRF antagonist inhibits disorder of a brain and brain wave abnormality due to brain ischemia and activation of NMDA receptor (Brain Res., 545, 339 (1991), Brain Res. 656, 405 (1994)).
13) CRF awakens a brain wave and induces convulsion (Brain Res., 278, 332 (1983)).
14) CRF in a cerebrospinal liquid of a schizophrenia patient is a higher value as compared with a healthy man (Am. J. Psychiatry, 144 (7), 873 (1987)).
15) CRF in a cerebral cortex in an Alzheimer disease, Parkinson disease or progressive supranuclear palsy is reduced (Neurology, 37, 905 (1987)).
16) CRF in a Huntington disease ganglion is reduced (Brain Res., 437, 355 (1987), Neurology, 37, 905 (1987)). In addition, it has been found that administration of CRF in a rat enhances learning and memory (Nature, 378, 384 (1995); Neuroendocrinology, 57, 1071 (1993)).
17) CRF in a cerebrospinal liquid in an amyotrophic lateral sclerosis patient. In a CRF overexpressing mouse, oversecretion of ACTH and adrenal gland steroid hormone occurs and abnormality similar to Cushing syndrome such as muscular atrophy, alopecia and infertility (Endocrinology, 130 (6), 3378 (1992)).
18) CRF in a cerebrospinal liquid in an anorexia nervosa patient is a higher value as compared with a healthy man, and a rise of ACTH in a plasma is small in an anorexia nervosa upon administration of CRF (J. Clin. Endocrinol. Metab., 62, 319 (1986)).
19) CRF suppresses eating in an experimental animal (Neuropharmacology, 22 (3A), 337 (1983)). In addition, α-helical CRF (9-41) of a peptidic CRF antagonist improved decrease in eating in an animal model due to stress load (Brain Res. Bull., 17 (3), 285 (1986)).
20) CRF suppressed weight gain in a hereditary obesity animal (Physiol. Behav., 45, 565 (1989)).

21) It is suggested that the lowness of a CRF value and obesity syndrome are related (Endocrinology, 130, 1931 (1992)).
22) It is suggested that eating inhibition and weight loss action of a serotonine reuptake inhibiting agent is via release of CRF (Pharmacol. Rev., 43, 425 (1991)).
23) CRF acts on centralness and peripherallness, weakens constriction of a stomach and reduces stomach excretion ability (Regulatory Peptides, 21, 173 (1983); Am. J. Physiol., 253, G241 (1987)). In addition, α-helical CRF (9-41) of a peptidic CRF antagonist has the recovery action on the functional decrease of stomach due to abdominal operation (Am. J. Physiol., h, G616 (1992)).
24) CRF promotes secretion of bicarbonate ions in stomach, decreases gastric acid secretion, and at the same time, inhibits cold constraint stress ulcer (Am. J. Physiol., 258, G152 (1990)). In addition, ulcer is increased in a non-constraint animal by CRF administration (Life Sci., 45, 907 (1989)).
25) CRF suppresses small intestine transport, promotes large intestine transport and induces defecation. In addition, α-helical CRF (9-41) of a peptidic CRF antagonist has the inhibitory action on decrease in gastric acid secretion, decrease in stomach excretion, decrease in small intestine transport and asthenia in large intestine (Gastroenterology, 99, 1510 (1988)).
26) In a healthy man, mental stress increases a gas and bellyache due to anxiety and gastrectasis and CRF reduces a threshold of uncomfort (Gastroenterol., 109, 1772 (1995); Neurogastroenterol. Mot., 8, 9 (1996)).
27) In an irritable bowel syndrome patient, large intestine movement is excessively exasperated by administration of CRF as compared with a healthy man (Gut., 42, 845 (1998)).
28) Administration of CRF increases blood pressure, heart rate and body temperature. In addition, α-helical CRF (9-41) of a peptidic CRF antagonist inhibits elevation of blood pressure, heart rate and body temperature (J. Physiol., 460, 221 (1993)).
29) In an inflammatory part of an experimental animal and a joint liquid of a rheumatoid arthritis patient, production of CRF is locally increased (Science, 254, 421 (1991); J. Clin. Invest., 90, 2555 (1992); J. Immunol., 151, 1587 (1993)).
30) CRF induces degranulation of a mast cell and exasperates vessel permeability (Endocrinology, 139 (1), 403 (1998); J. Parmacol. Exp. Ther., 288, 3), 1349 (1999)).
31) Also in an autoimmune thyroiditis patient, CRF is detected (Am. J. Pathol., 145, 1159 (1994)).
32) When CRF is administered to an experimental autoimmune cerebrospinal meningitis rat, progression of symptom of palsy and the like was remarkably inhibited (J. Immunol., 158, 5751 (1997)).
33) In a system for culturing pituitary gland adenocarcinoma of an acromegaly patient, urocortin (analogue of CRF) increased secretion of a growth hormone (Endocri, J., 44, 627 (1997)). In addition, CRF stimulates secretion of cytokin such as interleukin 1 and interleukin 2 (J. Neuroimmunol., 23, 256 (1989); Neurosci. Lett., 120, 151 (1990)).
34) Activity of natural killer cell and increase of T lymphocyte are decreased by administration of CRF and load of stress. α-Helical CRF (9-41) of a peptidic CRF antagonist improves decrease in the function of immune cells due to administration of CRF and stress load (Endocrinology, 128 (3), 1329 (1991)).
35) Breathing is remarkably increased by administration of CRF (Eur. J. Pharmacol., 182, 405 (1990)). In an advanced aged patient equipped with a long term artificial inhaler, animus of breathing and insomnia were recognized by administration of CRF (Acta Endcrinol. Copenh., 127, 200 (1992)).

From the above study reports, a CRF antagonist can be expected to exert the excellent effects in treating or preventing depression and depressive symptom including great depression, monostotic depression, recurrent depression, infant tyrannism by depression and postpartum depression, mania, anxiety, generalized anxiety disorder, panic disorder, phobia, compulsive disorder, posttraumatic stress disorder, Tourette syndrome, autism, emotional disorder, sentimental disorder, bipolar disorder, cyclothymia, schizophrenia, Alzheimer disease, Alzheimer type senile dementia, neurodegenerative disease such as Parkinson disease and Huntington disease, multi-infarct dementia, senile dementia, neurotic anorexia, appetite asthenia and other diet disorder, obesity, diabetes, alcohol dependence, pharmacophilia to cocaine, heroin, benzodiazepine etc., drug or alcohol withdrawal, sleep disorder, insomnia, migraine, stress headache, myotonic headache, ischemic neuropathy, excitation toxic neuropathy, cerebral apoplexy, progressive supranuclear palsy, amyotrophic lateral sclerosis, multiple sclerosis, muscular convulsion, chronic fatigue syndrome, mental social growth failure, epilepsy, head trauma, spinal trauma, graphospasm, spasmodic torticollis, muscular convulsion, neck-shoulder-arm syndrome, primary glaucoma, Meniere syndrome, autonomic imbalance, alopecia, neurosis including cardioneurosis, intestinal neurosis and bladder neurosis, peptic ulcer, irritable bowel syndrome, ulcerative colitis, Crohn's disease, diarrhea, coprostasis, postoperational ileus, gastrointestinal function abnormality associated with stress and neural vomiting, hypertension, cardiovascular disorder including neural angina, tachycardia, congestive cardioplegia, hyperpnea syndrome, bronchial asthma, apnea syndrome, infant sudden death syndrome, inflammatory disorder (for example, rheumatoid arthritis, bone arthritis, lumbago etc.), pain, allergic disease (for example, atopic dermatis, eczema, urticaria, psoriasis etc.), impotence, climacteric disorder, fertilization disorder, infertility, cancer, immune function abnormality upon infection with HIV, immune function abnormality by stress, hemorrhagic stress, Cushing syndrome, thyroid function disorder, encephalomyelitis, acromegaly, incontinence, osteoporosis etc. There is a report on a CRF antagonist, for example, a peptide-type CRF receptor antagonist in which a part of an amino acid sequence of a human being or other mammal is altered or deleted, and it is reported that the antagonist shows the ACTH release inhibitory action and anti-anxiety action of the antagonist (Science, 224, 889 (1984), J. Pharmacol. Exp. Ther., 269, 564 (1994), Brain Research Reviews, 15, 71 (1990)). However, it must be said that, from a viewpoint of pharmacokinetics such as the chemical stability in vivo, the bioavailability and the transferability to brain, the utility value thereof as a medicament is low.

On the other hand, regarding a non-peptide type CRF antagonist, there is the following report:

1) A compound represented by the formula:

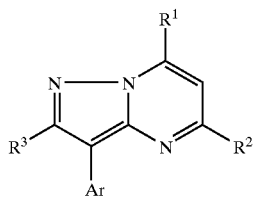

(wherein $R^1$ represents $NR^4R^5$ etc.; $R^2$ represents a $C_{1-6}$ alkyl group etc.; $R^3$ represents a $C_{1-6}$ alkyl group etc.; $R^4$ represents a $C_{1-6}$ alkyl group etc.; $R^5$ represents a $C_{1-6}$ alkyl group etc.; and Ar represents phenyl etc.), a stereoisomer thereof, or pharmaceutically acceptable acid addition salts thereof (WO97/29109).

2) A compound represented by the formula:

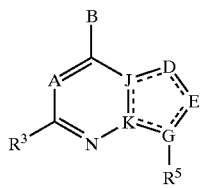

(wherein a broken line represents a single or double bond; A represents $CR^7$ etc.; B represents $NR^1R^2$ etc.; J and K are the same as or different from each other and each represents nitrogen atom etc.; D and E are the same as or different from each other and each represents nitrogen atom etc.; G denotes nitrogen atom etc.; $R^1$ represents a $C_{1-6}$ alkyl group etc.; $R^2$ represents a $C_1$–$C_{12}$ alkyl group etc.; and $R^7$ represents hydrogen atom etc.) or a pharmacologically acceptable salt thereof (WO98/08847).

3) An anilinopyrimidine compound described in WO95/10506, a pyrazolopyrimidine compound described in WO95/34563, a pyrazole compound described in WO94/13661, a pyrazole and pyrazolopyrimidine compound described in WO94/13643, aminopyrazole described in WO94/18644, a pyrazolopyrimidine compound described in WO94/13677, a pyrrolopyrimidine compound described in WO94/13676, a thiazole compound described in EP-659747, EP-611766, an anilinopyrimidine compound described in J. Med. Chem., 39, 4358 (1996), an anilinotriazine compound described in ibid. 39, 3454 (1996), a thienopyrimidine compound described in WO97/29110 etc.

As described above, there is desired the provision of a CRF receptor antagonist which is useful as a medicament. However, a medicament which shows the excellent CRF receptor antagonism, and satisfies the pharmacological activity, the dose, the safety etc. as a medicament and effectively acts clinically has not been found. That is, an object of the present invention is to search and find such the excellent CRF receptor antagonist.

DISCLOSURE OF THE INVENTION

According to the above-mentioned, circumstances, the present inventors studied intensively. As a result, they successfully synthesized a novel tricyclic fused heterocyclic compound represented by the following formula, a pharmacologically acceptable salt thereof or hydrates thereof and, further surprisingly, found that the compound has an excellent CRF antagonist action and the object can be attained. Thus, they have accomplished the present invention.

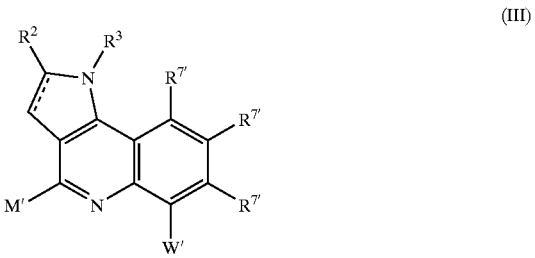

Wherein A, B and D are the same as or different from each other and each represents:
(1) heteroatom selected from nitrogen atom, oxygen atom and sulfur atom;
(2) formula —$(CR^1R^2)_m$— (wherein $R^1$ and $R^2$ are:
  (i) the same as or different from each other and each represents hydrogen atom, a $C_{1-6}$ alkyl group, a $C_{2-6}$ alkenyl group, a $C_{2-6}$ alkynyl group, a $C_{1-6}$ alkoxy group, a $C_{3-8}$ cycloalkyl group, a $C_{1-6}$ alkoxy $C_{1-6}$ alkyl group, a $C_{3-8}$, cycloalkyl $C_{1-6}$ alkyl group or a $C_{1-6}$ alkyl-aryl group, or $R^1$ and $R^2$ may be bound together to form a 3- to 8-membered ring;
  (ii) $R^1$s are bound together so that adjacent —$CR^1R^2$-s form a carbon-carbon double bond, that is, a partial structure represented by formula —$CR^2$=$CR^2$—; or
  (iii) $R^1$ and nitrogen atom may form a bond so that an adjacent nitrogen atom and —$CR^1R^2$— form a partial structure represented by the formula —N=$CR^2$— ($R^2$ is as defined above); and m is 0 or an integer of 1 to 4);
(3) —CO—;
(4) —CS—;
(5) —$NR^3$— (wherein $R^3$ represents:
  (i) hydrogen atom;
  (ii) formula —$COR^4$ (wherein $R^4$ represents a $C_{1-6}$ alkyl group, an optionally substituted aryl $C_{1-4}$ alkyl group, an optionally substituted aryl group, an optionally substituted heteroaryl $C_{1-4}$ alkyl group or an optionally substituted heteroaryl group);
  (iii) —$S(O)_nR^5$ (wherein $R^5$ represents a $C_{1-6}$ alkyl group, an optionally substituted aryl $C_{1-4}$ alkyl group, an optionally substituted aryl group, an optionally substituted heteroaryl $C_{1-4}$ alkyl group or an optionally substituted heteroaryl group; and n is an integer of 0, 1 or 2);
  (iv) a $C_{1-10}$ alkyl group optionally substituted with any of one or more groups defined in the following A group;
  (v) a $C_{2-10}$ alkenyl group optionally substituted with any of one or more groups defined in the following A group;
  (vi) a $C_{2-10}$ alkynyl group optionally substituted with any of one or more groups defined in the following A group;
  (vii) an optionally substituted aryl group; or
  (viii) a $C_{3-8}$ cycloalkyl group optionally fused with optionally substituted benzene ring and optionally substituted with a $C_{1-4}$ alkyl group);
(6) —SO—; or
(7) —$SO_2$—,
E and G are the same as or different from each other and each represents:
(1) a heteroatom selected from nitrogen atom, oxygen atom and sulfur atom;
(2) formula —$(CR^6R^7)_p$— (wherein $R^6$ and $R^7$ are:
  (i) the same as or different from each other and each represents hydrogen atom, a $C_{1-6}$ alkyl group, a $C_{3-8}$ cycloalkyl group optionally substituted with a $C_{1-4}$ alkyl group, an optionally substituted aryl group or an optionally substituted heteroaryl group;
(ii) $R^6$s are bound together so that adjacent —$CR^6R^7$—s form a carbon-carbon double bond, that is, a partial structure represented by formula —$CR^7$=$CR^7$— ($R^7$ is as defined above); or
(iii) $R^6$ and nitrogen atom may form a bond so that an adjacent nitrogen atom and a group —$CR^6R^7$— form a partial structure represented by —N=$CR^7$— ($R^7$ is as defined above); and p is an integer of 0, 1 or 2,
provided that when both E and G are groups —$(CR^6R^7)_p$— at the same time, p dose not represent 0 and at least one of E and G represent group —$CR^6R^7$—);
(3) —CO—;
(4) —CS—;
(5) —$NR^8$— (wherein $R^8$ represents:
(i) hydrogen atom;
(ii) formula —$COR^9$ (wherein $R^9$ represents a $C_{1-6}$ alkyl group, an optionally substituted aryl $C_{1-4}$ alkyl group, an optionally substituted aryl group, an optionally substituted heteroaryl $C_{1-4}$ alkyl group or an optionally substituted heteroaryl group);
(iii) —$S(O)_nR^{10}$ (wherein $R^{10}$ represents a $C_{1-6}$ alkyl group, an optionally substituted aryl $C_{1-4}$ alkyl group, an optionally substituted aryl group, an optionally substituted heteroaryl $C_{1-4}$ alkyl group or an optionally substituted heteroaryl group; and n is an integer of 0, 1 or 2);
(iv) a $C_{1-10}$ alkyl group optionally substituted with any of one or more groups defined in the following A group;
(v) a $C_{2-10}$ alkenyl group optionally substituted with any of one or more groups defined in the following A group;
(vi) a $C_{2-10}$ alkynyl group optionally substituted with any of one or more groups defined in the following A group; or
(vii) a $C_{3-8}$ cycloalkyl group optionally fused with an optionally substituted benzene ring and optionally substituted with a $C_{1-4}$ alkyl group);
(6) —SO—; or
(7) —$SO_2$—;
J represents:
(1) nitrogen atom or
(2) carbon atom or nitrogen atom which is substituted with any one or more selected from:
(i) hydrogen atom;
(ii) amino group;
(iii) cyano group;
(iv) a $C_{1-6}$ alkyl group optionally substituted with a halogen atom;
(v) a $C_{1-6}$ alkylaminosulfonyl group;
(vi) an optionally substituted aryl group; and
(vii) an optionally substituted saturated or unsaturated heterocyclic ring,
K and L are the same as or different from each other and each represents carbon atom or nitrogen atom,
a ring formed by K, E, G, J and L in the above formula (I) represents a saturated or unsaturated 5- or 6-membered ring,
M represents:
(1) hydrogen atom;
(2) halogen atom;
(3) cyano group;
(4) a $C_{1-6}$ alkyl group optionally substituted with any of one or more groups defined in the following A group;
(5) formula —$NR^{11}R^{12}$— (wherein $R^{11}$ and $R^{12}$ are the same as or different from each other and each represents:
(i) hydrogen atom;
(ii) any group defined in the following A group;
(iii) a $C_{1-6}$ alkyl group optionally substituted with any of one or more groups defined in the following A group;
(iv) a $C_{1-4}$ alkylacyl group;
(v) an optionally substituted aryl $C_{1-4}$ alkyl group;
(vi) an optionally substituted heteroaryl $C_{1-4}$ alkyl group;
(vii) an optionally substituted aryl group; or
(viii) an optionally substituted heteroaryl group);
(6) —$OR^{13}$ (wherein $R^{13}$ represents hydrogen atom, a $C_{1-6}$ alkyl group optionally substituted with any of one or more groups defined in the following A group, a $C_{1-4}$ alkylacyl group, an optionally substituted aryl $C_{1-4}$ alkyl group, an optionally substituted heteroaryl $C_{1-4}$ alkyl group, an optionally substituted aryl group or an optionally substituted heteroaryl group);
(7) —$S(O)_qR^{14}$ (wherein $R^{14}$ represents a $C_{1-6}$ alkyl group, an optionally substituted aryl $C_{1-4}$ alkyl group, an optionally substituted aryl group, an optionally substituted heteroaryl $C_{1-4}$ alkyl group or an optionally substituted heteroaryl group; and q is an integer of 0, 1 or 2);
(8) an optionally substituted $C_{2-10}$ alkenyl group;
(9) an optionally substituted $C_{2-10}$ alkynyl group;
(10) a $C_{1-6}$ alkoxy group optionally substituted with any of one or more groups defined in the following A group;
(11) a $C_{1-6}$ alkylthio group optionally substituted with any of one or more groups defined in the following A group;
(12) an optionally substituted aryl group; or
(13) an optionally substituted heteroaryl group,
the partial structure --- represents a single or double bond, and
the A group defined above represents the group consisting of:
(1) halogen atom,
(2) hydroxy group,
(3) nitro group,
(4) cyano group,
(5) carboxy group,
(6) a $C_{1-6}$ alkyloxycarbonyl group,
(7) a group represented by the formula —$S(O)_rR^{15}$ (wherein r is an integer of 0, 1 or 2; and $R^{15}$ represents:
(i) hydrogen atom;
(ii) a $C_{1-6}$ alkyl group;
(iii) a group represented by the formula —$NR^{16}R^{17}$ (wherein $R^{16}$ and $R^{17}$ are the same as or different from each other and each represents hydrogen atom, a $C_{1-6}$ alkyl group optionally substituted with an optionally substituted aryl group, a $C_{1-4}$ alkylacyl group, an optionally substituted aryl $C_{1-4}$ alkyl group, an optionally substituted heteroaryl $C_{1-4}$ alkyl group, an optionally substituted aryl group or an optionally substituted heteroaryl group);
(iv) an optionally substituted aryl $C_{1-4}$ alkyl group;
(v) an optionally substituted aryl group;
(vi) an optionally substituted heteroaryl $C_{1-4}$ alkyl group; or
(vii) an optionally substituted heteroaryl group);
(8) a group represented by the formula —$NR^{18}R^{19}$ (wherein $R^{18}$ and $R^{19}$ are the same as or different from each other and each represents hydrogen atom, a $C_{1-6}$ alkyl group or a $C_{1-4}$ alkylacyl group);
(9) a $C_{1-6}$ alkyl group;

(10) a $C_{1-6}$ alkoxy group;

(11) a $C_{3-8}$ cycloalkyl group optionally substituted with a $C_{1-4}$ alkyl group;

(12) a $C_{1-4}$ alkoxy $C_{1-6}$ alkyl group;

(13) a saturated 3- to 8-membered heterocyclic ring optionally substituted with a $C_{1-4}$ alkyl group;

(14) an optionally substituted aryl group; and

(15) an optionally substituted heteroaryl group, provided that in the above definition, (1) the case where both K and L are nitrogen atoms; and (2) the case where K is nitrogen atom, L is carbon atom, A and B are groups represented by the formula —$(CR^1R^2)_m$— (wherein both $R^1$ and $R^2$ represent hydrogen atoms; and m is 1), and J is carbon atom substituted with any group selected from:

(i) amino group;

(ii) cyano group;

(iii) aminosulfonyl group in which the nitrogen atom is substituted with a straight or branched $C_{1-6}$ alkyl group; and (iv) 1H-tetrazol-5-yl group, are excluded.

That is, the first essential feature of the present invention is:

(1) a compound represented by the above formula (I), a pharmacologically acceptable salt thereof or hydrates thereof, and further, (2) in the above (1), B and/or D may be nitrogen atom, oxygen atom, sulfur atom, or a group represented by the formula —$NR^3$—, —CO— or —$(CR^1R^2)_m$— (wherein $R^1$, $R^2$, $R^3$ and m have the same meanings as defined above);

(3) in the above (1), A and/or B may be a group represented by the formula —$(CR^1R^2)_m$— (wherein $R^1$, $R^2$ and m have the same meanings as defined above);

(4) in the above (1), D may be nitrogen atom, oxygen atom, sulfur atom or a group represented by the formula —$NR^3$— (wherein $R^3$ has the same meaning as defined above);

(5) in the above (1), D may be a group represented by the formula —$NR^3$— (wherein $R^3$ is as defined above);

(6) in the above (1), the partial structure —A- - -B- - -D— may be a group represented by the formula:

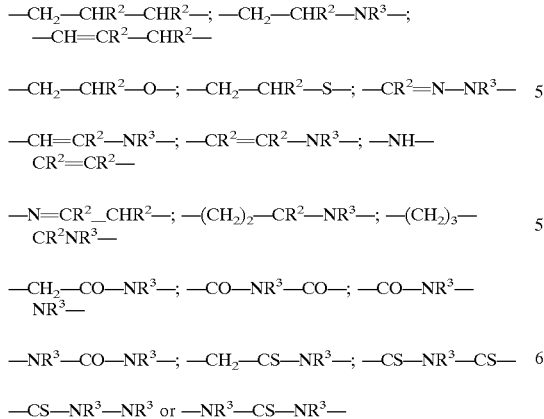

wherein $R^2$ and $R^3$ are as defined above, and $R^2$ and $R^3$ are the same as or different from each other;

(7) in the above (6), $R^2$ and/or $R^3$ are the same as or different from each other and each may be hydrogen atom, a $C_{1-6}$ alkyl group, a $C_{2-6}$ alkynyl group, a $C_{1-6}$ alkoxy $C_{1-6}$ alkyl group or a $C_{1-6}$ alkyl-aryl group;

(8) in the above (1), K may be nitrogen, and L may be carbon;

(9) in the above (1), K and L may be carbon;

(10) in the above (1), E or G may be nitrogen;

(11) in the above (1), E or G may be a group represented by the formula —$(CR^6R^7)_p$— (wherein $R^6$ and $R^7$ have the same meanings as defined above);

(12) in the above (1), the partial structure - - -E- - -G- - - may be a group represented by the formula —$[CH(R^7)]_2$—, —$N=CR^7$—, —$CR^7=N$—, —$[CH(R^7)]_3$—, —$CR^7=CR^7$——$CR^7=$, —$N=R^7$—$CR^7=$ or —$CR^7$—$CR^7$—$N=$ (wherein $R^7$ has the same meaning as defined above);

(13) in the above (12), $R^7$ may be the same as or different from each other and each may be hydrogen atom or a $C_{1-6}$ alkyl group;

(14) in the above (1), J may be a carbon atom or nitrogen atom substituted with any one group selected from (1) aryl group and (2) saturated or unsaturated heterocyclic ring,

(15) in the above (1), J may be a carbon atom or nitrogen atom substituted with any one group selected from phenyl group, pyridyl group, thienyl group and furyl group;

(16) in the above (1), J may be a carbon atom or nitrogen substituted with a phenyl group optionally substituted with one to three groups selected from a halogen atom, a $C_{1-6}$ alkyl group optionally substituted with a halogen atom and a $C_{1-6}$ alkoxy group;

(17) in the above (1), M may be (1) hydrogen atom, (2) a halogen atom, (3) cyano group, (4) a $C_{1-6}$ alkyl group optionally substituted with any one or more groups listed in the above A group, (5) a $C_{1-6}$ alkoxy group optionally substituted with any one or more groups listed in the above A group or (6) an amino group optionally substituted with any one or more groups listed in the above A group;

(18) in the above (1), M may be hydrogen, a $C_{1-6}$ alkyl group, a $C_{1-6}$ alkoxy group or a $C_{1-6}$ alkylthio group;

(19) in the above (1), M may be methyl group;

(20) in the above (1), A and B may be a group represented by the formula —$(CR^{1'}R^{2'})_{m'}$— (wherein $R^{1'}$ and $R^{2'}$ are the same as or different from each other and each represents hydrogen atom or a $C_{1-6}$ alkyl group; and m' represents an integer from 1 to 3) D may be a group represented by the formula —$NR^3$— (wherein $R^3$ has the same meaning as defined above), E may be nitrogen atom, and G may be a group represented by the formula =$CR^8$— (wherein $R^8$ has the same meaning as defined above);

(21) in the above (1), the partial structure —A- - -B- - - may be a group represented by the formula —$CR^2=CR^2$— (wherein $R^2$ represents hydrogen atom or a $C_{1-6}$ alkyl group), D may be a group represented by the formula —$NR^3$— (wherein $R^3$ has the same meaning as defined above), E may be nitrogen atom, and G may be a group represented by the formula =$CR^8$— (wherein $R^8$ has the same meaning as defined above); and

(22) in the above (1), A may be a group represented by the formula —$(CR^1R^2)_{m'}$— (wherein $R^1$ and $R^2$ are the same as or different from each other and each represents a $C_{1-6}$ alkyl group; and m' represents an integer from 1 to 3), B may be a group represented by the formula —CO— or —CS—, D may be a group represented by the formula —NR³— (wherein R³ has the same meaning as defined above), E may be nitrogen atom and G may be a group represented by the formula =CR⁸— (wherein R⁸ has the same meaning as defined above), a compound relating to the present invention may be:
(23) a compound represented by the formula:

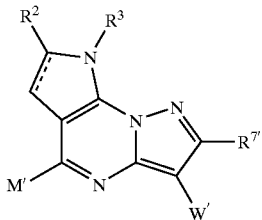

(II)

(wherein R², R³ and the partial structure --- has the same meanings as defined above; M' represents hydrogen atom, a halogen atom or a $C_{1-6}$ alkyl group; R⁷' represents hydrogen atom or a $C_{1-6}$ alkyl group; W represents hydrogen atom, amino group, cyano group, a $C_{1-6}$ alkyl group, a $C_{1-6}$ alkylaminosulfonyl group, an optionally substituted aryl group, or an optionally substituted saturated or unsaturated heterocyclic ring), a pharmacologically acceptable salt thereof, or hydrates thereof;
(24) a compound represented by the formula:

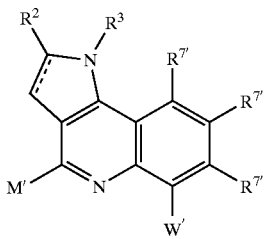

(III)

(wherein R², R³, R⁷', M', W' and the partial structure --- are as defined above), a pharmacologically acceptable salt thereof or hydrates thereof;
(25) a compound represented by the formula:

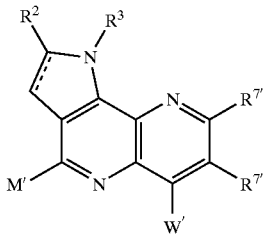

(IV)

(wherein R², R³, R⁷', M', W' and the partial structure --- are as defined above), a pharmacologically acceptable salt thereof or hydrates thereof;

(26) a compound represented by the formula:

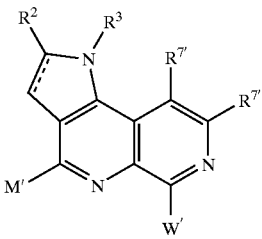

(V)

(wherein R², R³, R⁷', M', W' and the partial structure --- are as defined above), a pharmacologically acceptable salt thereof or hydrates thereof;
(27) a compound represented by the formula:

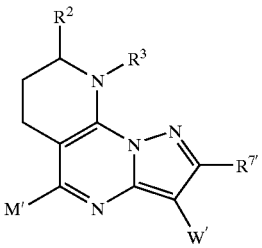

(VI)

(wherein R²₁R³, R⁷', M', W' and the partial structure --- are as defined above), a pharmacologically acceptable salt thereof or hydrates thereof; and
(28) a compound represented by the formula:

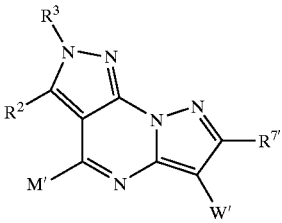

(VII)

(wherein R², R³, R⁷', M', W' and the partial structure --- are as defined above), a pharmacologically acceptable salt thereof or hydrates thereof, and
(29) in the above (1), the compound may be any one selected from:
8-(1-ethylpropyl)-3-mesityl-2,5-dimethyl-8H-pyrazolo[1,5-a]pyrrolo[3,2-e]pyrimidine;
8-(1-ethylpropyl)-3-mesityl-2,5-dimethyl-7,8-dihydro-6H-pyrazolo[1,5-a]pyrrolo[3,2-e]pyrimidine;
3-mesityl-8-[2-methoxy-1-(methoxymethyl)ethyl]-2,5-dimethyl-7,8-dihydro-6H-pyrazolo[1,5-a]pyrrolo[3,2-e]pyrimidine;
8-benzyl-3-mesityl-2,5-dimethyl-7,8-dihydro-6H-pyrazolo[1,5-a]pyrrolo[3,3-e]pyrimidine;
3-mesityl-8-[1-(methoxymethyl)propyl]-2,5-dimethyl-7,8-dihydro-6H-pyrazolo[1,5-a]pyrrolo[3,2-e]pyrimidine;
3-mesityl-2,5-dimethyl-8-(1-propylbutyl)-7,8-dihydro-6H-pyrazolo[1,5-a]pyrrolo[3,2-e]pyrimidine;
2-ethyl-8-(1-ethylpropyl)-3-mesityl-5-methyl-7,8-dihydro-6H-pyrazolo[1,5-a]pyrrolo[3,2-e]pyrimidine;
8-(1-ethylpropyl)-2,5-dimethyl-3-(2,4,6-trimethyl-3-pyridyl)-8H-pyrazolo[1,5-a]pyrrolo[3,2-e]pyrimidine;

6-mesityl-2,4,7-trimethyl-2H-dipyrazolo[1,5-a:4,3-e]
  pyrimidine;
9-(cyclopropylmethyl)-8-ethyl3-mesityl-2,5-dimethyl-6,7,
  8,9-tetrahydropyrazolo[1,5-a]pyrido[3,2-e]pyrimidine;
2-(6-mesityl-4-methyl-1H-pyrrolo[3,2-c]quinolin-1-yl)
  butyl methyl ether;
1-(1-ethylpropyl)-6-mesityl-4-methyl-1H-pyrrolo[3,2-c][1,
  7]naphthyridine; and
2-(6-mesityl-4-methyl-1H-pyrrolo[3,2-c][1,5-naphthyridin-
  1-yl]butyl methyl ether.

In addition, the second essential feature of the present invention is:

(30) a medicament which comprises the compound as described in the above (1), a pharmacologically acceptable salt thereof or hydrates thereof, and further,
(31) the medicament described in the above (30) may be an agent for treating or preventing diseases to which corticotrophin-releasing factor (hereinafter, referred to as "CRF") and/or a CRF receptor relate;
(32) the medicament described in the above (30) may be a CRF receptor antagonist;
(33) the medicament described in the above (30) may be an agent for treating or preventing depression, depressive symptom or mania;
(34) in the above (33), the depressive symptom may be great depression, monostotic depression, recurrent depression, infant tyrannism by depression or postpartum depression;
(35) the medicament described in the above (30) may be an agent for treating or preventing anxiety, generalized anxiety disorder, panic disorder, phobia, compulsive disorder, posttraumatic stress disorder, Tourette syndrome, autism, emotional disorder, sentimental disorder, bipolar disorder, cyclothymia or schizophrenia;
(36) the medicament described in the above (30) may be an agent for treating or preventing peptic ulcer, irritable bowel syndrome, ulcerative colitis, Crohn's disease, diarrhea, coprostasis, postoperational ileus, gastrointestinal function abnormality associated with stress or neural vomiting; and
(37) the medicament described in the above (30) may be an agent for treating or preventing Alzheimer disease, Alzheimer type senile dementia, neurodegenerative disease, multi-infarct dementia, senile dementia, neurotic anorexia, diet disorder, obesity, diabetes, alcohol dependence, pharmacophilia, withdrawal, sleep disorder, insomnia, migraine, stress headache, myotonic headache, ischemic neuropathy, excitation toxic neuropathy, cerebral apoplexy, progressive supranuclear palsy, amyotrophic lateral sclerosis, multiple sclerosis, muscular convulsion, chronic fatigue syndrome, mental social growth failure, epilepsy, head trauma, spinal trauma, graphospasm, spasmodic torticollis, muscular convulsion, neck-shoulder-arm syndrome, primary glaucoma, Meniere syndrome, autonomic imbalance, alopecia, neurosis, hypertension, cardiovascular disorder, tachycardia, congestive cardioplegia, hyperpnea syndrome, bronchial asthma, apnea syndrome, infant sudden death syndrome, inflammatory disorder (for example, rheumatoid arthritis, bone arthritis and lumbago), pain, allergic disease (for example, atopic dermatis, eczema, urticaria and psoriasis), impotence, climacteric disorder, fertilization disorder, infertility, cancer, immune function abnormality upon infection with HIV, immune function abnormality by stress, hemorrhagic stress, Cushing syndrome, thyroid function disorder, encephalomyelitis, acromegaly, incontinence or osteoporosis.

The present invention provides a method for treating or preventing diseases against which CRF and/or CRF receptor relate, diseases against which CRF receptor antagonism is efficacious, depressive symptoms such as depression, great depression, monostotic depression, recurrent depression, infant tyrannism by depression, postpartum depression etc., mania, anxiety, generalized anxiety disorder, panic disorder, phobia, compulsive disorder, posttraumatic stress disorder, Tourette syndrome, autism, emotional disorder, sentimental disorder, bipolar disorder, cyclothymia, schizophrenia, peptic ulcer, irritable bowel syndrome, ulcerative colitis, Crohn's disease, diarrhea, coprostasis, postoperational ileus, gastrointestinal function abnormality associated with stress, neural vomiting, Alzheimer disease, Alzheimer-type senile dementia, neurodegenerative disease, multi-infarct dementia, senile dementia, neurotic anorexia, diet disorder, obesity, diabetes, alcohol dependence, pharmacophilia, drug abstinence symptoms, alcohol abstinence symptoms, sleep disorder, insomnia, migraine, stress headache, myotonic headache, ischemic neuropathy, excitation toxic neuropathy, cerebral apoplexy, progressive supranuclear palsy, amyotrophic lateral sclerosis, multiple sclerosis, muscular convulsion, chronic fatigue syndrome, mental social growth failure, epilepsy, head trauma, spinal trauma, graphospasm, spasmodic torticollis, muscular convulsion, neck-shoulder-arm syndrome, primary glaucoma, Meniere syndrome, autonomic imbalance, alopecia, neurosis, hypertension, cardiovascular disorder, tachycardia, congestive cardioplegia, hyperpnea syndrome, bronchial asthma, apnea syndrome, infant sudden death, syndrome, inflammatory disorder, pain, allergic disease, impotence, climacteric disorder, fertilization disorder, infertility, cancer, immune function abnormality upon infection with HIV, immune function abnormality by stress, hemorrhagic stress, Cushing syndrome, thyroid function disorder, encephalomyelitis, acromegaly, incontinence or osteoporosis, by administering a pharmacologically effective dose of the compound represented by the above formula (I), a pharmacologically acceptable salt thereof or hydrates thereof to a patient.

Further, the present invention provides use of the compound represented by the above formula (I), a pharmacologically acceptable salt thereof or hydrates thereof, for producing an agent for treating or preventing diseases against which CRF and/or CRF receptor relate, diseases against which CRF receptor antagonism is efficacious, depressive symptoms such as depression, great depression, monostotic depression, recurrent depression, infant tyrannism by depression, postpartum depression etc., mania, anxiety, generalized anxiety disorder, panic disorder, phobia, compulsive disorder, posttraumatic stress disorder, Tourette syndrome, autism, emotional disorder, sentimental disorder, bipolar disorder, cyclothymia, schizophrenia, peptic ulcer, irritable bowel syndrome, ulcerative colitis, Crohn's disease, diarrhea, coprostasis, postoperational ileus, gastrointestinal function abnormality associated with stress, neural vomiting, Alzheimer disease, Alzheimer-type senile dementia, neurodegenerative disease, multi-infarct dementia, senile dementia, neurotic anorexia, diet disorder, obesity, diabetes, alcohol dependence, pharmacophilia, drug abstinence symptoms, alcohol abstinence symptoms, sleep disorder, insomnia, migraine, stress headache, myotonic headache, ischemic neuropathy, excitation toxic neuropathy, cerebral apoplexy, progressive supranuclear palsy, amyotrophic lateral sclerosis, multiple sclerosis, muscular convulsion, chronic fatigue syndrome, mental social growth failure, epilepsy, head trauma, spinal trauma, graphospasm, spasmodic torticollis, muscular convulsion, neck-shoulder-arm syndrome, primary glaucoma, Meniere syndrome, autonomic imbalance, alopecia, neurosis, hypertension, cardiovascular disorder, tachycardia, congestive cardioplegia, hyperpnea syndrome, bronchial asthma, apnea syndrome, infant sudden death, syndrome, inflammatory disorder, pain, allergic disease, impotence, climacteric disorder, fertilization disorder, infertility, cancer, immune function abnormality upon infection with HIV, immune function abnormality by stress, hemorrhagic stress, Cushing syndrome, thyroid function disorder, encephalomyelitis, acromegaly, incontinence or osteoporosis.

The meanings of symbols, terms and the like described in the present specification will be explained below and the present invention will be explained in detail.

In the present specification, the structural formula of the compound represents a certain isomer for convenience in some cases, but the present invention includes all isomers such as geometrical isomer, optical isomer based on an asymmetrical carbon, stereoisomer, tautomer and the like which occur structurally and an isomer mixture and is not limited to the description of the formula for convenience, and may be any one of isomer or a mixture. Therefore, an asymmetrical carbon atom may be present in the molecule and an optically active compound and a racemic compound may be present in the present compound, but the present invention is not limited to them and includes any one. In addition, a crystal polymorphism may be present but is not limiting, but any crystal form may be single or a crystal form mixture, or an anhydride or hydrate. Further, so-called metabolite which is produced by degradation of the present compound in vivo is included in the scope of the present invention.

The term 'and/or' in the present specification is used to include both the case of 'and' and case of 'or'. Therefore, for example, 'A and/or B' includes both the case of 'A and B' and the case of 'A or B' and indicates that any case may be.

As used herein, 'neural degenerative disease' means acute degenerative disease or chronic degenerative disease, specifically, means neural disorder derived from subarachnoidal hemorrhage, cerebrovascular disorder acute phase and the like, Alzheimer disease, Perkinson disease, Huntington's chorea, amyotrophic lateral sclerosis, spinal cerebellar degenerative disease and the like. As used herein, 'diet disorder' means appetite sthenia, cibophobia and the like. As used herein, 'cardiovascular disorder' means neural angina and the like. As used herein, 'inflammatory disorder' means, for example, rheumatoid arthritis, bone arthritis, lumbago and the like. 'Allergy disease' denotes, for example, atopic dermatis, eczema, urticaria, psoriasis and the like.

Meaning of A Group

'A group' in 'optionally substituted with any one or more groups listed in A group' used in the definition of each symbol in the above formula (I) means a group consisting of (1) halogen, (2) hydroxy group, (3) nitro group, (4) cyano group, (5) carboxyl group, (6) a $C_{1-6}$ alkyloxycarbonyl group, (7) the formula —S(O)$_r$R$^{13}$ (wherein r is an integer of 0, 1 or 2; and R$^{13}$ represents (i) hydorogen atom, (ii) a $C_{1-6}$ alkyl group, (iii) the formula —NR$^{14}$R$^{15}$ (wherein R$^{14}$ and R$^{15}$ are the same as or different from each other and each represents hydrogen atom, a $C_{1-6}$ alkyl group optionally substituted with an optionally substituted aryl group, a $C_{1-4}$ alkylacy group, an optionally substituted aryl $C_{1-4}$ alkyl group, an optionally substituted heteroaryl $C_{1-4}$ alkyl group, an optionally substituted aryl group or an optionally substituted heteroaryl group), (iv) an optionally substituted aryl $C_{1-4}$ alkyl group, (v) an optionally substituted aryl group, (vi) an optionally substituted heteroaryl $C_{1-4}$ alkyl group or (vii) an optionally substituted heteroaryl group), (8) —NR$^{16}$R$^{17}$ (wherein R$^{16}$ and R$^{17}$ are the same as or different from each other and each represents hydrogen, a $C_{1-6}$ alkyl group or a $C_{1-4}$ alkylacyl group), (9) a $C_{1-6}$ alkyl group, (10) a $C_{1-6}$ alkoxy group, (11) a $C_{3-8}$ cycloalkyl group optionally substituted with a $C_{1-4}$ alkyl group, (12) a $C_{1-4}$ alkoxy $C_{1-6}$ alkyl group, (13) a saturated 3- to 8-membered heterocyclic ring optionally substituted with a $C_{1-4}$ alkyl group, (14) an optionally substituted aryl group and (15) an optionally substituted heteroaryl group.

As a preferable atom in the above 'halogen atom', for example, fluorine, chlorine, bromine and iodine, more preferably fluorine, chlorine and bromine may be proposed.

'$C_{1-6}$ alkyl group' in the above '$C_{1-6}$ alkyloxycarbonyl group' means an alkyl group having 1 to 6 of carbon number, and preferably a liner or branched alkyl group such as methyl group, etheyl group, n-propyl group, iso-propyl group, n-butyl group, iso-butyl group, sec-butyl group, tert-butyl group, n-pentyl group, 1,1-dimethylpropyl group, 1,2-dimethylpropyl group, 2,2-dimethylpropyl group, 1-ethylpropyl group, 2-ethylpropyl group, n-hexyl group, 1-methyl-2-ethylpropyl group, 1-ethyl-2-methylpropyl group, 1,1,2-trimethylpropyl group, 1-propylpropyl group, 1-methylbutyl group, 2-methylbutyl group, 1-1-dimethylbutyl group, 1,2-dimethylbutyl group, 2,2-dimethylbutyl group, 1,3-dimethylbutyl group, 2,3-dimethylbutyl group, 2-ethylbutyl group, 2-methylpentyl group and 3-methylpentyl group. Preferable examples in the above '$C_{1-6}$ alkyloxycarbonyl group' are carbonyl groups with attached any $C_{1-6}$ alkyloxy group selected from methoxy group, ethoxy group, n-propoxy group, iso-propoxy group, sec-propoxy group, n-butoxy group, iso-butoxy group, sec-butoxy group, tert-butoxy group, n-pentyloxy group, iso-pentyloxy group, sec-pentyloxy group, n-hexoxy group, iso-hexoxy group, 1,1-dimethylpropyloxy group, 1,2-dimethylpropoxy, 2,2-dimethylpropyloxy group, 2-ethylpropoxy group, 1-methyl-2-ethylpropoxy group, 1-ethyl-2-methylpropoxy group, 1,1,2-trimethylpropoxy group, 1,1-dimethylbutoxy group, 1,2-dimethylbutoxy group, 2,2-dimethylbutoxy group, 2,3-dimethylbutyloxy group, 1,3-dimethylbutyloxy group, 2-ethylbutoxy group, 1,3-dimethylbutoxy group, 2-methylpentoxy group, 3-methylpentoxy group, hexyloxy group and the like.

'$C_{1-6}$ alkyl group' in the definition of A group has the same meaning of '$C_{1-6}$ alkyl group' as defined above. '$C_{1-4}$ alkyl group' in the above '$C_{1-4}$ alkylacyl group' represents an alkyl group having 1 to 4 of carbon number, and preferable example of the group are a group corresponding to an alkyl group having 1 to 4 carbon number among groups listed in the above '$C_{1-6}$ alkyl group '.

'Aryl group' in the above, 'optionally substituted aryl group' or 'optionally substituted aryl $C_{1-4}$ alkyl group' means '$C_{6-14}$ aromatic hydrocarbon ring group'. As the preferable examples of the group, monocyclic, dicyclic or tricyclic $C_{6-14}$ aromatic hydrocarbon rings such as phenyl group, indenyl group, 1-naphthyl group, 2-naphthyl group, azulenyl group, heptalenyl group, biphenyl group, indacenyl group, acenaphthyl group, fluorenyl group, phenalenyl group, phenanthrenyl group, anthracenyl group, cyclopenta cyclooctenyl group and benzocyclooctenyl group.

'Heteroaryl group' in the above 'optionally substituted heteroalyl group' or 'an optionally substituted heteroaryl $C_{1-4}$ alkyl group' means '5- to 14-membered aromatic heterocyclic ring' derived from a single ring or a fused ring, and preferable examples of the group include (1) nitrogen-containing aromatic heterocyclic ring such as pyrrolyl group, pyridyl group, pyridazinyl group, pyrimidinyl group, pyrazinyl group, triazolyl group, tetrazolyl group, benzotriazolyl group, pyrazolyl group, imidazolyl group, benzimidazolyl group, indolyl group, isoindolyl group, indolizinyl group, purinyl group, indazolyl group, quinolinyl group, isoquinolinyl group, quinolizinyl group, phthalazinyl group, naphthylidinyl group, quinoxalinyl group, quinazolinyl group, cinnolinyl group, pteridinyl group, imidazotriazinyl group, pyrazinopyridazinyl group, acridinyl group, phenanthridinyl group, carbazolyl group, carbazolinyl group, pyrimidinyl group, phenanthrolinyl group, phenacynyl group, imidazopyridinyl group, imidazopyrimidinyl group, pyrazolopyridinyl group and pyrazolopyridinyl group; (2) sulfur-containing aromatic heterocyclic ring such as thienyl group and benzothienyl group; (3) oxygen-containing aromatic heterocyclic ring such as furyl group, pyranyl group, cyclopentapyranyl group, benzofuranyl group and isobenzofuranyl group; and (4) aromatic heterocyclic rings containing two or more heteroatoms selected from nitrogen, sulfur and oxygen, such as thiazolyl group, isothiazolyl group, benzothiazolyl group, benzthiadiazolyl group, phenothiazinyl group, isoxazolyl group, furazanyl group, phenoxazinyl group, oxazolyl group, benzooxazolyl group, oxadiazolyl group, pyrazoloxazolyl group, imidazothiazolyl group, thienofuranyl group, furopyrrolyl group and pyridoxazinyl group.

The preferable examples of the above 'optionally substituted aryl $C_{1-4}$ alkyl group' include a $C_{1-4}$ alkyl group (for example, methyl group, ethyl group, n-propyl group, iso-propyl group, n-butyl group, iso-butyl group, sec-butyl group, tert-butyl group and the like) substituted with an optionally substituted aryl group (for example, phenyl group, indenyl group, 1-naphthyl group, 2-naphthyl group, azulenyl group, heptalenyl group, biphenyl group, indacenyl group, acenaphthyl group, fluorenyl group, phenalenyl group, phenanthrenyl group, anthracenyl group, cyclopentacyclooctenyl group, benzocyclooctenyl group and the like, which may be substituted, respectively), more preferably benzyl group, phenethyl group, naphthylmethyl group, naphthylethyl group and the like. In addition, the preferable examples of the above 'optionally substituted heteroaryl $C_{1-4}$ alkyl group' include a $C_{1-4}$ alkyl group (for example, methyl group, ethyl group, n-propyl group, iso-propyl group, n-butyl group, iso-butyl group, sec-butyl group, tert-butyl group and the like) substituted with an optionally substituted heteroaryl group (for example, pyrrolyl group, pyridyl group, pyridazinyl, pyrimidinyl group, pyrazinyl group, thienyl group, thiazolyl group, furyl group and the like which may be substituted, respectively), more preferably pyridylmethyl group, pyridylethyl group, thienylmethyl group, thienylethyl group and the like.

Examples of preferable groups in the above '$C_{1-6}$alkoxy group' are methoxy group, ethoxy group, n-propoxy group, iso-propoxy group, sec-propoxy group, n-butoxy group, iso-butoxy group, sec-butoxy group, tert-butoxy group, n-pentyloxy group, iso-pentyloxy group, sec-pentyloxy group, n-hexoxy group, iso-hexoxy group, 1,1-dimethylpropyloxy group, 1,2-dimethylpropoxy group, 2,2-dimethylpropyloxy group, 2-ethylpropoxy group, 1-methyl-2-ethylpropoxy group, 1-ethyl-2-methylpropoxy, 1,1,2-trimethylpropoxy group, 1,1,2-trimethylpropoxy group, 1,1-dimethylbutoxy group, 1,2-dimethylbutoxy group, 2,2-dimethylbutoxy group, 2,3-dimethylbutyloxy group, 1,3-dimethylbutyloxy group, 2-ethylbutoxy group, 1,3-dimethylbutoxy group, 2-methylpentoxy group, 3-methylpentoxy group, hexyloxy group and the like.

'$C_{1-4}$ alkoxy group' in the above '$C_{1-4}$ alkoxy $C_{1-6}$ alkyl group' means a group corresponding to an alkoxy group having 1 to 4 of carbon number among groups listed in the above '$C_{1-6}$alkoxy group'. Preferable examples of '$C_{1-4}$ alkoxy $C_{1-6}$ alkyl group' are $C_{1-6}$ alkyl groups (for example, methyl group, ethyl group, n-propyl group, iso-propyl group, n-butyl group, iso-butyl group, sec-butyl group, tert-butyl group, n-pentyl group, 1,1-dimethylpropyl group, 1,2-dimethylpropyl group, 2,2-dimethylpropyl group, 1-ethylpropyl group, 2-ethylpropyl group, n-hexyl group, 1-methyl-2-ethylptopyl group, 1-ethyl-2-methylpropyl group, 1,1,2-trimethylpropyl group, 1-propylpropyl group, 1-methylbutyl group, 2-methylbutyl group, 1,1-dimethylbutyl group, 1,2-dimethylbutyl group, 2,2-dimethylbutyl group, 1,3-dimethylbutyl group, 2,3-dimethylbutyl group, 2-ethylbutyl group, 2-methylpentyl group, 3-methylpentyl group and the like) in which the carbon atom is substituted with any two or more groups selected from methoxy group, ethoxy group, n-propoxy group, i-propoxy group, sec-propoxy group, n-butoxy group, iso-butoxy group, sec-butoxy group, tert-butoxy group and the like.

'$C_{3-8}$ cycloalkyl group' in the above '$C_{3-8}$ cycloalkyl group optionally substituted with a $C_{1-4}$ alkyl group' means a cycloalkyl group in which 3 to 8 carbon atoms form a ring, and preferable examples thereof include cyclopropyl group, cyclobutyl group, cyclopentyl group, cyclohexyl group, cycloheptyl group, cyclooctyl group and the like.

'Saturated 3- to 8-membered heterocyclic ring' in the above 'saturated 3- to 8-membered heterocyclic ring optionally substituted with a $C_{1-4}$ alkyl group' means a 3- to 8-membered saturated ring containing one or more heteroatoms selected from nitrogen, oxygen and sulfur, and preferable examples of the ring are aziridine, azetidine, pyrrolidine, piperidine, perhydroazepine, perhydroazocine, piperazine, homopiperazine, morpholine, thiomorpholine, tetrahydrofuran, tetrahydrothiopyran, perhydropyran, perhydrothiopyran, butyrolactone, butyrolactam and the like.

Preferable examples as the 'substituent' in the above 'optionally substituted aryl', 'optionally substituted aryl group', 'optionally substituted heteroaryl' or 'optionally substituted heteroaryl group', any one or more groups selected from (1) halogen atom (for example, fluorine atom, chlorine atom, bromine atom, iodine atom and the like); (2) hydroxy group; (3) thiol group; (4) nitro group; (5) cyano group; (6) a $C_{1-6}$ alkyl group, $C_{2-6}$ alkenyl group or $C_{2-6}$ alkynyl group which may be substituted with any one or more groups selected from a halogen atom and hydroxy group (for example, methyl, ethyl, n-propyl, isopropyl, fluoromethyl group, difluoromethyl group, trifluoromethyl group, 2,2,2-trifluoroethyl group, hydroxymethyl group, hydroxyethyl group, hydroxypropyl group and the like) (7) a $C_{1-6}$ alkoxy group, $C_{2-6}$ alkenyloxy group or $C_{2-6}$ alkynyloxy group which may be each substituted with a halogen atom or the like (for example, methoxy, ethoxy, n-propoxy, isopropoxy, butoxy group and the like); (8) a $C_{1-6}$ alkylthio group, $C_{2-6}$ alkenylthio group or $C_{2-6}$ alkynylthio group which may be each substituted with halogen atom or the like (for example, methylthio group, ethylthio group, isopropylthio group and the like); (9) acyl group (for example, acetyl group, propionyl group, benzoyl group and the like); (10) amino group; (11) an amino group substituted with any 1 or 2 groups selected from $C_{1-6}$ alkyl group, $C_{2-6}$ alkenyl group and $C_{2-6}$ alkynyl group (for example, methylamino group, ethylamino group, isopropylamino group, dimethylamino group, diethylamino group and the like); (12) cyclic amino group (for example, aziridinyl group, azetidinyl group, pyrrolidinyl group, piperidinyl group, perhydroazepinyl group, piperazinyl group and the like); (13) carboxyl group;

(14) a $C_{1-6}$ alkoxycarbonyl group, a $C_{2-6}$ alkenyloxycarbonyl group or a $C_{2-6}$ alkynyloxycarbonyl group (for example, methoxycarbonyl group, ethoxycarbonyl group, propylcarbonyl group and the like); (15) carbamoyl group optionally substituted with any group selected from a $C_{1-6}$ alkyl group, a $C_{2-6}$ alkenyl group and a $C_{2-6}$ alkynyl group (for example, carbamoyl group, methylcarbamoyl group, dimethylcarbamoyl group and the like); (16) acylamino group (for example, acetylamino group, benzoylamino group and the like); (17) sufamoyl group optionally substituted with any group selected from $C_{1-4}$ alkyl group, $C_{2-6}$ alkenyl group and $C_{2-6}$ alkynyl group; (18) $C_{1-6}$ alkylsulfonyl group, $C_{2-6}$ alkenylsulfonyl group or $C_{2-6}$ alkynylsulfonyl group (for example, methylsulfonyl group, ethylsulfonyl group and the like); (19) optionally substituted arylsulfonyl group (for example, benzenesulfonyl group, p-toluenesulfonyl group and the like); (20) optionally substituted aryl group (phenyl group, tolyl group, anisolyl group and the like); (21) optionally substituted heteroaryl group (for example, pyrrole group, pyrazolyl group, imidazolyl group, triazolyl group, tetrazolyl group, thiazolyl group, pyridyl group, pyrimidyl group, pyrazinyl group and the like); (22) $C_{1-6}$ alkyl group, $C_{2-6}$ alkenyl group or $C_{2-6}$alkynyl group substituted with carboxy group; (23) $C_{1-6}$ alkyloxycarbonyl $C_{1-6}$ alkyl group (for example, methoxycarbonylmethyl group, ethoxycarbonylmethyl group, methoxycarobonylethyl group and the like); (24) $C_{1-6}$alkoxy group substituted with carboxyl group (for example, carboxymethoxy group and the like); (25) $C_{1-6}$ alkyl group, $C_{2-6}$ alkenyl group or $C_{2-6}$ alkynyl group substituted with aryl group (for example, benzyl group, 4-chlorobenzyl group and the like); (25) $C_{1-6}$ alkyl group, $C_{2-6}$ alkenyl group or $C_{2-6}$ alkynyl group substituted with heteroaryl group (for example, pyridylmethyl group, pyridylethyl group and the like); (26) alkylenedioxy group (for example, methylenedioxy group, ethylenedioxy group and the like); (27) optionally substituted $C_{3-8}$ cycloalkyl group; (28) optionally substituted $C_{3-1}$ cycloalkenyl group; and (29) optionally substituted 5- to 14-membered non-aromatic heterocyclic ring may be proposed.

Meaning of A, B and D

A, B and D in the above formula (I) are the same as or different from each other and each represents (1) a heteroatom selected from nitrogen atom, oxygen atom and sulfur atom; (2) —$(CR^1R^2)_m$— (wherein $R^1$ and $R^2$ (i) are the same as or different from each other and each represents hydrogen atom, a $C_{1-6}$ alkyl group, a $C_{2-6}$ alkenyl group, a $C_{2-6}$ alkynyl group, a $C_{1-6}$alkoxy group, a $C_{3-8}$ cycloalkyl group, a $C_{1-6}$ alkoxy $C_{1-6}$ alkyl group, a $C_{3-8}$ cycloalkyl $C_{1-6}$ alkyl group or a $C_{1-6}$ alkyl-aryl group, or $R^1$ and $R^2$ may be taken together to form a 3- to 8-membered ring, (ii) $R^1$s are binded so that adjacent —$CR^1R^2$-s form a carbon-carbon double bond, that is, the partial structure represented by the formula —$CR^2$=$CR^2$—, or (iii) $R^1$ and nitrogen atom may form a bond so that adjacent nitrogen atom and a group —$CR^1R^2$— form the partial structure represented by the formula —N=$CR^2$— ($R^2$ is as defined above); and m means an integer from 0 to 4); (3) —CO—; (4) —CS—; (5) —$NR^3$— (wherein $R^3$ represents (i) hydrogen atom, (ii) formula —$COR^4$ (wherein $R^4$ represents a $C_{1-6}$ alkyl group, an optionally substituted aryl $C_{1-4}$ alkyl group, an optionally substituted aryl group, an optionally substituted heteroaryl $C_{1-4}$ alkyl group or an optionally substituted heteroaryl group), (iii) —$S(O)_nR^5$ (wherein $R^5$ represents a $C_{1-6}$ alkyl group, an optionally substituted aryl $C_{1-4}$ alkyl group, an optionally substituted aryl group, an optionally substituted heteroaryl $C_{1-4}$ alkyl group or an optionally substituted heteroaryl group; and n means an integer of 0, 1 or 2), (iv) a $C_{1-10}$, alkyl group optionally substituted with any one or more groups listed in the following A group, (v) a $C_{2-10}$ alkenyl group optionally substituted with any one or more groups listed in the following A group, (vi) a $C_{2-10}$ alkynyl group optionally substituted with any one or more groups listed in the following A group, (vii) an optionally substituted aryl group or (viii) a $C_{3-8}$ cycloalkyl group fused with an optionally substituted benzene ring, and optionally substituted with a $C_{1-4}$ alkyl group; (6) —SO—; or (7) —$SO_2$ (1) The above '$C_{1-6}$ alkyl group' has the same meaning as '$C_{1-6}$ alkyl group' as defined in the A group.

(2) The above '$C_{2-6}$ alkenyl group' means an alkenyl group having 2 to 6 of a carbon number, and preferable examples of the group are linear or branched alkenyl groups such as vinyl group, allyl group, 1-propenyl group, 2-propenyl group, isopropenyl group, 2-methyl-1-propenyl group, 3-methyl-1-propenyl group 2-methyl-2-propenyl group, 3-methyl-2-propenyl group, 1-butenyl group, 2-butenyl group, 3-butenyl group, 1-pentenyl group, 1-hexenyl group, 1,3-hexanedienyl group and 1,6-hexanedienyl group. Hereinafter, '$C_{2-6}$ alkenyl group' in the present specification has the same meaning as defined above.

(3) The above '$C_{2-6}$ alkynyl group' means an alkynyl group having 2 to 6 of a carbon number, and preferable examples of the group are linear or branched alkynyl groups such as ethynyl group, 1-propynyl group, 2-propynyl group, 1-butynyl group, 2-butynyl group, 3-butynyl group, 3-methyl-1-propynyl group, 1-ethynyl-2-propynyl group, 2-methyl-3-propynyl group, 1-pentynyl group, 1-hexynyl group, 1,3-hexanediynyl group and 1,6-hexanediynyl group. Hereinafter, '$C_{2-6}$ alkynyl group' in the present specification has the same meaning as defined above.

'$C_{1-6}$ alkoxy group', '$C_{3-8}$ cycloalkyl group', 'optionally substituted aryl $C_{1-4}$ alkyl group', 'optionally substituted aryl group', 'optionally substituted heteroaryl $C_{1-4}$ alkyl group' and 'optionally substituted heteroaryl group' in the definition A, B and D have, respectively, the same meaning as '$C_{1-6}$ alkoxy group', '$C_{3-8}$ cycloalkyl group', 'optionally substituted aryl $C_{1-4}$ alkyl group', 'optionally substituted aryl group', 'optionally substituted heteroaryl $C_{1-4}$ alkyl group' and 'optionally substituted heteroaryl group' in the A group. In addition, the above '$C_{1-6}$ alkoxy $C_{1-6}$ alkyl group' means '$C_{1-6}$ alkyl group'substituted with a group having the same meaning as '$C_{1-6}$ alkoxy group' in the above definition and, further, the above '$C_{3-8}$ cycloalkyl $C_{1-6}$ alkyl group' means '$C_{1-6}$ alkyl group'substituted with a group having the same meaning as '$C_{3-8}$ cycloalkyl group' in the above definition In the definition of A, B and D, '3- to 8-membered ring' in '$R^1$ and $R^2$ may be taken together to form a 3- to 8-membered ring' means a $C_{3-8}$ carbocycle or heterocycle. The above '$C_{3-8}$ carbocycle' means $C_{3-1}$ cycloalkane, $C_{3-8}$ cycloalkene or $C_{3-8}$ cyclo alkyne, and the above 'heterocycle', means a 3- to 8-membered ring containing any one or more hetero atoms selected from nitrogen atom, oxygen atom and sulfur atom.

(1)'$C_{1-10}$ alkyl group' in the above '$C_{1-10}$ alkyl group optionally substituted with any one or more groups listed in A group' means an alkyl group having 1 to 10 of a carbon number. Preferable examples of the group include, in addition to groups listed in '$C_{1-6}$ alkyl group' in the above definition, n-heptyl group, 1,2-dimethylpentyl group, 2,3-dimethylpentyl group, 1,3-dimethylpentyl group, 1-ethyl-2-methylbutyl group, 1-methyl-2-ethylbutyl group, 1,2-diethylpropyl group, 2,3- diethylpropyl group, 1,3-diethylpropyl group, 1-ethyl-2-propylethyl group, 1-propyl-2-methylpropyl group, 1-propylbutyl group, n-octyl group, 1,2-dimethylhexyl group, 2,3-dimethylhexyl group, 1,3-dimethylhexyl group, 1-methyl-2-ethylpentyl group, 1-methyl-2-ethylpentyl group, 1,2-diethylbutyl group, 2,3-dietylbutyl group, 1,3-diethylbutyl group, 1-ethyl-2-propylpropyl group, 1-propyl-2-methylbutyl group, 1-butylbutyl group, n-nonyl group, 1,2-dimethylheptyl group, 2,3-dimethylheptyl group, 1,3-dimethylheptyl group, 1-ethyl-2-methylhexyl group, 1-methyl-2-ethylhexyl group, 1,2-diethylpentyl group, 2,3-diethylpentyl group, 1,3-diethylpentyl group, 1-ethyl-2-propylbutyl group, 1-propyl-2-methylpentyl group, 1-propylhexyl group, 1-butylpentyl group, n-decanyl group, 1,2-dimethyloctyl group, 2,3-demethyloctyl group, 1,3-dimethyloctyl group, 1-ethyl-2-methylheptyl group, 1-methyl-2-ethylheptyl group, 1,2-diethylhexyl group, 2,3-diethylhexyl group, 1,3-diethylhexyl group, 1-ethyl-2-propylpentyl group, 1-propyl-2-methylhexyl group, 1-propylheptyl group, 1-butylhexyl group, 1-pentylpentyl group and the like. Hereinafter, '$C_{1-10}$ alkyl group' in the present specification has the same meaning as defined above.

(2) '$C_{2-10}$ alkenyl group' in the above '$C_{2-10}$ alkenyl group optionally substituted with any one or more groups listed in the A group' means an alkenyl group having 2 to 10 of a carbon number, and preferable groups for the group include linear or branched alkenyl groups such as vinyl group, allyl group, 1-propenyl group, 2-propenyl group, isopropenyl group, 2-methyl-1-propenyl group, 3-methyl-1-propenyl group, 2-methyl-2-propenyl group, 3-methyl-2-propenyl group, 1-butenyl group, 2-butenyl group, 3-butenyl group, 1-pentenyl group, 1-hexenyl group, 1,3-hexanedienyl group, 1,6-hexanedienyl group, 1-heptenyl group, 1-octenyl group, 5-ethylenyl-1-hexenyl group, 1-nonenyl group and 1-decenyl group. Hereinafter, '$C_{2-10}$ alkenyl group' in the present specification has the same meaning as defined above.

(3) '$C_{2-10}$ alkynyl group' in the above '$C_{2-10}$ alkynyl group optionally substituted with any one or more groups listed in the A group' means an alkynyl group having 2 to 10 of a carbon number, and preferable examples of the group include linear or branched alkynyl groups such as ethynyl group, 1-propynyl group, 2-propynyl group, 1-butynyl group, 2-butynyl group, 3-butynyl group, 3-methyl-1-propynyl group, 1-ethynyl-2-propynyl group, 2-methyl-3-propynyl group, 1-pentynyl group, 1-hexynyl group, 1,3-hexanediynyl group, 1,6-hexanediynyl group, 1-heptynyl group, 1-octynyl group, 5-ethylenyl-1-hexynyl group, 1-nonyneyl group and 1-decynyl group. Hereinafter, '$C_{2-10}$ alkynyl group' in the present specification has the same meaning as defined above.

(4) As the most preferable group in the above 'any one or more groups listed in the A group', a halogen atom, hydroxy group, a $C_{1-6}$ alkoxy, 'a $C_{3-8}$ cycloalxyl group optionally substituted with a $C_{1-4}$ alkyl group', 'a saturated 3- to 8-membered heterocyclic ring optionally substituted with a $C_{1-4}$ alkyl group', an optionally substituted aryl group, and an optionally substituted heteroaryl group may be proposed. Respective groups have the same meanings as defined above for the same term, respectively, in the above 'A group'.

'$C_{3-8}$ cycloalkyl group optionally fused with optionally substituted benzene ring, and optionally substituted with $C_{1-4}$ alkyl group' represented by $R^3$ in the definition of A, B and D means '$C_{3-9}$ cycloalkyl group' optionally fused with 'optionally substituted benzene ring, and further optionally substituted with '$C_{1-4}$ alkyl group'. The '$C_{3-8}$ cycloalkyl group' has the same meaning as defined above, and the example of '$C_{3-8}$ cycloalkyl group optionally fused with optionally substituted benzene ring and optionally substituted with $C_{1-4}$ alkyl group' is 2,3-dihydroindenyl group.

As a preferable aspect of A, B and D in the compound represented by the above formula (I) relating to the present invention, there is a case where A, B and/or D are nitrogen atom, oxygen atom, sulfur atom, or a group represented by the formula —$NR^3$— (wherein $R^3$ has the same meaning as defined above), CO—, —CS— or —$(CR^1R^2)_m$— (wherein $R^1$, $R^2$ and m has the same meaning as defined above), more preferably the case where A, B and/or D are nitrogen, oxygen, sulfur, a group represented by the formula —$NR^3$— (wherein $R^3$ has the same meaning as defined above) —CO—, —CS— or —$(CR^1R^2)_{m'}$— (wherein $R^1$ and $R^2$ have the same meanings as defined above; and m' represents an integer from 0 to 2). More preferably, there is the case where the partial structure represented by the formula:

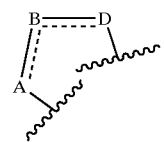

means a group represented by the formula:

—$CH_2$—$CHR^2$—$CHR^2$—; —$CH_2$—$CHR^2$—$NR^3$—;
—$CH$=$CR^2$—$CHR^2$—

—$CH_2$—$CHR^2$—O—; —$CH_2$—$CHR^2$—S—; —$CR^2$=N—$NR^3$—

—$CH$=$CR^2$—$NR^3$—; —$CR^2$=$CR^2$—$NR^3$—; —NH—$CR^2$=$CR^2$—

—N=$CR^2$—$CHR^2$—; —$(CH_2)_2$—$CR^2$—$NR^3$—; —$(CH_2)_3$—$CR^2$—$NR^3$—

—$CH_2$—CO—$NR^3$—; —CO—$NR^3$—CO—; —CO—$NR^3$—$NR^3$—

—$NR^3$—CO—$NR^3$—; —$CH_2$—CS—$NR^3$; —CS—$NR^3$—CS—

—CS—$NR^3$—$NR^3$— or —$NR^3$—CS—$NR^3$— wherein $R^2$ and $R^3$, respectively, have the same meaning as defined above, and $R^2$ and $R^3$ represent the same or different groups. In such the case, the most preferable groups in $R^2$ are hydrogen atom, methyl group, ethyl group, n-propyl group, iso-propyl group, n-butyl group, tert-butyl group, n-pentyl group, 1-ethylpropyl group, methoxymethyl group, 2-methoxyethyl group, 2-methoxy-n-propyl group, ethoxymethyl group, 2-ethoxyethyl group, 2-ethoxy-n-propyl group, cyclopropylmethyl group, 1-cyclopropylethyl group, 2-cyclopropylethyl group and the like, and examples of the most preferable groups in $R^3$ are (1) hydrogen atom, (2) a $C_{1-10}$ alkyl group, $C_{2-10}$ alkenyl group or $C_{2-10}$ alkynyl group optionally substituted with any one or more groups selected from hydroxy group; a halogen atom; a $C_{1-6}$ alkoxy group; an optionally substituted $C_{3-8}$ cycloalkyl group; an optionally substituted aryl group; an optionally substituted hetroaryl group; a mono $C_{1-6}$ alkyl-amino group; a di $C_{1-6}$ alkyl-amino group; and 3- to 5-membered saturated heterocyclic ring, (3) a $C_{1-6}$ alkylacyl group, (4) a $C_{1-6}$ alkylsulfonyl group and the like. Respective groups have the same meanings as defined above.

Meaning of E, G, J, K and L

In the above formula (I),

E and G are the same as or different from each other and each represents (1) a hetroatom selected from nitrogen atom, and oxygen atom and sulfur atom, (2) formula —$(CR^6R^7)_p$— (wherein $R^6$ and $R^7$ (i) are the same as or different from each other and each represents hydrogen atom, a $C_{1-6}$ alkyl group, a $C_{3-8}$ cycloalkyl group optionally substituted with a $C_{1-4}$ alkyl group, an optionally substituted aryl group or an optionally substituted heteroaryl group, (ii) $R^6$s are binded so that adjacent —$CR^6R^7$-s form a carbon-carbon double bond, that is, the partial structure represented by the formula —$CR^7$=$CR^7$— (wherein $R^7$ has the same meaning as defined above), or (iii) $R^6$ and nitrogen atom may form a bond so that adjacent nitrogen atom and group —$CR^6R^7$— form the partial structure represented by the formula —N=$CR^7$— ($R^7$ has the same meaning as defined above); p means an integer of 0, 1 or 2, provided that, when both E and G are —$(CR^6R^7)_p$—, p does not mean 0; and at least one of E and G represent —$CR^6R^7$—), (3) —CO—, (4) —CS—, (5) —$NR^8$— (wherein $R^8$ represents (i) hydrogen atom, (ii) formula —$COR^9$ (wherein $R^9$ means a $C_{1-6}$ alkyl group, an optionally substituted aryl $C_{1-4}$ alkyl group, an optionally substituted aryl group, an optionally substituted hetroaryl $C_{1-4}$ alkyl group or an optionally substituted heteroaryl group), (iii) —$S(O)_nR^{10}$ (wherein $R^{10}$ represents a $C_{1-6}$ alkyl group, an optionally substituted aryl $C_{1-4}$ alkyl group, an optionally substituted aryl group, an optionally substituted heteroaryl $C_{1-4}$ alkyl group or an optionally substituted heteroaryl group; and n means an integer of 0, 1 or 2), (iv) a $C_{1-10}$ alkyl group optionally substituted with any one or more groups listed in the following A group, (v) a $C_{2-10}$ alkenyl group optionally substituted with any one or more groups listed in the following. A group, (vi) a $C_{2-10}$ alkynyl group optionally substituted with any one or more groups listed in the following A group, or (vii) a $C_{3-8}$ cycloalkyl group optionally fused with an optionally substituted benzene ring, and optionally substituted with a $C_{1-4}$ alkyl group), (6) —SO—, or (7) —$SO_2$—;

J represents (1) nitrogen atom or (2) a carbon or nitrogen atom substituted with any one or more groups selected from the group consisting of (i) hydrogen atom, (ii) amino group, (iii) cyano, (iv) a $C_{1-6}$ alkyl group optionally substituted with a halogen atom, (v) a $C_{1-6}$ alkylaminosulfonyl group, (vi) an optionally substituted aryl group and (vii) an optionally substituted saturated or unsaturated heterocyclic ring; and K and L are the same as or different from each other and each represents carbon or nitrogen atom, respectively (provided that the case where both K and L are a nitrogen atom is excluded).

'$C_{1-4}$ alkyl group', '$C_{1-6}$ alkyl group', '$C_{3-8}$ cycloalkyl group', 'optionally substituted aryl group', 'optionally substituted heteroaryl group', 'optionally substituted aryl $C_{1-4}$ alkyl group', 'optionally substituted heteroaryl $C_{1-4}$ alkyl group', '$C_{1-10}$ alkyl group optionally substituted with any one or more groups listed in the A group', '$C_{2-10}$ alkenyl group optionally substituted with any one or more groups listed in the A group', '$C_{2-10}$ alkynyl group optionally substituted with any one or more groups listed in the A group' and '$C_{3-8}$ cycloalkyl group optionally fused with optionally substituted benzene group, and optionally substituted with $C_{1-4}$ alkyl group' in the definition of E and G respectively have the same meanings as those of '$C_{1-4}$ alkyl group', '$C_{1-6}$ alkyl group', '$C_{3-8}$ cycloalkyl group', 'optionally substituted aryl group', 'optionally substituted heteroaryl group', 'optionally substituted aryl $C_{1-4}$ alkyl group', 'optionally substituted heteroaryl $C_{1-4}$ alkyl group', '$C_{1-10}$ alkyl group optionally substituted with any one or more groups listed in the A group', '$C_{2-10}$ alkenyl group optionally substituted with any one or more groups listed in the A group', '$C_{2-10}$ alkynyl group optionally substituted with any one or more groups listed in the A group'and '$C_{3-8}$ cycloalkyl group optionally fused with optionally substituted benzene group, and optionally substituted with $C_{1-4}$ alkyl group'described in the definition of the above A group, A, B and D.

A preferable group in E and G is different depending upon an aspect of J and its substituent and K and L, and not particularly limited but includes the same or different group represented by (1) a heteroatom selected from nitrogen atom, oxygen atom and sulfur atom, (2) the formula —$(CR^6R^7)_p$— (wherein $R^6$, $R^7$ and p have the same meanings as defined above) or (3) —$NR^8$— (where $R^8$ has the same meaning as defined above). More preferably, there is the case where the partial structure - - -E- - -G- - - is a group represented by the formula —$(CHR^7)_2$—, —N=$CR^7$—, —$CR^7$=N—, —$(CHR^7)_3$—, —$CR^7$=$CR^7$—$CR^7$=, —N=$CR^7$—$CR^7$— or —$CR^7$=$CR^7$—N= (wherein $R^7$ has the same meaning as defined above). In such the case, a more preferable group in $R^7$ is also different depending upon an aspect of J and its substituent, and K and L are not particularly limited but includes hydrogen, a $C_{1-6}$alkyl group (for example, methyl group, ethyl group, n-propyl group, isopropyl group, 1-ethyl-n-propyl group and the like), a $C_{3-8}$ cycloalkyl group (for example, cyclopropyl group, cyclobutyl group, cyclopentyl group, cyclohexyl group and the like), aryl group (for example, phenyl group and the like), heteroaryl group (for example, pyridyl group, pyrimidinyl group, pyridazinyl group, pyrazinyl group, thienyl group, furyl group, imidazolyl group, thiazolyl group and the like.

'Halogen atom', '$C_{1-6}$ alkyl group' and 'an optionally substituted aryl group' in the definition of J have the same meanings as those of 'halogen atom', '$C_{1-6}$ alkyl group' and 'an optionally substituted aryl group' described in the definitions of the above A group, A, B and D, respectively.

'$C_{1-6}$ alkylaminosulfonyl group' in the definition of J means a sulfonyl group substituted with 'an amino group substituted with a $C_{1-6}$ alkyl group', and a preferable example includes methyl aminosulfonyl group, ethylaminosulfonyl group, n-propylaminosulfonyl group, isopropylaminosulfonyl group, n-butylaminosulfonyl group, tert-butylaminosulfonyl group and the like.

As a preferable group in J, for example, there is a carbon atom or nitrogen atom substituted with any one selected from (1) an aryl group and (2) a saturated or unsaturated heterocyclic ring which may be substituted, respectively. The above 'aryl group' has the same meaning as 'aryl group' in the above definition and, on the other hand, 'saturated or unsaturated heterocyclic ring' represents more specifically '5- to 14-membered non-aromatic heterocyclic ring' or '5- to 14-membered aromatic heterocyclic ring'.

As a preferable ring in the above '5- to 14-membered non-aromatic heterocyclic ring', for example, there are 5- to 14-membered heterocyclic ring such as pyrrolidine, pyrroline, piperidine, piperazine, imidazoline, pyrazolidine, imidazolidine, morpholine, tetrahydrofuran, tetrahydropyran, aziridine, oxirane, oxathiolane, pyridone ring; unsaturated fused ring such as phthalimide ring and succinimide ring, and the like.

'5- to 14-membered aromatic heterocyclic ring' means a ring corresponding to a group listed in the above 'heteroaryl', and, preferably, pyrrole, pyridine, pyridazine, pyrimidine, pyrazine, pyrazole, imidazole, indole, isoindole, indolizine, purine, indazole, quinoline, isoquinoline, quinolizine, phthalazine, naphthyridine, quinoxaline, quinazoline, cinnoline, pteridine, imidazotriazine, pyrazinopyridazine, acridine, phenanthridine, carbazole, carbazoline, perimidine, phenanthroline, phenazine, thiophene, benzothiophene, furan, pyran, cyclopentapyran, benzofuran, isobenzofuran, thiazole, isothiazole, benzthiazole, benzthiadiazole, phenothiazine, isoxazole, furazane, phenoxazine, pyrazoloxazole, imidazothiazole, thienofuran, furopyrrole, pyridooxazine, 3-benzo[b]furan ring and the like.

Preferable examples of 'aryl group' or 'heterocyclic ring' in the case where J is a carbon atom or nitrogen atom substituted with any one group selected from (1) an aryl group and (2) a saturated or unsaturated heterocyclic ring which may be substituted, respectively, are phenyl group and naphthyl group which may be substituted, respectively, and pyrrolidine, pyrroline, piperidine, piperazine, imidazoline, morpholine, tetrahydrofuran, pyridone, pyrrole, pyridine, pyridazine, pyrimidine, pyrazine, pyrazole, imidazole, indole, isoindole, thiophene, benzothiophene, furan, thiazole, isothiazole, benzthiazole, benzthiadiazole ring and the like which may be substituted, respectively. More preferable groups or rings are phenyl group, pyridine ring, thiophene ring, furan ring and the like which may be substituted, respectively. Still preferable rings or groups are phenyl group and pyridine ring which may be substituted, respectively.

Preferable groups as 'substituent' in the above optionally substituted aryl group' or 'optionally substituted saturated or unsaturated heterocyclic ring' include, for example, one or more same or different groups selected from (1) a halogen atom (for example, fluorine atom, chlorine atom, bromine atom and the like), (2) a $C_{1-6}$ alkyl group optionally substituted with a halogen atom (for example, methyl group, ethyl group, n-propyl group, iso-propyl group, trifluoromethyl group and the like), (3) a $C_{1-6}$ alkoxy group (for example, methoxy group, ethoxy group, n-propoxy group, iso-propoxy group and the like) and (4) an amino group optionally substituted with one or more linear hydrocarbon group (a $C_{1-6}$ alkyl group, a $C_{2-6}$ alkenyl group and/or a $C_{2-6}$ alkynyl group) (for example, methylamino group, ethylamino group, dimethylamino group, diethylamino group, methylethylamino group and the like).

A preferable aspect in K and L is not particularly limited except for the case where K and L are nitrogen atom, and includes the case where K and L are carbon atom, the case where K is carbon atom and L is nitrogen atom, and the case where L is nitrogen atom and L is carbon atom. The most preferable is the case where K is nitrogen atom and L is carbon atom or the case where K and L are carbon atom.

A ring represented by the formula:

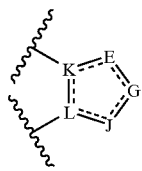

which is constituted by K, E, G, J and L in the above formula (I) represents an unsaturated 5- or 6-membered ring, and the ring may be a hydrocarbon ring or a heterocyclic ring containing a nitrogen atom. As the most preferable aspect in the ring, there is a ring represented by the formula:

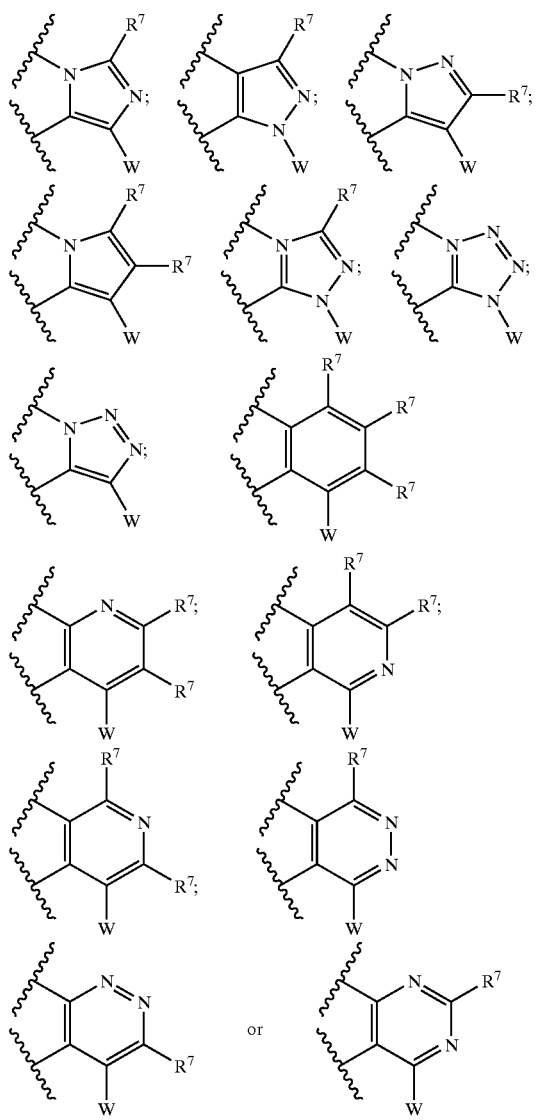

wherein $R^7$ has the same meaning as defined above; and W represents any one group selected from the group consisting of (i) hydrogen atom, (ii) amino group, (iii) cyano group, (iv) a $C_{1-6}$ alkyl group optionally substituted with a halogen atom, (v) a $C_{1-6}$ alkylaminosulfonyl group, (vi) an optionally substituted aryl group and (vii) an optionally substituted saturated or unsaturated heterocyclic ring. Examples of preferable $R^7$ in such the case are described for $R^7$ as defined above. In addition, examples of preferable W are an optionally substituted aryl group and saturated or unsaturated heterocyclic ring. And preferable examples of the group or ring are as defined for substituents of J in the above definition. Provided that, in the foregoing, the case where K is nitrogen, L is carbon, A and B are a group represented by the formula —$(CR^1R^2)_m$— (wherein both $R^1$ and $R^2$ represents hydrogen; and m is 1), respectively, and J is a carbon substituted with any group selected from (i) amino group; (ii) cyano group; (iii) an aminosulfonyl group in which the nitrogen atom is substituted with a linear or branched $C_{1-6}$ alkyl group; and (iv) 1H-tetrazol-5-yl group, is excluded.

Meaning of M

In the above formula (I), M represents (1) hydrogen atom, (2) a halogen atom, (3) cyano group, (4) a $C_{1-6}$ alkyl group optionally substituted with any one or more groups listed in the above A group, (5) the formula —NR$^{11}$R$^{12}$— (wherein R$^{11}$ and R$^{12}$ are the same as or different from each other and each represents (i) hydrogen atom, (ii) any group listed in the following A group, (iii) a C$_{1-6}$ alkyl group optionally substituted with any one or more groups listed in the following A group, (iv) a C$_{1-4}$ alkylacyl group, (v) an optionally substituted aryl C$_{1-4}$ alkyl group, (vi) an optionally substituted heteroaryl C$_{1-4}$ alkyl group, (vii) an optionally substituted aryl group or (viii) an optionally substituted heteroaryl group), (6) —OR$^{11}$ (where R$^{11}$ represents hydrogen atom, a C$_{1-6}$ alkyl group optionally substituted with any one or more groups listed in the above A group, a C$_{1-4}$ alkylacyl group, an optionally substituted aryl C$_{1-4}$ alkyl group, an optionally substituted heteroaryl C$_{1-4}$ alkyl group, an optionally substituted aryl group or an optionally substituted heteroaryl group), (7) —S(O)$_q$R$^{12}$ (wherein R$^{12}$ represents a C$_{1-6}$ alkyl group, an optionally substituted aryl C$_{1-4}$ alkyl group, an optionally substituted aryl group, an optionally substituted heteroaryl C$_{1-4}$ alkyl group, an optionally substituted aryl group, an optionally substituted heteroaryl C$_{1-4}$ alkyl group or an optionally substituted heteroaryl group; q means an integer of 0, 1 or 2), (8) an optionally substituted C$_{2-10}$ alkenyl group, (9) an optionally substituted C$_{2-10}$ alkynyl group, (10) a C$_{1-6}$ alkoxy group optionally substituted with one or more groups listed in the following A group, (11) a C$_{1-6}$ alkylthio group optionally substituted with one or more groups listed in the following A group, (12) an optionally substituted aryl group or (13) an optionally substituted heteroaryl group.

'Halogen atom', 'C$_{1-6}$ alkyl group', 'C$_{1-4}$ alkylacyl group', 'an optionally substituted aryl C$_{1-4}$ alkyl group', 'an optionally substituted heteroaryl C$_{1-4}$ alkyl group', 'an optionally substituted aryl group', 'an optionally substituted heteroaryl group', 'C$_{2-10}$ alkenyl group', 'C$_{2-10}$ alkynyl group' and 'C$_{1-6}$ alkoxy group' in the definition of M have, respectively, the same meanings as those of 'halogen atom', 'C$_{1-6}$ alkyl group', 'C$_{1-4}$ alkylacyl group', 'an optionally substituted aryl C$_{1-4}$ alkyl group', 'an optionally substituted heteroaryl C$_{1-4}$ alkyl group', 'an optionally substituted aryl group', 'an optionally substituted heteroaryl group', 'a C$_{2-10}$ alkenyl group', 'C$_{2-10}$ alkynyl group' and 'C$_{1-6}$ alkoxy group' described in the above definitions of A group, A, B and D.

Preferable groups in 'C$_{1-6}$ alkylthio group' in the definition of M are methylthio group, ethylthio group, n-propyl group, iso-propylthio group, n-butylthio group, iso-butylthio group, sec-butylthio group, tert-butylthio group, n-pentylthio group, 1,1-dimethylpropylthio group, 1,2-dimethylpropylthio group, 2,2-dimethylpropylthio group, 1-ethylpropylthio group, 2-ethylpropylthio group, n-hexylthio group, 1-methyl-2-ethylpropylthio group, 1-ethyl-2-methylpropylthio group, 1,1,2-trimethylpropylthio group, 1-propylpropylthio group, 1-methylbutylthio group, 2-methylbutylthio group, 1,1-dimethylbutylthio group, 1,3-dimethylbutylthio group, 2,3-dimethylbutylthio group, 2-ethylbutylthio group, 2-methylpentylthio group, 3-methylpentylthio group and the like. More preferred are methylthio group, ethylthio group, n-propylthio group, iso-propylthio group, n-butylthio group, iso-butylthio group, sec-butylthio group and tert-butylthio group.

Preferable groups in M are not particularly limited, but examples of more preferred are a halogen atom (for example, fluorine, chlorine, bromine and the like), a C$_{1-6}$ alkyl group optionally substituted with any one or more groups selected from the above A group, the formula —NR$^9$R$^{10}$— (wherein R$^9$ and R$^{10}$ are the same as or different from each other and each represents hydrogen, a C$_{1-6}$ alkyl group optionally substituted with any one or more groups listed in the above A group, a C$_{1-4}$ alkylacyl group, an optionally substituted aryl C$_{1-4}$ alkyl group, an optionally substituted heteroaryl C$_{1-4}$ alkyl group, an optionally substituted aryl group or an optionally substituted heteroaryl group), an optionally substituted C$_{2-10}$ alkenyl group, an optionally substituted C$_{2-10}$ alkynyl group and the like. Still preferable groups in M are a halogen atom (for example, fluorine, chlorine, bromine and the like), a C$_{1-6}$ alkyl group, a C$_{2-10}$ alkenyl group, a C$_{2-10}$ alkynyl group and the like, and the most preferred are a halogen atom, methyl group, ethyl group, n-propyl group, iso-propyl group and the like.

An aspect of the compound represented by the above formula (I) relating to the present invention is not particularly limited, and a person in the art can arbitrarily combine groups listed regarding A, B, D, E, G, J, K, L and M in the above definition and implement all compounds in the range. Among them, a more preferable aspect is, for example, a compound represented by the formula:

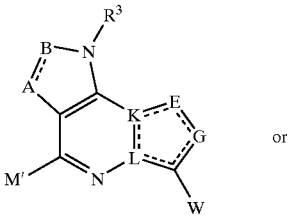

(VIII-1)

or

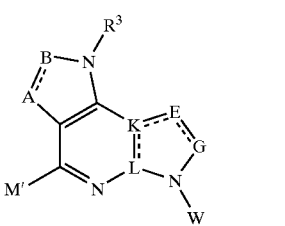

(VIII-2)

(wherein A, B, K, E, G, J, L and R$^3$ have the same meanings as defined above; M' represents halogen atom, a C$_{1-6}$ alkyl group optionally substituted with any one or more groups selected from the above A group, the formula —NR$^9$R$^{10}$— (wherein R$^9$ and R$^{10}$ have the same meanings as defined above), an optionally substituted C$_{2-10}$ alkenyl group or an optionally substituted C$_{2-10}$ alkynyl group; W represents hydrogen atom, amino group, cyano group, a C$_{1-6}$ alkyl group, a C$_{1-6}$ alkylaminosufonyl group, an optionally substituted aryl group or an optionally substituted saturated or unsaturated heterocyclic ring), a salt thereof or hydrates thereof. A still preferable aspect is a compound represented by the formula:

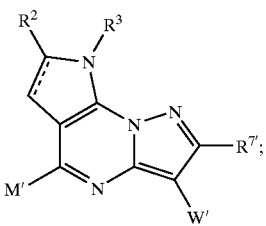

-continued

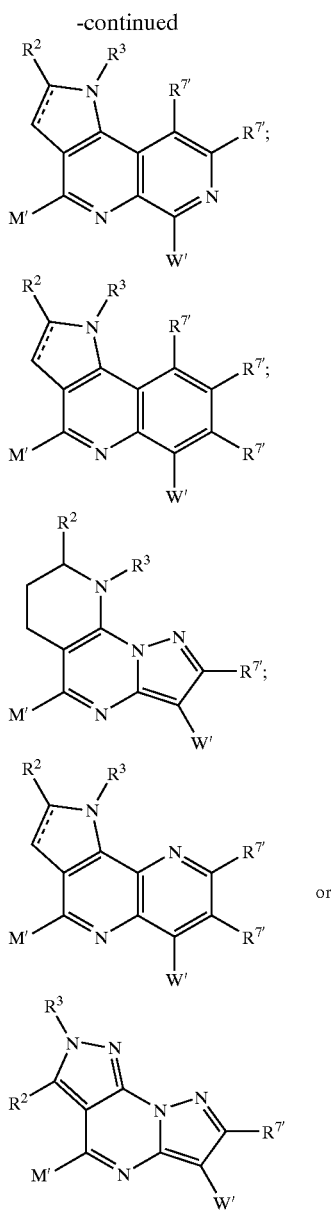

(wherein M', R² and R³ have the same meanings as defined above; R⁷ represents hydrogen or a $C_{1-6}$ alkyl group; and W' represents an optionally substituted aryl group or an optionally substituted saturated or unsaturated heterocyclic ring), a salt thereof or hydrates thereof.

As an specific embodiment in a compound relating to the present invention, there are the following suitable compounds:

8-(1-ethylpropyl)-3-mesityl-2,5-dimethyl-8H-pyrazolo[1,5-a]pyrrolo[3,2-e]pyrimidine;

8-(1-ethylpropyl)-3-mesityl-2,5-dimethyl-7,8-dihydro-6H-pyrazolo[1,5-a]pyrrolo[3,2-e]pyrimidine;

3-mesityl-8-[2-methoxy-1-(methoxymethyl)ethyl]-2,5-dimethyl-7,8-dihydro-6H-pyrazolo[1,5-a]pyrrolo[3,2-e]pyrimidine;

8-benzyl-3-mesityl-2,5-dimethyl-7,8-dihydro-6H-pyrazolo[1,5-a]pyrrolo[3,2-e]pyrimidine;

3-mesityl-8-[1-(methoxymethyl)propyl]-2,5-dimethyl-7,8-dihydro-6H-pyrazolo[1,5-a]pyrrolo[3,2-e]pyrimidine;

3-mesityl-2,5-dimethyl-8-(1-propylbutyl)-7,8-dihydro-6H-pyrazolo[1,5-a]pyrrolo[3,2-e]pyrimidine;

2-ethyl-8-(1-ethylpropyl)-3-mesityl-5-methyl-7,8-dihydro-6H-pyrazolo[1,5-a]pyrrolo[3,2-e]pyrimidine;

8-(1-ethylpropyl)-2,5-dimethyl-3-(2,4,6-trimethyl-3-pyridyl)-8H-pyrazolo[1,5-a]pyrrolo[3,2-e]pyrimidine;

6-mesityl-2,4,7-trimethyl-2H-dipyrazolo[1,5-a:4,3-e]pyrimidine;

9-(cyclopropylmethyl)-8-ethyl-3-mesityl-2,5-dimethyl-6,7,8,9-tetrahydropyrazolo[1,5-a]pyrido[3,2-e]pyrimidine;

2-(6-mesityl-4-methyl-1H-pyrrolo[3,2-c]quinolin-1-yl)butyl methyl ether;

1-(1-ethylpropyl)-6-mesityl-4-methyl-1H-pyrrolo[3,2-c][1,7]naphthyridine; and 2-(6-mesityl-4-methyl-1H-pyrrolo[3,2-c][1,5]naphthyridine-1-yl)butyl methyl ether.

'Pharmacologically acceptable salt' in the present specification is not particularly limited as long as it forms a salt with a compound of the present invention and pharmacologically acceptable. Preferable examples include hydrogen halide salts (for example, hydrofluoride, hydrochloride, hydrobromide, hydroiodide and the like), inorganic acid salts (for example, sulfate, nitrate, perchlorate, phosphate, carbonate, bicarbonate and the like) organic acid salts (for example, acetate, trifluoroacetate, oxalate, maleate, tartate, fumarate, citrate and the like), organic sulfonic acid salts (for example, methanesulfonate, trifluoromethanesulfonate, ethanesulfonate, benzenesulfonate, camphorsulfonate and the like), amino acid salts (for example, aspartate, glutamate and the like), quaternary amine salt, alkali metal salts (for example, sodium salt, potassium salt and the like), alkaline earth metal salts (magnesium salt, calcium salt and the like) and the like. As the 'pharmacologically acceptable salt', more preferred are hydrochloride, oxalate, trifluoroacetate and the like.

A representative process for preparing the compound according to the present invention represented by the above formula (I) will be described below.

(1) A compound (I-1) wherein D is a nitrogen atom in a compound according to the present invention represented by the above formula (I) can be prepared via steps 1-A to E shown in the formula:

Producing Process 1

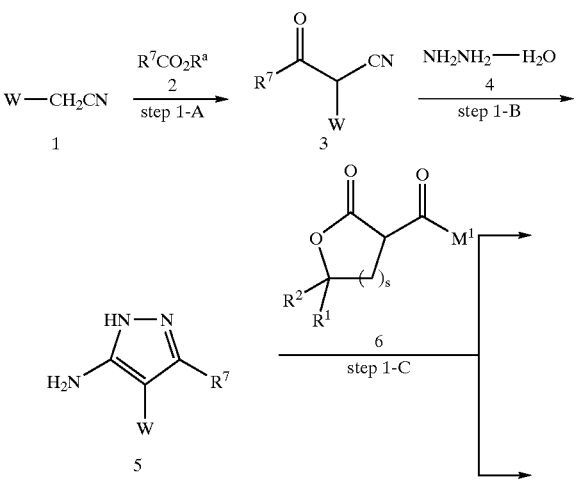

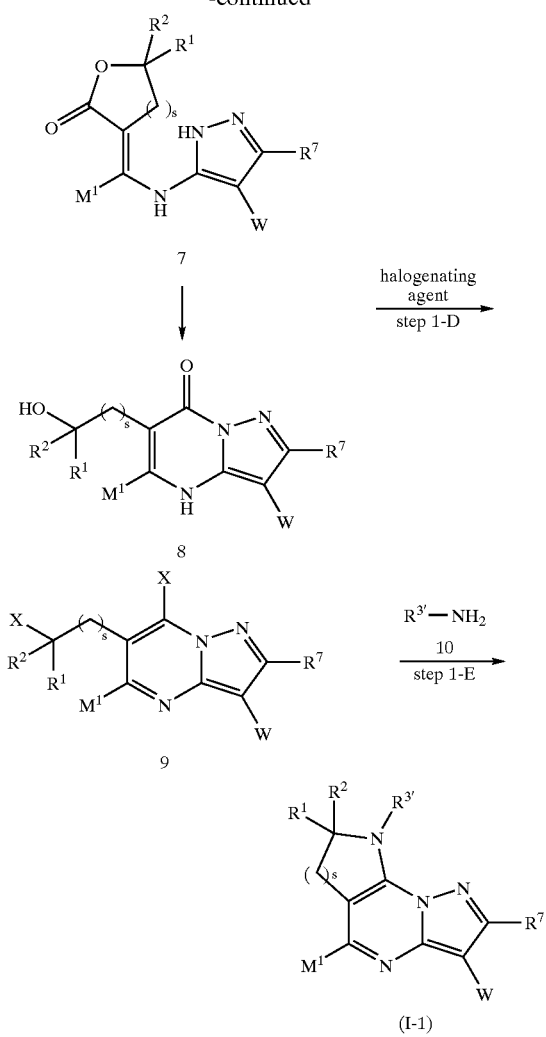

wherein
R[1], R[2] and R[7] have the same meanings as defined above;
R[3'] represents hydrogen atom, a $C_{1-10}$ alkyl group optionally substituted with any one or more groups listed in the above A group, a $C_{2-10}$ alkenyl group optionally substituted with any one or more groups listed in the above A group, a $C_{2-10}$ alkynyl group optionally substituted with any one or more groups listed in the above A group or a $C_{3-8}$ cycloalkyl group optionally fused with an optionally substituted benzene ring and optionally substituted with a $C_{1-4}$ alkyl group;
R[3] represents a $C_{1-6}$ alkyl group; X represents chlorine, bromine or iodine; W represents hydrogen atom, amino group, cyano group, a $C_{1-6}$ alkyl group, a $C_{1-6}$ alkylaminosulfonyl group, an optionally substituted aryl group or an optionally substituted saturated or unsaturated heterocyclic ring; M[1] represents a $C_{1-6}$ alkyl group optionally substituted with any one or more groups listed in the above A group, an optionally substituted aryl group or an optionally substituted heteroaryl group; and s means an integer from 1 to 4.

A compound (3) can be obtained by reacting acetonitrile compound (1) with a compound (2) at −78 to 200° C. in the presence of a base in a solvent (Step 1-A). A base used is different depending upon a starting raw material, the solvent used and the like, and is not particularly limited as long as it dose not inhibit the reaction. Preferably, amines such as triethylamine, diisopropylamine, N,N-diisopropylethylamine, N,N-diisopropylethylamine and pyridine; inorganic salts such as sodium carbonate, potassium carbonate and sodium bicarbonate; alcoholates such as sodium methoxide, sodium ethoxide and potassium tert-butoxide; metal amides such as sodium amide and lithium diisopropylamide; metal hydrides such as sodium hydride, potassium hydride and calcium hydride etc. may be proposed. A solvent used is different depending upon a starting raw material, a reagent and the like, and is not particularly limited as long as it dose not inhibit the reaction and dissolves a starting material to some extent. Suitable solvents are alcohols such as methanol, ethanol, isopropylalcohol and ethylene glycol; ethers such as diethyl ether, tetrahydrofuran, dioxane and 1,2-dimethoxyethane; hydrocarbons such as benzene and toluene; amides such as N,N-dimethylformamide; acetonitrile; water, or a mixed solvent of them.

An aminopyrazole derivative (5) can be obtained by reacting a compound (3) and hydrazine hydrate (4) at 0 to 200° C. in the presence or absence of an acid in a solvent (Step 1-B). An acid used is different depending upon a raw material, a reagent, the solvent used and the like, and is not particularly limited as long as it dose not inhibit the reaction. Suitable acids are inorganic acids such as hydrochloric acid, hydrobromic acid and sulfuric acid; organic acids such as p-toluenesulfonic acid, methanesulfonic acid, acetic acid and trifluoroacetic acid. A solvent used is different depending upon a raw material, a reagent used and the like, and is not particularly limited as long as it dose not inhibit the reaction and dissolves a raw material to some extent. Suitable solvents are alcohols such as methanol, ethanol, isopropylalcohol and ethylene glycol; ethers such as diethyl ether, tetrahydrofuran, dioxane and 1,2-dimethoxyethane; hydrocarbons such as benzene and toluene; amides such as N,N-dimethylformamide; acetonitrile; water, or a mixed solvent thereof.

Pyrazolo[1,5-a]pyrimidine derivative (8) can be obtained by reacting am aminopyrazole derivative (5) and an acyl-lactone derivative (6) at 0 to 200° C. in the presence or absence of an acid in a solvent (Step 1-C). An acid used is different depending upon a raw material used, a reagent, the solvent and the like to be used, and is not particularly limited as long as it dose not inhibit the reaction. Suitable acids are inorganic acids such as hydrochloric acid, hydrobromic acid and sulfuric acid; and organic acids such as p-toluenesulfonic acid, methanesulfonic acid, acetic acid and trifluoroacetic acid. A solvent used is different depending upon a raw material used, a reagent and the like to be used, and is not particularly limited as long as it dose not inhibit the reaction and dissolves a raw material to some extent. Preferably, alcohols such as methanol, ethanol, isopropyl alcohol and ethylene glycol; ethers such as diethyl ether, tetrahydrofuran, dioxane and 1,2-dimethoxyethane; hydrocarbons such as benzene, toluene and xylene; amides such as N,N-dimethylformamide; acetonitrile; water, or a mixed solvent of them etc. may be proposed. Pyrazoloaminomethylenelactone (7) is precipitated during the present reaction is some cases but isolation and heating in a solvent again afford (8).

A dihalogeno compound (9) can be obtained in one stage or two stage reaction by reacting a compound (8) and a halogenating agent at −80 to 250° C. in the presence or absence of a base and in the presence or absence of a quaternary salt in a solvent or without a solvent (Step 1-D). A halogenating agent, a base and a quaternary salt used are different depending upon a raw material, a reagent and the solvent used. Preferable examples of a halogenating agent are thionyl chloride, phosphorus oxychloride, phosphorus trichloride, phosphorus pentachloride, phosphorus oxybromide, phosphorus tribromide, phosphorus pentabromide, oxalyl chloride and the like. Preferable bases are triethylamine, diisopropylamine, N,N-diisopropylethylamine, N,N-diisopropylethylamine, pyridine, dimethylaniline, diethylaniline and the like. Preferable quaternary salts are tetraethylammonium chloride, tetraethylammonium bromide, triethylmethylammonium chloride, triethylmethylammonium bromide and the like. A solvent used is different depending upon a raw material, a reagent and the like to be used, and is not particularly limited as long as it dose not inhibit the reaction and dissolves a raw material to some extent. Suitable solvents are ethers such as diethyl ether, tetrahydrofuran, dioxane and 1,2-dimethoxyethane; and hydrocarbons such as benzene, toluene and xylene, or a mixed solvent of them.

A pyrazolo[1,5-a]pyrrolo[3,2-e]pyrimidine (I-1) of the present invention can be obtained by adding an amine derivative (10) to a dihalogeno compound (9) in a solvent or without a solvent (Step 1-E). When the reaction is performed in a solvent, such the solvent is different depending upon a raw material, a reagent and the like to be used, and is not particularly limited as long as it dose not inhibit the reaction and dissolves a raw material to some extent. Preferably, alcohols such as methanol, ethanol, isopropyl alcohol and ethylene glycol; ethers such as diethyl ether, tetrahydrofuran, dioxane and 1,2-dimethoxyethane; hydrocarbons such as benzene, toluene and xylene; amides such as N,N-dimethylformamide; alkylnitriles such as acetonitrile; ketones such as methyl ethyl ketone; a mixed solvent of them etc. may be proposed. The present reaction is conducted in the presence or absence of a base and, when a base is used, such the base is different depending upon raw material, other reagents to be used, and is not particularly limited. Preferably, amines such as triethylamine, diisopropylamine, N,N-diisopropylethylamine, N,N-diisopropylethylamine and pyridine; inorganic salts such as sodium carbonate, potassium carbonate and sodium bicarbonate; alcoholates such as sodium methoxide, sodium ethoxide and potassium tert-butoxide; metal amides such as sodium amide and lithium diisopropylamide; metal hydrides such as sodium hydride, potassium hydride and calcium hydride etc. may be proposed. In addition, an amine (10) which is a reaction reagents may be also used a base by using it an excessive amount. A reaction temperature is usually −80 to 250° C.

Regarding the above Preparation method 1, a compound wherein the ring constituted by A, B and D in the above formula (I) is 6- or 7-membered ring can be prepared as follows;

Preparation Method 1'

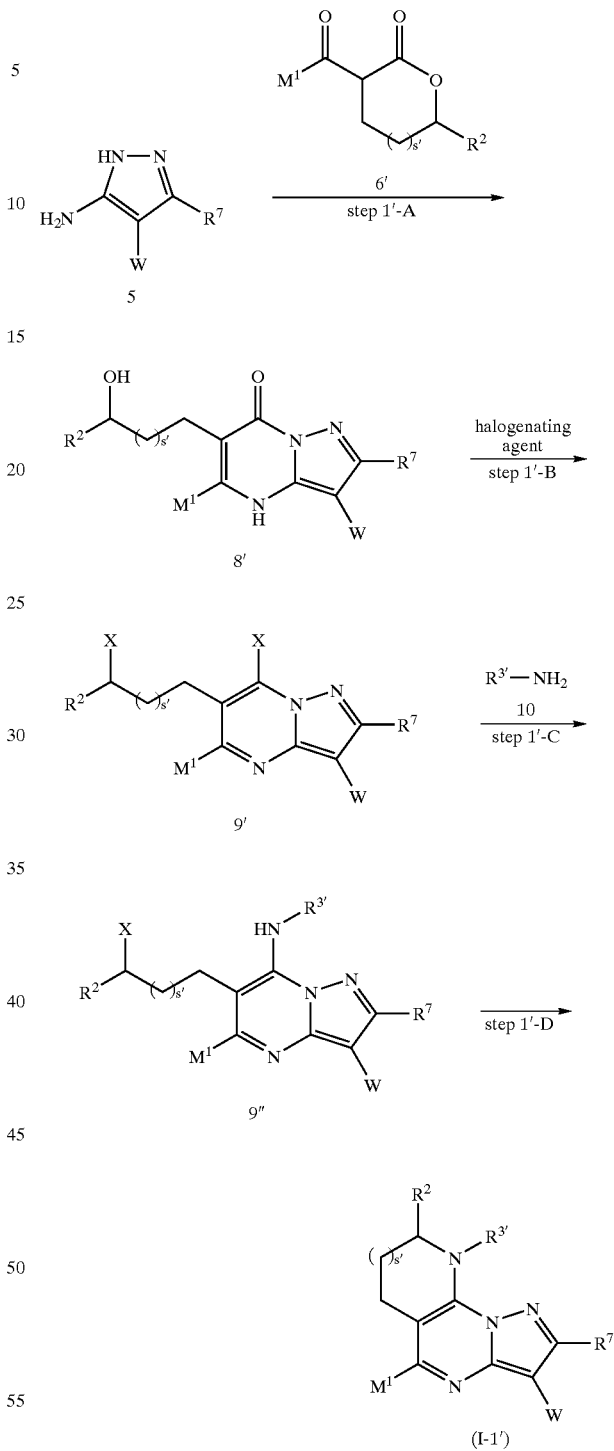

A compound (9") can be obtained by adding an amine derivative (10) to a dihalogeno compound (9') in an inert solvent or without solvent (step 1-C). An inert solvent used is different depending upon a raw material, a reagents and the like to be used, and is not particularly limited as long as it does not inhibit the reaction and desolves a raw material to some extent. Preferably, xylene, toluene, benzene, tetrahydrofuran, N-methylpyrrolidone, N,N-dimethylformamide, 1,4-dioxane, dimethoxyethane, ethanol, acetonitrile etc. may be proposed. Alternatively, an amine (10) which is a raw material may be used as a solvent. A reaction temperature is usually a room temperature to the boiling point of the solvent.

A pyrozolo[1,5-a]pyrrolo[3,2-e]pyrimidine compound (I-1') of the present invention can be obtained by cyclizing intramolecularly the compound (9'') prepared in Step 1'-C (Step 1'-D). A reaction solvent used different depending upon a raw material, a reagents and the like to be used, and is not particularly limited as long as it does not inhibit the reaction and dissolves a starting material to some extent. Suitable reaction solvents are tetrahydrofuran, N-methylpyrrolidone, N,N-dimethylformamide, dimethylsulfoxide, 1,4-dioxane, dimethoxyethane, ethanol, acetonitrile and the like. It is preferable that the present reaction can be performed by adding a base (for example, triethylamine, pyridine, potassium carbonate and the like) and the better results can be obtained. Alternatively, the addition of sodium iodide as a catalyst to the reaction system is also a preferable method. A reaction temperature is usually room temperature to the boiling point of the solvent.

Although a commercial derivative can be usually used as lactone (6) used in the above Step 1-C, when substituents are introduced to parts of $R^1$ and $R^2$ of (6), the lactone may be also prepared by an easy method by a person skilled in the art as follows:

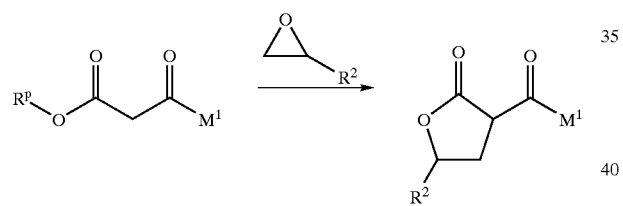

The reaction is usually performed in the presence or absence of a base in an inert solvent. An inert solvent used is different depending upon a raw material, a reagent and the like to be used, and is not particularly limited as long as it does not inhibit the reaction and dissolves a starting materials to some extent. Suitable inert solvents are xylene, toluene, benzene, tetrahydrofuran, N-methylpyrrolidone, N,N-dimethylformamide, 1,4-dioxane, 1,2-dimethoxyethan, methanol, acetonitrile and the like. A base used is different depending upon a starting material, a reagent, the solvent and the like, and is not particularly limited. Suitable bases are sodium hydride, sodium methoxide, sodium t-butoxide, lithium diisopropylamide, butylrithium and the like. A reaction temperature is usually room temperature to the boiling point of the solvent.

A compound of the present invention can be prepared using as a starting raw material the above aminopyrazole derivative (5) by another method different from a preparation method 1 that is, a method represented by the formula:

Producing Process 2

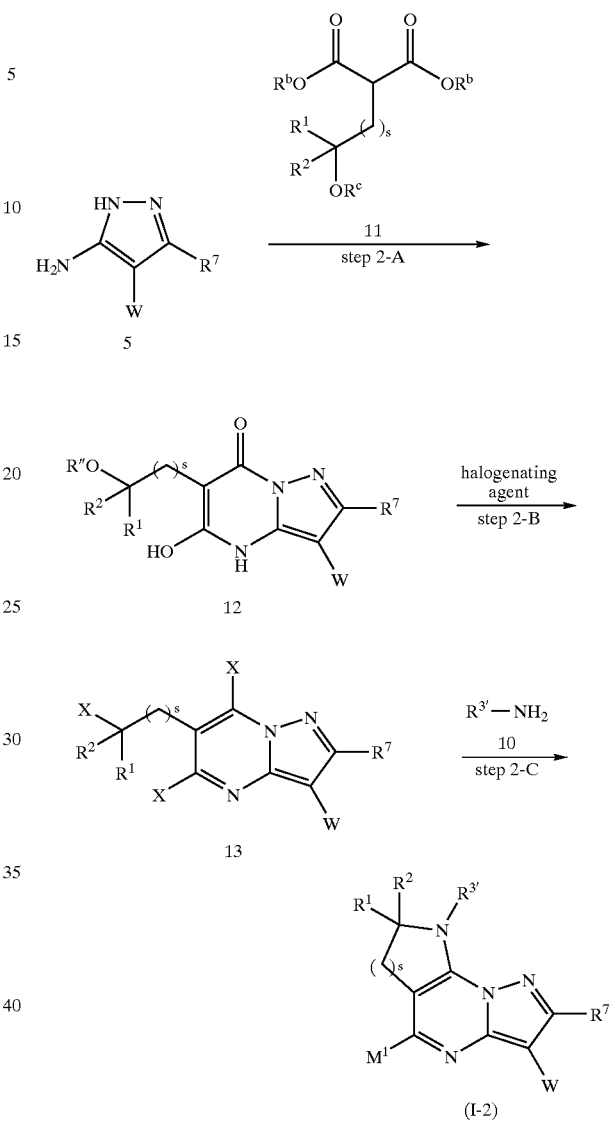

wherein $R^1$, $R^2$, $R^{3'}$, $R^7$, W, $M^1$, X and s have the same meanings as defined above; $R^b$ and $R^c$ are the same as or different from each other and each represents a $C_{1-6}$ alkyl group.

First, a pyrazolo[1,5-a]pyrimidine derivative (12) which is an intermediate can be prepared by reacting a compound (5) and a compound (11) at 0 to 200° C. in the presence or absence of an acid in an inert solvent (Step 2-A). An acid used is different depending upon a raw material, other reagents, the solvent and the like to be used, and is notparticularly limited. Suitable acids are inorganic acids such as hydrochloric acid, hydrobromic acid and sulfuric acid; and organic acids such as p-toluenesulfonic acid, methanesulfonic acid, acetic acid and trifluoroacetic acid. Preferable examples in an inert solvent used are alcohols such as methanol, ethanol, isopropyl alcohol and ethylene glycol; ethers such as diethyl ether, tetrahydrofuran, dioxane and 1,2-dimethoxyethan; hydrocarbons such as benzene, toluene and xylene; amides such as N,N-dimethylformamide; acetonitrile; water, or a mixed solvent of them.

A compound (13) can be obtained by reacting a compound (12) and a halogenating reagent in the presence or absence of a base, and in the presence or absence of a quaternary salt in an inert solvent or without a solvent (Step 2-B). A halogenating agent, a base and a quaternary salt to be used are different depending upon a raw material, a reagent, the solvent and the like to be used. Preferable examples of the halogenating agent are thionyl chloride, phosphorus oxychloride, phosphorus trichloride, phosphorus pentachloride, phosphorus oxybromide, phosphorus tribromide, phosphorus pentabromide, oxalylchloride and the like. Preferable examples of the base are amines such as triethylamine, diisopropylamine, N,N-diisopropylethylamine, pydidine, dimethylaniline and diethylaniline; in organic salts such as sodium carbonate, potassium carbonate and sodium bicarbonate; alcoholates such as sodium methoxide, sodium ethoxide and potassium tert-butoxide; metal amides such as sodium amide and lithium diisopropylamide; metal hydrides such as sodium hydride, potassium hydride and calcium hydride, and the like. Preferable quaternary salts are tetraethylammonium chloride, tetraethylammonium bromide, triethylmethylammonium chloride, triethylmethylammonium bromide and the like. An inert solvent used is different depending upon a raw material, a reagent and the like to be used, and is not particularly limited as long as it does not inhibit the reaction and dissolves a starting material to some extent. Preferably, alcohols such as methanol ethanol, isopropyl alcohol and ethylene glycol; ethers such as diethyl ether, tetrahydrofuran, dioxane and 1,2-dimethoxyethan; hydrocarbons such as benzene, toluene and xylene; amides such as N,N-dimethylformamide; acetonitrile; water, or a mixed solvent of them may be proposed.

A pyrazolo[1,5-a]pyrrolo[3,2-e]pyrimidine derivative (I-2) of the present invention can be obtained by reacting a compound (13) and a primary amine (10) at −80 to 250° C. in the presence or absence of a base in a solvent or without a solvent (Step 2-C). A base used is different depending upon a raw material, a reagent, the solvent and the like to be used. Preferably, amines such as triethylamine, diisopropylamine, N,N-diisopropylethylamine and pydidine; inorganic salts such as sodium carbonate, potassium carbonate and sodium bicarbonate; alcoholates such as sodium methoxide, sodium ethoxide and potassium tert-butoxide; metal amides such as sodium amide and lithium diisopropylamide; metal hydrides such as sodium hydride, potassium hydride and calcium hydride may be proposed. Amine (10) which is a reaction reagent may be also acted as a base in the present reaction. An inert solvent to be used is different depending upon a raw material, a reagent and the like to be used, and is not particularly limited as long as it does not inhibit the reaction and dissolves a starting a material to some extent. Preferably, alcohols such as methanol ethanol, isopropyl alcohol and ethylene glycol; ethers such as diethyl ether, tetrahydrofuran, dioxane and 1,2-dimethoxyethan; hydrocarbons such as benzene, toluene and xylene; amides such as N,N-dimethylformamide; alkylnitriles such as acetonitrile; ketones such as methyl ethyl ketone; water, or a mixed solvent of them may be proposed.

A compound wherein D is nitrogen atom, and A and B are a group represented by the formula —CO— in a compound represented by the above formula (I) of the present invention can be obtained by a method represented by the formula:

Preparation Method 3

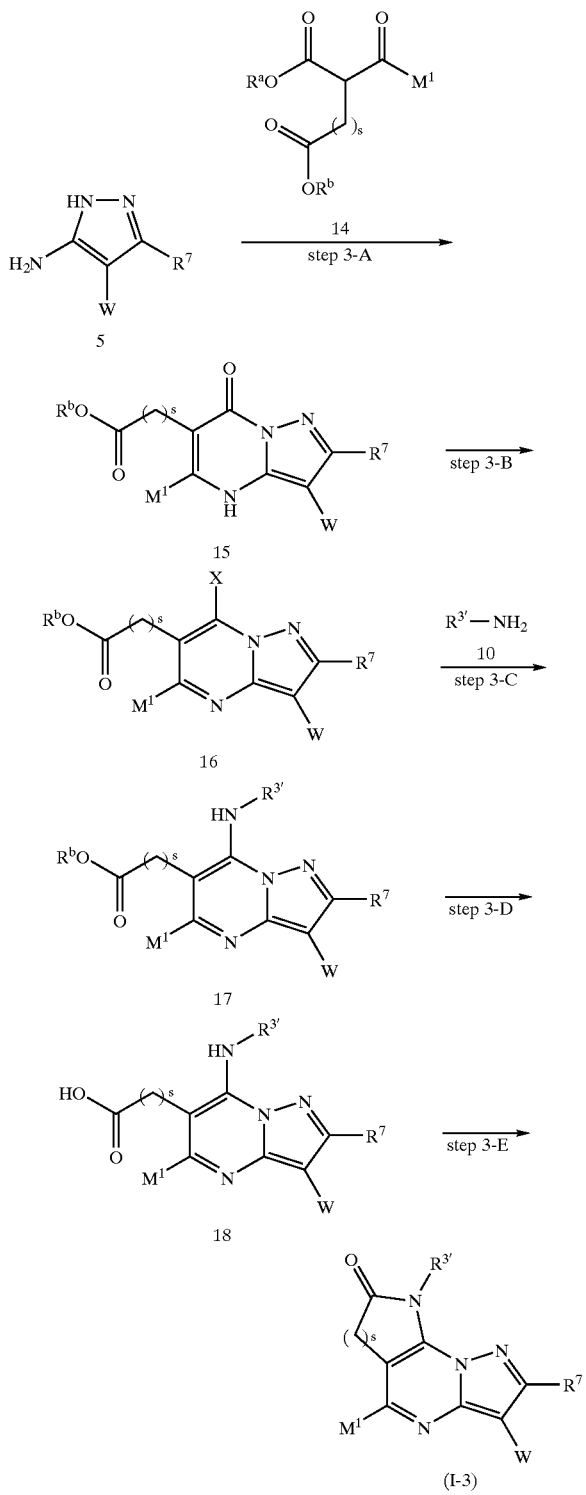

wherein $R^a$, $R^d$, J, W, $M^1$, R", X and s have the same meanings as defined above.

A pyrazolo[1,5-a]pyrimidine derivative (15) can be obtained by reacting a compound (5) and a compound (14) at −80 to 300° C. in the presence or absence of a base in a solvent or without a solvent (Step 3-A). A base used is different depending upon a starting raw material, a reagent, the solvent and the like to be used, and is not particularly limited. Preferably, amines such as triethylamine, diisopropylamine, N,N-diisopropylethylamine and pyridine; inorganic salts such as sodium hydroxide, potassium hydroxide, sodium carbonate, potassium carbonate and sodium bicarbonate; alcoholates such as sodium methoxide, sodium ethoxide and potassium tert-butoxide; metal amides such as sodium amide, lithium diisopropylamide, lithium bis(trimethylsilyl)amide; metal hydrides such as sodium hydride, potassium hydride and calcium hydride; organic magnesium compounds such as methylmagnesium bromide and ethylmagnesium bromide; organic lithium compounds such as butyllithium and methyllithium may be proposed. An inert solvent used is different depending upon a raw material, a reagent and the like to be used, and is notparticularly limited as long as it does not inhibit the reaction and dissolves a starting material to some extent. Preferably, alcohols such as methanol ethanol, isopropyl alcohol and ethylene glycol; ethers such as diethyl ether, tetrahydrofuran, dioxane, 1,2-dimethoxyethan and diphenyl ether; hydrocarbons such as benzene, toluene and xylene; amides such as N,N-dimethylformamide and 1-methyl-2-pyrrolidinone; alkylnitriles such as acetonitrine; ketones such as methyl ethyl ketone; water, and a mixed solvent of them may be proposed.

An intermediate (16) can be obtained by reacting a compound (15) and a halogenating reagent at −80 to 250° C. in the presence or absence of a base and in the presence or absence n a quaternary salt in a solvent or without a solvent (Step 3-B). A halogenating agent, a base and a quaternary salt to be used are different depending upon a starting raw material, a reagent, the solvent and the like, and are not particularly limited. Preferable examples of the halogenating agent are thionyl chloride, phosphorus oxychloride, phosphorus trichloride, phosphorus pentachloride, phosphorus oxybromide, phosphorus tribromide, phosphorus pentabromide, oxalyl chloride and the like. Suitable examples of the base are amines such as triethylamine, diisopropylamine, N,N-diisopropylethylamine, pydidine, dimethylaniline and diethylaniline; inorganic salts such as sodium carbonate, potassium carbonate and sodium bicarbonate; alcoholates such as sodium methoxide, sodium ethoxide and potassium tert-butoxide; metal amides such as sodium amide and lithium diisopropylamide; metal hydrides such as sodium hydride, potassium hydride and calcium hydride. Preferable examples of a quaternary salt are tetraethylammonium chloride, tetraethylammonium bromide, triethylmethylammonium chloride, triethylmethylammonium bromide and the like. An inert solvent used is different depending upon a raw material, a reagent and the like to be used, and is notparticularly limited as long as it does not inhibit the reaction and dissolves a starting material to some extent. Suitable are alcohols such as methanol ethanol, isopropyl alcohol and ethylene glycol; ethers such as diethyl ether, tetrahydrofuran, dioxane and 1,2-dimethoxyethane; hydrocarbons such as benzene, toluene and xylene; amides such as N,N-dimethylformamide; acetonitrile; water, or a mixed solvent of them.

An aminopyrimidine derivative (17) can be obtained by reacting a compound (16) and a primary amine (10) at −80 to 250° C. in the presence or absence of a base in a solvent or without a solvent (Step 3-C). A base used is different depending upon a starting raw material, a reagent, the solvent and the like, and is not particularly limited. Suitable are amines such as triethylamine, diisopropylamine, N,N-diisopropylethylamine and pydidine; inorganic salts such as sodium carbonate, potassium carbonate and sodium bicarbonate; alcoholates such as sodium methoxide, sodium ethoxide and potassium tert-butoxide; metal amides such as sodium amide and lithium diisopropylamide; metal hydrides such as sodium hydride, potassium hydride and calcium hydride. Alternatively, amine (10) which is a reaction reagent may be acted as the base. A solvent used is different depending upon a raw material, a reagent and the like to be used, and is not particularly limited as long as it does not inhibit the reaction and dissolves a starting material to some extent. Suitable are alcohols such as methanol ethanol, isopropyl alcohol and ethylene glycol; ethers such as diethyl ether, tetrahydrofuran, dioxane and 1,2-dimethoxyethane; hydrocarbons such as benzene, toluene and xylene; amides such as N,N-dimethylformamide; alkylnitriles such as acetonitrile; ketons such as methyl ethyl keton; water, or a mixed solvent of them.

A carboxylic acid (18) can be obtained by hydrolyzing an ester (17) at 0 to 200° C. in the presence of an acid or a base in a solvent (Step 3-D). An acid used is different depending upon a starting raw material, a reagent, the solvent and the like, and is not particularly limited. Suitable are inorganic acids such as hydrochloric acid, hydrobromic acid and sulfuric acid; and organic acids such as p-toluenesulfonic acid, methanesulfonic acid, acetic acid and trifluoroacetic acid. A base to be used is also not particularly limited. Suitable are inorganic salts such as sodium carbonate, potassium carbonate and sodium bicarbonate; alcoholates such as sodium methoxide, sodium ethoxide and potassium tert-butoxide; metal amides such as sodium amide and lithium diisopropylamide. A solvent used is different depending upon a raw material, a reagent and the like to be used, and is not particularly limited as long as it does not inhibit the reaction and dissolves a starting material to some extent. Suitable solvents are alcohols such as methanol ethanol, isopropyl alcohol and ethylene glycol; ethers such as diethyl ether, tetrahydrofuran, dioxane and 1,2-dimethoxyethane; hydrocarbons such as benzene and toluene; amides such as N,N-dimethylformamide; acetonitrile; water, or a mixed solvent of them.

A compound (I-3) of the present invention can be obtained by reacting a carboxylic acid (18) at normal pressure or under pressure at −80 to 250° C. in the presence of absence of a condensing agent and in the presence or absence of a base in a solvent or without a solvent. The condensing agent used is different depending upon a starting raw material, a reagent, the solvent and the like, and is not particularly limited. Suitable condensing agents are dicyclohexylcarbodiimide, N-ethyl-N'-(3-dimehylaminopropyl)carbodiimide, carbonyldiimidazole, 2-ethoxy-1-ethoxycarbonyl-1,2-dihydroquinoline, a combination of triphenylphosphine and carbon tetrachloride, diethyl chlorophosphate and the like. The base used is different depending upon a starting raw material, a reagent, the solvent and the like, and is not particularly limited. Suitable bases are amines such as triethylamine, diisopropylamine, N,N-diisopropylethylamine and pyridine; inorganic salts such as sodium carbonate, potassium carbonate and sodium bicarbonate; alcoholates such as sodium methoxide, sodium ethoxide and potassium tert-butoxide; metal amides such as sodium amide and lithium diisopropylamide. A solvent used is different depending upon a raw material, a reagent and the like to be used, and is not particularly limited as long as it does not inhibit the reaction and dissolves a starting material to some extent. Suitable solvents are alcohols such as methanol, ethanol, isopropyl alcohol and ethylene glycol; ethers such as diethyl ether, tetrahydrofuran, dioxane and 1,2-dimethoxyethane; hydrocarbons such as benzene, toluene and xylene; amides such as N,N-dimethylformamide; acetonitrile; water, or a mixed solvent of them.

Among compounds represented by the above formula (I) according to the present invention, the compound (I-4) in which the partial structure —A—B—D— is represented by the formula —CH=C($R^2$) —N($R^{3''}$)— (wherein $R^{3''}$ represents hydrogen atom, the formula —$COR^{10}$ (wherein $R^{10}$ represents a $C_{1-6}$ alkyl group, an optionally substituted aryl $C_{1-4}$ alkyl group, an optionally substituted aryl group, an optionally substituted heteroaryl $C_{1-4}$ alkyl group or an optionally substituted heteroaryl group), a group represented by the formula —S(O)$_p$$R^{11}$ (wherein $R^{11}$ represents a $C_{1-6}$ alkyl group, an optionally substituted aryl $C_{1-4}$ alkyl group or an optionally substituted aryl group, an optionally substituted heteroaryl $C_{1-4}$ alkyl group or an optionally substituted heteroaryl group; and p means an integer of 0, 1 or 2), a $C_{1-10}$ alkyl group optionally substituted with anyone or more groups listed in the above A group, a $C_{2-10}$ alkyenyl group optionally substituted with any one or more groups listed in the above A group, a $C_{2-10}$ alkynyl group optionally substituted with any one or more groups listed in the above A group, or a $C_{3-8}$ cycloalkyl group optionally fused with an optionally substituted benzene ring and optionally substituted with a $C_{1-4}$ alkyl group) can be prepared by the following method:

Preparation Method 4

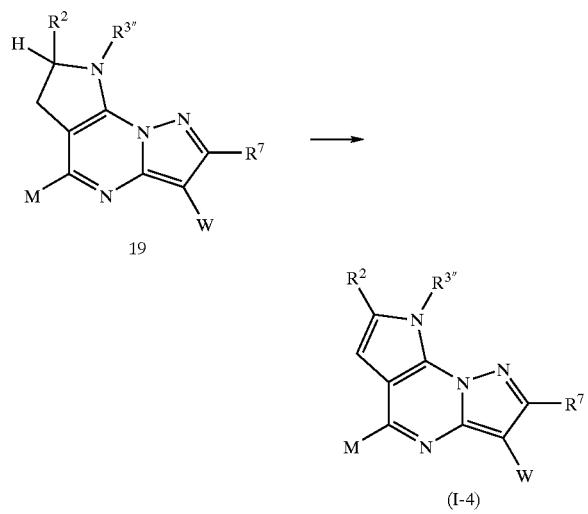

wherein $R^2$, $R^{3''}$, $R^7$, M and W have the same meanings as defined above.

The present reaction is usually performed in the presence of a base or in the presence of an oxidizing agent and in the solvent or without a solvent. A base used is different depending upon a starting raw material, a reagent, the solvent used and the like, and is not particularly limited. Suitable bases are amines such as triethylamine, diisopropylamine, N,N-diisopropylethylamine and pyridine; inorganic salts such as sodium hydroxide, potassium hydroxide, sodium carbonate, potassium carbonate and sodium bicarbonate; alcoholates such as sodium methoxide, sodium ethoxide and potassium tert-butoxide; metal amides such as sodium amide, lithium diisopropylamide and lithium bis(trimethylsilyl)amide; metal hydrides such as sodium hydride, potassium hydride and calcium hydride; organic magnesium compounds such as methylmagnesium bromide and ethylmagnesium bromide; organic lithium compounds such as butyllithium and methyllithium. As an oxidizing agent used, for example, a metal reagent such as activated maganese dioxide; and organic compounds such as DDQ are preferable. A solvent used is different depending upon a raw material, a reagent and the like to be used, and is not particularly limited as long as it does not inhibit the reaction and dissolves a starting material to some extent. Suitable solvents are alcohols such as methanol ethanol, isopropyl alcohol and ethylene glycol; ethers such as diethyl ether, tetrahydrofuran, dioxane, 1,2-dimethoxyethane and diphenyl ether; hydrocarbons such as benzene, toluene and xylene and the like; halogenated hydrocarbons such as dichloromethane and chloroform; amides such as N,N-dimethylformamide and 1-methyl-2-pyrrolidinone; alkylnitriles such as acetonitrile; ketons such as acetone and methyl ethyl keton; water, or a mixed solvent thereof. A reaction temperature is different depending upon a law material, a reagent, the solvent and the like to be used, and is usually −80 to 300° C.

A compound wherein the partial structure —A—B— is represented by the formula —$CH_2$—CH($R^2$)—$CH_2$—; and D is a substituted nitrogen atom in a compound represented by the above formula (I) of the present invention can be prepared by the following method:

Preparation Method 5

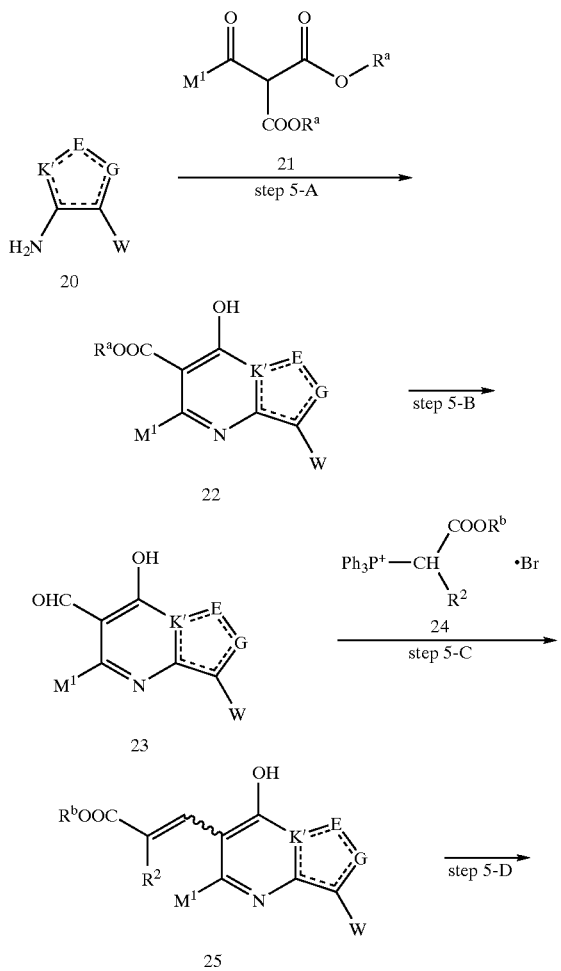

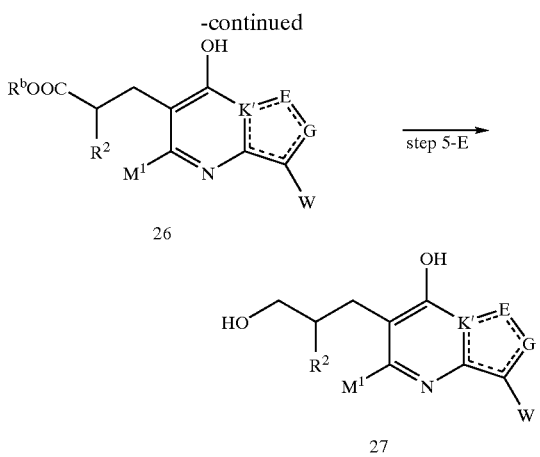

wherein $R^2$, $R^{3'}$, $R^a$, $R^b$, E, G, W, $M^1$ and X have the same meanings as defined above; and K' represents nitrogen atom or NH.

An intermediate compound (22) can be obtained by heating compounds (20) and (21) in the presence of an acid or Lewis acid in a solvent not involved in the reaction (Step 5-A). The present reaction is usually performed by heating in the presence of p-toluenesulfonic acid, sulfuric acid or hydrogen chloride in benzene, toluene or xylene, or heating in the presence of stannic chloride, zinc chloride/hydrogen chloride or aluminium chloride in a solvent such as dichloroethane, chloroform or diphenyl ether, or heating in a polyphosphoric acid.

A formyl compound (23) can be obtained by reducing a carboxylic acid compound (22) (Step 5-B). A reducing agent used is different depending upon a starting raw material, reagent, the solvent and the like, and is not particularly limited. Suitable reducing agents are diisobutylaluminum hydride, lithium borohydride and the like. A solvent used is different depending upon a raw material, a reagent and the like to be used, and is not particularly limited as long as it does not inhibit the reaction and dissolves a starting material to some extent. Suitable solvents are tetrahydrofuran, dichloromethane and the like. A reaction temperature is usually −78° C. to the boiling point of the solvent, preferably −78 to 20° C.

A compound (25) can be obtained by subjecting a compound (23) together with a compound (24) to Horner-Emmons reaction or Wittig-Horner reaction in the presence of a base (Step 5-C) A base used is different depending upon a starting raw material, a reagent, the solvent and the like, and is not particularly limited. Suitable bases are sodium hydride, sodium alkoxide, n-butyllithium, potassium t-butoxide, lithium bistrimethylsilylamide and the like. A solvent used is different depending upon a raw material, a reagent and the like to be used, and is not particularly limited as long as it does not inhibit the reaction and dissolves a starting material to some extent. Suitable solvents are N,N-dimethylformamide, n-hexane, tetrahydrofuran, diethyl ether and the like. A reaction temperature is usually −78° C. to the boiling point of the solvent, preferably −78 to 20° C.

A compound (26) can be obtained by reducing a double bond of an ene compound (25) (Step 5-D). As the reducing method used, for example, there is a hydrogenation using a metal catalyst such as Pd—C, Raney nickel and the like. A reaction solvent used is different depending upon a raw material, a reagent and the like to be used, and is not particularly limited as long as it does not inhibit the reaction and dissolves a starting material to some extent. Suitable solvents are ethanol, ethanol, tetrahydrofuran and the like. A reaction temperature is usually −78° C. to the boiling point of the solvent, preferably 0 to 20° C.

An alcohol compound (27) can be obtained by reducing a carboxylic acid of a compound (26) (Step 5-E). Preferable examples of the reducing agent used are diisobutylaluminium hydride, lithium borohydride and the like. A reaction solvent used is different depending upon a raw material, a reagent and the like to be used, and is not particularly limited as long as it does not inhibit the reaction and dissolves a starting material to some extent. Preferred are tetrahydrofuran, dichloromethane and the like. A reaction temperature is usually −78° C. to the boiling point of the solvent, preferably −78 to 20° C.

Dihalogeno compound (28) can be obtained by reacting a compound (27) and a halogenating agent in the presence or absence of a base and the presence or absence of a quaternary salt (Step 5-F). As the halogenating agent and the reaction solvent used, and a reaction temperature, those similar to the reagent, solvent and temperature described in Step 1-D in the above preparation method 1 can be used, respectively.

A compound (I-5) of the present invention can be obtained by reacting a dihalogeno compound (28) and a primary amine (10) at −80 to 250° C. in the presence or absence of a base and in the presence or absence of a solvent (Step 5-G). The present reaction can be performed according to the same as or similar to the condition for the above Steps 1-E, 1'-C and 1'-D.

A compound wherein A is a group represented by the formula —CH$_2$—CH($R^2$)—, B is a group represented by the formula —CO— and D is a group represented by the formula —N($R^{3'}$)— in a compound represented by the above formula (I) of the present invention can be prepared by a method represented by the formula:

Preparation Method 6

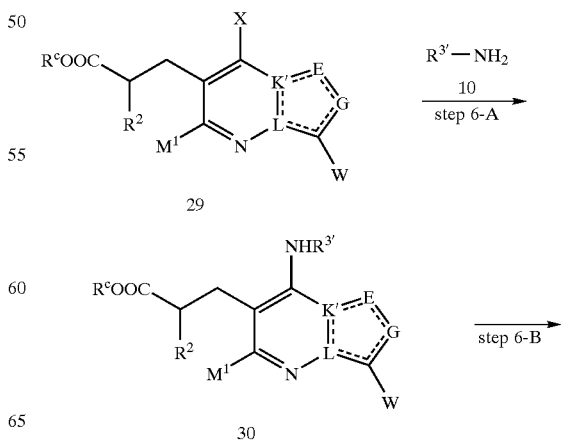

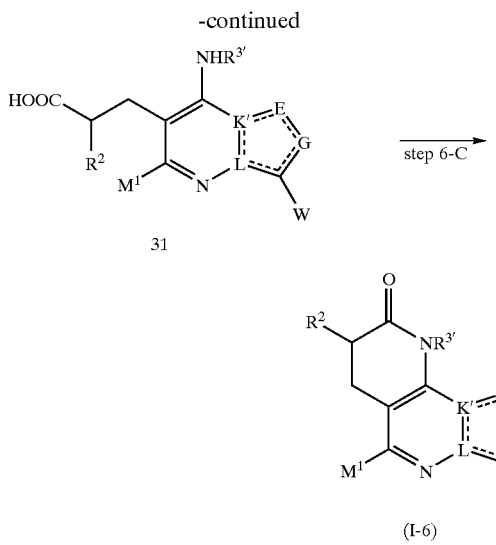

wherein $R^2$, $R^{3'}$, $R^c$, E, G, W, $M^1$, X and K', have the same meanings as defined above.

That is, first, a compound (26) obtained in Step 5-D in the above Preparation method 5 is halogenated with a halogenating agent, to prepare a compound (29). The (29) is treated with a primary amine (10), to give an aminoester compound (30) (Step 6-A; the same reaction conditions as those described in the above Step 5-F). Next, an ester part of the compound (30) is hydrolyzed, to prepare an animocarboxylic acid compound (31) (Step 6-B) the same procedures as those described in the above Step 3-D) and, finally, the compound (31) is treated according to the procedures described in the above Step 3-E, to give a δ lactam compound (I-6) of the present invention.

When a compound (32) having as a substituent at 3-position a ring Ar having a leaving group (a group represented by the symbol -Lev in the following formula) is used as a raw material, a compound (I-7) of the present invention can be prepared by converting a leaving group -Lev on a ring Ar into a desired substituent $R^d$ in accordance with a method represented by the formula:

Preparation Method 7

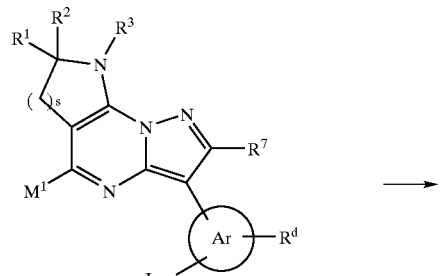

wherein $M^1$, $R^1$, $R^2$, $R^3$ and $R^7$ have the same meanings as defined above; the ring Ar represents an aromatic group such as phenyl group, naphthyl group and heteroaryl group; Lev represents a leaving group such as a halogen atom and trifluoromethanesulfonyl group; $R^d$ and $R^{d'}$ are the same as or different from each other and each represents hydrogen atom, hydroxyl, nitro group, cyano group, carboxyl group, a $C_{1-6}$ alkyloxycarbonyl group, formula —$S(O)_pR^{12}$ (wherein $R^{12}$ represents hydrogen, a $C_{1-6}$ alkyl group, an optionally substituted aryl $C_{1-4}$ alkyl group, an optionally substituted aryl group, an optionally substituted heteroaryl $C_{1-4}$ alkyl group or an optionally substituted heteroaryl group; and p means an integer of 0, 1 or 2), —$NR^{13}R^{14}$ (wherein $R^{13}$ and $R^{14}$ are the same as or different from each other and each represents hydrogen atom, a $C_{1-6}$ alkyl group or a $C_{1-4}$ alkylacyl group), a $C_{1-6}$ alkyl group, a $C_{1-6}$ alkoxy group, a $C_{3-8}$ cycloalkyl group optionally substituted with a $C_{1-4}$ alkyl group, a $C_{1-4}$ alkoxy $C_{1-6}$ alkyl group, a $C_{2-10}$ alkenyl group, a saturated 3- to 8-membered heterocyclic ring optionally substituted with a $C_{2-10}$ alkynyl group, an optionally substituted aryl group or an optionally substituted heteroaryl group; $R^d$ represents an alkyl group, cyano group, an optionally substituted aryl group, an optionally substituted alkynyl group, an alkoxycarbonyl group, N-monosubstituted carbamoyl group and the like.

That is, 1) a compound represented by the formula (32) is heating together with cuprous cyanide, zinc cyanide or the like in a high boiling point solvent such as N-pyrrolidinone, dimethylsulfoxide and N,N-dimethylformamide. Then, 2) it is subjected to an oxidative-reductive leaving reaction using a palladium catalyst to a leaving group Lev into $R^d$. In such the conversion reaction, a palladium catalyst used is different depending upon a starting raw material and the like, and is not particularly limited. Preferred are $Pd(PPh_3)$, $Pd_2(dba)_3+L$, $Pd(OCOCH_3)_2+L$, $PdCl_2L_2$ and the like (wherein L means $PPh_3$, ddpe, dppf and the like). The reaction is usually performed at room temperature or under heating in the presence of a tertiary amine in a solvent. The tertiary amine used is different depending upon a starting raw material, a reagent, a solvent and the like, and is not particularly limited. Preferably, triethylamine, diisopropylethylamine, DBU, dimethylaniline and the like may be proposed. A solvent used is different depending upon a raw material, a reagent and the like, and is not particularly limited as long as it dose not inhibit the reaction and dissolves a starting material to some extent. Preferably, ethers such as tetrahydrofuran, dioxane, dimethoxyethane and diethylene glycol, dimethylformamide, 1-methylpyrrolidine and the like may be proposed. A suitable reaction temperature is 0 to 250° C. More suitable is under reflux.

In the compound according to the present invention represented by the above formula (I), a compound wherein the partial structure -A-B-D- is represented by the formula —N=N—N(R³')— is obtained by the method shown by the formula:

Preparation Method 8

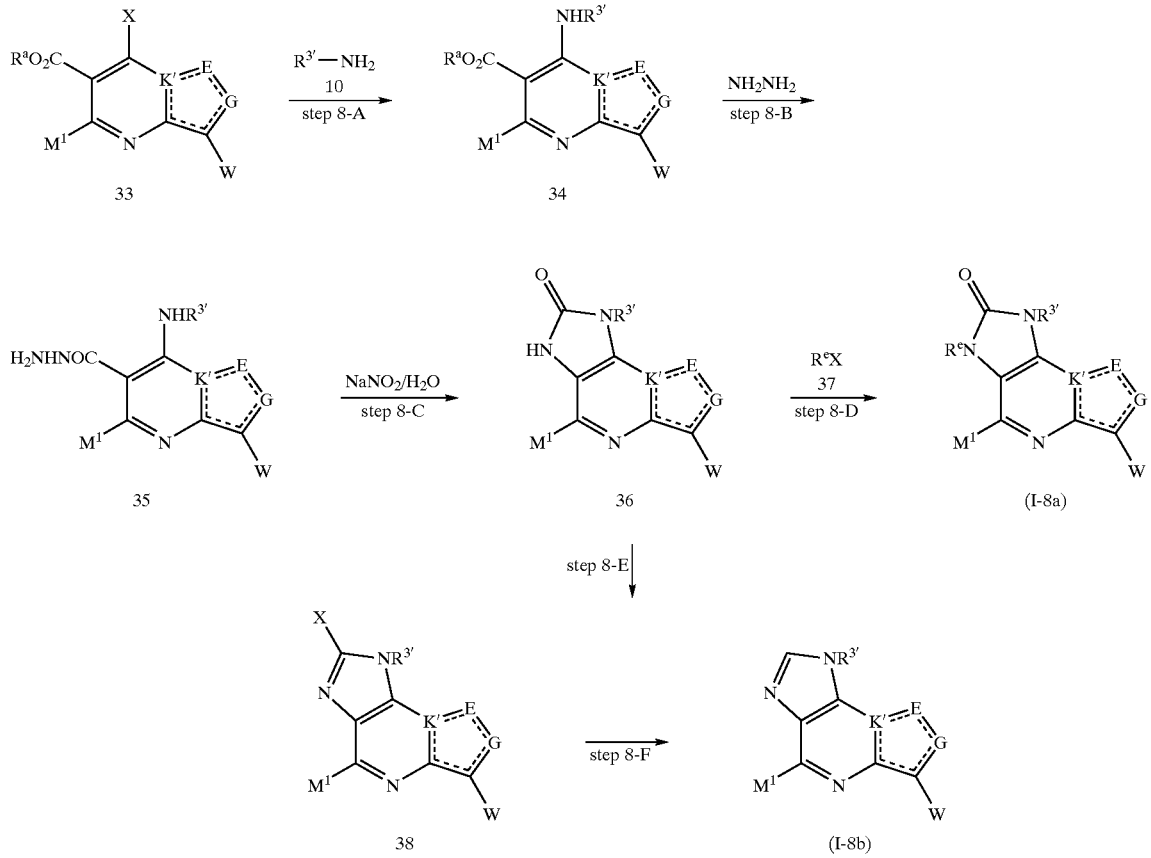

wherein R³', R^a, E, G, W, M¹, X and K' have the same meanings as defined above; and R^eX represents an alkyl halide, a sanchloride, acid anhydride and the like.

First, a halogenated compound (33) which is a starting material is obtained by halogenating a compound (22) obtained by the above Step 5-B with a halogenating agent. The (33) is treated with (10), to give an aminoester compound (34) (Step 8-A). Such the step can be performed under the same conditions as those for the above Step 5-F.

A hydrazide compound (35) is obtained by heating a compound (34) with hydrazinein a solvent (Step 8-B). Such the hydrazine is preferably used at an excessive amount in an equivalent relationship relative to a compound (34). A reaction solvent used is different depending upon a raw material used, a reagent used and the like and is not particularly limited as long as it dose not dissolves a starting material to some extent. Suitable are alcohols such as methanol, ethanol, propanol, isopropanol and butanol, tetrahydrofuran, N-pyrrolidone, dimethylsulfoxide, N,N-dimethylformamide and the like.

An imidazolone compound (36) is obtained by acting sodium nitrite to a compound (35) (Step 8-C). The present reaction is performed by applying the conditions for Curtius rearrangement reaction. A reaction solvent used is different depending upon a raw material, a reagent and the like to be used, and is not particularly limited as long as it dose not inhibit the reaction and dissolves a starting material to some extent. Suitable are alcohols such as methanol, ethanol, propanol, isopropanol and butanol, tetrahydrofuran, N-pyrrolidinone, dimethylsulfoxide, N,N-dimethylformamide and the like.

Pyrazolo[1,5-a]pyrrolo[3,2-e]pyrimidine compound can be prepared by two methods using an imidazolone compound (36) as a raw material.

That is, first, the first method is a method of reacting a compound (36) with an alkylating agent containing a leaving group such as alkyl halide, or an acylating agent such as acid chloride, acid anhydride and the like at −70 to 200° C., to give the compound (I-8a) according to the present invention. A solvent used is different depending upon a raw material used, a reagent and the like to be used, and is notparticularly limited as long as it dose not inhibit the reaction and dissolves a starting material to some extent. Suitable are tetrahydrofuran, diethyl ether, N,N-dimethylformamide, dimethylsulfoxide and the like. In addition, a base used is different depending upon a raw material, a reagent, a solvent and the like to be used, and is not particularly limited. Suitable are sodium hydride, potassium hydride, potassium carbonate, sodium carbonate, cesium carbonate, potassium hydroxide, sodium hydroxide and the like.

The second method is a method of preparing a compound (38) by halogenating a compound (36) (Step 8-E), then subjecting the (38) to a hydrogenation reaction, to give an imidazole derivative (I-8b) according to the present invention (Step 8-F) Step 8-E is performed in the presence or absence of a base, and in the presence or absence of a quaternary salt. A base, a quaternary salt and a halogenating agent to be used are different depending upon a starting raw material, a reagent, a solvent and the like, and are not particularly limited. Suitable bases are N,N-dimethylaniline, N,N-diethylaniline, N,N-diisopropylethylamine and the like. Suitable quaternary amines are tetraethylammonium bromide, tetraethylammonium chloride, triethylmethylammonium bromide, triethylmethylammonium chloride and the like. In addition, suitable halogenating agents are thionyl chloride, phosphorus oxychloride, phosphorus trichloride, phosphorus pentachloride, phosphorous oxybromide, phosphorous tribromide, phosphorous pentabromide, oxazolyl chloride and the like. A reaction temperature is usually −20 to 150° C. A hydrogenation reaction in Step 8-F is usually performed in a solvent or without a solvent, in the presence or absence of an acid, and in the hydrogen atmosphere. A pressure of hydrogen is preferably 1 to 100 atm. Suitable examples of solvent used are methanol, ethanol, propanol, butanol, tetrahydrofuran, dioxane, ethyl acetate, acetone, N,N-dimethylformamide and the like. An acid used preferably is acetic acid, hydrochloric acid and the like. In addition, the hydrogenation reaction usually uses a metal catalyst and suitable examples thereof are Pd—C, PtO$_2$, Pt—C, Raney-Ni and the like. A reaction temperature is usually 0 to 200° C. In addition, as a method according to this method, the compound according to the present invention may be prepared by generating hydrogen in situ by heating ammonium formate and the like in a solvent.

By using as a starting material the compound (I-2) of the present invention obtained in the above Preparation method 2, a compound of the present invention can be prepared newly by the following Preparation method 9.

Preparation Method 9

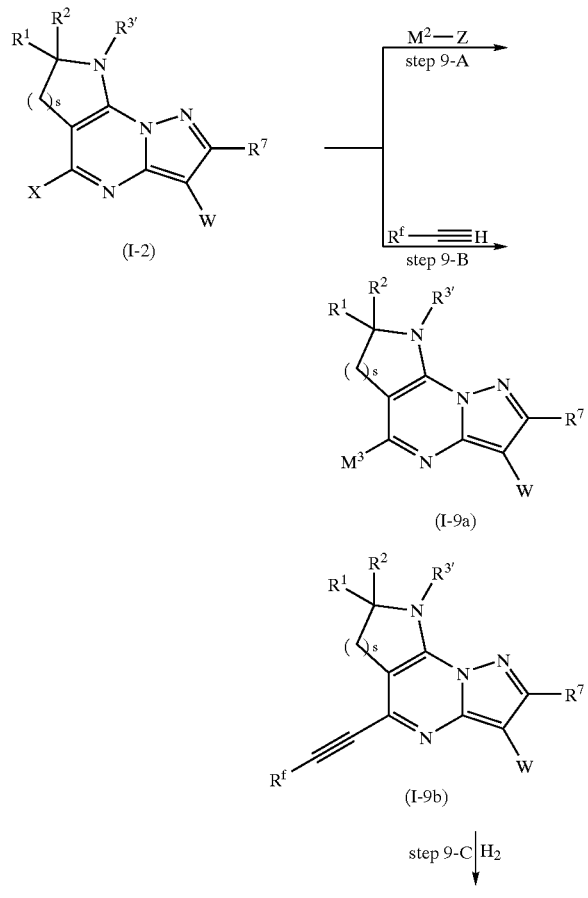

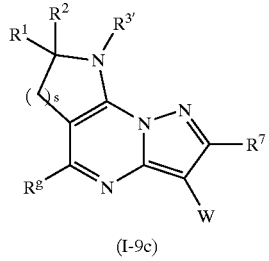

wherein $R^1$, $R^2$, $R^{3'}$, $R^7$, X, W and S have the same meanings as defined above; $M^2$ represents cyano group, or a group represented by the formula —NR$^{13}$R$^{14}$ (wherein $R^{13}$ and $R^{14}$ have the same meanings as defined above), —OR$^{15}$ (wherein $R^{15}$ has the same meaning as defined above), —SH or —SR$^{16}$ (wherein $R^{16}$ has the same meaning as defined above); $M^3$ represents cyano group, or a group represented by the formula —NR$^{13}$R$^{14}$ (wherein $R^{13}$ and $R^{14}$ have the same meanings as defined above), —OR$^{15}$ (wherein $R^5$ has the same meaning as defined above), —SH or —S(O)$_q$R$^{16}$ (wherein q and $R^{16}$ have the same meanings as defined above); z represents hydrogen atom or an alkali metal (for example, sodium, potassium and the like); $R^f$ represents (i) hydrogen atom, (ii) a $C_{3-8}$ cycloalkyl group optionally fused with an optionally substituted benzene ring, and optionally substituted with a $C_{1-4}$ alkyl group or (iii) a $C_{1-4}$ alkyl group optionally substituted with any one or more groups listed in the above A group; and $R^g$ represents (i) a $C_{3-8}$ cycloalkylethyl group optionally fused with an optionally substituted benzene ring, and optionally substituted with a $C_{1-4}$ alkyl group or (ii) a $C_{2-6}$ alkyl group optionally substituted with any one or more groups listed in the above A group.

1) As the first method, there is a method of treating a compound (I-2) with a nuclephole represented by the formula M$^2$-Z, to give a compound represented by the formula (I-9a) according to the present invention (Step 9-A). The present reaction can be performed by the similar reaction conditions to those for the above Step 5-F. In addition, a sulfinyl compound and a sulfonyl compound can be obtained by oxidizing a thiol compound or a sulfide compound obtained by the present preparation method by the conventional method known to a person skilled in the art.

2) The second method is a method of reacting a compound (I-2) with an alkynyl compound represented by the formula R$^f$—C≡CH, to give an ethynyl compound (I-9B) according to the present invention (Step 9-B), or a method of reducing a compound (I-9b) to give a compound (I-9c) (Step 9-C). Step 9-B is usually performed at room temperature or under heating in the presence of cuprous iodide and a tertiary amine. A reaction solvent used is different depending upon a raw material, a reagent and the like to be used, and is not particularly limited as long as it dose not inhibit the reaction and dissolves a starting material to some extent. Suitable are tetrahydrofuran, dioxane, dimethoxyethane, diethylene glycol dimethylether, N,N-dimethylformamide, 1-methylpyrrolidinone and the like. Preferable examples in a tertiary amine used are triethylamine, diisopropylethylamine, DBU, dimethylaniline and the like. A preferable reaction temperature is 0 to 100° C., and a more preferable is room temperature. In addition, Step 9-C can be performed by the conventional method by which a person skilled in the art can be easily performed.

The compound represented by the following formula (I-10) according to the present invention is obtained via Steps 10-A to D shown by the following formula:

Preparation Method 10

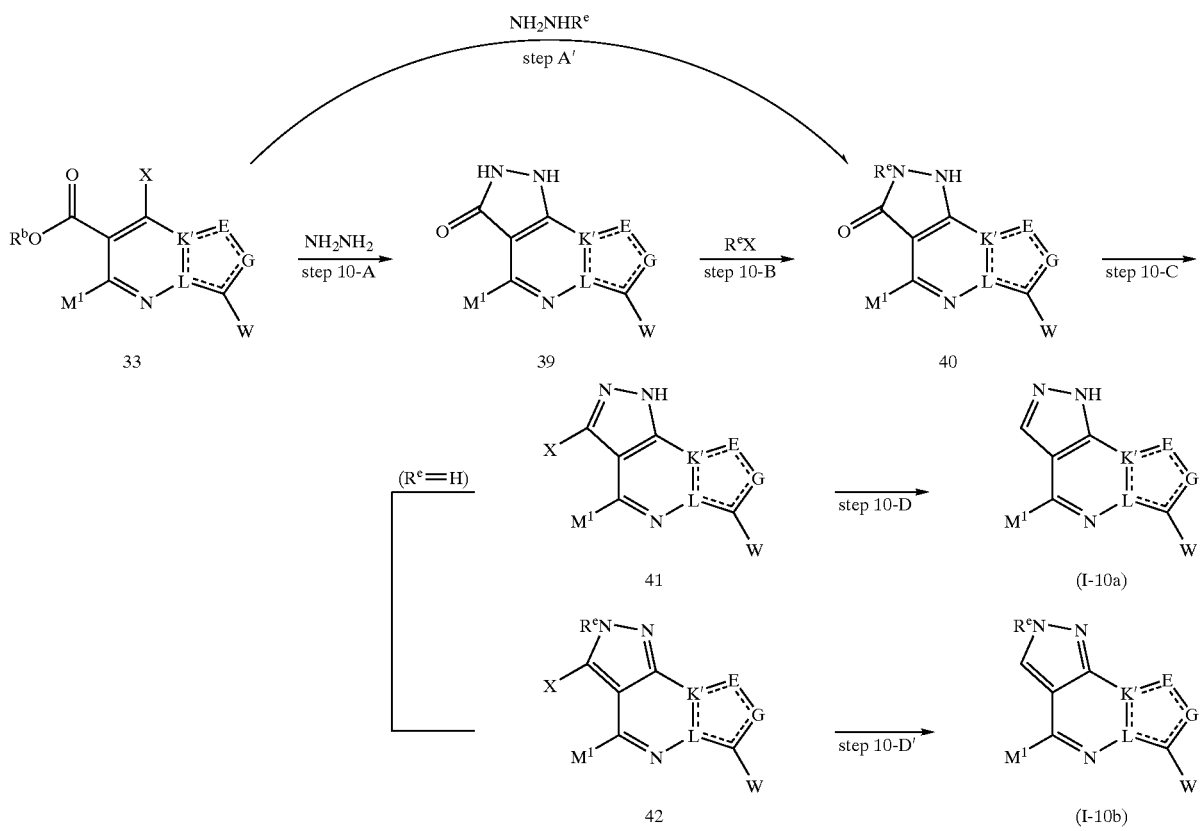

wherein $R^b$, E, G, K', L, $M^1$, W, X and $R^eX$ have the same meanings as defined above.

In order to obtain a pyrazolone derivative (39) which is an intermediate, a compound (33) is reacted with hydrazine at 0 to 200° C. in the presence or absence of an acid in an inert solvent (Step 10-A). An acid used is different depending upon a starting raw material, reagents, the solvent and the like, and is not particularly limited. Suitable are inorganic acids such as hydrochloric acid, hydrobromic acid and sulfuric acid; organic acids such as p-toluenesulfonic acid, methanesufonic acid, acetic acid and trifluoroacetic acid. An inert solvent used is different depending upon a raw material, reagents and the like to be used, and is not particularly limited as long as it dose not inhibit the reaction and dissolves a starting material to some extent. Suitable are alcohols such as methanol, ethanol, isopropanol and ethylene glycol; ethers such as diethyl ether, tetrahydrofuran, dioxane and 1,2-dimethoxyethane; hydrocarbons such as benzene, toluene and xylene; amides such as N,N-dimethylformamide; acetonitrile; water, or a mixed solvent thereof.

In order to prepare (40) from a compound (39), the compound (39) is reacted with an alkylating agent containing a leaving group (for example, alkyl halide and the like) or an acylating agent and the like (for example, acid chloride, acid anhydride and the like) at −70 to 200° C. in the presence or absence of a base in a solvent or without a solvent (Step 10-B). A solvent used is different depending upon a raw material, reagents and the like to be used, and is not particularly limited as long as it dose not inhibit the reaction and dissolves a starting material to some extent.

Suitable are tetrahydrofuran, diethyl ether, dimethylformamide, dimethyl sulfoxide and the like. In addition, a base used is different depending upon a starting raw material, reagents, the solvent and the like, and is not particularly limited. Suitable are sodium hydride, potasssium hydride, potasssium carbonate, sodium carbonate, cesium carbonate, potasssium hydroxide, sodium hydroxide and the like.

In addition, (40) can be prepared directly from a compound (33) instead of Steps 10-A and B (Step 10-A'). In such the reaction, hydrazine having a substituent on the nitrogen atom is used instead of hydrazine used in Step 10-A.

Next, in Step 10-C, a pyrazolone compound (40) is reacted with a halogenating agent at −20 to 150° C. in the presence or absence of a base and in the presence or absence of a quaternary salt, to give an intermediate (41) or (42). Abase, a quaternary salt and a halogenating agent to be used are different depending upon a starting raw material, reagents, the solvent and the like, and are not particularly limited. Suitable bases are dimethylaniline, diethylaniline, N,N-diisopropylethylamine and the like. Suitable quaternary salts are tetraethylammonium bromide, tetraethylammonium chloride, triethylmethylammonium bromide, triethylmethylammonium chloride and the like. Suitable halogenating agents are thionyl chloride, phosphorus oxychloride, phosphorus trichloride, phosphorus pentachloride, phosphorous oxybromide, phosphorous tribromide, phosphorus pentabromide, oxalyl chloride and the like.

Finally, a compound (41) or a compound (42) is subjected to a hydrogenation reaction, to give a compound (I-10a or 10b) of the present invention (Step 10-D or D'). Such the reaction is conducted in the presence or absence of an acid in a solvent or without a solvent in hydrogen atmosphere. A hydrogen pressure is preferably 1 to 100 atm. Suitable examples of the solvent used are methanol, ethanol, propanol, butanol, tetrahydrofuran, dioxane, ethyl acetate, acetone, N,N-dimethylformamide and the like. An acid used is preferably acetic acid, hydrochloric acid and the like. In addition, the hydrogenation reaction usually uses a metal catalyst, and suitable examples of the metal catalyst are Pd—C, $PtO_2$, Pt—C, Raney-Ni and the like. A reaction temperature is usually 0 to 200° C. In addition, as an alternative method for the present method, the present compound may be prepared also by generating hydrogen in situ by heating ammonium formate and the like in a solvent.

In compounds of the present invention, a compound wherein A and D are a group represented by the formula —CO— and B is represented by the formula —N($R^{3'}$) can be prepared by a method represented by the following formula:

Preparation Method 11

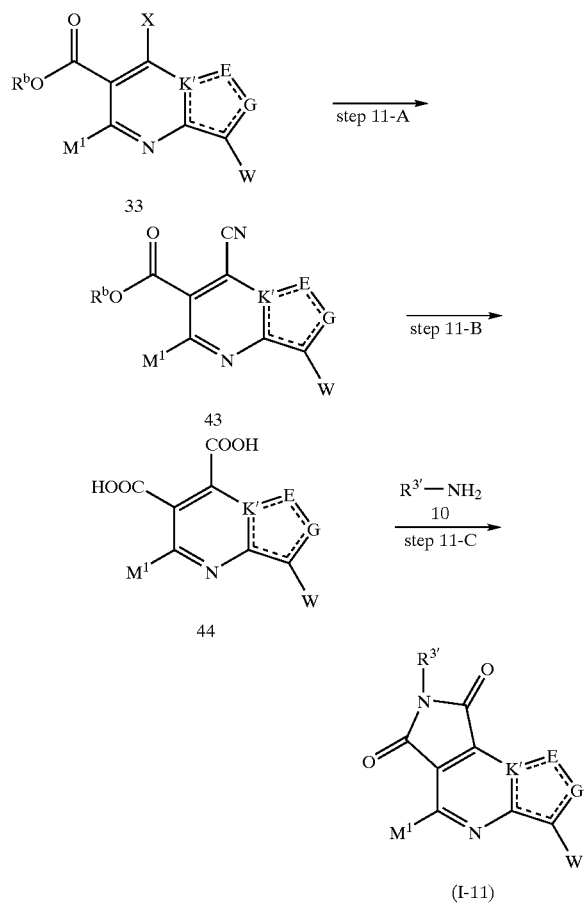

wherein $R^{3'}$, $R^b$, E, E, G, K', $M^1$, W and X have the same meanings as defined above.

The first intermediate (43) is obtained by reacting a compound (33) with zinc cyanide at 0 to 200° C. in the presence of a 0 valent palladium catalyst in N,N-dimethylformamide (Step-A).

Next, a compound (43) is hydrolyzed to prepare a compound (44) (Step 11-B) and, finally, such the (44) is reacted with an amine compound (10), to give a phthalimide compound (I-11) of the present invention (Step 11-C). The above Step 11-B is performed in the presence of an acid or a base, and in an inert solvent. An acid or a base used is different depending upon a starting raw material, reagents, the solvent and the like, and is not particularly limited. Suitable acids are inorganic acids such as hydrochloric acid, hydrobromic acid, sulfuric acid and the like, and suitable bases are inorganic salts such as potassium hydroxide, sodium hydroxide, lithium hydroxide, sodium carbonate, potassium carbonate, sodium bicarbonate and the like; alcoholates such as sodium methoxide, sodium ethoxide, potassium tert-butoxide, and the like. An inert solvent used is different depending upon a raw material, reagents and the like to be used and is not particularly limited as long as it dose not inhibit the reaction and dissolves a starting material to some extent. Suitable are alcohols such as methanol, ethanol, isopropyl alcohol and ethylene glycol; ethers such as diethyl ether, tetrahydrofuran, dioxane and 1,2-dimethoxyethane; hydrocarbons such as benzene, toluene and xylene; amides such as N,N-dimethylformamide; acetonitrile, water or a mixed solvent thereof. A reaction temperature is usually 0 to 200° C. The above Step-C is usually performed in a solvent such as acetic acid and the like. A reaction temperature is usually 0 to 200° C.

In compounds represented by the formula (I) according to the present invention, a compound wherein D is oxygen atom is obtained by the following preparation method:

Preparation Method 12

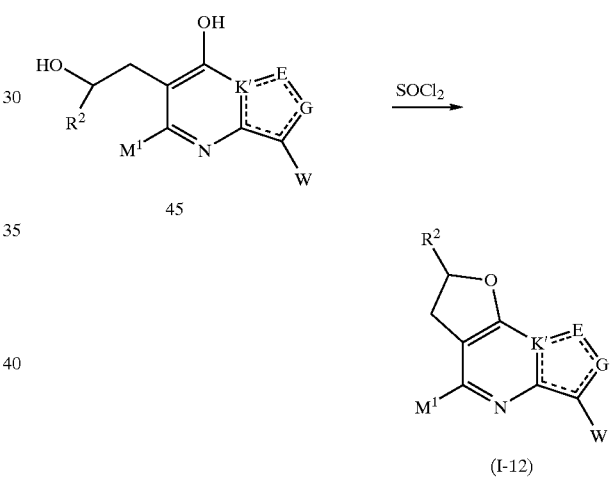

wherein $R^2$, E, G, K', $M^1$ and W have the same meanings as defined above.

The present reaction is performed by reacting a dihydroxy compound (45) with thionyl chloride and the like in an inert solvent. After the reaction, the reaction system is cooled to room temperature, the precipitated crystals are collected by filtration, and the resulting crystals are reacted with a base, to give finally a dihydrofuran compound (I-11) of the present invention. Preferable examples in the solvent used are ethers such as diethyl ether, tetrahydrofuran, dioxane and 1,2-dimethoxyethane; hydrocarbons such as benzene and toluene; acetonitrile, or a mixed solvent thereof. Preferable examples in a base used are inorganic salts such as sodium carbonate, potassium carbonate and sodium bicarbonate; alcoholates such as sodium methoxide, sodium ethoxide and potassium tert-butoxide. A reaction temperature is usually 0 to 200° C.

Further, compounds represented by the above formula (I) of the present invention, a compound wherein D is sulfur is obtained by the following preparation method:

Preparation Method 13

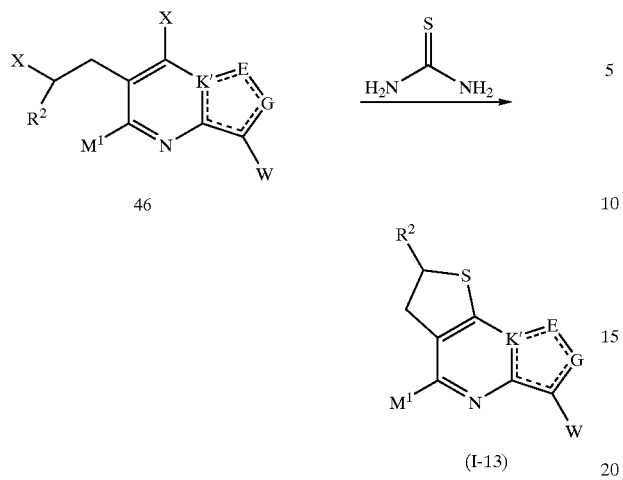

wherein $R^2$, E, G, K', $M^1$ and W have the same meanings as defined above.

The present reaction is usually performed in the presence of a base in an inert solvent. A base used is different depending upon a starting raw material, reagents, the solvent and the like, and is not particularly limited. Suitable are amines such as triethylamine, diisopropylamine, N,N-diisopropylethylamine and pyridine; inorganic salts such as sodium carbonate, potassium carbonate and sodium bicarbonate; alcoholates such as sodium methoxide, sodium ethoxide and potassium tert-butoxide; and the like. In addition, an inert solvent used is different depending upon a raw material, reagents and the like to be used, and is not particularly limited as long as it dose not inhibit the reaction and dissolves a starting material to some extent. Suitable are alcohols such as methanol, ethanol, isopropyl alcohol and ethylene glycol; ethers such as diethyl ether, tetrahydrofuran, dioxane and 1,2-dimethoxyethane; amides such as N,N-dimethylformamide; acetonitrile; water, or a mixed solvent thereof. A reaction temperature is usually 0 to 200° C.

A compound wherein the partial structure -A-B-D- is an optionally substituted alkylene group in the above formula (I) can be prepared, for example, by a method represented by the formula:

Preparation Method 14

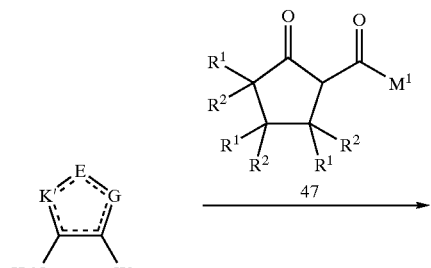

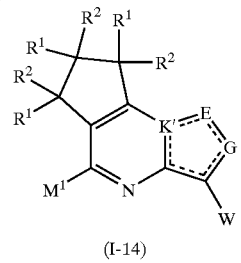

wherein $R^1$, $R^2$, E, G, K', $M^1$ and W have the same meanings as defined above.

A reaction is usually performed in an inert solvent and such the inert solvent is different depending upon a raw material, reagents and the like to be used, and is not particularly limited as long as it does not inhibit the reaction and dissloves a starting material to some extent. Suitable are alcohols such as methanol, ethanol, isopropyl alcohol and ethylene glycol; ethers such as diethyl ether, tetrahydrofuran, dioxane and 1,2-dimethoxyethane; hydrocarbons such as benzene and toluene; amides such as N,N-dimethylformamide; acetonitrile; water, or a mixed solvent thereof, and the like. A reaction temperature is usually 0 to 200° C.

Synthesis of a skeleton of a compound of the present invention can be conducted by the following method in addition to methods described in the above preparation methods.

Preparation Method 15

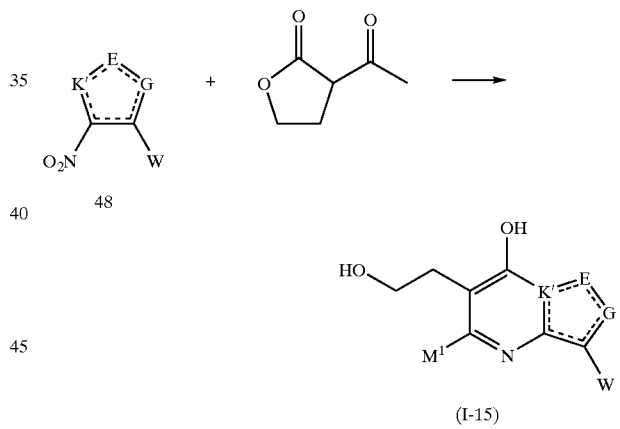

wherein E, G, K', $M^1$ and W have the same meanings as defined above.

The present preparation method is a method of cyclization while reducing a nitro group of a compound (48), and is performed in the presence of a metal powder such as zinc powder and the like and an acid in an inert solvent or without a solvent. An acid used is different depending upon a starting material, reagents, the solvent and the like, and is not particularly limited. Suitable are inorganic acids such as hydrochloric acid, hydrobromic acid and sulfuric acid; and organic acids such as p-toluenesulfonic acid, methanesulfonic acid, acetic acid and trifluoroacetic acid. An inert solvent used is different depending upon a raw material, reagents and the like to be used, and is not particularly limited as long as it does not inhibit the reaction and dissolves a starting material to some extent. Suitable are alcohols such as methanol, ethanol, isopropyl alcohol and ethylene glycol; ethers such as diethyl ether, tetrahydrofuran, dioxane and 1,2-dimethoxy ethane; hydrocarbons such as benzene and toluene; amides such as N,N-dimethylformamide; acetonitrile; water, or a mixed solvent thereof and the like. A reaction temperature is usually 0 to 200° C.

Alternatively, a hydrogenation reaction may be used in order to prepare an end compound (I-15) from a starting material in the present preparation method. Such the hydrogenation reaction is performed in the presence or absence of an acid in the hydrogen atmosphere. A hydrogen pressure is preferably 1 to 100 atom. An acid and a solvent to be used are different depending upon a starting material, reagents, the solvent and the like, and are not particularly limited. Suitable acids are acetic acid, hydrochloric acid and the like, and suitable solvents are methanol, ethanol, propanol, butanol, tetrahydrofuran, dioxane, ethyl acetate, acetone, N,N-dimethylformamide and the like. In the hydrogenation reaction, a metal catalyst is usually used, and suitable examples of such the metal catalysts are Pd—C, $PtO_2$, Pt—C, Raney-Ni and the like. A reaction temperature is usually 0 to 200° C. In addition, as an alternative method for the present method, a compound of the present invention may be prepared also by generating in situ by heating ammonium formate and the like in a solvent.

According to Preparation method 15, for example, an imidazole ring can be introduced in a skeleton by a method shown in the formula:

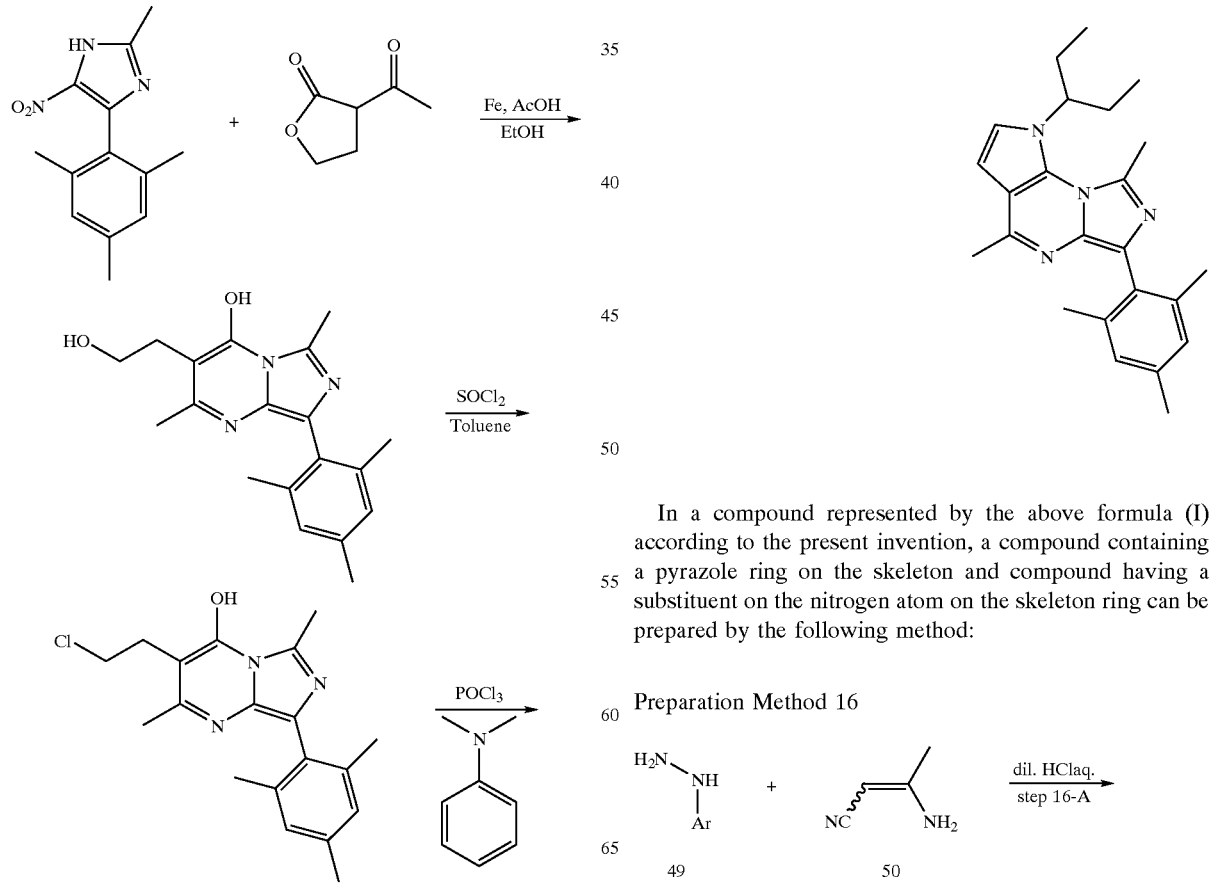

In a compound represented by the above formula (I) according to the present invention, a compound containing a pyrazole ring on the skeleton and compound having a substituent on the nitrogen atom on the skeleton ring can be prepared by the following method:

Preparation Method 16

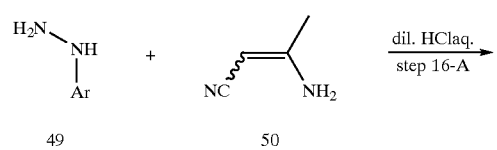

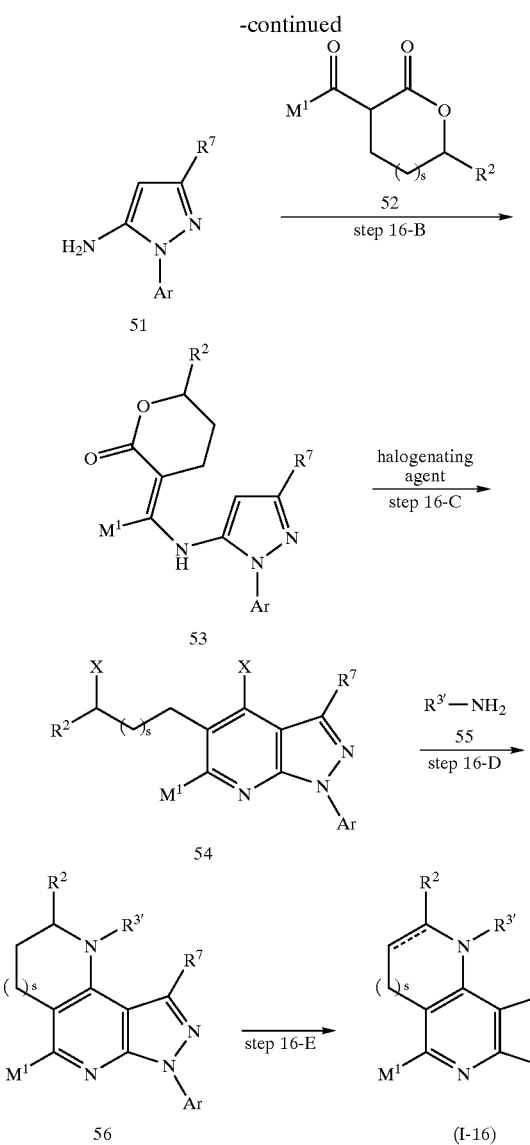

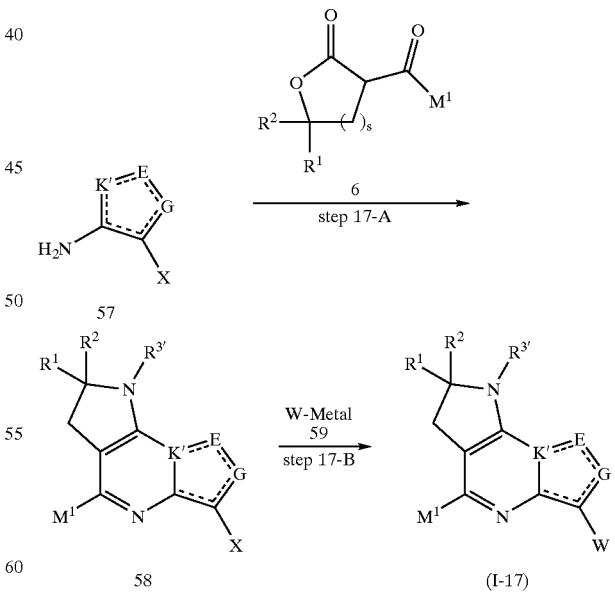

wherein $R^2$, $R^{3'}$, $R^7$, $M^1$ and s have the same meanings as defined above; and Ar represents an aromatic group having a substituent.

A pyrazole ring compound (51) as a starting material can be prepared according to the method described in WO99/10350 (Step 16-A).

A compound (53) is obtained by dehydration condensation of the (51) and α-ketoester (52) (Step 16-D). A solvent used is different depending upon a raw material, reagents and the like, and is not particularly limited as long as it does not inhibit the reaction and dissolves a starting material to some extent. Suitable are xylene, toluene, benzene, tetrahydrofuran, 1,4-dioxane, dimethoxyethane, ethanol and the like. In addition, the present reaction can afford the better results by adding a dehydration agent, and preferable examples in such the dehydration agent are acids such as hydrochloric acid, sulfuric acid, p-toluenesulfonic acid, acetic acid, trifluoroacetic acid, oxalic acid and phosphoric acid. A reaction temperature is usually room temperature to the boiling point of the solvent, preferably the boiling point of the solvent.

Next, a compound (54) is obtained by halogenating a compound (53) (Step 16-C). A halogenating agent used is different depending upon a starting material, reagents, a solvent and the like, and is not particularly limited. Suitable are phosphorus oxychloride, phosphorus oxybromide and the like. Halogenation is performed in a solvent or without a solvent, and such the solvent is different depending upon a raw material, reagents and the like to be used, and is not particularly limited as long as it does not inhibit the reaction and dissolves a starting material to some extent. Suitable are acetonitrile and the like. Further, the present reaction is performed by adding a base and preferable examples in such the base are triethylamine, diethylisopropylamine, pyridine, N,N-dimethylaminopyridine, N,N-dimethylaniline, N,N-diethylaniline and the like. A reaction temperature is usually 0 to 120° C.

Further, in Step 16-D, a cyclizing reaction of a compound (54) and an amine compound (55) can be performed, to give a compound (56) (Step 16-D). A solvent used is different depending upon a raw material, reagents and the like to be used, and is not particularly limited as long as it does not inhibit the reaction and dissolves a starting material to some extent. Suitable are xylene, toluene, benzene, tetrahydrofuran, N-methylpyrrolidone, N,N-dimethylformamide, 1,4-dioxane, dimethoxyethane, ethanol, acetonitrile and the like. Alternatively, an amine compound (55) may be used as a solvent. The present reaction is preferably performed by adding p-toluenesulfonic acid, phenol and the like. A reaction temperature is usually room temperature to the boiling point of the solvent. However, when a pressure-resistant vessel is used, a reaction may be performed in a range of the boiling point of the solvent to 200° C.

Finally, a compound (I-16) of the present invention is obtained by subjecting a compound (56) to an oxidation reaction (Step 16-G). As a preferable example in such the oxidation reaction, there are oxidation with manganese dioxide, 2,3-dichloro-5,6-dicyano-1,4-benzoquinone (DDQ), air oxidation and the like.

Preparation Method 17

In the formula, $R^1$, $R^2$, $R^{3'}$, E, G, K', $M^1$, W, X and s have the same meanings as defined above. A dihydropyrrole compound (58) can be prepared by a method according to the above Preparation method 1 and the like (Step 17-A). A compound (I-17) of the present invention can be obtained by reacting the compound (58) with a heteroaryl-boric acid compound, an aryl-boric acid compound, an aryl-metal compound or a compound (59) (for example, a heteroaryl-tin compound, an aryl-tin compound and the like) (Step 17-B). The reaction is performed by using a palladium or nickel metal complex. Preferable examples thereof are Pd(PPh$_3$)$_4$, Pd(OAc)$_2$/PPh$_3$, PdCl$_2$, PdCl$_2$(dppf), Ni (dpp)$_2$Cl$_2$ and the like. A solvent used is different depending upon a raw material, reagents and the like to be used and is not particularly limited as long as it does not inhibit the reaction and dissolves a starting material to some extent. Suitable are benzene, toluene, xylene, anisole, N,N-dimethylformamide, 1,2-dimethoxyethane, tetrahydrofuran, dioxane, n-butanol, ethanol, methanol, N-methyl-2-pyridone or water, or a mixed solvent thereof. A reaction temperature is usually 0 to 250° C. In addition, the present reaction is a reaction which is performed in the presence of a base, such the base is different depending upon a starting material, reagents, the solvent and the like, and is not particularly limited. Suitable are potassium carbonate, sodium carbonate, cesium fluoride, potassium fluoride, sodium bicarbonate, triethylamine and the like.

As an alternative method for the above preparation methods 15 and 15', there is a method of adding iodine to a position of W in the formula (Preparation method 18).

Preparation Method 18

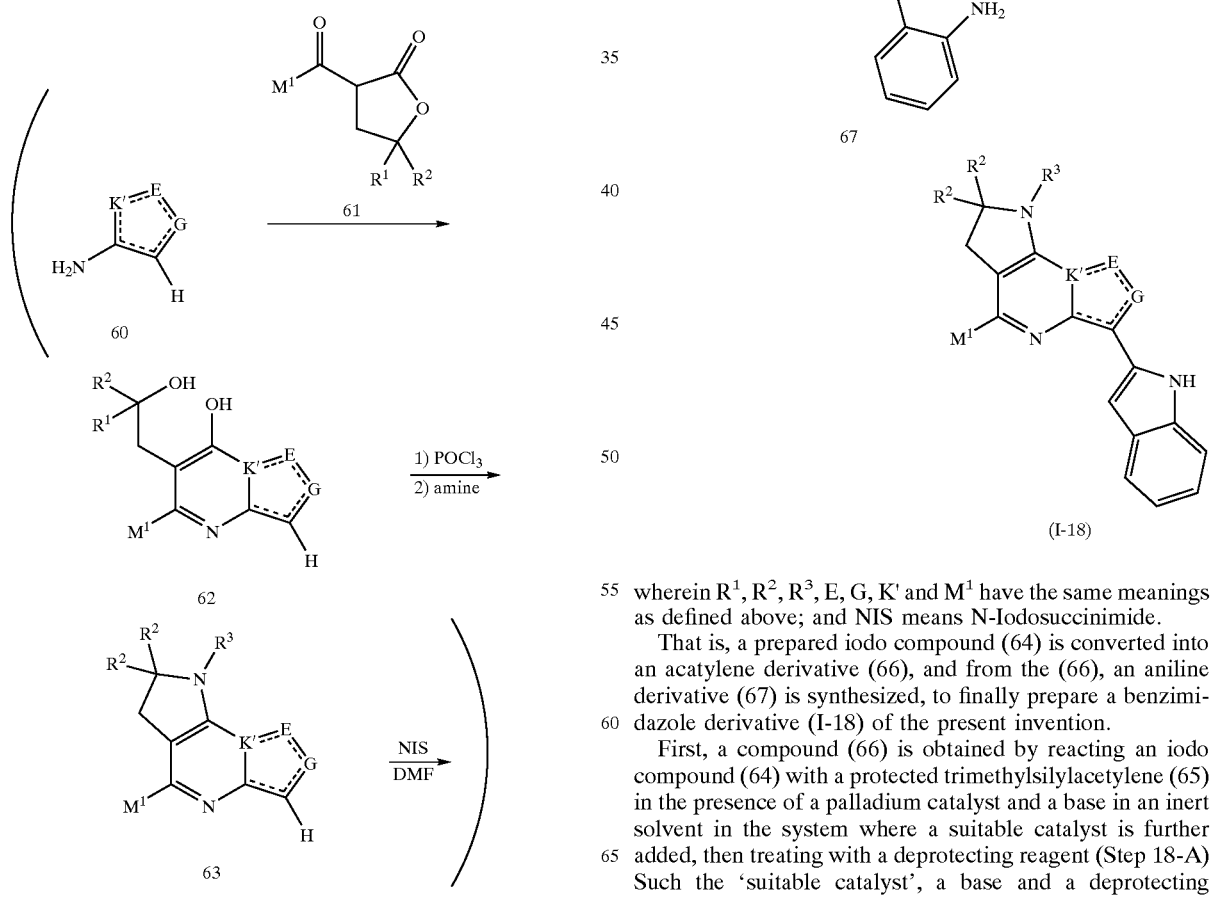

wherein R$^1$, R$^2$, R$^3$, E, G, K' and M$^1$ have the same meanings as defined above; and NIS means N-Iodosuccinimide.

That is, a prepared iodo compound (64) is converted into an acatylene derivative (66), and from the (66), an aniline derivative (67) is synthesized, to finally prepare a benzimidazole derivative (I-18) of the present invention.

First, a compound (66) is obtained by reacting an iodo compound (64) with a protected trimethylsilylacetylene (65) in the presence of a palladium catalyst and a base in an inert solvent in the system where a suitable catalyst is further added, then treating with a deprotecting reagent (Step 18-A) Such the 'suitable catalyst', a base and a deprotecting reagent to be used are different depending upon a starting material, reagents, the solvent and the like, and are not particularly limited. Preferable examples in 'suitable catalyst' are cuprous iodide and the like. Suitable bases are potassium carbonate, sodium carbonate, cesium fluoride, potassium fluoride, sodium bicarbonate, triethylamine and the like. In addition, suitable deprotecting reagents are fluorine anion and the like, more preferably tetrabutylammonium fluoride, cesium fluoride and the like. Suitable examples in a palladium catalyst or a nickel metal complex used are Pd(PPh$_3$)$_4$, Pd(OAc)$_2$/PPh$_3$, PdCl$_2$, PdCl$_2$(dppf), Ni (dpp)$_2$Cl$_2$ and the like. A solvent used is different depending upon a raw material, reagents and the like to be used, and is not particularly limited as long as it does not inhibit the reaction and dissolves a starting material to some extent. Suitable are benzene, toluene, xylene, anisole, N,N-dimethylformamide, 1,2-dimethoxyethane, tetrahydrofuran, n-butanol, ethanol, methanol, N-methyl-2-pyridone, water, or a mixed solvent thereof and the like. A reaction temperature is usually 0 to 250° C.

An aniline derivative (67) which is a next intermediate is obtained by reacting an acetylene compound (66) with 2-iodoaniline in the presence of a palladium catalyst and a base in an inert solvent in the system where a suitable catalyst is further added (Step 18-B). 'Suitable catalyst' used is different depending upon a starting material, reagents, the solvent and the like, and is not particularly limited. Suitable examples of 'suitable catalyst' are cuprous iodide and the like. Suitable bases are potassium carbonate, sodium carbonate, cesium fluoride, potassium fluoride, sodium bicarbonate, triethylamine and the like. In addition, suitable examples in a palladium or a nickel metal complex used are Pd(PPh$_3$)$_4$, Pd(OAc)$_2$/PPh$_3$, PdCl$_2$, PdCl$_2$(dppf), ni(dpp)$_2$Cl$_2$ and the like. A solvent used is different depending upon a raw material, reagents and the like to be used, and is not particularly limited as long as it does not inhibit the reaction and dissolves a starting material to some extent. Suitable are benzene, toluene, xylene, anisole, N,N-dimethylformamide, 1,2-dimethoxyethane, tetrahydrofuran, N-butanol, ethanol, methanol, N-methyl-2-pyridone, water, or a mixed solvent thereof and the like. A reaction temperature is usually 0 to 250° C.

Finally, in order to obtain a benzimidazole derivative (I-18) of the present invention form the above compound (67), an aniline compound (67) is reacted at 0 to 250° C. in the presence of a catalyst such as cuprous iode and the like in an inert solvent. A solvent used is different depending upon a raw material, reagents and the like to be used, and is not particularly limited as long as it does not inhibit the reaction and dissolves a starting material to some extent. Suitable are benzene, toluene, xylene, anisole, N,N-dimethylformamide, 1,2-dimethoxyethane, tetrahydrofuran, dioxane, n-butanol, ethanol, methanol, N-methyl-2-pyridone, water, or a mixed solvent thereof and the like.

In addition, there is a method of preparing a compound of the present invention via an aldehyde intermediate (Preparation method 19).

Preparation Method 19

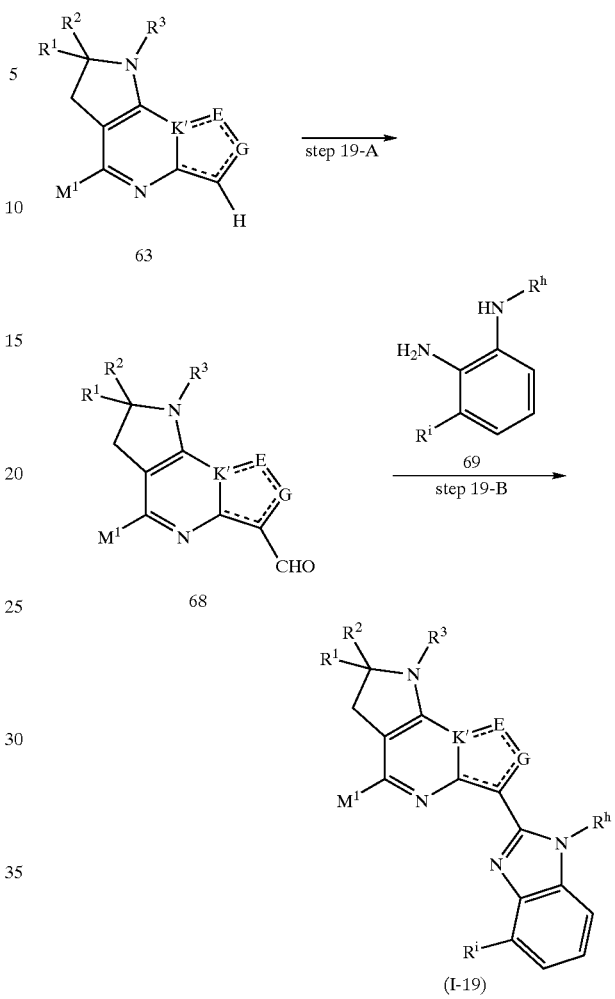

wherein $R^1$, $R^2$, $R^3$, E, G, K' and $M^1$ have the same meanings as defined above; and $R^h$ and $R^i$ represent a substituent.

That is, first, a benzimidazole derivative (I-19) of the present invention is prepared by formylating a compound (63) by a method such as Vilsmeier method (compound (68); Step 19-A), then reacting the aldehyde compound with 1,2-phenylenediamine derivative (69) (Step 19-B). The above formylating reaction (Step 19-A) is usually performed at a reaction temperature of 0 to 100° C. When a Vilsmeier method is used in the formylating reaction, phosphoryl chloride and N,N-dimethylformamide are reacted, to synthesize a Vilsmeier reagent, and such the reagent is used to perform a reaction. A reaction of an aldehyde compound (68) and a 1,2-phenylenediamine derivative (69) is performed at 0 to 250° C. in the presence of a catalyst in an inert solvent (Step 19-B). A catalyst used is different depending upon a starting raw material, reagents, the solvent and the like, and is not particularly limited. Suitable are 2,3-dichloro-5,6-dicyano-1,4-benzoquinone (DDQ) and the like. In addition, the solvent used is different depending upon a starting material, reagents, the solvent and the like, and is not particularly limited. Suitable are N,N-dimethylformamide, 1,2-dimethoxyethane, tetrahydrofuran, dioxane, n-butanol, ethanol, methanol, N-methyl-2-pyridone, water, or a mixed solvent thereof and the like.

A compound having a skeleton of a 6-6-5-membered ring system in compounds of the present invention can be prepared, for example, by the following method (Preparation method 20).
Preparation Method 20
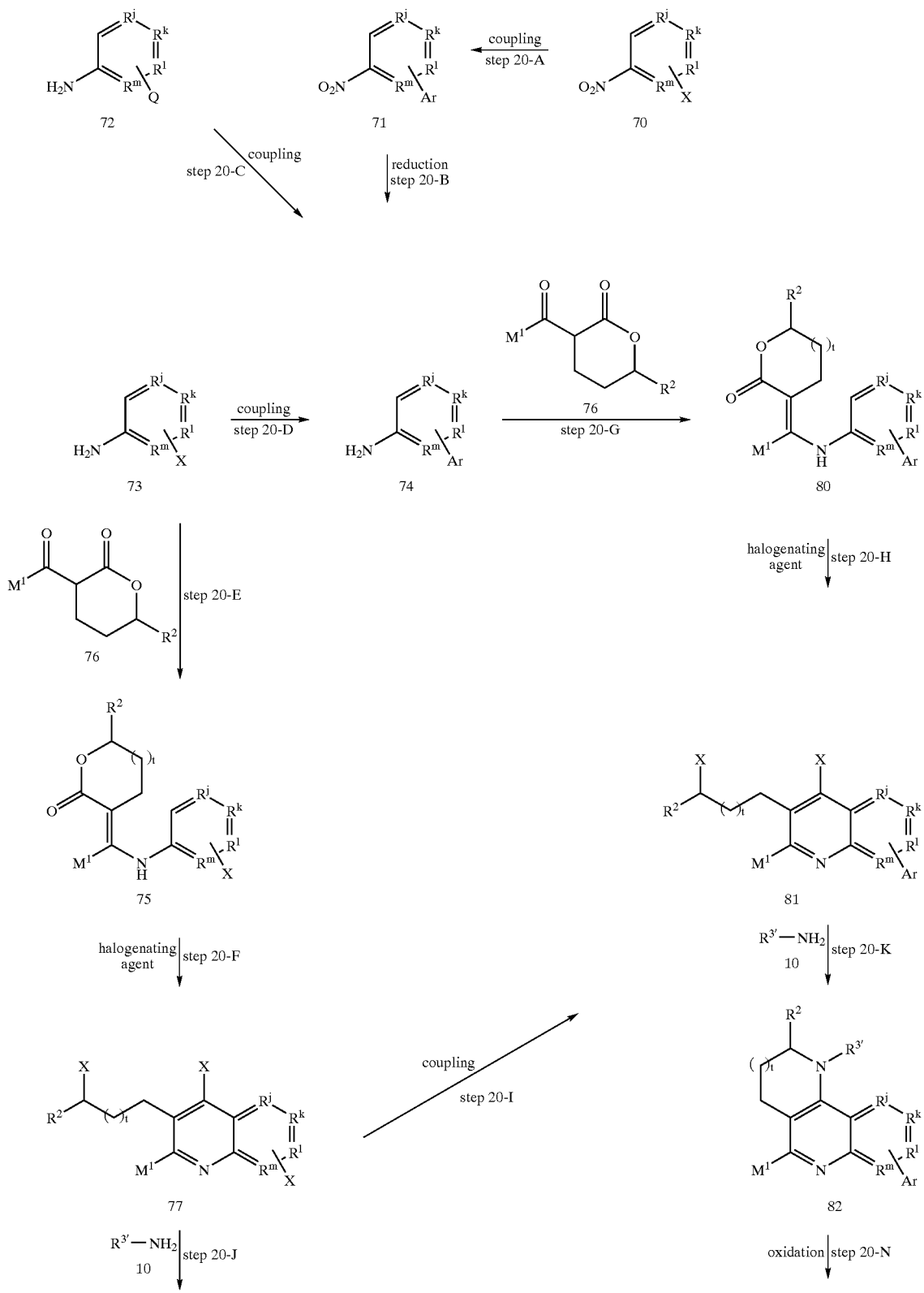

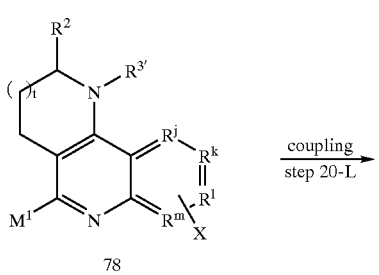 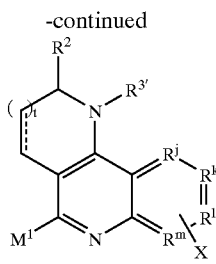 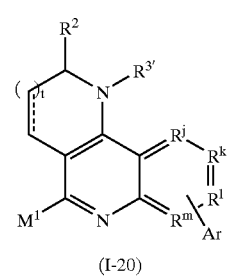

wherein R², R³', M¹, X and Ar have the same meanings as defined above; $R^j$, $R^k$, $R^l$ and $R^m$ represent nitrogen atom or a group represented by the formula —C(R⁷)— (wherein R⁷ has the same meaning as defined above); Q represents a group represented by the formula —B(R")₂, —Sn(R°)₃ (wherein R" and R° are the same as or different from each other and each represents an alkyl group and the like), —ZnX' or —MgX" (wherein X' and X" represent the same or different halogen atom); and t means an integer of 0, 1 or 2.

In order to prepare a compound (74), there are a method via compounds (70) and (71) (Step 20-A, B), a method of deriving from a compound (72) (Step 20-C), and a method of deriving from a compound (73) (Step 20-D).

A compound (71) is obtained by a palladium catalyst cross-coupling reaction of (70) and an organometal compound (20-A). An organometal compound used is different depending upon a starting material, reagents, the solvent and the like, and is not particularly limited. Suitable are an organic boron compound, an organic tin compound, an organic zinc compound, Grignard reagent and the like. A solvent used is different depending upon a raw material, reagents and the like to be used, and is not particularly limited as long as it does not inhibit the reaction and dissolves a starting material to some extent. Suitable are organic solvents such as toluene, benzene and tetrahydrofuran; hydrophilic organic solvents such as N,N-dimethylformamide, 1,4-dioxane, 1,2-dimethoxyethan, ethanol and acetonitrile; a mixed solvent of a hydrophilic organic solvent and water, and the like. A catalyst used is different depending upon a starting material, reagents, the solvent and the like, and is not particularly limited. Suitably, tetrakistriphenylphosphine palladium, dichlorobistriphenylphosphine palladium and the like are used alone, or a mixture of palladium acetate, bisdibenzylydene aceton palladium and the like with a phosphine compound such as triphenylphosphine is used. A suitable example of a reaction temperature is room temperature to a boiling point of the solvent. In addition, when an organic boron compound is used as an organometal compound, this cross-coupling reaction is usually performed in the presence of a base. As a preferable example in the base, there are triethylamine, sodium carbonate, potassium carbonate, cesium carbonate, potassium tert-butoxide, sodium hydroxide, barium hydroxide, potassium acetate, potassium phosphate and the like.

A compound (74) can be obtained by reduction of a nitro compound (71) (Step 20-B), by a palladium catalyst cross-coupling reaction of an organometal compound (72) and halogenated allyl (Step 20-C), or a palladium catalyst cross-coupling reaction of a compound (73) and an organometal compound. As a preferable reduction reaction in step 20-B, for example, there are a catalytic hydrogenation reaction and a reduction reaction using a metal salt such as iron, zinc and tin. A coupling reaction in Steps 20-C and D can be performed under the same conditions as the reaction conditions in the above Step 20-A.

In order to prepare a compound (I-20) of the present invention from a compound (74), one can pass successively through Steps 20-G, H, K and N in the formula.

First, a compound (80) can be obtained by dehydration condensation of a compound (74) and α-ketoester (76) (Step 20-G). A solvent used is different depending upon a raw material, reagents and the like to be used, and is not particularly limited as long as it does not inhibit the reaction and dissolves a starting material to some extent. Suitable are xylene, toluene, benzene, tetrahydrofuran, 1,4-dioxane, dimethoxyethane, ethanol and the like. The present reaction can also afford the better results by adding an acid such as hydrochloric acid, sulfuric acid, p-toluenesulfonic acid, acetic acid, trifluoroacetic acid, oxalic acid, phosphoric acid and the like as a dehydration agent. A reaction temperature is usually room temperature to a boiling point of the solvent, preferably a boiling point of the solvent.

A compound (81) can be obtained by halogenating a compound (80) (Step 20-H) and, additionally, also can be obtained by a palladium catalyst cross-coupling reaction of a compound (77) derived from a compound (73) and an organometal compound (Step 20-I). A halogenating agent and a solvent used in Step 20-H are different depending upon a starting material, reagents, a solvent and the like, and are not particularly limited. Suitable halogenating agents are phosphorous oxychloride, phosphorous oxybromide and the like. Suitable solvents are acetonitrile and the like. In addition, such the halogenating reaction can be also performed without a solvent. Further, the present halogenating reaction can afford more preferable results by adding a base such as triethylamine, diethylisopropylamine, pyridine, N,N-dimethylaminopyridine, N,N-dimethylaniline, N,N-diethylaniline and the like. A reaction temperature is usually 0 to 120° C., but the reaction may be also performed at 120 to 180° C., when an pressure-resistance vessel is used. A cross-coupling reaction in Step 20-I can be performed under the same conditions as the reaction conditions for the above Step 20-A.

A compound (82) can be obtained by a cyclization using an amine (10) (Step 20-K). The present reaction is usually performed in the presence of a solvent, and is also preferable by adding p-toluenesulfonic acid, phenol and the like. A solvent used is different depending upon a raw material, reagents and the like to be used, and is not particularly limited so long as it does not inhibit the reaction and dissolves a starting material to some extent. Suitable examples are xylene, toluene, benzene, tetrahydrofuran, N-methylpyrrolidone, N,N-dimethylformamide, 1,4-dioxane, dimethoxyethane, ethanol, acetonitrile and the like. Alternatively, an amine (10) may be used as a solvent instead of them. A reaction temperature is usually room temperature to a boiling point of the solvent, and the reaction may be also performed at a boiling point of the solvent to 200° C., when a pressure-resistant vessel is used.

Finally, a compound (I-20) of the present invention can be obtained by oxidizing a compound (82) (Step 20-N). As a preferable example in such the oxidation reaction, there are a manganese dioxide oxidation, a 2,3-dichloro-5,6-dicyano-1,4-benzoquinone (DDQ) oxidation, an air oxidation and the like.

In order to prepare a compound (I-20) of the present invention from a compound (73), one may pass successively thorough Steps 20-E, F, J, L and M in the formula or one may pass successively through Steps 20E, F, I, K and N.

First, a compound (75) is obtained by dehydration condensation of a compound (73) and α-ketoester (76) (Step 20-E). Such the condensation reaction can be performed under the same conditions as the reaction conditions for the above Step 20-G.

A compound (77) is obtained by halogenating a compound (75) (Step 20-F). Such the halogenating reaction can be performed under the same conditions as the reaction conditions for the above Step 20-H.

A compound (78) can be obtained by a cyclization using an amine (10) (Step 20-J). Such the reaction can be performed under the same conditions as the reaction conditions for the above Step 20-K.

A compound (79) can be obtained by oxidizing a compound (78). As a preferable example in such the oxidation reaction, there are a manganese dioxide oxidation, a 2,3-dichloro-5,6-dicyano-1,4-benzoquinone (DDQ) oxidation, an air oxidation and the like.

Finally, the compound (I-20) according to the present invention can be obtained by a palladium catalyst cross-coupling reaction of a compound (79) and an organometal compound. Such the cross-coupling reaction can be performed under the same conditions as the reaction conditions for the above Step 20-A.

The foregoing are methods of preparing a compound (I) of the present invention, raw material compounds listed in the above preparation methods may form a salt or a hydrate, and the kind of such the salt and whether hydrate or an hydride are not particularly limited as long as they do not inhibit the reaction. When a compound of the present invention is prepared as a free compound, it can be converted into the state of a salt according to the conventional method. In addition, a variety of isomers (for example, geometrical isomer, optical isomer based on an asymmetrical carbon, stereoisomer, tautomer and the like) regarding a compound (I) of the present invention can be purified and isolated using the conventional separating means (for example, recrystallization, diastereomer salt method, enzyme dissolution method, a variety of chromatographies and the like).

A compound represented by the above formula (I) of the present invention, a salt thereof or hydrates thereof can be formulated into preparations by the conventional method. As a preferable dosage form, there are tablets, powders, fine granules, granules, coated tablets, capsules, syrups, troches, inhalants, suppositories, injections, ointments, ocular ointments, eye drops, nasal drops, ear drops, cataplasms, lotions and the like. For the formulation into preparations, excipient, binding agent, disintegrating agent, lubricant, colorant and flavoring agent which are generally used and, if needed, stabilizer, emulsifier, absorption promoter, surfactant, pH adjusting agent, preservative and anti-oxidant can be used. Generally, ingredients used as a raw material for pharmaceutical preparations can be blended and formulated into preparations by the conventional method. As these ingredients, there are animal and vegetable oils such as soy bean oil, beef tallow and synthetic glycerin; hydrocarbons such as liquid paraffin, squalene and solid paraffin; ester oils such as octyldodecyl myristate and isopropyl myristate; higher alcohols such as cetostearyl alcohol and behenyl alcohol; silicone resin; silicone oil; surfactants such as polyoxyethylene fatty ester, sorbitan fatty ester, glycerin fatty ester, polyoxyethylenesorbitan fatty ester, polyoxyethylene hydrogenated castor oil and polyoxyethylene polyoxypropylene block copolymer; water-solublepolymers such as hydroxyethyl cellulose, polyacrylic acid, carboxyvinil polymer, polyethylene glycol, polyvinylpyrrolidole and methyl celluose; lower alcohols such as ethanol and isopropanol; polyhydric alcohol such as glycerin, propylene glycol, dipropylene glycol and sorbitol; sugar such as grucose and sucrose; inorganic powders such as anhydrous silicic acid, aluminium magnesium silicate and alminium silicate; purified water, and the like. Specifically, there can be used, for example, lactose, cornstarch, sucrose, glucose, mannitol, sorbitol, crystalline celluose, silicon dioxide and the like as an excipient; for example, polyvinyl alcohol, polyvinyl ether, methyl celluose, ethyl celluose, gum arabic, tragacant, gelatin, shellac, hydroxypropyl celluose, hydroxypropylmethyl celluose, polyvinylpyrrolidone, polypropylene glycol polyoxiethylene block polymer, meglumine, calcium citrate, dextrin, pectin and the like as a binding agent; for example, starch, agar, gelatin powder, crystalline celluose, calcium carbonate, sodium bicarbonate, calcium citrate, dextrin, pectin, calcium carboxymethyl celluose and the like as a disintegrating agent; for example, magnesium stearate, talc, polyethylene glycol, silica, hydrogenated vegetable oil and the like as a lubricant; any ones which are permitted to add to medicaments as a colorant; cacao powder, 1-menthol, aromatic powder, mentha oil, Borneo camphor, powdered cinnamon bark and the like as flavoring agent; and any ones which are permitted to add to phermaceuticals such as ascorbic acid and α-tocopherol as an anti-oxidant.

(1) For example, for oral preparations, a compound of the present invention, a salt thereof or hydrates thereof and an excipient, if needed, a binding agent, disintegrating agent, lubricant, colorant, flavoring agent and the like are added, and thereafter, formulated into powders, fine granules, granules, tablets, coated tablets, capsules and the like by the conventional method. (2) In the case of tablets or granules, coating such as sugar coating, gelatin coating, and others may be of course performed conveniently. (3) In the case of syrups, injectable preparations, eye drops and the like, a pH adjusting agent, dissolving agent, isotonic and the like and, if needed, a solubilizer, stabilizer, buffer, suspending agent and anti-oxidant are added and formulated in preparations by the conventional method. In the preparations, it may be freeze-dried, and an injectable can be admired intravenously, subcutaneously or intramascularly. There are methyl cellose, polysorbate 80, hydroxyethyl cellouse, gum arabic, tragacant powder, sodium carboxymethyl cellouse, polyoxyethylenesorbitan monolaurate and the like as a preferable example in a suspending agent; polyoxyethylene hydrogenated castor oil, polysorbate 80, nicotinic amide, polyoxyethylenesorbitan monolaurate and the like as a preferable example of a solubilizer; sodium sulfite, sodium methasulfite, ether and the like as a preferable example of a stabilizer; and methyl paraoxybenzoate, ethyl paraoxybenzoate, sorbic acid, phenol, cresol, chlorocresol and the like as a preferable example of a preservative. (4) In addition, in the case of an external preparation, a method of preparing it is not particularly limited but it can be prepared by the conventional method. As a base raw material used, a variety of raw materials which are usually used for a drug, a quasi-drug or a cosmetic can be used and, for example, there are raw materials such as animal and vegetable oils, mineral oils, ester oils, waxes, higher alcohols, fatty acids, silicone oils, surfactants, phospholipids, alcohols, polyhydric alcohols, water-soluble polymers, clay minerals, purified water. If needed, a pH adjusting agent, anti-oxydant, chelating agent, antiseptic and anti-mold agent, colorant and flavor and the like may be added. Further, if needed, an ingredient having the differentiation inducing activity, ingredients such as a blood flow promoter, sterilizer, anti-inflammatory, cell activating agent, vitamins, aminoacid, humectant, corneum dissolving agent and the like may be incorporated. A dose of a drug of the present invention is different depending upon severity of the symptom, age, sex, weight, dosage form, kind of salt, difference in sensitivity to a drug, particular kind of disease and the like, and generally about 30 μg to 1000 mg, preferably 100 μg to 500 mg, more preferably 100 μg to 100 mg is administered orally per day in an adult, and about 1 to 3000 μg/kg, preferably 3 to 1000 μg/kg is administered by injection once or in several times.

EXAMPLES

The following Reference Examples, Examples (pharmacologically acceptable salts, hydrates thereof and pharmaceuticals containing them) and Test Examples are only illustrative and compounds of the present invention are not limited by the following embodiments. A person skilled in the art can implement the present invention to maximum by way of Examples and by modifying claims and such the modification is included in the claims.

Reference Examples 1

4-Mesityl-3-methyl-1H-5-pyrazoleamine

In tetrahydrofuran (700 mL) was dissolved 2-mesitylacetonitrile (50 g, 314 mmol). Under ice-cooling, sodium hydride (31 g (60%), 785 mmol) was slowly added thereto, followed by stirring at room temperature for one hour. Under ice-cooling, ethyl acetate (92 mL, 942 mmol) was added thereto, followed by stirring at room temperature overnight. Methanol (100 mL) was added to the reaction mixture, followed by overnight. The residue was subjected to silica gel column chromatography (20% methanol/ethyl acetate), to give a crude purified product of 2-mesityl-3-oxobutanenitrile. A mixture of the resulting 2-mesityl-3-oxobutanenitrile, hydrazine dihydrobromide (300 g), water (200 ml) and ethanol (1000 mL) was heated under reflux for six days. The reaction mixture was evaporated and neutralized with an aqueous saturated sodium bicarbonate solution. The resulting crystals were collected by filtration, washed well with water and air-dried at 50° C., to give the title compound (65 g) as gray-white crystals.

$^1$H-NMR (400 MHz, CDCl$_3$) δ 2.03 (s, 3H), 2.07 (s, 6H), 2.32 (s, 3H), 6.95 (s, 2H).

Reference Example 2

6-(2-Hydroxyethyl)-3-mesityl-2,5-dimethyl-4,7-dihydropyrazolo[1,5-a]pyrimidin-7-one A mixture of 4-mesityl-3-methyl-1H-5-pyrazoleamine (20 g, 99.2 mmol) obtained in Reference Example 1, 2-acetylbutyrolactone (10.5 mL, 97.5 mmol) and xylene (150 mL) was heated under reflux for five hours. It was cooled to room temperature, and the resulting crystals were collected by filtration, to give the title compound (22.7 g) as white crystals.

$^1$H-NMR (400 MHz, CDCl$_3$) δ 2.03 (s, 6H), 2.15 (s, 3H), 2.33 (s, 3H), 2.34 (s, 3H), 2.40 (br s, 1H), 2.86 (t, J=6.0 Hz, 2H), 3.85 (t, J=6.0 Hz, 2H), 6.98 (s, 2H), 8.13 (s, 1H).

According to the procedures described in the above Reference Examples, the following compounds were synthesized.

Reference Example 3

3-[6-(Dimethylamino)-4-methyl-3-pyridyl]-6-(2-hydroxyethyl)-2,5-dimethyl-4,7-dihydropyrazolo[1,5-a]pyrimidin-7-one Flesh Colored Crystals $^1$H-NMR (400 MHz, DMSO-d$_6$) δ 1.99 (s, 3H), 2.06 (s, 3H), 2.27 (s, 3H), 2.59 (t, J=6.8 Hz, 2H), 3.04 (s, 6H), 3.45 (dt, J=6.0 Hz, 2H), 4.58 (t, J=6.0 Hz, 1H), 6.61 (s, 1H), 7.83 (s, 1H), 11.46 (s, 1H).

Reference Example 4

6-(2-Hydroxyethyl)-2,5-dimethyl-3-(3-methyl-2-naphthyl)-4,7-dihydropyrazolo[1,5-a]pyrimidin-7-one White Crystals $^1$H-NMR (400 MHz, CDCl$_3$+DMSO-d$_6$) δ 2.21 (s, 3H), 2.26 (s, 3H), 2.28 (s, 3H), 2.82 (t, J=6.4 Hz, 2H), 3.78 (t, J=6.0 Hz, 2H), 4.71 (br s, 1H), 7.38–7.48 (m, 2H), 7.67 (s, 1H), 7.73 (s, 1H), 7.75–7.78 (m, 2H).

Reference Example 5

3-(4-Bromophenyl)-6-(2-hydroxyethyl)-2,5-dimethyl-4,7-dihydropyrazolo[1,5-a]pyrimidin-7-one White Crystals $^1$H-NMR (400 MHz, DMSO-d$_6$) δ 2.24 (s, 3H), 2.32 (s, 3H), 2.60 (t, J=7.0 Hz, 2H), 3.44 (t, J=7.0 Hz, 2H), 4.59 (t, J=5.6 Hz, 1H), 7.34 (d, J=8.5 Hz, 2H), 7.63 (d, J=8.5 Hz, 2H), 11.55 (s, 1H).

Reference Example 6

6-(2-Hydroxyethyl)-2,5-dimethyl-3-(2,4,6-trimethoxyphenyl)-4,7-dihydropyrazolo[1,5-a]pyrimidin-7-one White Crystals Reference Example 7

3-(1,3-Benzodioxol-5-yl)-6-(2-hydroxyethyl)-2,5-dimethyl-4,7-dihydropyrazolo[1,5-a]pyrimidin-7-one White Crystals $^1$H NMR (400 MHz, DMSO-d$_6$) δ 2.22 (s, 3H), 2.32 (s, 3H), 2.60 (t, J=7.1 Hz, 2H), 3.44 (t, J=7.0 Hz, 2H), 4.58 (t, J=5.6 Hz, 1H), 6.04 (s, 2H), 6.81 (d, J=8.1 Hz, 1H), 6.93 (s, 1H), 6.99 (d, J=8.1 Hz, 1H), 11.45 (s, 1H).

Reference Example 8

6-(2-Hydroxyethyl)-2,5-dimethyl-3-phenyl-4,7-dihydropyrazolo[1,5-a]pyrimidin-7-one White Crystals Reference Example 9

3-(2,4-Dichlorophenyl)-6-(2-hydroxyethyl)-2,5-dimethyl-4,7-dihydropyrazolo[1,5-a]pyrimidin-7-one Brown Crystals ¹H NMR (400 MHz, DMSO-d₆) δ 2.11 (s, 3H), 2.29 (s, 3H), 2.60 (t, J=6.8 Hz, 2H), 3.45 (t, J=6.8 Hz, 2H), 4.2 (br s, 1H), 7.40–7.50 (m, 2H), 7.77 (s, 1H).

Reference Example 10

3-(2-Chlorophenyl)-6-(2-hydroxyethyl)-2,5-dimethyl-4,7-dihydropyrazolo[1,5-a]pyrimidin-7-one
White Crystals Reference Example 11

3-(2,4-Dimethoxyphenyl)-6-(2-hydroxyethyl)-2,5-dimethyl-4,7-dihydropyrazolo[1,5-a]pyrimidin-7-one
Brown Crystals
¹H NMR (400 MHz, DMSO-d₆) δ 2.12 (s, 3H), 2.30 (s, 3H), 2.59 (t, J=7.2 Hz, 2H), 3.44 (t, J=6.8 Hz, 2H), 3.72 (s, 3H), 3.80 (s, 3H), 6.60 (br d, J=8.4 Hz, 1H), 6.64 (br s, 1H), 7.13 (d, J=8.4 Hz, 1H).

Reference Example 12

6-(2-Hydroxyethyl)-2,5-dimethyl-3-(2-methylphenyl)-4,7-dihydropyrazolo[1,5-a]pyrimidin-7-one
White Crystals
¹H NMR (400 MHz, DMSO-d₆) δ 2.06 (s, 3H), 2.08 (s, 3H), 2.29 (s, 3H), 2.60 (t, J=6.8 Hz, 2H), 3.46 (t, J=7.2 Hz, 2H), 7.20–7.35 (m, 4H).

Reference Example 13

6-(2-Hydroxyethyl)-3-(2-methoxy-4-methylphenyl)-2,5-dimethyl-4,7-dihydropyrazolo[1,5-a]pyrimidin-7-one
White Crystals
¹H NMR (400 MHz, DMSO-d₆) δ 2.14 (s, 3H), 2.30 (s, 3H), 2.36 (s, 3H), 2.60 (t, J=7.2 Hz, 2H), 3.45 (t, J=6.8 Hz, 2H), 3.72 (s, 3H), 6.83 (d, J=7.2 Hz, 1H), 6.91 (s, 1H), 7.11 (d, J=7.6 Hz, 1H).

Reference Example 14

3-(3-Chlorophenyl)-6-(2-hydroxyethyl)-2,5-dimethyl-4,7-dihydropyrazolo[1,5-a]pyrimidin-7-one
White Crystals
¹H NMR (400 MHz, DMSO-d₆) δ 2.24 (s, 3H), 2.34 (s, 3H), 2.61 (t, J=6.8 Hz, 2H), 3.42–3.49 (m, 2H), 4.59 (br s, 1H), 7.34 (d, 1=7.2 Hz, 1H), 7.39 (dd, J=1.2, 8.0 Hz, 1H), 7.42 (d, J=1.6 Hz, 1H), 7.47 (dd, J=7.6, 8.0 Hz, 1H), 11.61 (s, 1H).

Reference Example 15

3-(4-Chlorophenyl)-6-(2-hydroxyethyl)-2,5-dimethyl-4,7-dihydropyrazolo[1,5-a]pyrimidin-7-one
White Crystals
¹H NMR (400 MHz, DMSO-d₆) δ 2.23 (s, 3H), 2.33 (s, 3H), 2.60 (t, J=7.2 Hz, 2H), 3.42–3.49 (m, 2H), 4.59 (br s, 1H), 7.39 (dd, J=2.0, 6.4 Hz, 2H), 7.49 (dd, J=2.0 Hz, 6.4, 21H), 11.55 (s, 1H).

Reference Example 16

3-(2,6-Dimethylphenyl)-6-(2-hydroxyethyl)-2,5-dimethyl-4,7-dihydropyrazolo[1,5-a]pyrimidin-7-one
Pale Brown Crystals
¹H NMR (400 MHz, DMSO-d₆); δ 1.95 (s, 3H), 1.97 (s, 6H), 2.27 (s, 3H), 2.60 (t, J=7.2 Hz, 2H), 3.47 (dt, J=7.2, 5.6 Hz, 2H), 4.59 (t, J=5.6 Hz, 1H), 7.15 (d, J=7.2 Hz, 2H), 7.15–7.22 (m, 1H), 11.47 (s, 1H).

Reference Example 17

3-(4-Bromo-2-methylphenyl)-6-(2-hydroxyethyl)-2,5-dimethyl-4,7-dihydropyrazolo[1,5-a]pyrimidin-7-one
White Crystals
¹H NMR (400 MHz, DMSO-d₆) δ 2.07 (s, 6H), 2.28 (s, 3H), 2.59 (t, J=6.7 Hz, 2H), 3.45 (t, J=6.6 Hz, 2H), 4.58 (t, J=5.4 Hz, 1H), 7.14 (d, J=8.1 Hz, 1H), 7.43 (d, J=8.1 Hz, 1H), 7.56 (s, 1H), 11.45 (s, 1H).

Reference Example 18

3-(2,4-Dimethylphenyl)-6-(2-hydroxyethyl)-2,5-dimethyl-4,7-dihydropyrazolo[1,5-a]pyrimidin-7-one
White Crystals
¹H NMR (400 MHz, DMSO-d₆); δ 2.06 (s, 3H), 2.07 (s, 3H), 2.30 (s, 3H), 2.33 (s, 3H), 2.61 (t, J=7.2 Hz, 2H), 3.47 (dt, J=7.2, 5.6 Hz, 2H), 4.59 (t, J=5.6 Hz, 1H), 7.08 (s, 2H), 7.16 (s, 1H), 11.43 (s, 1H).

Reference Example 19

7-Chloro-6-(2-chloroethyl)-3-mesityl-2,5-dimethylpyrazolo[1,5-a]pyrimidine

A mixture of 6-(2-hydroxyethyl)-3-mesityl-2,5-dimethyl-4,7-dihydropyrazolo[1,5-a]pyrimidin-7-one (22.7 g, 69.8 mmol), N,N-dimethylaniline (6 drops) and phosphorus oxychloride (45 g) was heated under reflux for three hours. The reaction mixture was poured onto ice (400 g), followed by extracting with ethyl acetate. The organic layer was washed with brine, dried over anhydrous magnesium sulfate and evaporated. The residue was purified by silica gel column chromatography (67% ethyl acetate/hexane), to give a crude purified title compound (9.7 g). The compound was further recrystallized from 50% ethyl acetate/hexane, to give the title compound (5.4 g) as white crystals.
¹H NMR (400 MHz, CDCl₃) δ 1.56 (s, 6H), 2.00 (s, 3H), 2.31 (s, 3H), 2.34 (s, 3H), 2.60 (s, 3H), 3.32 (t, J=7.6 Hz, 2H), 3.74 (t, J=7.6 Hz, 2H), 6.98 (s, 2H).

Reference Example 20

3-(4-Bromophenyl)-7-chloro-6-(2-chloroethyl)-2,5-dimethylpyrazolo[1,5-a]pyrimidine
Pale Yellow Crystals
¹H NMR (400 MHz, CDCl₃) δ 2.64 (s, 3H), 2.69 (s, 3H), 3.33 (t, J=7.5 Hz, 2H), 3.74 (t, J=7.5 Hz, 2H), 7.59 (d, J=1.1 Hz, 2H), 7.59 (d, J=1.1 Hz, 2H).

Reference Example 21

7-Chloro-6-(2-chloroethyl)-2,5-dimethyl-3-(2,4,6-trimethoxyphenyl)pyrazolo[1,5-a]pyrimidine
Pale Yellow Crystals
¹H NMR (400 MHz, CDCl₃) δ 2.36 (s, 3H), 2.60 (s, 3H), 3.29 (t, J=7.7 Hz, 2H), 3.70 (t, J=7.7 Hz, 2H), 3.72 (s, 6H), 3.87 (s, 3H), 6.26 (s, 2H).

Reference Example 22

3-(1,3-Benzodioxol-5-yl)-7-chloro-6-(2-chloroethyl)-2,5-dimethylpyrazolo[1,5-a]pyrimidine
Pale Yellow Crystals
¹H NMR (400 MHz, CDCl₃) δ 2.63 (s, 3H), 2.68 (s, 3H), 3.32 (t, J=7.5 Hz, 2H), 3.74 (t, J=7.5 Hz, 2H), 6.00 (s, 2H), 6.93 (d, J=8.0 Hz, 1H), 7.11 (dd, J=1.7, 8.0 Hz, 1H), 7.22 (d, J=1.7 Hz, 1H).

Reference Example 23

3-(4-Bromo-2-methylphenyl)-7-chloro-6-(2-chloroethyl)-2,5-dimethylpyrazolo[1,5-a]pyrimidine Pale Yellow Crystals $^1$H NMR (400 MHz, CDCl$_3$) δ 2.17 (s, 3H), 2.41 (s, 3H), 2.63 (s, 3H), 3.33 (t, J=7.5 Hz, 2H), 3.74 (t, J=7.5 Hz, 2H), 7.10 (d, J=8.1 Hz, 1H), 7.39 (d d, J=2.1, 8.2 Hz, 1H), 7.49 (d, J=2.2 Hz, 1H).

Reference Example 24

7-Chloro-6-(2-chloroethyl)-3-(2,4-dimethylphenyl)-2,5-dimethylpyrazolo[1,5-a]pyrimidine Pale Yellow Crystals $^1$H NMR (400 MHz, CDCl$_3$) δ 2.16 (s, 3H), 2.38 (s, 3H), 2.42 (s, 3H), 2.62 (s, 3H) 3.32 (t, J=7.6 Hz, 2H), 3.74 (t, J=7.6 Hz, 2H), 7.08 (d, J=7.6 Hz, 1H), 7.13 (d, J=7.6 Hz, 1H), 7.16 (s, 1H).

Reference Example 25

7-Chloro-6-(2-chloroethyl)-3-mesityl-5-methylpyrazolo[1,5-a]pyrimidine $^1$H NMR (400 MHz, CDCl$_3$) δ 2.09 (s, 6H), 2.33 (s, 3H), 2.65 (s, 3H), 3.35 (t, J=7.6 Hz, 2H), 3.77 (t, J=7.6 Hz, 2H), 6.98 (s, 2H), 8.06 (s, 1H).

Reference Example 26

7-Chloro-6-(2-chloroethyl)-2-ethyl-3-mesityl-5-methylpyrazolo[1,5-a]pyrimidine $^1$H NMR (400 MHz, CDCl$_3$) δ 1.16 (t, J=7.6 Hz, 3H), 1.99 (s, 6H), 2.34 (s, 3H), 2.59 (s, 3H), 2.67 (q, J=7.6 Hz, 2H), 3.32 (t, J=7.7 Hz, 2H), 3.74 (t, J=7.7 Hz, 2H), 6.97 (s, 2H).

Reference Example 27

Ethyl 2-(3-mesityl-2-dimethyl-7-oxo-4,7-dihydropyrazolo[1,5-a]pyrimidin-6-yl]acetate Diethyl acetylsuccinate (0.3 mL) and a catalytic amount of 4-toluenesulfonic acid monohydrate were added to a solution of 4-mesityl-3-methyl-1H-5-pyrazoleamine (100 mg) of Reference Example 1 in xylene (5 mL). Under heating under reflux, the mixture was stirred for three hours while distilling water off with Dean-Stark. The reaction solution was cooled, water was added thereto. The mixture was extracted twice with ethyl acetate, and washed twice with an aqueous saturated solution of sodium bicarbonate. The organic layer was separated and dried over anhydrous magnesium sulfate. The solvent was evaporated, and the residue was purified by silica gel column chromatography, to give the title compound (200 mg) as a yellow amorphous material.

$^1$H NMR (400 MHz, CDCl$_3$) δ 1.27 (t, J=6.8 Hz, 3H), 2.01 (s, 6H), 2.06 (s, 3H), 2.22 (s, 3H), 2.35 (s, 3H), 3.57 (s, 2H), 4.16 (q, J=7.2 Hz, 2H), 6.81 (s, 2H), 9.84 (s, 1H).

Reference Example 28

Ethyl 2-(7-chloro-3-mesityl-2,5-dimethylpyrazolo[1,5-a]pyrimidin-6-yl)acetate

Phosphorus oxychloride (1.7 g) was added to ethyl 2-(3-mesityl-2,5-dimethyl-7-oxo-4,7-dihydropyrazolo[1,5-a]pyrimidin-6-yl)acetate (120 mg) of Reference Example 27 at room temperature, followed by stirring for one hour under heating under reflux. After cooling, the reaction solution was poured onto ice. The reaction mixture was basified with an aqueous saturated solution of sodium bicarbonate, and then extracted twice with ethylacetate. The organic layer was washed with brine, and then dried over anhydrous magnesium sulfate. The solvent was evaporated, to give the title compound (130 mg) as a reddish brown oil.

$^1$H NMR (400 MHz, CDCl$_3$) δ 1.29 (t, J=7.2 Hz, 3H), 2.00 (s, 6H), 2.31 (s, 3H), 2.34 (s, 3H), 2.52 (s, 3H), 3.88 (s, 2H), 4.22 (q, J=7.2 Hz, 2H), 6.98 (s, 2H).

Reference Example 29

Ethyl 2-[7-[(1-Ethylpropyl)amino]-3-mesityl-2,5-dimethylpyrazolo[1,5-a]pyrimidin-6-yl]acetate 3-Aminopentane (0.6 mL) was added to a solution of ethyl 2-(7-chloro-3-mesityl-2,5-dimethylpyrazolo[1,5-a]pyrimidin-6-yl)acetate (130 mg) in acetonitrile (5 mL), followed by heating under reflux overnight. After cooling the reaction solution, water was added thereto. The mixture was extracted twice with ethylacetate, and the organic layer was washed with an aqueous saturated solution of sodium bicarbonate, and then dried over anhydrous magnesium sulfate. The solvent was evaporated, and the residue was purified by silica gel column chromatography, to give the title compound (84 mg) as a green oil.

$^1$H NMR (400 MHz, CDCl$_3$) δ 1.00 (t, J=7.2 Hz, 6H), 1.29 (t, J=7.2 Hz, 3H), 1.58–1.80 (m, 4H), 2.03 (s, 6H), 2.20 (s, 3H), 2.32 (s, 3H), 2.43 (s, 3H), 3.69 (s, 2H) 3.85 (m, 1H), 4.22 (q, J=7.2 Hz, 2H), 6.11 (br s, 1H), 6.95 (s, 2H).

Reference Example 30

6-(2-Hydroxypropyl)-3-mesityl-2,5-dimethyl-4,7-dihydropyrazolo[1,5-a]pyrimidin-7-one White Crystals $^1$H NMR (400 MHz, DMSO-d$_6$) δ 1.07 (d, J=6.4 Hz, 3H), 1.93 (s, 3H), 1.95 (s, 6H), 2.26 (s, 3H), 2.27 (s, 3H), 2.38–2.41 (m, 1H), 2.52–2.56 (m, 1H), 3.82 (m, 1H), 4.50 (d, J=4.8 Hz, 1H), 6.96 (s, 2H), 11.40 (s, 1H).

Reference Example 31

7-Chloro-6-(2-chloropropyl)-3-mesityl-2,5-dimethyl-4,7-dihydropyrazolo[1,5-a]pyrimidine Yellow Amorphous $^1$H NMR (400 MHz, CDCl$_3$) δ 1.67 (d, J=6.4 Hz, 3H), 2.00 (s, 3H), 2.01 (s, 3H), 2.31 (s, 3H), 2.34 (s, 3H), 2.61 (s, 3H), 3.00–3.35 (m, 2H), 4.39 (m, 1H), 6.98 (s, 2H).

Reference Example 32

6-(2-Hydropentyl)-3-mesityl-2,5-dimethyl-4,7-dihydropyrazolo[1,5-a]pyrimidin-7-one White Crystals $^1$H NMR (400 MHz, DMSO-d$_6$) δ 0.86 (t, J=6.8 Hz, 3H), 1.26–1.39 (m, 3H), 1.39–1.50 (m, 1H), 1.93 (s, 3H), 1.95 (s, 6H), 2.26 (s, 3H), 2.27 (s, 3H), 2.35 (dd, J=4.4, 13.6 Hz, 1H), 2.59 (dd, J=8.0, 13.6 Hz, 1H), 3.63 (br s, 1H), 4.42 (d, J=5.2 Hz, 1H), 6.96 (s, 2H), 11.39 (s, 1H).

Reference Example 33

6-(3-Hydroxypropyl)-3-mesityl-2,5-dimethyl-4,7-dihydropyrazolo[1,5-a]pyrimidin-7-one White Crystals $^1$H NMR (400 MHz, DMSO-d$_6$) δ 1.57 (t t, J=7.6, 7.2 Hz, 2H), 1.93 (s, 6H), 1.95 (s, 3H), 2.25 (s, 3H), 2.27 (s, 3H), 2.45 (t, J=8.0 Hz, 1H), 3.38–3.43 (m, 2H), 4.38 (t, J=5.6 Hz, 1H), 6.96 (s, 2H), 11.40 (s, 1H).

Reference Example 34

3-Bromo-6-(2-hydroxyethyl)-2,5-dimethylpyrazolo[1,5-a]pyrimidin-7-ol

A solution of 5-amino-4-bromo-3-methylpyrazole hydrobromide (13 g, 51 mmol) and α-acetyl-γ-butyrolactone (6.8 g, 53 mmol) in ethanol (65 mL) was heated under reflux for nine hours. After cooling to room temperature, the resulting crystals were collected by filtration, to give the title compound (4.6 g) as white crystals.

$^1$H NMR (400 MHz, DMSO-d$_6$) δ 2.24 (s, 3H), 2.39 (s, 3H), 2.97 (t, J=7.6 Hz, 2H), 3.56 (t, J=7.6 Hz, 2H).

Reference Example 35

3-Bromo-8-(1-ethylpropyl)-2,5-dimethyl-7,8-dihydro-6H-pyrazolo[1,5-a]pyrrolo[3,2-e]pyrimidine Phosphorus oxychloride (3.3 mL) was added to a solution of 3-bromo-6-(2-hydroxyethyl)-2,5-dimethylpyrazolo[1,5-a]pyrimidin-7-ol (1.0 mg, 3.50 mmol) in N,N-dimethyaniline (5 mL), followed by stirring at 120° C. for 20 minutes. After cooling to room temperature, the mixture was added dropwise slowly into ice-water under vigorously stirring. Then, the mixture was stirred for two hours while raising a temperature gradually to room temperature, followed by diluting with ethyl acetate. The organic layer was washed with brine, dried over anhydrous magnesium sulfate and evaporated. 3-Aminopentane (10 mL) was added to a solution of the residue in acetonitrile (30 mL), followed by heating under reflux for three hours. The mixture was diluted with ethylacetate, and the organic layer was washed with water and brine, dried over anhydrous magnesium sulfate and evaporated. The resulting crystals were collected by filtration, to give the title compound (700 mg) as white crystals.

$^1$H NMR (400 MHz, CDCl$_3$) δ 0.89 (t, J=7.6 Hz, 6H), 1.50–1.68 (m, 4H), 2.37 (s, 3H), 2.39 (s, 3H), 3.09 (t, J=9.2 Hz, 2H), 3.67 (t, J=9.2 Hz, 2H), 5.50–5.60 (m, 1H).

Reference Example 36

6-(2-Hydroxyethyl)-2,5-dimethylpyrazolo[1,5-a]pyrimidin-7-ol

A solution of 3-amino-5-methylpyrazole (25.0 g, 0.26 mole) α-acetyl-γ-butyrolactone (34.5 g, 0.27 mmol) and acetic acid (5 mL) in toluene (350 mL) was heat ed under reflux for three hours. After cooling to room temperature, the resulting crystals w ere collected by filtration and washed with ethyl acetate, to give the title compound (48.0 g) as white crystals.

$^1$H NMR (400 MHz, DMSO-d$_6$) δ 2.24 (s, 3H), 2.29 (s, 31), 2.57 (t, J=6.8 Hz, 2H), 3.42 (t, J=6.8 Hz, 2H), 5.83 (s, 1H).

Reference Example 37

7-Chloro-6-(2-chloroethyl)-2,5-dimethylpyrazolo[1,5-a]pyrimidine

A solution of 6-(2-hydroxyethyl)-2,5-dimethylpyrazolo[1,5-a]pyrimidin-7-ol (10.0 g, 48 mmol) and phosphorus oxychloride (45 mL, 0.48 mol) in N,N-dimethylaniline (50 mL) was stirred at room temperature for 30 minutes and further at 120 for one hour. After cooling to room temperature, the mixture was added dropwise into ice-water while stirring vigorously. The mixture was stirred for two hours while gradually raising a temperature to room temperature. The mixture was diluted with ethyl acetate, and the organic layer was washed with brine, dried over magnesium anhydrous sulfate and evaporated. The residue was purified by silica gel column chromatography (10% ethyl acetate/hexane), to give the title compound (6.5 g) as white crystals.

$^1$H NMR (400 MHz, CDCl$_3$) δ 2.54 (s, 3H), 2.67 (s, 3H), 3.31 (t, J=7.6 Hz, 2H), 3.72 (t, J=7.6 Hz, 2H), 6.44 (s, 1H).

Reference Example 38

8-(1-Ethylpropyl)-2,5-dimethyl-7,8-dihydro-6H-pyrazolo[1,5-a]pyrrolo[3,2-e]pyrimidine A solution of 7-chloro-6-(2-chloroethyl)-2,5-dimethylpyrazolo[1,5-a]pyrimidine (4.0 g, 16 mmol), 3-aminopentane (40 mL) in acetonitryl (120 mL) was heated under reflux for nine hours. After overnight, the residue was purified by silica gel column chromatography (20% ethyl acetate/hexane), to give the title compound (3.7 g) as white crystals.

$^1$H NMR (400 MHz, CDCl$_3$) δ 0.90 (t, J=7.6 Hz, 6H), 1.50–1.65 (m, 4H), 2.31 (s, 3H), 2.39 (s, 3H), 3.07 (t, J=9.2 Hz, 2H), 3.65 (t, J=9.2 Hz, 2H), 5.53–5.63 (m, 1H), 6.02 (s, 1H).

Reference Example 39

8-(1-Ethylpropyl)-3-iodo-2,5-dimethyl-7,8-dihydro-6H-pyrazolo[1,5-a]pyrrolo[3,2-e]pyrimidine N-Iodosuccinimide (3.5 g, 15 mmol) was added to a solution of 8-(1-ethylpropyl)-2,5-dimethyl-7,8-dihydro-6H-pyrazolo[1,5-a]pyrrolo[3,2-e]pyrimidine (3.7 g 15 mmol) in N,N-dimethylformamide (40 mL) at room temperature, followed by stirring for one hour. Hypo water was added, and the mixture was diluted with ethyl acetate, washed with an aqueous saturated solution of ammonium chloride and brine, dried over anhydrous magnesium sulfate and evaporated. The residue was purified by silica gel column chromatgraphy (20–40% ethyl acetate/hexane), to give the title compound (4.37 g) as white crystals.

$^1$H NMR (400 MHz, CDCl$_3$) δ 0.88 (t, J=7.6 Hz, 6H), 1.48–1.66 (m, 4H), 2.37 (s, 3H), 2.40 (s, 3H), 3.09 (t, J=9.2 Hz, 2H), 3.67 (t, J=9.2 Hz, 2H), 5.48–5.60 (m, 1H).

Reference Example 40

8-(1-Ethylpropyl)-3-(1-ethynyl)-2,5-dimethyl-7,8-dihydro-6H-pyrazolo[1,5-a]pyrrolo[3,2-e]pyrimidine A solution of 8-(1-ethylpropyl)-3-iodo-2,5-dimethyl-7,8-dihydro-6H-pyrazolo[1,5-a]pyrrolo[3,2-e]pyrimidine (2.0 g, 5.29 mmol), trimethylsilylacetylene (0.8 mL, 5.82 mmol), Cl$_2$Pd(PPh$_3$)$_2$ (0.19 g, 0.26 mmol) and copper(I) iodide (50 mg, 0.26 mmol) in triethylamine (20 mL) was stirred at room temperature for two hours. The solution was filtered through Celite, and the filtrate was evaporated. Tetramethylammonium fluoride (1.0 M tetrahydrofuran solution 6.3 mL, 6.3 mmol) was added to a solution of the residue in tetrahydrofuran (20 mL) at room temperature, followed by stirring for 10 minutes. Water was added thereto, and the mixture was diluted with ethyl acetate, washed with brine, dried over anhydrous magnesium sulfate and evaporated.

The residue was purified by silica gel column chromatography (10–20% ethyl acetate/hexane), to give the title compound (727 mg) as pale brown crystals.

$^1$H NMR (400 MHz, CDCl$_3$) δ 0.88 (t, J=7.6 Hz, 6H), 1.50–1.68 (m, 4H), 2.37 (s, 3H), 2.45 (s, 3H), 3.09 (t, J=9.2 Hz, 2H), 3.40 (s, 1H), 3.67 (t, J=9.2 Hz, 2H), 5.48–5.60 (m, 1H).

Reference Example 41

2-2-[8-(1-Ethynylpropyl)-2,5-dimethyl-7,8-dihydro-6H-pyrazolo[1,5-a]pyrrolo[3,2-e]pyrimidin-3-yl]-1-ethynylaniline A solution of 8-(1-ethylpropyl)-3-(1-ethynyl)-2,5-dimethyl-7,8-dihydro-6H-pyrazolo[1,5-a]pyrrolo[3,2-e]pyrimidine (600 mg, 2.13 mmol), 2-iodoaniline (465 mg, 2.13 mmol), Cl$_2$Pd(PPh$_3$)$_2$ (75 mg, 0.11 mmol) and copper (I) iodide (20 mg, 0.11 mmol) in triethylamine (6 mL) and N,N-dimethylformamide (3 mL) was stirred at room temperature for three hours. The solution was filtered through Celite, and the filtrate was evaporated. The residue was purified by silica gel column chromatography (30–50% ethyl acetate/hexane), to give the title compound (540 mg) as white crystals.

$^1$H NMR (400 MHz, CDCl$_3$) δ 0.90 (t, J=7.6 Hz, 6H), 1.50–1.70 (m, 4H), 2.36 (s, 3H), 2.50 (s, 3H), 3.10 (t, J=9.2 Hz, 2H), 3.68 (t, J=9.2 Hz, 2H), 4.33–4.50 (m, 2H), 5.50–5.61 (m, 1H), 6.68 (dd, J=7.6 Hz, 1.2 Hz, 1H), 6.70 (dt, J=7.6 Hz, 1.2 Hz, 1H), 7.07 (dt, J=7.6 Hz, 1.2 Hz, 1H), 7.39 (dd, J=7.6 Hz, 1.2 Hz, 1H).

Reference Example 42

8-(1-Ethylpropyl)-2,5-dimethyl-7,8-dihydro-6H-pyrazolo[1,5-a]pyrrolo[3,2-e]pyrimidin-3-carbaldehyde Phosphorus oxychloride (5.5 mL, 60 mmol) was added to a solution of 8-(1-ethylpropyl)-2,5-dimethyl-7,8-dihydro-6H-pyrazolo[1,5-a]pyrrolo[[3,2-e]pyrimidine (5.0 g, 20 mmol) in N,N-dimethylformamide (25 mL) at room temperature, followed by stirring for one hour. The reaction solution was poured slowly into a 2N aqueous solution of sodium hydroxide, followed by stirring at room temperature for 30 minutes. The reaction mixture was extracted with ethyl acetate, washed with brine, dried over anhydrous magnesium sulfate and evaporated. The residue was purified by silica gel column chromatography (50–70% ethyl acetate/hexane), to give the title compound (6.48 g) as white crystals.

$^1$H NMR (400 MHz, CDCl$_3$) δ 0.90 (t, J=7.6 Hz, 6H), 1.50–1.69 (m, 4H), 2.37 (s, 3H), 2.62 (s, 3H), 3.13 (t, J=9.2 Hz, 2H), 3.71 (t, J=9.2 Hz, 2H), 5.48–5.60 (m, 1H), 10.19 (s, 1H).

Reference Example 43

Ethyl 7-amino-mesityl-2,5-dimethylpyrazolo[1,5-a]pyrimidin-6-carboxylate

Concentrated dihydrochloric acid (0.1 mL) was added to a solution of 4-mesityl-3-methyl-1H-5-pyrazoleamine (2.5 g, 11.61 mmol) and ethyl 2-cyano-3-ethoxy-2-butenoate (2.13 g, 11.61 mmol) in ethanol (30 mL), followed by heating under reflux for 18 hours. The reaction mixture was evaporated as it was. Then, water was added and a 5N aqueous solution of sodium hydroxide was added under ice-cooling, to neutralize. Further, the mixture was extracted with ethyl acetate, and the organic layer was washed with brine, dried over anhydrous magnesium sulfate and evaporated. The residue was purified by silica gel column chromatography (15% ethyl acetate/hexane), to give the title compound (835 mg).

$^1$H NMR (400 MHz, CDCl$_3$) δ 1.41 (t, J=7.1 Hz, 3H), 2.02 (s, 6H), 2.21 (s, 3H), 2.32 (s, 3H), 2.68 (s, 3H), 4.39 (q, J=7.1 Hz, 2H), 6.95 (s, 2H).

Reference Example 44

Ethyl 3-mesityl-2,5-dimethyl-7-oxo-4,7-dihydropyrazolo[1,5-a]pyrimidin-6-carboxylate Acetic acid (5 mL) was added to a solution of 4-mesityl-3-methyl-1H-5-pyrazoleamine (5 g, 23.22 mmol) and diethyl 2-acetylmalonate (4.7 g, 23.22 mmol) in xylene (40 mL), followed by heating under reflux for seven hours. The reaction mixture was evaporated as it was, and water was added thereto. After extracting with ethyl acetate, the organic layer was washed with an aqueous saturated sodium bicarbonate and brine, dried over anhydrous magnesium sulfate and evaporated. The residue was purified by silica gel column chromatography (20% ethyl acetate/hexane), to give the title compound (3 g).

$^1$H NMR (400 MHz, CDCl$_3$) δ 1.39 (t, J=7.1 Hz, 3H), 2.00 (s, 6H), 2.13 (s, 3H), 2.33 (s, 3H), 2.75 (s, 3H), 4.41 (q, J=7.1 Hz, 2H), 6.96 (s, 2H), 8.20 (br s, 1H).

Reference Example 45

Ethyl 7-chloro3-mesityl-2,5-dimethylpyrazolo[1,5-a]pyrimidin-6-carboxylate

Five droplets of N,N-dimethylaniline was added to a solution of ethyl 3-mesityl-2,5-dimethyl-7-oxo-4,7-dihydropyrazolo[1,5-a]pyrimidin-6-carboxylate (3 g, 8.49 mmol) in phosphorus oxychloride (80 g), followed by heating under reflux for four hours. The reaction mixture was added to ice and stirred for a while. Then, the mixture was extracted with ethyl acetate, and the organic layer was washed with an aqueous saturated solution of sodium bicarbonate and brine, dried over anhydrous magnesium sulfate and evaporated. The residue was purified by silica gel column chromatography (15–30% ethyl acetate/hexane), to give the title compound (1.94 g).

$^1$H NMR (400 MHz, CDCl$_3$) δ 1.44 (t, J=7.3 Hz, 3H), 1.97 (s, 6H), 2.29 (s, 3H), 2.33 (s, 3H), 2.86 (s, 3H), 4.47 (q, J=7.1 Hz, 2H), 6.96 (s, 2H).

Reference Example 46

3-Chloro-6-mesityl-2,4,7-trimethyl-2H-dipyrazolo[1,5-a:4,3-e]pyrimidine

Methylhydrazine (1 mL) was added to a solution of ethyl 7-chloro-3-mesityl-2,5-dimethylpyrazolo[1,5-a]pyrimidin-6-carboxylate (209 mg, 0.562 mmol) in ethanol (5 mL), followed by stirring at room temperature for two hours. The reaction mixture was evaporated as it was. Two droplets of N,N-dimethylaniline was added to a solution of the resulting crude compound in phosphorus oxychloride (14 g), followed by heating under reflux for five hours. The reaction mixture was added to ice, followed by stirring for a while. Then, the mixture was extracted with ethyl acetate, and the organic layer was washed with an aqueous saturated solution of sodium bicarbonate and brine, dried over anhydrous magnesium sulfate and evaporated. The residue was purified by silica gel column chromatography (12% ethyl acetate/hexane), to give the title compound (14 mg).

¹H NMR (400 MHz, CDCl₃) δ 2.02 (s, 6H), 2.34 (s, 3H), 2.37 (s, 3H), 3.28 (s, 3H) 3.87 (s, 3H), 7.01 (s, 2H).

Reference Example 47

Ethyl 7-cyano-3-mesityl-2,5-dimethylpyrazolo[1,5-a]pyrimidin-6-carboxylate

Tetrakis(triphenylphosphine)palladium (0) (691 mg, 0.592 mmol) and zinc cyanide (402 mg, 3.25 mmol) were added to a solution of ethyl 7-chloro-3-mesityl-2,5-dimethylpyrazolo[1,5-a]pyrimidin-6-carboxylate (1.1 g, 2.96 mmol) in N,N-dimethylformamide (10 mL), followed by stirring at 150° C. for four hours. Water was added to the reaction mixture, and the mixture was extracted with ethyl acetate. The organic layer was washed with brine, dried over anhydrous magnesium sulfate and evaporated, and the residue was purified by silica gel column chromatography (15% ethyl acetate/hexane), to give the title compound (1 g).

¹H NMR (400 MHz, CDCl₃) δ 1.49 (t, J=7.1 Hz, 3H), 1.96 (s, 6H), 2.35 (s, 3H), 2.36 (s, 3H), 3.13 (s, 3H), 4.52 (q, J=7.1 Hz, 2H), 7.00 (s, 2H).

Reference Example 48

3-Mesityl-2,5-dimethylpyrazolo[1,5-a]pyrimidin-6,7-dicarboxylic acid

Potassium hydroxide (441 mg, 11.04 mmol) was added to a solution of ethyl 7-cyano-3-mesityl-2,5-dimethylpyrazolo[1,5-a]pyrimidin-6-carboxylate (800 mg, 2.21 mmol) in ethanol (15 mL), followed by heating under reflux for two hours. The reaction mixture was evaporated, water was added. Under ice-cooling, 2N hydrochloric acid was added to adjust the pH of the mixture to pH 1. The mixture was extracted with ethyl acetate, and the organic layer was washed with brine, dried over anhydrous magnesium sulfate and evaporated, to give the title compound (780 mg).

¹H NMR (400 MHz, CDCl₃) δ 1.96 (s, 6H), 2.37 (s, 6H), 3.01 (s, 3H), 7.01 (s, 2H).

MS (ESI) m/z 354 MH⁺.

Reference Example 49

6-(3-Hydroxyhexyl)-3-mesityl-2,5-dimethyl-4,7-dihydropyrazolo[1,5-a]pyrimidin-7-one 3-Amino-4-mesityl-5-methylpyrazole (2 g, 9.29 mmol) and 2-acetyl-5-propylpropiolactone (2.05 g, 11.1 mmol) were suspended in xylene (40 mL), followed by heating under reflux for 16 hours. After cooling, the resulting crystals were collected by filtration, washed with diethyl ether and then dried under reduced pressure, to give the tile compound (1.54 g, 4.04 mmol) as a white solid.

¹H NMR (400 MHz, DMSO-d₆) δ 0.85 (t, J=7.6 Hz, 3H), 1.30–1.55 (m, 4H), 1.93 (s, 6H), 1.95 (s, 3H), 2.24 (s, 3H), 2.27 (s, 3H), 2.30–2.60 (m, 4H), 3.35–3.45 (m, 1H), 6.95 (s, 2H).

Reference Example 50

7-Chloro-6-(3-chlorohexyl)-3-mesityl-2,5-dimethylpyrazolo[1,5-a]pyrimidine 6-(3-Hydroxyhexyl)-3-mesityl-2,5-dimethyl-4,7-dihydropyrazolo[1,5-a]pyrimidin-7-one (900 mg, 2.36 mmol) was dissolved in toluene (9 mL). Thionyl chloride (0.18 mL, 2.48 mmol) was added thereto, followed by stirring at 80° C. for one hour. The resulting crystals were collected by filtration, washed with toluene and then dried under reduced pressure, to give a white solid. The solid was dissolved in phosphorus oxychloride (4 mL). N,N-Dimethylaniline (0.4 mL) was added thereto, followed by heating under reflux for 2 hr. After overnight phosphorus oxychloride, water was added to the residue. The mixture was extracted with ethyl acetate, and the organic layer was washed successively with an aqueous saturated solution of sodium bicarbonate, water and brine, dried over anhydrous magnesium sulfate and then evaporated, to give the title compound (850 mg, 2.03 mmol) as a pale yellow oil.

¹H NMR (400 MHz, CDCl₃) δ 0.96 (t, J=7.2 Hz, 3H), 1.42–1.55 (m, 1H), 1.56–1.66 (m, 1H), 1.72–1.84 (m, 2H), 1.88–1.99 (m, 1H), 1.99 (s, 6H), 2.00–2.10 (m, 1H), 2.30 (s, 3H), 2.34 (s, 3H), 2.58 (s, 3H), 2.86–2.96 (m, 1H), 3.08–3.17 (m, 1H), 4.00–4.08 (m, 1H), 6.98 (s, 2H).

Reference Example 51

2-(3-Mesityl-2,5-dimethyl-7-oxo-4,7-dihydropyrazolo[1,5-a]pyrimidin-6-yl)acetaldehyde Des Martin reagent was added gradually to a solution of 6-(2-hydroxyethyl)-3-mesityl-2,5-dimethyl-4,7-dihydropyrazolo[1,5-a]pyrimidin-7-one (2.65 g, 8.14 mmol) in dichloromethane (200 mL) at room temperature, followed by stirring for three hours. A saturated solution of sodium thiosulfate was added to the reaction mixture, extracted with ethyl acetate, dried over anhydrous magnesium sulfate and evaporated. The residue was purified by silica gel column chromatography (50% ethyl acetate/hexane, 10% ethyl acetate/methanol), to give the title compound (1.78 g) as a yellow amorphous.

¹H NMR (400 MHz, CDCl₃) δ 2.01 (s, 6H), 2.05 (s, 3H), 2.19 (s, 3H), 2.34 (s, 3H), 3.60 (s, 2H), 6.76 (s, 2H), 9.64 (s, 1H).

Reference Example 52

Ethyl 4-(3-mesityl-2-dimethyl-7-oxo-4,7-dihydropyrazolo[1,5-a]pyrimidin-6-yl)butanoate In nitrogen stream, sodium hydride (900 mg, 22.5 mmol) was added to a solution of triethyl phosphonoacetate (5.9 mL, 29.7 mmol) in dimethyl formamide (150 ml), followed by stirring at room temperature for 10 minutes. Thereafter, 2-(3-mesityl-2,5-dimethyl-7-oxo-4,7-dihydropyrazolo[1,5-a]pyrimidin-6-yl)acetaldehyde (2.4 g, 7.4 mmol) was added, followed by stirring at room temperature for two hours. Water was added to the reaction mixture, extracted with ethyl acetate, dried over anhydrous magnesium sulfate and evaporated. The residue was purified by silica gel column chromatography (25–100% ethyl acetate/hexane), to give an olefin compound (2.5 g). The product was dissolved in methanol (200 mL) and water-containing palladium-carbon was added, followed by stirring in hydrogen atmosphere for three days. After filtering through Celite, the mixture was evaporated and the residue was washed with diethyl ether, to give the title compound (1.2 g) as white crystals.

¹H NMR (400 MHz, CDCl₃) δ 1.25 (t, J=7.2 Hz, 3H), 1.80–1.90 (m, 2H), 2.01 (s, 6H), 2.10 (s, 3H), 2.26 (s, 3H), 2.36 (s, 3H), 2.40 (t, J=7.2 Hz, 2H), 2.57 (dd, J=7.6, 9.6 Hz, 2H), 4.11 (q, J=7.2 Hz, 2H), 6.87 (s, 2H), 9.02 (br s, 1H).

Reference Example 53

Ethyl 4-(7-(butyl)-3-mesityl-2,5-dimethylpyrazolo[1,5-a]pyrimidin-6-yl)butanoate Phosphorus oxychloride (11.3 g) and N,N-dimethylaniline (3 droplets) were added to ethyl 4-(3- mesityl-2,5-dimethyl-7-oxo-4,7-dihydropyrazolo[1,5-a]pyrimidin-6-yl)butanoate (700 mg, 1.77 mmol), followed by heating under reflux for 1.5 hours. After the reaction, it was treated with ice-water, neutralized with potassium carbonate, extracted with ethyl acetate, dried over anhydrous magnesium sulfate and evaporated. The resulting reaction residue was dissolved in acetonitrile (5 ml) and n-butylamine (2 mL) was added, followed by heating under reflux for six hours. After the reaction, it was treated with water, and then neutralized with potassium carbonate, extracted with ethyl acetate, dried over anhydrous magnesium sulfate and evaporated. The residue was purified by silica gel column chromatography (10–25% ethyl acetate/hexane), to give the title compound (2.5 g) as a yellow oil.

$^1$H NMR (400 MHz, CDCl$_3$) δ 1.01 (t, J=7.6 Hz, 3H), 1.28 (dt, J=0.8, 7.6 Hz, 3H), 1.50–1.55 (m, 2H), 1.72–1.82 (m, 2H), 1.82–1.92 (m, 2H), 2.02 (s, 6H), 2.20 (s, 3H), 2.31 (s, 3H), 2.44 (t, J=7.2 Hz, 2H), 2.45 (s, 3H), 2.71–2.76 (m, 2H), 3.74 (dd, J=6.8, 13.2 Hz, 2H), 4.17 (q, J=7.2 Hz, 2H), 6.26 (t, J=5.6 Hz, 2H), 6.94 (s, 2H).

Reference Example 54

4-(7-(Butyl)-3-mesityl-2,5-dimethylpyrazolo[1,5-a]pyrimidin-yl)-1-butanol

A 1.0M solution of diisobutylaluminium hydride in hexane was added dropwise into a solution of ethyl 4-(7-(butyl)-3-mesityl-2,5-dimethylpyrazolo[1,5-a]pyrimidin-6-yl)butanoate (320 mg, 0.71 mmol) in tetrahydrofuran (10 mL) under nitrogen stream, followed by stirring for 30 minutes. After Celite was added, the mixture was treated by adding ethyl acetate and water dropwise, and the insoluble matters were filtered off. The solution was extracted with ethyl acetate, dried over anhydrous magnesium sulfate and evaporated, to give the title compound (320 mg) as a brown oil.

$^1$H NMR (400 MHz, CDCl$_3$) δ 1.01 (s, 3H), 1.46–1.57 (m, 2H), 1.60–1.70 (m, 3H), 1.72–1.83 (m, 3H), 2.02 (s, 6H), 2.20 (s, 3H), 2.31 (s, 3H), 2.45 (s, 3H), 2.71–2.76 (m, 2H), 3.60–3.71 (m, 4H), 6.25 (t, J=5.2 Hz, 1H), 6.94 (s, 2H).

Reference Example 55

N-Butyl-N-(6-(4-chlorobutyl)-3-mesityl-2,5-dimethylpyrazolo[1,5-a]pyrimidin-6-yl)amine Phosphorus oxychloride (11.3 g) and N,N-dimethylaniline (3 droplets) were added to 4-(7-(butyl)-3-mesityl-2,5-dimethylpyrazolo[1,5-a]pyrimidin-6-yl)-1-butanol (320 mg, 0.78 mmol), followed by heating under reflux for 0.5 hour. After the reaction, the mixture was treated with ice-water, neutralized with potassium carbonate, extracted with ethyl acetate, dried over anhydrous magnesium sulfate and evaporated. The residue was purified by silica gel column chromatography (10–15% ethyl acetate/hexane), to give the title compound (254 mg) as a pale yellow oil.

$^1$H NMR (400 MHz, CDCl$_3$) δ 1.02 (t, J=7.6 Hz, 3H), 1.48–1.58 (m, 2H), 1.60–1.84 (m, 4H), 1.86–1.96 (m, 2H), 2.02 (s, 6H), 2.20 (s, 3H), 2.32 (s, 3H), 2.46 (s, 3H), 2.74 (t, J=8.0 Hz, 2H), 2.60–3.67 (m, 4H), 6.26 (t, J=5.6 Hz, 1H), 6.95 (s, 2H).

Reference Example 56

3-((E)-1-[3-Methyl-1-(2,4,6-trichlorophenyl)-1H-5-pyrazolyl]aminoethylidene)tetrahydro-2-furanone 3-Amino-2-(2,4,6-trichlorophenyl)-5-methylpyrazole (1 g, 3.62 mmol) was dissolved in ethanol (10 mL). α-Acetyl-γ-butyrolactone (0.409 mL, 3.80 mmol) was added, followed by heating under reflux for two days. After ethanol was evaporated, the residue was purified by silica gel column chromatography (10% ethyl acetate/hexane), to give the title compound (700 mg, 1.80 mmol) as a pale yellow oil.

$^1$H NMR (400 MHz, CDCl$_3$) δ 2.06 (s, 3H), 2.33 (s, 3H), 2.85 (t, J=8.0 Hz, 2H), 4.30 (t, J=8.0 Hz, 2H), 5.90 (s, 1H), 7.47 (s, 2H), 9.77 (brs, 1H).

Reference Example 57

4-Chloro-5-(2-chloroethyl)-3,6-dimethyl-1-(2,4,6-trichlorphenyl 1H-pyrazolo[3,4-b]pyridine 3-((E)-1-[3-Methyl-1-(2,4,6-trichlorophenyl)-1H-5-pyrazolyl]aminoethylidene)tetrahydro-2-furanone (500 mg, 1.29 mmol) was dissolved in phosphorus oxychloride (4 mL), and heated under reflux for two hours. After phosphorus oxychloride was evaporated, water was added to the residue. The mixture was extracted with ethyl acetate, and the organic layer was washed with an aqueous saturated solution of sodium bicarbonate, water and brine, dried over anhydrous magnesium sulfate, and then evaporated. The residue was purified by silica gal column chromatogrpahy (10% ethyl acetate/hexane), to give the title compound (166 mg, 0.392 mmol) as a pale yellow oil.

$^1$H NMR (400 MHz, CDCl$_3$) δ 2.66 (s, 3H), 2.79 (s, 3H), 3.39 (t, J=8.0 Hz, 2H), 3.72 (t, J=8.0 Hz, 2H), 7.52 (s, 2H).

Reference Example 58

Mesityl-2-methyl-4-nitro-1H-imidazole

A solution of 5-bromo-2-methyl-4-nitroimidazole (5.0 g, 24 mmol), mesitylboric acid (3.96 g, 24 mmol), Pd(PPh$_3$)$_4$ (1.4 g, 1.2 mmol) and barium hydroxide octahydrate (19.1 g, 61 mmol) in 2,2-dimethoxyethane (150 mL) and water (25 mL) was heated at reflux for four hours. After filtered through Celite, the filtrate was diluted with ethyl acetate, washed with brine, dried over anhydrous magnesium sulfate and evaporated. The resulting crystals were washed with ethyl acetate, to give the title compound (4.17 g) as white crystals.

$^1$H NMR (400 MHz, DMSO-d$_6$) δ 1.97 (s, 6H), 2.27 (s, 3H), 2.33 (s, 3H), 6.97 (s, 2H).

Reference Example 59

3-(2-Hydroxyethyl)-8-mesityl-2,6-dimethylimidazo[1,5-a]pyrimidin-4-ol

A solution of 5-mesityl-2-methyl-4-nitro-1H-imidazole (2.1 g, 8.56 mmol), α-acetyl-γ-butyrolactone (1.21 g, 9.42 mmol), and iron powder (2.39 g, 42.8 mmol) in ethanol (40 mL) and acetic acid (10 mL) was stirred at 80° C. for one day. The mixture was filtered through Celite and evaporated. The resulting crystals were washed with ethyl acetate, to give the title compound (0.95 g) as white crystals.

$^1$H NMR (400 MHz, DMSO-d$_6$) δ 2.05 (s, 6H), 2.30 (s, 6H), 2.71 (t, J=6.8 Hz, 2H), 2.85 (s, 3H), 3.68 (t, J=6.8 Hz, 2H), 6.95 (s, 2H).

Reference Example 60

3-(2-Chloroethyl)-8-mesityl-2,6-dimethylimidazo[1,5-a]pyrimidin-4-ol

Thionyl chloride (112 mL, 1.54 mmol) was added to a solution of 3-(2-hydroxyethyl)-8-mesityl-2,6- dimethylimidazo[1,5-a]pyrimidin-4-ol (500 mg, 1.54 mmol) in toluene (5 mL) at 80° C., followed by stirring for one hour. After cooling to room temperature, the resulting crystals were washed with diethyl ether, to give the title compound (360 mg) as pale brown crystals.

$^1$H NMR (400 MHz, CD$_3$OD) δ 2.15 (s, 6H), 2.35 (s, 3H), 2.40 (s, 3H), 3.00 (t, J=6.8 Hz, 2H), 3.09 (s, 3H), 3.76 (t, J=6.8 Hz, 2H), 7.08 (s, 2H).

Reference Example 61

4-Chloro-3-(2-chloroethyl)-8-mesityl-2,6-dimethylimidazo[1,5-a]pyrimidine

A solution of 3-(2-chloroethyl)-8-mesityl-2,6-dimethylimidazo[1,5-a]pyrimidin-4-ol (200 mg, 0.58 mmol) and N,N-dimethylaniline (0.3 mL) in phosphorus oxychloride (3 mL) was heated under reflux for six hours. After overnight, 3-aminopentane (2 mL) was added to a solution of the residue in acetonitrile (5 mL), followed by stirring at 80° C. for three hours. Water was added, and the mixture was extracted with ethyl acetate, washed with brine, dried over anhydrous magnesium sulfate and evaporated. The residue was purified by silica gel column chromatogrpahy (10–20% ethyl acetate/hexane), to give the title compound (139 mg) as pale yellow crystals.

$^1$H NMR (400 MHz, CDCl$_3$) δ 2.08 (s, 6H), 2.30 (s, 3H), 2.48 (s, 3H), 3.05 (s, 3H), 3.21 (t, J=7.6 Hz, 2H), 3.71 (t, J=7.6 Hz, 2H), 6.92 (s, 2H).

Reference Example 62

4-Chloro-3-(2-chloroethyl)-8-iodo-2-methylquinoline

2-Iodoaniline (25 g, 114 mmol) and α-acetyl-γ-butyrolactone (43.8 g, 342 mmol) were dissolved in ethanol (250 mL), followed by heating under reflux for two days. The solvent was removed, and diethyl ether was added for crystallization. The crystals were collected by filtration and dried under reduced pressure, to give a pale yellow solid (28 g). This was dissolved in phosphorus oxychloride (60 mL), followed by heating under reflux for three hours. After phosphorus oxychloride was evaporated, water was added to the residue, and extracted with ethyl acetate. The organic layer was washed with an aqueous saturated solution of sodium bicarbonate, water and brine, dried over anhydrous magnesium sulfate, and then evaporated. The residue was purified by silica gel column chromatogrpahy (3% ethyl acetate/hexane), to give the title compound (19 g, 50.0 mmol) as brown crystals.

$^1$H NMR (400 MHz, CDCl$_3$) δ 2.90 (s, 3H), 3.50 (t, J=7.6 Hz, 3H), 3.76 (t, J=7.6 Hz, 3H), 7.28 (t, J=8.0 Hz, 1H), 8.19 (d, J=8.0 Hz, 1H), 8.33 (d, J=8.0 Hz, 1H).

Reference Example 63

1-(1-Ethylpropyl)-6-iodo-4-methyl-2,3-dihydro-1H-pyrrolo[3,2-c]quinoline

4-Chloro-3-(2-chloroethyl)-8-iodo-2-methylquinoline (900 mg, 2.46 mmol) was dissolved in 3-aminopentane (10 mL), followed by adding p-toluenesulfonic acid (900 mg). The mixture was sealed at 200° C. for six hours. Water was added to the reaction mixture, extracted with ethyl acetate, and the organic layer was washed with water and brine, dried over magnesium sulfate, and then evaporated. The residue was purified by silica gel column chromatography (10% ethyl acetate/hexane), to give the title compound (450 mg, 1.18 mmol) as white crystals.

$^1$H NMR (400 MHz, CDCl$_3$) δ 0.93 (t, J=7.6 Hz, 6H), 1.48–1.70 (m, 4H), 2.55 (s, 3H), 3.08 (t, J=9.6 Hz, 3H), 3.70 (t, J=9.6 Hz, 3H), 4.18–4.26 (m, 1H), 6.92 (dd, J=7.6, 8.4 Hz, 1H), 8.02 (dd, J=1.0, 8.4 Hz, 1H), 8.16 (dd, J=1.0, 7.6 Hz, 1H).

Reference Example 64

1-(1-Ethylpropyl)-6-iodo-4-methyl-1H-pyrrolo[3,2-c]quinoline 1-(1-Ethylpropyl)-6-iodo-4-methyl-2,3-dihydro-1H-pyrrolo[3,2-c]quinoline (450 mg, 1.18 mmol) was dissolved in toluene (10 mL). To the mixture was added activated manganese dioxide (4.95 g), followed by heating at 40° C. overnight. The reaction mixture was filtered through Celite and washed with ethyl acetate. The filtrate was evaporated, and the residue was purified by silica gel column chromatogrpahy (5% ethyl acetate/hexane), to give the title compound (334 mg, 0.884 mmol) as a white oil.

$^1$H NMR (400 Hz, CDCl$_3$) δ 2.90 (s, 3H), 3.50 (t, J=7.6 Hz, 3H), 3.76 (t, J=7.6 Hz, 3H), 7.28 (t, J=8.0 Hz, 3H), 8.19 (d, J=8.0 Hz, 3H), 8.33 (d, J=8.0 Hz, 3H).

Reference Example 65

2-Mesityl-3-nitropyridine

A solution of 2-chloro-3-nitropyridine (5.0 g, 31.5 mmol), mesitylboric acid (5.65 g, 34.7 mmol), Pd(PPh$_3$)$_4$ (1.82 g, 1.58 mmol) and barium hydroxide octahydrate (14.9 g, 47.3 mmol) in 2,2-dimethoxyethane (150 mL) and water (25 mL) was heated under reflux for one day. The mixture was filtered through Celite, and the filtrate was diluted with ethyl acetate, washed with brine, dried over anhydrous magnesium sulfate and evaporated. The residue was purified by silica gel column chromatogrpahy (10% ethyl acetate/hexane), to give the title compound (5.99 g) as pale yellow oil.

$^1$H NMR (400 MHz, CDCl$_3$) δ 1.95 (s, 6H), 2.32 (s, 3H), 6.92 (s, 2H), 7.51 (dd, J=8.0 Hz, 4.8 Hz, 1H), 8.31 (dd, J=8.0 Hz, 1.2 Hz, 1H), 8.36 (dd, J=4.8 Hz, 1.2 Hz, 1H).

Reference Example 66

2-Mesityl-pyridinamine

Palladium-carbon (10%, 0.6 g) was added to a solution of 2-mesityl-3-nitropyridine (5.99 g, 23 mmol) methanol (120 mL), followed by stirring for one day in hydrogen atmosphere. The mixture was filtered through Celite and evaporated, to give the title compound (5.2 g) as white crystals.

$^1$H NMR (400 MHz, CDCl$_3$) δ 2.01 (s, 6H), 2.31 (s, 3H), 6.94 (s, 2H), 7.05 (dd, J=8.0 Hz, 1.6 Hz, 1H), 7.08 (dd, J=8.0 Hz, 4.4 Hz, 1H), 8.36 (dd, J=4.4 Hz, 1.6 Hz, 1H).

Reference Example 67

3-1-[(2-Mesityl-3-pyridyl)amino]ethylidenetetrahydro-2-furanone p-Toluenesulfonic acid monohydrate (39 mg, 0.20 mmol) was added to a solution of 2-mesityl-3-pyridinamine (3.9 g, 18 mmol) and α-acetyl-γ-butyrolactone (4.7 g, 37 mmol) in toluene (80 mL). The mixture was heated under reflux for seven days while removing water using Dean-Stark apparatus. The mixture was evaporated, and the resulting crystals were washed with 60% diethyl ether/ethyl acetate, to give the title compound (3.74 g) as white crystals.

¹H NMR (400 MHz, CDCl₃) δ 1.97 (s, 6H), 2.03 (s, 3H), 2.29 (s, 3H), 2.82 (t, J=7.6 Hz, 2H), 4.26 (t, J=7.6 Hz, 2H), 6.93 (s, 2H), 7.25 (dd, J=8.0 Hz, 4.8 Hz, 1H), 7.41 (dd, J=8.0 Hz, 1.2 Hz, 1H), 8.46 (dd, J=4.88 Hz, 1.2 Hz, 1H), 9.46 (s, 1H).

Reference Example 68

4-Chloro-3-(2-chloroethyl)-8-mesityl-2-methyl[1,7]naphthyridine

A solution of 3-1-[(2-mesityl-3-pyridyl)amino]ethylidenetetrahydro-2-furanone (2.0 g, 6.20 mmol) in phosphorus oxychloride (8.0 mL) was stirred at 120° C. for one hour. After cooling to room temperature, the mixture was slowly added dropwise into ice-water while stirring vigorously and stirred for one hour while raising a temperature to room temperature. The mixture was diluted with ethylacetate, and the organic layer was washed with brine, dried over anhydrous magnesium sulfate and evaporated. The residue was purified by silica gel column chromatography (0–2% ethyl acetate/hexane), to give the title compound (500 mg) as white crystals. ¹H NMR (400 MHz. CDCl₃) δ 1.87 (s, 6H), 2.36 (s, 3H), 2.71 (s, 3H), 3.50 (t, J=7.6 Hz, 2H), 3.79 (t, J=7.6 Hz, 2H), 6.96 (s, 2H), 7.96 (d, J=6.0 Hz, 1H), 8.73 (d, J=6.0 Hz, 1H).

Reference Example 69 tert-Butyl N-(3-pyridyl)cabamate

Sodium bis(trimethylsilyl)amide (1.0M tetrahydrofuran solution 800 mL, 0.80M) was added to a solution of 3-aminopyridine (34.2 g, 0.36 mmol) in tetrahydrofuran (800 mL), followed by stirring for two hours. A solution of di-tert-butyl dicarbonate in tetrahydrofuran (200 mL) was added thereto and stirred for 30 minutes. Water was added, extracted with ethyl acetate, and the organic layer was washed with 1N hydrochloric acid, water and brine, dried over anhydrous magnesium sulfate and evaporated. The resulting crystals were washed with hexane, to give the title compound (55.0 g) as white crystals.

¹H NMR (400 MHz, CDCl₃) δ 1.52 (s, 9H), 6.85 (br s, 1H), 7.24 (ddd, J=8.4 Hz, 4.8 Hz, 0.8 Hz, 1H), 7.95–8.04 (m, 1H), 8.28 (dd, J=4.8 Hz, 1.6 Hz, 1H), 8.35 (dd, J=2.8 Hz, 0.8 Hz, 1H).

Reference Example 70 tert-Butyl N-(4-iodo-3-pyridyl)carbamate

N-Butyllithium (1.6M hexane solution 400 mL, 0.64 mol) was added to a solution of tert-butyl N-(3-pyridyl)carbamate (51.8 g, 0.27 mol) and tetramethylethylenediamine (96.6 mL, 0.64 ml) in diethyl ether (1.5 L) at −78° C., followed by stirring at −20° C. for 2.5 hr. After cooling to −78° C. again, a solution of iodine (94.8 g, 0.37 mol) in diethyl ether (200 mL) was added and stirred for one day while raising a temperature to room temperature. Water was added, extracted with diethyl ether, and the organic layer was washed with hypo-water and brine, dried over anhydrous magnesium sulfate and evaporated. The resulting crystals were washed with hexane, to give the title compound (53.0 g) as white crystals.

¹H NMR (400 MHz, CDCl₃) δ 1.54 (s, 9H), 6.67 (br s, 1H), 7.69 (d, J=4.8 Hz, 1H), 7.90 (d, J=4.8 Hz, 1H), 9.14 (s, 1H).

Reference Example 71 tert-Butyl N-(4-mesityl-3-pyridyl)carbamate

A solution of tert-butyl N-(4-iodo-3-pyridyl)carbamate (20.0 g, 62 mmol), mesitylboric acid (10.2 g, 62 mmol), Pd(PPh₃)₄ (3.6 g, 3.12 mmol), barium hydroxide octahydrate (49.3 g, 47.3 mmol) in 1,2-dimethoxyethane (400 mL) and water (67 mL) was heated under reflux for six hours. The mixture was filtered through Celite, and the filtrate was diluted with ethyl acetate, washed with brine, dried over magnesium sulfate and evaporated, to give the title compound (containing 22.3 g of impurities) as pale brown crystals.

¹H NMR (400 MHz, CDCl₃) δ 1.46 (s, 9H), 1.95 (s, 6H), 2.36 (s, 3H), 5.95 (br s, 1H), 6.97 (d, J=4.8 Hz, 1H), 7.00 (s, 2H), 8.35 (d, J=4.8 Hz, 1H), 9.42 (s, 1H).

Reference Example 72

4-Mesityl-3-pyridinamine

A 4N hydrochloric acid solution in ethyl acetate (100 mL) was added to a solution of tert-butyl N-(4-mesityl-3-pyridyl)carbamate (19.5 g, 62 mmol) in ethyl acetate (100 mL) followed by stirring for one hour. The solution was neutralized with a 5N aqueous solution of sodium hydroxide, extracted with ethyl acetate. The organic layer was washed with brine, dried over anhydrous magnesium sulfate and evaporated. The residue was purified by silica gel column chromatography (20% ethyl acetate/hexane), to give the title compound (500 mg) as white crystals.

¹H NMR (400 MHz, CDCl₃) δ 2.00 (s, 6H), 2.33 (s, 3H), 3.53 (br s, 2H), 6.88 (d, J=4.8 Hz, 1H), 6.97 (s, 2H), 8.06 (d, J=4.8 Hz, 1H), 8.19 (s, 1H).

Reference Example 73

3-1-[(4-Mesityl-3-pyridyl)amino]ethylidenetetrahydro-2-furanone p-Toluenesulfonic acid monohydrate (0.2 g, 1.18 mmol) was added to a solution of 4-mesityl-3-pyridinamine (5.0 g, 24 mmol) and α-acetyl-γ-butyrolactone (6.0 g, 47 mmol) in toluene (100 mL), followed by heating under reflux for three days while removing water using a Dean-Stark apparatus. The mixture was evaporated, and the resulting crystals were washed with 60% diethyl ether/ethyl acetate, to give the title compound (6.0 g) as white crystals.

¹H NMR (400 MHz, CDCl₃) δ 1.97 (s, 6H), 2.08 (s, 3H), 2.31 (s, 3H), 2.83 (t, J=8.0 Hz, 2H), 4.27 (t, J=8.0 Hz, 2H), 6.97 (s, 2H), 7.12 (d, J=4.8 Hz, 1H), 8.40 (d, J=4.8 Hz, 1H), 8.47 (s, 1H), 9.44 (s, 1H).

Reference Example 74

4-Chloro-3-(2-chloroethyl)-8-mesityl-2-methyl[1,5]naphthyridine

A solution of 3-1-[(4-mesityl-3-pyridyl)amino]ethylidenetetrahydro-2-furanone (2.0 g, 6.20 mmol), phosphorus oxychloride (5.8 mL, 6.2 mmol), N,N-dimethylaniline (98 mL, 0.78 mmol) and triethylmethylammonium chloride (0.94 g, 6.20 mmol) in acetonitrile (10 mL) was heated under reflux for 24 hours. After cooling to room temperature, the solution was slowly added dropwise into ice-water while stirring vigorously. The mixture was stirred for one hour while raising a temperature to room temperature. The mixture was diluted with ethyl acetate, and the organic layer was washed with brine, dried over anhydrous magnesium sulfate and evaporated. The residue was purified by silica gel column chromatography (10% ethyl acetate/hexane), to give the title compound (500 mg) as white crystals.

¹H NMR (400 MHz, CDCl₃) δ 1.87 (s, 6H), 2.39 (s, 3H), 2.71 (s, 3H), 3.52 (t, J=7.6 Hz, 2H), 3.82 (t, J=7.6 Hz, 2H), 6.99 (s, 2H), 7.45 (d, J=4.4 Hz, 1H), 9.04 (d, J=4.4 Hz, 1H).

Reference Example 75

1-(1-Ethylpropyl)-6-mesityl-4-methyl-2,3-dihydro-1H-pyrrolo[3,2-c][1,5]naphthyridine A solution of 4-chloro-3-(2-chloroethyl)-8-mesityl-2-methyl[1,5]naphthyridine (150 mg, 0.42 mmol) in 3-aminopentane (7.5 mL) was stirred at 200° C. for four hours in a sealed tube. After overnight, the residue was purified by silica gel column chromatography (30–50% ethyl acetate/hexane), to give the title compound (50 mg) as white crystals.

$^1$H NMR (400 MHz, CDCl$_3$) δ 0.96 (t, J=7.2 Hz, 6H), 1.55–1.70 (m, 4H), 1.92 (s, 6H), 2.32 (s, 3H), 2.36 (s, 3H), 3.08 (t, J=9.6 Hz, 2H), 3.72 (t, J=9.6 Hz, 2H), 5.86–5.98 (m, 1H), 6.97 (s, 2H), 7.14 (d, J=4.0 Hz, 1H), 8.58 (d, J=4.0 Hz, 1H).

Reference Example 76

1-Mesityl-2-methyl-1-nitrobenzene

A solution of 2-bromo-6-nitrotoluene (10.0 g, 46 mmol), mesitylboric acid (8.3 g, 51 mmol), Pd(PPh$_3$)$_4$ (2.7 g, 2.31 mmol) and barium hydroxide octahydrate (21.9 g, 69 mmol) in 2,2-dimethoxyethane (300 mL) and water (50 mL) was heated under reflux for six hours. The mixture was filtered through Celite, and the filtrate was diluted with ethyl acetate, washed with brine, dried over anhydrous magnesium sulfate and evaporated. The residue was purified by silica gel column chromatography (0–1% ethyl acetate/hexane), to give the title compound (11.0 g) as white crystals.

$^1$H NMR (400 MHz, CDCl$_3$) δ 1.90 (s, 6H), 2.15 (s, 3H), 2.34 (s, 3H), 6.96 (s, 2H), 7.28 (dd, J=7.6 Hz, 1.2 Hz, 1H), 7.38 (t, J=7.6 Hz, 1H), 7.84 (dd, J=7.6 Hz, 1.2 Hz, 1H).

Reference Example 77

3-Mesityl-2-methylaniline

Palladium-carbon (10%, 1.1 g) was added to a solution of 1-mesityl-2-methyl-3-nitrobenzene (11.0 g, 43 mmol) in ethanol (220 mL) at room temperature, followed by stirring for one day in hydrogen atmosphere. The mixture was filtered through Celite and evaporated. The residue was purified by silica gel column chromatography (10% ethyl acetate/hexane), to give the title compound (8.2 g) as white crystals.

$^1$H NMR (400 MHz, CDCl$_3$) δ 1.80 (s, 3H), 1.94 (s, 6H), 2.33 (s, 3H), 3.60–3.75 (br s, 2H), 6.49 (d, J=7.6 Hz, 1H), 6.69 (d, J=7.6 Hz, 1H), 6.93 (s, 2H), 7.08 (t, J=7.6 Hz, 1H).

Reference Example 78

3-[1-(3-Mesityl-2-methylanilino)ethylidene]tetrahydro-2-furanone

A solution of 3-mesityl-2-methylaniline (5.0 g, 22 mmol) and α-acetyl-γ-butyrolactone (14.2 g, 0.11 mol) in ethanol (100 mL) was heated at reflux for three days. The mixture was evaporated, and the residue was purified by silica gel column chromatography (10% ethyl acetate/hexane), to give the title compound (7.08 g) as white crystals.

$^1$H NMR (400 MHz, CDCl$_3$) δ 1.88 (s, 3H), 1.90 (s, 9H), 2.33 (s, 3H), 2.92 (t, J=8.0 Hz, 2H), 4.36 (t, J=8.0 Hz, 2H), 6.91 (dd, J=7.6 Hz, 1.2 Hz, 1H), 6.94 (s, 2H), 7.04 (dd, J=7.6 Hz, 1.2 Hz, 1H), 7.22 (t, J=7.6 Hz, 1H), 9.80 (s, 1H).

Reference Example 79

4-Chloro-3-(2-chloroethyl)-7-mesityl-2,8-dimethylquinoline

A solution of 3-[1-(3-mesityl-2-methylanilino)ethylidene]tetrahydro-2-furanone (2.0 g, 5.96 mmol) in phosphorus oxychloride (5.6 mL) was stirred at 120° C. for two hours. After cooling to room temperature, the mixture was slowly added dropwise into ice-water while stirring vigorously, and the mixture was stirred for one hour while raising a temperature gradually to room temperature. The mixture was diluted with ethyl acetate, and the organic layer was washed with brine, dried over anhydrous magnesium sulfate and evaporated. The residue was purified by silica gel column chromatography (0–5% ethyl acetate/hexane), to give the title compound (210 mg) as white crystals.

$^1$H NMR (400 MHz, CDCl$_3$) δ 1.90 (s, 6H), 2.36 (s, 3H), 2.47 (s, 3H), 2.90 (s, 3H), 3.52 (t, J=8.0 Hz, 2H), 3.79 (t, J=8.0 Hz, 2H), 6.98 (s, 2H), 7.29 (d, J=8.4 Hz, 1H), 8.10 (d, J=8.4 Hz, 1H).

Reference Example 80

3-[1-(3-Iodoanilino)ethylidene]tetrahydro-2-furanone

A solution of 3-iodoaniline (5.0 g, 23 mmol), α-acetyl-γ-butyrolactone (14.6 g, 0.11 mol) in ethanol (100 mL) was heated under reflux for seven days. The mixture was evaporated, and the residue was purified by silica gel column chromatography (10% ethyl acetate/hexane), to give the title compound (7.54 g) as white crystals.

$^1$H NMR (400 MHz. CDCl$_3$) δ 2.03 (s, 3H), 2.90 (t, J=8.0 Hz, 2H), 4.36 (t, J=8.0 Hz, 2H), 6.99–7.07 (m, 2H), 7.41–7.48 (m, 2H), 9.96 (s, 1H).

Reference Example 81

4-Chloro-3-(2-chloroethyl)-7-iodo-2-methylquinoline

A solution of 3-[1-(3-iodoanilino)ethylidene]tetrahydro-2-furanone (3.0 g, 9.12 mmol) in phosphorus oxychloride (8.5 mL) was heated at reflux for two hours. After cooling to room temperature, the solution was slowly added dropwise into ice-water while stirring vigorously. The mixture was stirred for one hour while raising a temperature gradually to room temperature. The mixture was diluted with ethyl acetate, and the organic layer was washed with brine, dried over anhydrous magnesium sulfate and evaporated. The residue was purified by silica gel column chromatography (50% methylene chloride/hexane), to give the title compound (821 mg) as white crystals.

$^1$H NMR (400 MHz, CDCl$_3$) δ 2.82 (s, 3H), 3.46 (t, J=8.0 Hz, 2H), 3.76 (t, J=8.0 Hz, 2H), 7.83 (dd, J=8.8 Hz, 1.2 Hz, 1H), 7.87 (d, J=8.8 Hz, 1H), 8.44 (d, J=1.2 Hz, 1H).

Reference Example 82

1-(1-Ethylpropyl)-7-iodo-4-mesityl-2,3-dihydro-1H-1-pyrrolo[3,2-c]quinoline

A solution of 4-chloro-3-(2-chloroethyl)-7-iodo-2-methylquinoline (300 mg, 0.82 mmol) in 3-aminopentane (10.0 mL) was stirred at 200° C. for eight hours in a sealed tube. The mixture was evaporated, and the residue was purified by silica gel column chromatography (10–70% ethyl acetate/hexane), to give the title compound (39 mg) as a pale yellow oil.

$^1$H NMR (400 MHz, CDCl$_3$) δ 0.97 (t, J=7.6 Hz, 6H), 1.68–1.86 (m, 4H), 2.70 (s, 3H), 3.12 (t, J=9.6 Hz, 2H), 3.88 (t, J=9.6 Hz, 2H), 4.33–4.82 (m, 1H), 7.66 (dd, J=9.2 Hz, 1.2 Hz, 1H), 7.76 (d, J=9.2 Hz, 1H), 8.89 (d, J=1.2 Hz, 1H).

Reference Example 83

1-(1-Ethylpropyl)-7-iodo-4-methyl-1H-pyrrolo[3,2-c]quinoline

Activated manganese dioxide (45 mg, 0.51 mmol) was added to a solution of 1-(1-ethylpropyl)-7-iodo-4-mesityl- 2,3-dihydro-1H-pyrrolo[3,2-c]quinoline (39 mg, 0.10 mmol) in toluene (4.0 mL) and methylene chloride (4.0 mL), followed by heating under reflux for one day. The mixture was filtered through Celite and evaporated, to give the title compound (32 mg) as pale yellow crystals.

$^1$H NMR (400 MHz, CDCl$_3$) δ 0.87 (t, J=7.6 Hz, 6H), 1.90–2.12 (m, 4H), 2.90 (s, 3H), 4.92–5.00 (m, 1H), 6.83 (d, J=3.2 Hz, 1H), 7.32 (d, J=3.2 Hz, 1H), 7.77 (dd, J=8.8 Hz, 1.2 Hz, 1H), 8.06 (d, J=8.8 Hz, 1H), 8.61 (d, J=1.2 Hz, 1H).

Example 1

8-(1-Ethylpropyl)-3-mesityl-2,5-dimethyl-7,8-dihydro-6H-pyrazolo[1,5-a]pyrrolo[3,2-e]pyrimidine hydrochloride A solution of 7-chloro-6-(2-chloroethyl)-3-mesityl-2,5-dimethylpyrazolo[1,5-a]pyrimidine (1.5 g, 4.14 mmol) and 3-aminopentane (3 mL) in methyl ethyl ketone (15 mL) was heated under reflux for one hour. 3-Aminopentane (6 mL) was added thereto, followed by heating under reflux for further 4.5 hours. Water was added to the reaction mixture, followed by extcarting with ethyl acetate, The organic layer was washed with brine, dried over anhydrous magnesium sulfate and evaporated. The residue was purified by silica gel column chromatography (10–50% ethyl acetate/hexane), to give the title compound (1.02 g) as a pale yellow oil.

$^1$H NMR (400 MHz, CDCl$_3$) δ 0.95 (t, J=4.8 Hz, 6H), 1.54–1.70 (m, 4H), 2.02 (s, 6H), 2.16 (s, 3H), 2.27 (s, 3H), 2.31 (s, 3H), 3.08 (t, J=7.8 Hz, 2H), 3.68 (t, J=7.8 Hz, 2H), 5.60–5.69 (m, 1H), 6.94 (s, 2H).

The above-mentioned 8-(1-ethylpropyl)-3-mesityl-2,5-dihydro-6H-pyrazolo[1,5-a]pyrrolo[3,2-e]pyrimidine (1.02 g, 2.71 mmol) was dissolved in ether, and a 1 molar solution of hydrogen chloride in ether (2.71 mL) was added slowly. The resulting crystals were collected by filtration, washed with ether and dried, to give the title compound (1.09 g) as white crystals.

$^1$H NMR (400 MHz, CDCl$_3$) δ 0.95 (t, J=7.6 Hz, 6H), 1.64 (dq, J=6.0, 7.6 Hz, 4H), 2.02 (s, 6H), 2.16 (s, 3H), 2.27 (s, 3H), 2.31 (s, 3H), 3.08 (t, J=9.2 Hz, 2H), 3.67 (t, J=9.2 Hz, 2H), 5.64 (quint, 6.0 Hz 1H), 6.93 (s, 2H).

MS (ESI) m/z 377 MH$^+$.

According to the method described in the above Example 1, compounds of Examples 2 to 65 were synthesized.

Example 2

8-Butyl-3-mesityl-2,5-dimethyl-7,8-dihydro-pyrazolo[1,5-a]pyrrolo[3,2-e]pyrimidine hydrochloride White Crystals $^1$H NMR (400 MHz, CDCl$_3$) δ 0.94 (t, J=7.2 Hz, 3H), 1.38 (tq, J=7.2, 8.0 Hz, 2H), 1.75 (tt, J=8.0, 7.2 Hz, 2H), 1.93 (s, 6H), 2.07 (s, 3H), 2.25 (s, 3H), 2.29 (s, 3H), 3.10 (t, J=8.8 Hz, 2H), 4.10 (t, J=8.8 Hz, 2H), 4.29 (t, J=7.2 Hz, 2H), 7.01 (s, 2H).

MS (ESI) m/z 363 MH$^+$.

Example 3

N-5-[2,5-Dimethyl-8-(1-propylbutyl)-7,8-dihydro-6H-pyrazolo[1,5-a]pyrrolo[3,2-e]pyrimidin-3-yl]-4-methyl-2-pyridyl-N,N-dimethylamine hydrochloride White Crystals $^1$H NMR (400 MHz, CDCl$_3$) δ 0.97 (t, J=6.8 Hz, 6H), 1.20–1.70 (m, 8H), 2.25 (s, 3H), 2.37 (s, 3H), 2.61 (s, 3H), 3.17 (br s, 2H), 3.40 (s, 6H), 3.95 (t, J=9.6 Hz, 2H), 5.91–6.01 (m, 1H), 6.78 (s, 1H), 8.00 (s, 1H).

Example 4

N-5-[8-(1-Ethylpropyl)-2,5-dimethyl-7,8-dihydro-pyrazolo[1,5-a]pyrrolo[3,2-e]pyrimidin-3-yl]-4-methyl-2-pyridyl-N,N-dimethylamine hydrochloride White Crystals $^1$H NMR (400 MHz, CDCl$_3$) δ 0.89–1.05 (m, 6H), 1.50–1.85 (m, 4H), 2.26 (s, 3H), 2.37 (s, 3H), 2.61 (s, 3H), 3.12–3.25 (m, 2H), 3.40 (s, 6H), 3.94 (t, J=7.6 Hz, 2H), 5.71–5.85 (m, 1H), 6.78 (s, 1H), 7.99 (s, 1H).

Example 5

8-Cyclopentyl-3-mesityl-2,5-dimethyl-7,8-dihydro-6H-pyrazolo[1,5-a]pyrrolo[3,2-e]pyrimidine Grayish White Amorphous $^1$H NMR (400 MHz, CDCl$_3$) δ 1.65–1.82 (m, 6H), 1.92–2.06 (m, 2H), 2.18 (s, 3H), 2.26 (s, 3H), 2.31 (s, 3H), 3.06 (t, J=9.2 Hz, 2H), 3.78 (t, J=9.2 Hz, 2H), 6.04–6.15 (m, 1H), 6.94 (s, 2H).

MS (ESI) m/z 375 MH$^+$.

Example 6

3-Mesityl-2,5-dimethyl-8-(1-propylbutyl)-7,8-dihydro-6H-pyrazolo[1,5-a]pyrrolo[3,2]-pyrimidine hydrochloride Brown Crystals $^1$H NMR (400 MHz, DMSO-D$_6$) δ 0.88 (t, J=7.2 Hz, 6H), 1.22–1.36 (m, 4H), 1.54–1.64 (m, 2H), 1.64–1.76 (m, 2H), 1.93 (s, 6H), 2.07 (s, 3H), 2.27 (s, 3H), 2.29 (s, 3H), 3.12 (t, J=8.4 Hz, 2H), 3.99 (t, J=8.4 Hz, 2H), 5.82–5.90 (m, 1H), 7.01 (s, 2H), 12.79 (br s, 1H).

MS (ESI) m/z 405 MH$^+$.

Example 7

4-[2-(3-Mesityl-2,5-dimethyl-7,8-dihydro-6H-pyrazolo[1,5-a]pyrrolo[3,2-e]pyrimidin-8-yl)ethyl] morpholine Yellow Oil $^1$H NMR (400 MHz, CDCl$_3$) δ 2.01 (s, 6H), 2.15 (s, 3H), 2.28 (s, 3H), 2.31 (s, 3H), 2.59 (br s, 4H), 2.73 (t, J=6.4 Hz, 2H), 3.10 (t, J=9.2 Hz, 2H), 3.64 (t, J=4.4 Hz, 4H), 3.85 (J=9.2 Hz, 2H), 4.36 (t, J=6.4 Hz, 2H), 6.94 (s, 2H).

Example 8

8-(1-Ethylpropyl)-2,5-dimethyl-3-(3-methyl-2-naphthyl)-7,8-dihydro-6H-pyrazolo[1,5-a]pyrrolo[3,2-e]pyrimidine hydrochloride White Crystals $^1$H NMR (400 MHz, CDCl$_3$) δ 0.93–1.10 (m, 6H), 1.55–1.87 (m, 4H), 2.24 (s, 3H), 2.36 (s, 3H), 2.67 (s, 3H), 3.10–3.27 (m, 2H), 3.87–4.05 (m, 2H), 5.88 (br s, 1H), 7.33–7.48 (m, 2H), 7.70 (s, 1H), 7.73–7.83 (m, 3H).

Example 9

2,5-Dimethyl-3-(3-methyl-2-naphthyl)-8-(1-propylbutyl)-7,8-dihydro-6H-pyrazolo[1,5-a]pyrrolo[3,2-e]pyrimidine hydrochloride White Crystals $^1$H NMR (400 MHz, CDCl$_3$); δ (ppm) 0.93–1.05 (m, 6H), 1.23–1.78 (m, 8H), 2.24 (s, 3H), 2.36 (s, 3H), 2.66 (s, 3H), 3.10–3.23 (m, 2H), 3.90–4.00 (m, 2H), 6.00–6.10 (m, 1H), 7.35–7.48 (m, 2H), 7.70 (s, 1H), 7.73–7.83 (m, 3H).

Example 10

3-Mesityl-2,5-dimethyl-8-(2,2,6,6-tetramethyl-4-pipyridyl)-7,8-dihydro-6H-pyrazolo[1,5-a]pyrrolo[3,2-e]pyrimidine White Crystals $^1$H NMR (400 MHz, CDCl$_3$) δ 1.21 (S, 6H), 1.42 (s, 6H), 1.40–1.60 (m, 2H), 1.85 (dd, J=12.0, 2.8 Hz, 2H), 2.03 (s, 6H), 2.15 (s, 3H), 2.27 (s, 3H), 2.31 (s, 3H), 3.05 (t, J=9.2 Hz, 2H), 3.75 (t, J=9.2 Hz, 2H), 6.20 (tt, J=12.0, 2.8 Hz, 1H), 6.94 (s, 2H).

MS (ESI) m/z 446 MH$^+$.

Example 11

8-Isopropyl-3-mesityl-2,5-dimethyl-7,8-dihydro-6H-pyrazolo[1,5-a]pyrrolo-[3,2-e]pyrimidine hydrochloride Grayish White Solid $^1$H NMR (400 MHz, CDCl$_3$) δ 1.36 (d, J=6.8 Hz, 6H), 1.93 (s, 6H), 2.07 (s, 3H), 2.26 (s, 3H), 2.29 (s, 3H), 3.08 (t, J=8.4 Hz, 2H), 4.08 (t, J=8.4 Hz, 2H), 5.93 (hept., J=6.8 Hz, 1H), 7.00 (s, 2H), 12.69 (s, 1H).

MS (ESI) in/z 349 MH$^+$.

Example 12

9-(1-Ethylpropyl)-3-mesityl-2,5-dimethyl-6,7,8,9-tetrahydropyrazolo[1,5-a]pyrido[3,2-e]pyrimidine White Amorphous $^1$H NMR (400 MHz, CDCl$_3$) δ 0.94 (t, J=7.6 Hz, 6H), 1.60–1.73 (m, 4H), 1.96–2.05 (m, 2H), 2.03 (s, 6H), 2.18 (s, 3H), 2.31 (s, 3H), 2.33 (s, 3H), 2.68 (t, J=6.4 Hz, 2H), 3.32 (t, J=5.6 Hz, 2H), 6.04–6.12 (m, 1H), 6.94 (s, 2H).

Example 13

8-(1-Ethylpropyl)-mesityl-2,5,7-trimethyl-7,8-dihydro-6H-pyrazolo[1,5-a]pyrrolo[3,2-e]pyrimidine White Crystals $^1$H NMR (400 MHz, CDCl$_3$) δ 0.82 (t, J=6.8 Hz, 3H), 1.13 (t, J=6.8 Hz, 3H), 1.39 (d, J=5.6 Hz, 3H), 1.60–1.90 (m, 4H), 2.03 (s, 6H), 2.17 (s, 3H), 2.27 (s, 3H), 2.31 (s, 3H), 2.52–2.62 (m, 1H), 3.34–3.62 (m, 1H), 4.07–4.22 (m, 1H), 5.45 (br s, 1H), 6.93 (s, 2H).

Example 14

3-(4-Bromophenyl-8-(1-ethylpropyl)-2,5-dimethyl-7,8-dihydro-6H-pyrazolo[1,5-a]pyrrolo[3,2-e]pyrimidine White Crystals $^1$H NMR (400 MHz, CDCl$_3$) δ 0.93 (t, J=7.5 Hz, 6H), 1.50–1.75 (m, 4H), 2.35 (s, 3H), 2.52 (s, 3H), 3.10 (t, J=9.2 Hz, 2H), 3.68 (t, J=9.2 Hz, 2H), 5.55–5.70 (m, 1H), 7.52 (d, J=8.6 Hz, 2H), 7.66 (d, J=8.6 Hz, 2H).

MS (ESI) m/z 415 MH$^+$.

Example 15

3-(4-Bromophenyl)-8-[1-(methoxymethyl)propyl]-2,5-dimethyl-7,8-dihydro-6H-pyrazolo[1,5-a]-pyrrolo[3,2-e]pyrimidine White Crystals $^1$H NMR (400 MHz, CDCl$_3$) δ 0.98 (t, J=7.4 Hz, 3H), 1.58–1.78 (m, 2H), 2.35 (s, 3H), 2.51 (s, 3H), 3.09 (dd, J=3.7, 8.4 Hz, 1H), 3.34 (s, 3H), 3.51 (dd, J=4.3, 10.4 Hz, 1H), 3.62 (dd, J=7.6, 10.4 Hz, 1H), 3.69–3.91 (m, 2H), 5.88–6.04 (m, 1H), 7.51 (d, J=8.4 Hz, 2H), 7.65 (d, J=8.4 Hz, 2H).

Example 16

3-(4-Bromophenyl)-2,5-dimethyl-8-(1-propylbutyl)-7,8-dihydro-6H-pyrazolo[1,5-a]pyrrolo[3,2-e]pyrimidine White Crystals $^1$H NMR (400 MHz, CDCl$_3$) δ 0.92 (t, J=7.3 Hz, 6H), 1.22–1.44 (m, 4H), 1.45–1.65 (m, 4H), 2.35 (s, 3H), 2.51 (s, 3H), 3.09 (t, J=9.2 Hz, 2H), 3.68 (t, J=9.2 Hz, 2H), 5.80–5.91 (m, 1H), 7.51 (d, J=8.6 Hz, 2H), 7.66 (d, J=8.6 Hz, 2H).

Example 17

8-(1-Ethylpropyl)-2,5-dimethyl-3-(2,4,6-trimethoxyphenyl)-7,8-dihydro-6H-pyrazolo[1,5-a]pyrrolo[3,2-e]pyrimidine Pale Yellow Crystals $^1$H NMR (400 MHz, CDCl$_3$) δ 0.95 (t, J=7.4 Hz, 6H), 1.50–1.73 (m, 4H), 2.22 (s, 3H), 2.30 (s, 3H), 3.05 (t, J=9.0 Hz, 2H), 3.66 (t, J=9.0 Hz, 2H), 3.74 (s, 6H), 3.85 (s, 3H), 5.60–5.73 (m, 1H), 6.24 (s, 2H).

Example 18

8-[1-(Methoxymethyl)propyl]-2,5-dimethyl-3-(2,4,6-trimethoxyphenyl)-7,8-dihydro-6H-pyrazolo[1,5-a]pyrrolo[3,2-e]pyrimidine Pale Yellow Crystals $^1$H NMR (400 MHz, CDCl$_3$) δ 1.00 (t, J=7.4 Hz, 3H), 1.60–1.75 (m, 2H), 2.21 (s, 3H), 2.28 (s, 3H), 3.03 (dd, J=3.0, 7.2 Hz, 1H), 3.06 (dd, J=3.0, 7.2 Hz, 1H), 3.36 (s, 3H), 3.55 (dd, J=4.4, 10.4 Hz, 1H), 3.64 (dd, J=6.7, 10.4 Hz, 1H), 3.68–3.88 (m, 2H), 3.72 (s, 3H), 3.73 (s, 3H), 3.85 (s, 3H), 5.85–6.00 (m, 1H), 6.24 (s, 2H).

Example 19

2,5-Dimethyl-8-(1-propylbutyl)-3-(2,4,6-trimethoxyphenyl)-7,8-dihydro-6H-pyrazolo[1,5-a]pyrrolo[3,2-e]pyrimidine Yellow Crystals $^1$H NMR (400 MHz, CDCl$_3$) δ 0.93 (t, J=7.3 Hz, 6H), 1.26–1.64 (m, 8H), 2.21 (s, 3H), 2.27 (s, 3H), 3.03 (t, J=9.1 Hz, 2H), 3.64 (t, J=9.1 Hz, 2H), 3.73 (s, 6H), 3.85 (s, 3H), 5.80–5.92 (m, 1H), 6.24 (s, 2H).

Example 20

3-(1,3-Benzodioxol-5-yl)-yl-8-(1-ethylpropyl-2,5-dimethyl-7,8-dihydro-6H-pyrazolo[1,5-a]pyrrolo[3,2-e]pyrimidin Pale Yellow Crystals $^1$H NMR (400 MHz, CDCl$_3$) δ 0.93 (t, J=7.4 Hz, 6H), 1.50–1.71 (m, 4H), 2.34 (s, 3H), 2.50 (s, 3H), 3.09 (t, J=9.2 Hz, 2H), 3.67 (t, J=9.2 Hz, 2H), 5.58–5.73 (m, 1H), 5.96 (s, 2H), 6.87 (d, J=8.1 Hz, 1H), 7.14 (dd, J=1.6, 8.1 Hz, 1H), 7.31 (d, J=1.5 Hz, 1H).

Example 21

3-(1,3-Benzodioxol-5-yl)-2,5-dimethyl-8-(1-propylbutyl)-7,8-dihydro-6H-pyrazolo[1,5-a]pyrrolo[3,2-e]pyrimidine Pale Yellow Crystals $^1$H NMR (400 MHz, CDCl$_3$); δ (ppm) 0.92 (t, J=7.3 Hz, 6H), 1.24–1.44 (m, 4H), 1.45–1.68 (m, 4H), 2.34 (s, 3H), 2.49 (s, 3H), 3.08 (t, J=9.2 Hz, 2H), 3.67 (t, J=9.2 Hz, 2H), 5.80–5.94 (m, 1H), 5.95 (s, 2H), 6.86 (d, J=8.1 Hz, 1H), 7.14 (dd, J=1.7, 8.1 Hz, 1H), 7.32 (d, J=1.7 Hz, 1H).

Example 22

8-(1-Ethylpropyl)-2,5-dimethyl-3-phenyl-7,8-dihydro-6H-pyrazolo[1,5-a]pyrrolo[3,2-e]pyrimidine

Pale Yellow Crystal $^1$H NMR (400 MHz. CDCl$_3$) δ 0.94 (t, J=7.4 Hz, 6H), 1.50–1.66 (m, 4H), 2.35 (s, 3H), 2.54 (s, 3H), 3.10 (t, J=9.1 Hz, 2H), 3.68 (t, J=9.1 Hz, 2H), 5.60–5.74 (m, 1H), 7.20 (t, J=7.4 Hz, 1H), 7.41 (t, J=7.8 Hz, 2H), 7.76 (dd, J=1.2, 8.3 Hz, 2H).

Example 23

2-Ethyl-8-(1-ethylpropyl)-3-mesityl-5-methyl-7,8-dihydro-6H-pyrazolo[1,5-a]pyrrolo[3,2-e]pyrimidine

Pale Yellow Crystals $^1$H NMR (400 MHz, CDCl$_3$) δ 0.96 (t, J=7.4 Hz, 6H), 1.15 (t, J=7.5 Hz, 3H), 1.53–1.72 (m, 4H), 2.02 (s, 6H), 2.27 (s, 3H), 2.30 (s, 3H), 2.51 (q, J=7.5 Hz, 2H), 3.08 (t, J=9.1 Hz, 2H), 3.67 (t, J=9.1 Hz, 2H), 5.60–5.75 (m, 1H), 6.92 (s, 2H).

Example 24

8-(tert-Butyl)-3-mesityl-2,5-dimethyl-7,8-dihydro-6H-pyrazolo[1,5-a]pyrrolo[3,2-e]pyrimidine hydrochloride

Brown Crystals $^1$H NMR (400 MHz, CDCl$_3$) δ 1.83 (s, 9H), 2.03 (s, 6H), 2.18 (s, 3H), 2.32 (s, 3H), 2.63 (s, 3H), 3.07 (t, J=7.9 Hz, 2H), 4.27 (t, J=7.9 Hz, 2H), 6.98 (s, 2H).

MS (ESI) m/z 363 MH$^+$.

Example 25

3-Mesityl-2,5,8-trimethyl-7,8-dihydro-6H-pyrazolo[1,5-a]pyrrolo[3,2-e]pyrimidine

White Crystals $^1$H NMR (400 MHz, CDCl$_3$) δ 1.66 (s, 3H), 2.02 (s, 6H), 2.19 (s, 3H), 2.28 (s, 3H), 2.31 (s, 3H), 3.08 (t, J=9.2 Hz, 2H), 3.73 (t, J=9.2 Hz, 2H), 6.94 (s, 2H).

MS (ESI) m/z 321 MH$^+$.

Example 26

8-Benzyl-3-mesityl-2,5-dimethyl-7,8-dihydro-6H-pyrazolo[1,5-a]pyrrolo[3,2-e]pyrimidine hydrochloride

Brown Crystals $^1$H NMR (400 MHz, CDCl$_3$); δ (ppm) 2.05 (s, 6H), 2.20 (s, 3H), 2.33 (s, 3H), 2.68 (s, 3H), 3.14 (t, J=9.0 Hz, 2H), 3.95 (t, J=9.0 Hz, 2H), 5.65 (s, 2H), 7.00 (s, 2H), 7.32–7.47 (m, 5H).

MS (ESI) m/z 397 MH$^+$.

Example 27

3-Mesityl-8-(2-methoxyethyl)-2,5-dimethyl-7,8-dihydro-6H-pyrazolo[1,5-a]pyrrolo[3,2-e]pyrimidine hydrochloride

Brown Crystals $^1$H NMR (400 MHz, CDCl$_3$) δ 2.02 (s, 6H), 2.14 (s, 3H), 2.32 (s, 3H), 2.66 (s, 3H), 3.18 (t, J=9.2 Hz, 2H), 3.42 (s, 3H), 3.82 (t, J=4.8 Hz, 2H), 4.23 (t, J=9.2 Hz, 2H), 4.55 (t, J=4.8 Hz, 2H), 6.97 (s, 2H).

MS (ESI) m/z 365 MH$^+$.

Example 28

3-Mesityl-2,5-dimethyl-8-propyl-7,8-dihydro-6H-pyrazolo[1,5-a]pyrrolo[3,2-e]pyrimidine hydrochloride

Brown Crystals $^1$H NMR (400 MHz, CDCl$_3$) δ 1.06 (t, J=7.2 Hz, 3H), 1.88 (tq, J=7.2, 7.2 Hz, 2H), 2.01 (s, 6H), 2.16 (s, 3H), 2.32 (s, 3H), 2.62 (s, 3H), 3.21 (t, J=5.7 Hz, 2H), 4.13 (t, J=5.7 Hz, 2H), 4.34 (t, J=7.2 Hz, 2H), 6.97 (s, 2H).

MS (ESI) m/z 349 MH$^+$.

Example 29

8-(1-Ethylpropyl)-2-cyclopropyl-3-mesityl-5-methyl-7,8-dihydro-6H-pyrazolo[1,5-a]pyrrolo[3,2-e]pyrimidine

Example 30

4-[8-(1-Ethylpropyl)-2,5-dimethyl-7,8-dihydro-6H-pyrazolo[1,5-a]pyrrolo[3,2-e]pyrimidin-3-yl]benzonitrile

Pale Yellow Crystals $^1$H NMR (400 MHz, CDCl$_3$) δ 0.93 (t, J=7.4 Hz, 6H), 1.51–1.73 (m, 4H), 2.37 (s, 3H), 2.58 (s, 3H), 3.12 (t, J=9.2 Hz, 2H), 3.70 (t, J=9.2 Hz, 2H), 5.55–5.71 (m, 1H), 7.66 (dd, J=1.8, 6.8 Hz, 2H), 7.99 (dd, J=1.8, 6.8 Hz, 2H).

MS (ESI) m/z 360 MH$^+$.

Example 31

4-[8-(1-Ethylpropyl)-2,5-dimethyl-7,8-dihydro-6H-pyrazolo[1,5-a]pyrrolo[3,2-e]pyrimidin-3-yl]benzamide

White Crystals $^1$H NMR (400 MHz, CDCl$_3$) δ 0.93 (t, J=7.3 Hz, 6H), 1.50–1.75 (m, 4H), 2.37 (s, 3H), 2.57 (s, 3H), 3.11 (t, J=9.2 Hz, 2H), 3.69 (t, J=9.2 Hz, 2H), 5.60–5.73 (m, 1H), 7.85 (d, J=8.6 Hz, 2H), 7.92 (d, J=8.6 Hz, 2H).

MS (ESI) m/z 378 MH$^+$.

Example 32

8-(Ethylpropyl)-3-mesityl-5-methyl-7,8-dihydro-6H-pyrazolo[1,5-a]pyrrolo[3,2]pyrimidine hydrochloride

Pink Crystals $^1$H NMR (400 MHz, CDCl$_3$) δ 1.13 (t, J=7.3 Hz, 6H), 1.77–2.00 (m, 4H), 2.25 (s, 6H), 2.47 (s, 3H), 2.87 (s, 3H), 3.30–3.40 (m, 2H), 4.07–4.18 (m, 2H), 5.90–6.04 (m, 1H), 7.13 (s, 2H), 8.03 (s, 1H).

Example 33

3-(2,4-Dichlorophenyl)-8-(1 ethylpropyl)-2,5-dimethyl-7,8-dihydro-6H-pyrazolo[1,5-a]pyrrolo[3,2-e]pyrimidine hydrochloride

Yellow Crystals $^1$H NMR (400 MHz, CDCl$_3$) δ 0.96 (t, J=6.4 Hz, 3H), 1.00 (t, J=6.8 Hz, 3H), 1.55–1.82 (m, 4H), 2.28 (s, 3H), 2.69 (s, 3H), 3.10–3.22 (m, 2H), 3.87–4.00 (m, 2H), 5.74–5.87 (m, 1H), 7.40 (s, 2H), 7.53 (s, 1H).

Example 34

3-(2,4-Dichlorophenyl)-2,5-dimethyl-8-(1-propylbutyl)-7,8-dihydro-6H-pyrazolo[1,5-a]pyrrolo[3,2-e]pyrimidine hydrochloride White Crystals $^1$H NMR (400 MHz, CDCl$_3$) δ 0.92–1.01 (m, 6H), 1.18–1.72 (m, 8H), 2.27 (s, 3H), 2.67 (s, 3H), 3.15 (t, J=8.8 Hz, 2H), 3.94 (t, J=9.2 Hz, 2H), 6.00 (quint, 6.0 Hz, 1H), 7.40 (s, 2H), 7.53 (s, 1H).

Example 35

3-Mesityl-2,5-dimethyl-8-nonyl-7,8-dihydro-6H-pyrazolo[1,5-a]pyrrolo[3,2-e]pyrimidine hydrochloride Brown Oil $^1$H NMR (400 MHz, CDCl$_3$) δ 0.88 (t, J=7.2 Hz, 3H), 1.15–1.52 (m, 12H), 1.70–1.90 (m, 2H), 2.02 (s, 6H), 2.16 (s, 3H), 2.33 (s, 3H), 2.67 (s, 3H), 3.16 (br s, 2H), 4.09 (br s, 2H), 4.36 (t, J=7.2 Hz, 2H), 6.98 (s, 2H).

MS (ESI) m/z 433 MH$^+$.

Example 36

8-Cyclopropyl-3-mesityl-2,5-dimethyl-7,8-dihydro-6H-pyrazolo[1,5-a]pyrrolo[3,2-e]pyrimidine hydrochloride Pale Brown Crystals $^1$H NMR (400 MHz, CDCl$_3$) δ 1.04–1.14 (m, 4H), 2.03 (s, 6H), 2.17 (s, 3H), 2.33 (s, 3H), 2.63 (s, 3H), 3.10 (t, J=8.9 Hz, 2H), 3.94 (t, J=9.2 Hz, 2H), 4.00–4.10 (m, 1H), 6.98 (s, 2H).

MS (ESI) m/z 347 MH$^+$.

Example 37

8-Ethyl-3-mesityl-2,5-dimethyl-7,8-dihydro-6H-pyrazolo[1,5-a]pyrrolo[3,2-e]pyrimidine hydrochloride Brown Solid $^1$H NMR (400 MHz, CDCl$_3$) δ 1.47 (t, J=7.2 Hz, 3H), 2.02 (s, 6H), 2.16 (s, 3H), 2.33 (s, 3H), 2.67 (s, 3H), 3.19 (t, J=8.8 Hz, 2H), 4.11 (t, J=8.8 Hz, 2H), 4.45 (q, J 7.2 Hz, 2H), 6.98 (s, 2H).

MS (ESI) m/z 335 MH$^+$.

Example 38

8-(Cyclopropylmethyl)-3-mesityl-2,5-dimethyl-7,8-dihydro-6H-pyrazolo[1,5-a]pyrrolo[3,2-e]pyrimidine hydrochloride Brown Crystals $^1$H NMR (400 MHz, CDCl$_3$) δ 0.46 (dd, J=10.3, 3.8 Hz, 2H), 0.72 (dd, J=11.0, 3.8 Hz, 2H), 1.18–1.26 (m, 1H), 2.03 (s, 6H), 2.16 (s, 3H), 2.33 (s, 3H), 2.69 (s, 3H), 3.21 (t, J=8.4 Hz, 2H), 4.22 (t, J=8.4 Hz, 2H), 4.32 (d, J=7.2 Hz, 2H), 6.99 (s, 2H).

MS (ESI) m/z 361 MH$^+$.

Example 39

3-Mesityl-8-(3-methoxypropyl)-2,5-dimethyl-7,8-dihydro-6H-pyrazolo[1,5-a]pyrrolo[3,2-e]pyrimidine hydrochloride Brown Crystals $^1$H NMR (400 MHz, CDCl$_3$) δ 2.02 (s, 6H), 2.08 (tt, J 7.2, 5.6 Hz, 2H), 2.16 (s, 3H), 2.32 (s, 3H), 2.52 (s, 3H), 3.13 (t, J=8.8 Hz, 2H), 3.27 (s, 3H), 3.55 (t, J=5.6 Hz, 2H), 3.99 (t, J=8.8 Hz, 2H), 4.39 (t, J=0.2 Hz, 2H), 6.96 (s, 2H).

MS (ESI) in/z 379 MH$^+$.

Example 40

3-Mesityl-8-[1-(methoxymethyl)propyl]-2,5-dimethyl-7,8-dihydro-6H-pyrazolo[1,5-a]pyrrolo[3,2-e]pyrimidine hydrochloride Brown Crystals $^1$H NMR (400 MHz, CDCl$_3$) δ 1.05 (t, J=6.9 Hz, 3H), 1.68–1.84 (m, 2H), 2.02 (s, 3H), 2.04 (s, 3H), 2.16 (s, 3H), 2.33 (s, 3H), 2.69 (s, 3H), 3.10–3.22 (m, 2H), 3.38 (s, 3H), 3.62–3.68 (m, 2H), 3.80–4.40 (m, 4H), 6.06–6.14 (m, 1H), 6.98 (m, 2H).

MS (ESI) m/z 393 MH$^+$.

Example 41

3-(2-Chlorophenyl)-8-(1-ethylpropyl)-2,5-dimethyl-7,8-dihydro-6H-pyrazolo[1,5-a]pyrrolo[3,2-e]pyrimidine White Amorphous $^1$H NMR (400 MHz, CDCl$_3$) δ 0.95 (t, J=7.2 Hz, 6H), 1.55–1.72 (m, 4H), 2.30 (s, 3H), 2.32 (s, 3H), 3.09 (t, J=8.8 Hz, 2H), 3.68 (t, J=8.8 Hz, 2H), 5.68 (br s, 1H), 7.23 (ddd, J=1.6, 7.6, 7.6 Hz, 1H), 7.29 (ddd, J=1.6, 7.2, 7.6 Hz, 1H), 7.43 (dd, J=2.0, 7.6 Hz, 1H), 7.47 (dd, J=1.2, 7.6 Hz, 1H).

Example 42

3-(2-Chlorophenyl)-2,5-dimethyl-8-(1-propylbutyl)-7,8-dihydro-6H-pyrazolo[1,5-a]pyrrolo[3,2-e]pyrimidine Yellow Amorphous $^1$H NMR (400 MHz, CDCl$_3$) δ 0.94 (t, J=7.2 Hz, 6H), 1.28–1.45 (m, 4H), 1.46–1.66 (m, 4H), 2.30 (s, 3H), 2.31 (s, 3H), 3.08 (t, J=8.8 Hz, 2H), 3.69 (t, J=8.8 Hz, 2H), 5.86 (br s, 1H), 7.23 (ddd, J=1.2, 7.2, 8.0 Hz, 1H), 7.29 (ddd, J=1.2, 7.2, 7.6 Hz, 1H), 7.43 (dd, J=2.0, 7.6 Hz, 1H), 7.47 (dd, J=1.6, 8.0 Hz, 2H).

Example 43

8-Butyl-3-mesityl-2,5,7-trimethyl-7,8-dihydro-6H-pyrazolo[1,5-a]pyrrolo[3,2-e]pyrimidine hydrochloride Pale Yellow Crystals $^1$H NMR (400 MHz, DMSO-d$_6$) δ 0.94 (t, J=6.8 Hz, 3H), 1.32–1.43 (m, 2H), 1.42 (d, J=6.0 Hz, 3H), 1.62–1.74 (m, 1H), 1.75–1.86 (m, 1H), 1.93 (s, 6H), 2.06 (s, 3H), 2.26 (s, 3H), 2.29 (s, 3H), 2.65–2.76 (m, 1H), 3.28–3.40 (m, 1H), 3.73–3.83 (m, 1H), 4.52 (br s, 1H), 4.66–4.80 (m, 1H), 7.00 (s, 2H).

Example 44

3-Mesityl-8-(2-methoxyethyl)-2,5,7-trimethyl-7,5-dihydro-6H-pyrazolo[1,5-a]pyrrolo[3,2-e]pyrimidine hydrochloride Pale Yellow Crystals $^1$H NMR (400 MHz, DMSO-d$_6$) δ 1.42 (d, J=6.4 Hz, 3H), 1.929 (s, 3H), 1.933 (s, 3H), 2.07 (s, 3H), 2.27 (s, 3H), 2.29 (s, 3H), 2.72 (dd, J=4.8 Hz, 16.4, 11H), 3.28 (s, 3H), 3.35 (dd, J=10.4, 15.6 Hz, 1H), 3.63–3.79 (m, 2H), 3.83–3.92 (m, 1H), 4.50–4.60 (m, 1H), 5.10–5.20 (m, 1H), 7.00 (s, 2H), 12.84 (br s, H11).

Example 45

8-Cycloheptyl-3-mesityl-2,5-dimethyl-7,8-dihydro)-6H-pyrazolo[1,5-a]pyrrolo[3,2-e]pyrimidine hydrochloride Pale Brown Crystals $^1$H NMR (400 MHz, CDCl$_3$) δ 1.54–1.89 (m, 10H), 2.03 (s, 6H), 2.04–2.14 (m, 2H), 2.17 (s, 3H), 2.33 (s, 3H), 2.65 (s, 3H), 3.13 (t, J=8.8 Hz, 2H), 4.07 (t, J=8.8 Hz, 2H), 5.86–5.92 (m, 1H), 6.98 (s, 2H).

MS (ESI) m/z 403 MH$^+$.

Example 46

3-Mesityl-2,5-dimethyl-8-(2-pyridylmethyl)-7,8-dihydro-6H-pyrazolo[1,5-a]pyrrolo[2,3-e]pyrimidine hydrochloride Pale Brown Crystals $^1$H NMR (400 MHz, CDCl$_3$) δ 2.02 (s, 6H), 2.15 (s, 3H), 2.32 (s, 3H), 2.69 (s, 3H), 3.20 (t, J=8.8 Hz, 2H), 4.19 (t, J=8.8 Hz, 2H), 5.84 (s, 2H), 6.98 (s, 2H), 7.40 (t, J=6.0 Hz, 1H), 7.56–7.66 (m, 1H), 7.89 (t, J=6.0 Hz, 1H), 8.63 (d, J=3.6 Hz, 1H).

MS (ESI) m/z 398 MH$^+$.

Example 47

8-Cyclohexyl-3-mesityl-2,5-dimethyl-7,8-dihydro-6H-pyrazolo[1,5-a]pyrrolo[3,2-e]pyrimidine hydrochloride Brown Crystals $^1$H NMR (400 MHz, CDCl$_3$) δ 1.46–1.68 (m, 4H), 1.74–2.10 (m, 6H), 2.03 (s, 6H), 2.16 (s, 3H), 2.33 (s, 3H), 2.65 (s, 3H), 3.14 (t, J=8.8 Hz, 2H), 4.07 (t, J=8.8 Hz, 2H), 5.61–5.72 (m, 1H), 6.98 (s, 2H).

MS (ESI) m/z 389 MH$^+$.

Example 48

3-Mesityl-2,5-dimethyl-8-(2-methylcyclohexyl)-7,8-dihydro-6H-pyrazolo[1,5-a]pyrrolo[3,2-e]pyrimidine hydrochloride Gray Crystals $^1$H NMR (400 MHz, CDCl$_3$) δ 0.95–1.14 (d×2, J=7.2, 6.4 Hz, 3H), 1.23–2.00, 2.55–2.63 (m, 9H), 2.00–2.09 (s×3, 6H), 2.13–2.20 (s×2, 3H), 2.33 (s, 3H), 2.63–2.69 (s×2, 3H), 3.08–3.20 (m, 2H), 3.93–4.18 (m, 2H), 5.49–5.58 (m, 1H), 6.98 (s, 2H).

MS (ESI) m/z 403 MH$^+$.

Example 49

3-(2,4-Dimethoxyphenyl)-8-(1-ethylpropyl)-2,5-e]pyrimidine

Brown Oil $^1$H NMR (400 MHz, CDCl$_3$) δ 0.95 (t, J=7.2 Hz, 3H), 2.51–2.70. (m, 4H), 2.29 (s, 3H), 2.30 (s, 3H), 3.07 (t, J=8.8 Hz, 2H), 3.66 (t, J=9.6 Hz, 2H), 3, 78 (s, 3H), 3.84 (s, 3H), 5.65 (br s, 1H), 6.56 (d, J=2.8 Hz, 1H), 6.59 (dd, J=2.8, 10.8 Hz, 1H), 7.36 (d. J=8.0 Hz, 1H).

Example 50

8-(1-Ethylpropyl)-2,5-dimethyl-3-(2-methylphenyl)-7,8-dihydro-6H-pyrazolo[1,5-a]pyrrolo[3,2-e]pyrimidine hydrochloride White Crystals $^1$H NMR (400 MHz, CDCl$_3$) δ 0.98 (t, J=7.6 Hz, 3H), 1.00 (t, J=7.2 Hz, 3H), 1.65–1.85 (m, 4H), 2.20 (s, 3H), 2.25 (s, 3H), 2.68 (s, 3H), 3.10–3.22 (m, 2H), 3.85–3.97 (m, 2H), 5.78–5.92 (m, 1H), 7.17–7.40 (m, 4H).

Example 51

2,5-Dimethyl-3-(2-methylphenyl)-8-(1-propylbutyl)-7,8-dihydro-6H-pyrazolo[1,5-a]pyrrolo[3,2-e]pyrimidine hydrochloride White Crystals $^1$H NMR (400 MHz, CDCl$_3$) δ 0.97 (t, J=7.2 Hz, 3H), 0.98 (t, J=6.8 Hz, 3H), 1.20–1.50 (m, 8H), 2.20 (s, 3H), 2.24 (s, 3H), 2.67 (s, 3H), 3.15 (t, J=8.8 Hz, 2H), 3.93 (t, J=8.4 Hz, 2H), 6.03 (quint, J=6.0 Hz, 1H), 7.15–7.40 (m, 4H).

Example 52

8-[1-(Methoxymethyl)propyl]-2,5-dimethyl-3-(2-methylphenyl)-7,8-dihydro-6H-pyrazolo[1,5-a]pyrrolo[3,2-e]pyrimidine hydrochloride White Crystals $^1$H NMR (400 MHz, CDCl$_3$) δ 1.00–1.08 (m, 3H), 1.70–1.82 (m, 2H), 2.19 (d, J=3.6 Hz, 3H), 2.24 (s, 3H), 2.68 (s, 3H), 3.10–3.19 (m, 2H), 3.38 (d, J=3.2 Hz, 3H), 3.58–3.67 (m, 2H), 3.93–4.17 (m, 2H), 6.05–6.18 (m, 1H), 7.15–7.38 (m, 4H).

Example 53

3-(4-Chloro-2-methoxyphenyl)-8-(1-ethylpropyl)-2,5-dimethyl-7,8-dihydro-6H-pyrazolo[1,5-a]pyrrolo[3,2-e]pyrimidine Yellow Crystals $^1$H NMR (400 MHz, CDCl$_3$) δ 0.95 (t, J=7.2 Hz, 3H), 1.50–1.70 (m, 4H), 2.29 (s, 3H), 2.31 (s, 3H), 2.39 (s, 3H), 3.06 (t, J=9.6 Hz, 2H), 3.65 (t, J=8.4 Hz, 2H), 3.79 (s, 3H), 5.66 (br s, 1H), 6.78 (s, 1H), 6.85 (d, J=8.4 Hz, 1H), 7.33 (d, J=7.6 Hz, 1H).

Example 54

3-(3-Chlorophenyl)-8-(1-ethylpropyl)-2,5-dimethyl-7,8-dihydro-6-pyrazolo[1,5-a]pyrrol[3,2-e]pyrimidine Yellow Crystals $^1$H NMR (400 MHz, CDCl$_3$) δ 0.93 (t, J=7.6 Hz, 6H), 1.52–1.74 (m, 4H), 2.36 (s, 3H), 2.54 (s, 3H), 3.10 (t, J=8.8 Hz, 2H), 3.68 (t, J=8.8 Hz, 2H), 5.65 (br s, 1H), 7.16 (ddd, J=1.2, 2.0, 8.0 Hz, 1H), 7.32 (dd, J=8.0, 8.0 Hz, 1H), 7.67 (d, J=8.0 Hz, 1H), 7.79 (dd, J=1.6, 2.0 Hz, 1H).

Example 55

3-(4-Chlorophenyl)-8-(1-ethylpropyl)-2,5-dimethyl-7,8-dihydro-6H-pyrazolo[1,5-a]pyrrolo[3,2-e]pyrimidine Yellow Crystals $^1$H NMR (400 MHz, CDCl$_3$) δ 0.93 (t, J=7.6 Hz, 6H), 1.55–1.70 (m, 4H), 2.35 (s, 3H), 2.52 (s, 3H), 3.10 (t, J=8.8 Hz, 2H), 3.68 (t, J=8.8 Hz, 2H), 5.65 (br s, 1H), 7.37 (ddd, J=2.0, 2.8, 8.4 Hz, 2H), 7.72 (ddd, J=2.0, 2.4, 8.8 Hz, 2H).

Example 56

3-(2,6-Dimethylphenyl)-8-(1-ethylpropyl)-2,5-dimethyl-7,8-dihydro-6H-pyrazol[1,5-a]pyrrolo[3,2-e]pyrimidine Yellow Crystals $^1$H NMR (400 MHz, CDCl$_3$) δ 0.96 (t, J=7.2 Hz, 6H), 1.56–1.72 (m, 4H), 2.06 (s, 6H), 2.16 (s, 3H), 2.27 (s, 3H), 3.08 (t, J=8.8 Hz, 2H), 3.68 (t, J=8.8 Hz, 2H), 5.66 (br s, 1H), 7.07–7.18 (m, 3H).

Example 57

3-(2,6-Dimethylphenyl)-2,5-dimethyl-8-(1-propylbutyl)-7,8-dihydro-6H-pyrazolo[1,5-a]pyrrolo[3,2-e]pyrimidine hydrochloride Yellow Crystals $^1$H NMR (400 MHz, DMSO-d$_6$) δ 0.88 (t, J=6.4 Hz, 6H), 1.18–1.38 (m, 4H), 1.51–1.64 (m, 2H), 1.64–1.76 (m, 2H), 1.96 (s, 6H), 2.06 (s, 3H), 2.26 (s, 3H), 3.12 (br s, 2H), 3.96 (br s, 2H), 5.84 (br s. 1H), 7.10–7.20 (m, 2H), 7.20–7.30 (m, 1H).

Example 58

N-[2-(3-Mesityl-2,5-dimethyl-7,8-dihydro-6H-pyrazolo[1,5-a]pyrrolo[3,2-e]pyrimidin-8-yl)ethyl]-N,N-dimethylamine hydrochloride White Crystals $^1$H NMR (400 MHz, CDCl$_3$) δ 2.03 (s, 6H), 2.15 (s, 3H), 2.31 (s, 3H), 2.46 (s, 3H), 3.05 (s, 6H), 3.24 (br s, 2H), 3.74 (br s, 2H), 4.31 (br s, 2H), 4.90 (br s, 2H), 6.95 (s, 2H).

MS (ESI) m/z 378 MH$^+$.

Example 59

3-(3-Mesityl-2,5-dimethyl-7,8-dihydro-6H-pyrazolo[1,5-a]pyrrolo[3,2-e]pyrimidin-8-yl)-1-propanol hydrochloride White Crystals $^1$H NMR (400 MHz, CDCl$_3$) δ 2.00 (s, 6H), 2.00–2.11 (m, 2H), 2.17 (s, 3H), 2.32 (s, 3H), 2.58 (s, 3H), 3.14–3.28 (m, 2H), 3.73 (t, J=5.6 Hz, 2H), 4.15–4.25 (m, 2H), 4.46 (t, J=6.0 Hz, 2H), 6.97 (s, 2H).

MS (ESI) m/z 365 MH$^+$.

Example 60

3-(4-Bromo-2-methylphenyl)-8-(1-ethylpropyl)-2,5-dimethyl-7,8-dihydro-6H-pyrazolo[1,5-]pyrrolo[3,2-e]pyrimidine White Crystals $^1$H NMR (400 MHz, CDCl$_3$) δ 0.88–1.02 (m, 6H), 1.52–1.74 (m, 4H), 2.20 (s, 3H), 2.27 (s, 3H), 2.29 (s, 3H), 3.09 (t, J=9.2 Hz, 2H), 3.68 (t, J=9.2 Hz, 2H), 5.58–5.70 (m, 1H), 7.12 (d, J=8.1 Hz, 1H), 7.32 (dd, J=2.0, 8.1 Hz, 1H), 7.43 (d, J=2.0 Hz, 1H).

Example 61

8-Butyl-3-mesityl-2,5-dimethyl-7-propyl-7,8-dihydro-6H-pyrazolo[1,5-a]pyrrolo[3,2-e]pyrimidine hydrochloride Pale Yellow Crystals $^1$H NMR (400 MHz, CDCl$_3$) δ 0.95–1.12 (m, 6H), 1.36–1.56 (m, 4H), 1.63–1.80 (m, 2H), 1.80–2.00 (m, 2H), 2.03 (s, 6H), 2.16 (s, 3H), 2.32 (s, 3H), 2.65 (s, 3H), 2.83 (br s, 1H), 3.29 (br s, 1H), 3.69 (br s, 1H), 4.35 (br s, 1H), Example 62

3-Mesityl-8-(2-methoxyethyl)-2,5-dimethyl-7-propyl-7,8-dihydro-6H-pyrazolo[1,5-a]pyrrolo[3,2-e]pyrimidine hydrochloride Pale Yellowish White Powder $^1$H NMR (400 MHz, CDCl$_3$) δ 1.04 (t, J=6.8 Hz, 3H), 1.34–1.50 (m, 2H), 1.61–1.77 (m, 1H), 1.88–2.10 (m, 1H), 2.03 (s, 6H), 2.15 (s, 3H), 2.32 (s, 3H), 2.64 (s, 3H), 2.76–2.86 (m, 1H), 3.23–3.25 (m, 1H), 3.39 (s, 3H), 3.70–3.85 (m, 3H), 4.51 (br s, 1H), 5.25–5.38 (m, 1H), 6.97 (s, 2H).

Example 63

3-Mesityl-8-[2-methoxy-1-(methoxymethyl)ethyl]-2,5-dimethyl-7,8-dihydro-6H-pyrazolo[1,5-a]pyrrolo[3,2-e]pyrimidene White Crystals $^1$H NMR (400 MHz, CDCl$_3$) δ 2.01 (s, 6H), 2.14 (s, 3H), 2.26 (s, 3H), 2.30 (s, 3H), 3.07 (t, J=9.2 Hz, 2H), 3.38 (s, 6H), 3.67 (dd, J 10.0, 4.8 Hz, 2H), 3.78 (dd, J=10.0, 6.8 Hz, 2H), 3.92 (t, J=9.2 Hz, 2H), 6.17–6.27 (m, 1H), 6.93 (s, 2H).

MS (ESI) m/z 409 MH$^+$.

Example 64

3-(2,4-Dimethylphenyl)-8-[2-methoxy-1-(methoxymethyl)ethyl]-2,5-dimethyl-7,8-dihydro-6H-pyrazolo[1,5-a]pyrrolo[3,2-e]pyrimidene hydrochloride White Crystals $^1$H NMR (400 MHz, CDCl$_3$) δ 2.15 (s, 3H), 2.21 (s, 3H), 2.37 (s, 3H), 2.69 (s, 3H), 3.15 (t, J=9.2 Hz, 2H), 3.40 (s, 6H), 3.66–3.74 (m, 2H), 3.77–3.85 (m, 2H), 4.19 (t, J=9.2 Hz, 2H), 6.25–6.33 (m, 1H), 7.07 (s, 1H), 7.08 (s, 1H), 7.16 (s, 1H).

MS (ESI) m/z 395 MH$^+$.

Example 65

3-(2,4-Dimethylphenyl)-8-(1-ethylpropyl)-2,5-dimethyl-7,8-dihydro-6H-pyrazolo[1,5-a]pyrrolo[3,2-e]pyrimidine hydrochloride White Crystals $^1$H NMR (400 MHz, CDCl$_3$) δ 0.98 (t, J=7.6 Hz, 3H), 1.00 (t, J=7.6 Hz, 3H), 1.70–1.90 (m, 4H), 2.16 (s, 3H), 2.24 (s, 3H), 2.37 (s, 3H), 2.69 (s, 3H), 3.17 (br s, 2H), 3.94 (br s, 2H), 5.87 (br s, 1H), 7.08 (s, 2H), 7.17 (s, 1H).

MS (ESI) m/z 363 MH$^+$.

Example 66

8-(1-Ethylpropyl)-3-mesityl-2,5-dimethyl-7,8-dihydro-6H-pyrazolo[1,5-a]pyrrolo[3,2-e]pyrimiden-7-one Water (7 mg) was added to a solution of potassium tert-butoxide (43 mg) in tetrahydrofuran (10 mL), and a solution of ethyl 2-[7-[(1-ethylpropyl)amino-3-mesityl-2,5-dimethylpyrazolo[1,5-a]pyrimidin-6-yl]acetate (84 mg) obtained in Preparation Example 30 in tetrahydrofuran (5 mL) was added dropwise, followed by stirring at room temperature for two hours. The reaction mixture was adjusted to about pH 5 with acetic acid, extracted twice with ethyl acetate, and then washed twice with brine. After the organic layer was dried over anhydrous magnesium sulfate, the solvent was evaporated, to give 23 mg of carboxylic acid, (2-[7-[(1-ethylpropyl)amino]-3-mesityl-2,5-dimethylpyrazolo[1,5-a]pyrimidin-6-yl]acetic acid). Methylene chloride (5 mL) was added to the carboxylic acid, 1-ethyl-3-(3-dimethylaminopropyl)-carbodiimide hydrochloride (WSC) (12 mg) and a catalytic amount of 4-dimethylaminopyridine were further added successively, followed by stirring at room temperature for one hour. After the solvent was removed, water was added thereto and the mixture was extracted twice with ethyl acetate. The organic layer was washed twice with brine, dried over anhydrous magnesium sulfate and the solvent was evaporated. The residue was purified by silica column chromatography, to give the title compound (20 mg) as deep-red crystals.

$^1$H NMR (400 MHz, CDCl$_3$) δ 1.00 (t, J=7.2 Hz, 6H), 1.23–1.36 (m, 2H), 1.57 (m, 2H), 2.03 (s, 6H), 2.25 (s, 3H), 2.34 (s, 3H), 2.63 (s, 3H), 4.02–4.25 (m, 2H), 5.86 (m, 1H), 6.96 (s, 2H).

Example 67

8-(1-Ethylpropyl)-3-mesityl-2,5-dimethyl-8H-pyrazolo[1,5-a]pyrrolo[3,2-e]pyrimidine A solution of 8-(1-ethylpropyl)-3-mesityl-2,5-dimethyl-7,8-dihydro-6H-pyrazolo[1,5-a]pyrrolo[3,2-e]pyrimidine (468 mg, 1,24 mmol) in N-methyl-2-pyrrolidinone (10 mL) was heated at 200° C. for 15 hours. Water was added to the reaction solution, and the mixture was extracted with ethyl acetate, washed with brine, and then dried over anhydrous magnesium sulfate. The solvent was evaporated, and the residue was subjected to silica gel column chromatography (10% ethyl acetate/hexane), to give the title compound (168 mg, 36%) as pale yellow crystals.

$^1$H NMR (400 MHz, CDCl$_3$) δ 0.88 (t, J=7.3 Hz, 6H), 1.80–2.08 (m, 4H), 2.04 (s, 6H), 2.24 (s, 3H), 2.33 (s, 3H), 2.63 (s, 3H), 5.88–6.02 (m, 1H), 6.59 (d, J=3.5 Hz, 1H), 6.85 (d, J=3.6 Hz, 1H), 6.97 (s, 2H).

According to the method described in the above Example 67, compounds of Examples 68–71 were synthesized.

Example 68

8-(1-Ethylpropyl)-2,5-dimethyl-3-(2,4,6-trimethoxyphenyl)-8H-pyrazolo[1,5-a]pyrrolo[3,2-e]pyrimidine Pale Pink Crystals $^1$H NMR (400 MHz, CDCl$_3$) δ 0.87 (t, J=7.3 Hz, 6H), 1.76–2.04 (m, 4H), 2.32 (s, 3H), 2.63 (s, 3H), 3.75 (s, 6H), 3.87 (s, 3H), 5.85–6.03 (m, 1H), 6.28 (s, 2H), 6.55 (d, J=3.5 Hz, 1H), 6.81 (d, J=3.5 Hz, 1H).

Example 69

3-(2,4-Dichlorophenyl)-8-(1-ethylpropyl)-2,5-dimethyl-8H-pyrazolo[1,5-a]pyrrolo[3,2-e]pyrimidine hydrochloride White Crystals $^1$H NMR (400 MHz, CDCl$_3$) δ 0.79 (t, J=7.3 Hz, 6H), 1.70–1.99 (m, 4H), 2.33 (s, 3H), 2.60 (s, 3H), 5.79–5.97 (m, 1H), 6.54 (d, J=3.5 Hz, 1H), 6.81 (d, J=3.5 Hz, 1H), 7.25 (dd, J=2.2, 8.2 Hz, 1H), 7.34 (d, J=8.2 Hz, 1H), 7.46 (d, J=2.2 Hz, 1H).

Example 70

3-(2,4-Dichlorophenyl)-2,5-dimethyl-8-(1-propylbutyl)-8H-pyrazolo[1,5-a]pyrrolo[3,2-e]pyrimidine hydrochloride Pale Yellow Crystals $^1$H NMR (400 MHz, CDCl$_3$) δ 0.90 (t, J=7.3 Hz, 6H), 1.06–1.22 (m, 2H), 1.24–1.40 (m, 2H), 1.77–1.92 (m, 4H), 2.39 (s, 3H), 2.66 (s, 3H), 6.06–6.23 (m, 1H), 6.61 (d, J=3.5 Hz, 1H), 6.88 (d, J=3.5 Hz, 1H), 7.32 (dd, J=2.0, 8.2 Hz, 1H), 7.41 (d, J=8.2 Hz, 1H), 7.53 (d, J=2.0 Hz, 1H).

Example 71

3-(4-Bromophenyl)-8-(1-ethylpropyl)-2,5-dimethyl-8H-pyrazolo[1,5-a]pyrrolo[3,2-e]pyrimidine Yellow Crystals $^1$H NMR (400 MHz, CDCl$_3$) δ 0.84 (t, J=7.3 Hz, 6H), 1.76–2.06 (m, 4H), 2.65 (s, 3H), 2.75 (s, 3H), 5.87–6.02 (m, 1H), 6.65 (d, J=3.5 Hz, 1H), 6.91 (d, J=3.5 Hz, 1H), 7.72 (d, J=8.6 Hz, 2H), 8.02 (d, J=8.6 Hz, 2H).

MS (ESI) m/z 413 MH$^+$.

Example 72

3-Mesityl-2,5-dimethyl-7,8-dihydro-6H-pyrazolo[1,5-a]pyrrolo[3,2-e]pyrimidine

Concentrated hydrochloric acid (1 mL) was added to a mixture of 8-benzyl-3-mesityl-2,5-dimethyl-7,8-dihydro-6H-pyrazolo[1,5-a]pyrrolo[3,2-e]pyrimidine (4.7 g) which is a free compound of the compound prepared in Example 26, water-containing 5% palladium carbon (3.0 g) and ethanol (300 mL), followed by stirring at room temperature for two days in hydrogen atmosphere. After filtering through Celite, the filtrate was evaporated, which was neutralized with an aqueous solution of sodium bicarbonate. The resulting solid was filtered, and dissolved in a mixed solution of dichloromethane, methanol and ethyl acetate. After filtering off the insoluble matter, the mixture was purified by silica gel column chromatography (10–67% ethyl acetate/hexane), to give the title compound as white crystals (2.6 g). 1.0 g of a raw material was recovered.

$^1$H NMR (400 MHz, CDCl$_3$) δ 2.02 (s, 6H), 2.21 (s, 3H), 2.31 (s, 3H), 2.36 (s, 3H), 3.21 (t, J=8.8 Hz, 2H), 3.94 (t, J=8.8 Hz, 2H), 5.95 (br s, 1H), 6.95 (s, 2H).

MS (ESI) m/z 307 MH$^+$.

Example 73

3-Mesityl-2,5-dimethyl-8H-pyrazolo[1,5-a]pyrrolo[3,2-e]pyrimidine 1.0 M tert-BuOK/THF (0.29 mL, 0.29 mmol) was added to a solution of 3-mesityl-2,5-dimethyl-7,8-dihydro-6H-pyrazolo[1,5-a]pyrrolo[3,2-e]pyrimidine (80 mg, 0.261 mmol) prepared in Example 72 in THF (4 mL), which was at room temperature, followed by stirring at room temperature for 15 hours. Water was added, and the mixture was extracted with ethyl acetate, washed with brine, dried over MgSO$_4$ and the solvent was evaporated. The residue was subjected to silica gel column chromatography (25% ethyl acetate/hexane), to give the title compound (50 mg, 63%) as white crystals.

$^1$H NMR (400 MHz, CDCl$_3$) δ 2.05 (s, 6H), 2.32 (s, 3H), 2.34 (s, 3H), 2.69 (s, 3H), 6.63 (d, J=2.9 Hz, 1H), 6.96 (d, J=3.5 Hz, 1H), 6.99 (s, 2H), 11.1 (s, 1H).

MS (ESI) m/z 305 MH$^+$.

Example 74

1-(3-Mesityl-2,5-dimethyl-7,8-dihydro-6H-pyrazolo[1,5-a]pyrrolo[3,2-e]pyrimidin-8-yl)-1-butanone Triethylamine (0.091 mL, 0.652 mmol) was added to a solution of 3-mesityl-2,5-dimesityl-7,8-dihydro-6H-pyrazolo[1,5-a]pyrrolo[3,2-e]pyrimidine (100 mg, 0.326 mmol) which was prepared in Example 71 in dichloromethane (4 mL), butyryl chloride (0.037 mL, 0.358 mmol) was added dropwise at room temperature, followed by stirring for two hours. Water was added to the reaction solution, and the mixture was extracted with ethyl acetate, washed with brine, and then dried over $MgSO_4$. The solvent was evaporated, and the residue was subjected to silica gel column chromatography (7 g), to give the title compound (52 mg, 42%) as a pale yellow oil from a fraction of ethyl acetate-hexane (1:4 v/v).

$^1$H NMR (400 MHz, $CDCl_3$) δ 0.98 (t, J=7.3 Hz, 3H), 1.71–1.86 (m, 2H), 2.00 (s, 6H), 2.25 (s, 3H), 2.33 (s, 3H), 2.43 (s, 3H), 2.99 (t, J=7.3 Hz, 2H), 3.06 (t, J=8.0 Hz, 2H), 4.38 (t, J=8.0 Hz, 2H), 6.97 (s, 2H).

Example 75

8-(Butylsulfonyl)-3-mesityl2,5-dimethyl-7,8-dihydro-6H-pyrazolo[1,5-a]pyrrolo[3,2-e]pyrimidine Triethylamine (0.091 mL, 0.652 mmol) was added to a solution of 3-mesityl-2,5-dimethyl-7,8-dihydro-6H-pyrazolo[1,5-a]pyrrolo[3,2-e]pyrimidine (100 mg, 0.326 mmol) prepared in Example 72 in dichloromethane (5 mL). Butanesulfonyl chloride (0.047 mL, 0.358 mmol) was added dropwise at room temperature, followed by stirring for two hours. Water was added to the reaction solution, extracted with ethyl acetate, washed with brine, dried over $MgSO_4$, and the solvent was evaporated. The residue was subjected to silica gel column chromatography, to give the title compound (38 mg, 27%) as white crystals from a fraction of ethyl acetate-hexane (1:4 v/v).

$^1$H NMR (400 MHz, $CDCl_3$) δ 1.03 (t, J=7.3 Hz, 3H), 1.54–1.65 (m, 2H), 1.99 (s, 6H), 1.94–2.07 (m, 2H), 2.24 (s, 3H), 2.32 (s, 3H), 2.41 (s, 3H), 3.17 (t, J=8.2 Hz, 2H), 4.34 (t, J=7.9 Hz, 2H), 4.44 (t, J=8.2 Hz, 2H), 6.96 (s, 2H).

MS (ESI) m/z 427 $MH^+$.

Example 76

4-[8-1-Ethylpropy)-2,5-dimethyl-7,8-dihydro-6H-pyrazolo[1,5-a]pyrrolo[3,2-e]pyrimidin-3-yl]benzonitrile CuCN (585 mg, 6.53 mmol) was added to a solution of 3-(4-buromophenyl)-8-(1-ethylpropyl)-2,5-dimethyl-7,8-dihydro-6H-pyrazolo[1,5-a]pyrrolo[3,2-e]pyrimidine (1.5 g, 3.63 mmol) which was prepared in Example 14 in N-methyl-2-pyrrolidinone, followed by stirring under heating under reflux for six hours. The reaction mixture was cooled to room temperature, water was added to the reaction solution. The resulting solid was collected by filtration and subjected to silica gel column chromatography (100 g), to give the title compound (332 mg, 25%) as a pale yellow powder from a fraction of ethyl acetate-hexane (1:2 v/v).

Example 77

2-Chloro-2-(2-furyl)-7,8-dihydro-6H-pyrrolo[3,2-e][1,2,4]triazolo[1,5-a]pyrimidine $^1$H NMR (400 MHz, DMSO-$d_6$) δ 3.22 (t, J=6.8 Hz, 2H), 3.72 (t, J=6.8 Hz, 2H), 6.71 (d, J=3.7 Hz, 1H), 7.17 (d, J=3.7 Hz, 1H), 7.93 (s, 1H), 8.25 (br s, 1H).

Example 78

N5-(2-Pyridylmethyl)-2-(2-furyl)-7,8-dihydro-6H-pyrrolo[3,2-e][1,2,4]triazolo[1,5-a]pyrimidin-5-amine

Example 79

8-(1-Ethylpropyl)-2,5-dimethyl-3-(4-methyl-1,3-benzodioxol-5-yl)-7,8-dihydro-6H-pyrazolo[1,5-a]pyrrolo[3,2-e]pyrimidine Pale Yellow Crystals $^1$H NMR (400 MHz, $CDCl_3$) δ 0.84–1.04 (m, 6H), 1.50–1.70 (m, 4H), 2.06 (s, 3H), 2.28 (s, 3H), 2.30 (s, 3H), 3.08 (t, J=9.2 Hz, 2H), 3.67 (t, J=9.2 Hz, 2H), 5.58–5.72 (m, 1H), 5.97 (d, J=9.5 Hz, 2H), 6.71 (dd, J=7.9, 0.6 Hz, 1H), 6.76 (d, J=7.9 Hz, 1H).

MS (ESI) m/z 393 $MH^+$.

Example 80

8-(1-Ethylpropyl)-2,5-dimethyl-3-(4-methyl-1,3-benzodioxol-5-yl)-8H-pyrazolo[1,5-a]pyrrolo[3,2-e]pyrimidine Pale Yellow Amorphous $^1$H NMR (400 MHz, $CDCl_3$) δ 0.84 (t, J 7.3 Hz, 3H), 0.89 (t, J=7.3 Hz, 3H), 1.76–2.05 (m, 4H), 2.09 (s, 3H), 2.37 (s, 3H), 2.66 (s, 3H), 6.00 (d, J=6.0 Hz, 2H), 5.88–6.04 (m, 1H), 6.60 (d, J=3.5 Hz, 1H), 6.75 (d, J=7.9 Hz, 1H), 6.81 (d, J=8.0 Hz, 1H), 6.86 (d, J=3.5 Hz, 1H).

Example 81

2,5-Dimethyl-3-(4-methyl-1,3-benzodioxol-5-yl)-8H-pyrazolo[1,5-a]pyrrolo[3,2-e]pyrimidine Pale Yellow Crystals $^1$H NMR (400 MHz, $CDCl_3$) δ 2.12 (s, 3H), 2.48 (s, 3H), 2.75 (s, 3H), 6.01 (d, J=9.7 Hz, 2H), 6.64 (s, 1H), 6.77 (d, J=7.9 Hz, 1H), 6.85 (d, J=7.9 Hz, 1H), 6.98 (s, 1H), 12.90 (s, 1H).

Example 82

3-Mesityl-2,5,7-trimethyl-8H-pyrazolo[1,5-a]pyrrolo[3,2-e]pyrimidine

Pale Yellow Crystals $^1$H NMR (400 MHz, $CDCl_3$) δ 2.06 (s, 6H), 2.32 (d, J=1.1 Hz, 3H), 2.33 (s, 3H), 2.34 (s, 3H), 2.64 (s, 3H), 6.25 (s, 1H), 6.98 (s, 2H), 11.50 (s, 1H).

Example 83

3-Mesityl-2,5,8-trimethyl-8H-pyrazolo[1,5-a]pyrrolo[3,2-e]pyrimidine

Pale Yellow Crystals $^1$H NMR (400 MHz, $CDCl_3$) δ 2.02 (s, 6H), 2.26 (s, 3H), 2.33 (s, 3H), 2.62 (s, 3H), 4.40 (s, 3H), 6.52 (d, J=3.6 Hz, 1H), 6.72 (d, J=3.2 Hz, 1H), 6.97 (s, 2H).

MS (ESI) m/z 319 $MH^+$.

Example 84

8-Ethyl-3-mesityl-2,5-dimethyl-8H-pyrazolo[1,5-a]pyrrolo[3,2-e]pyrimidine hydrochloride Pale Yellow Crystals MS (ESI) m/z 333 $MH^+$.

Example 85

3-Mesityl-2,5-dimethyl-8-propyl-8H-pyrazolo[1,5-a]pyrrolo[3,2-e]pyrimidine hydrochloride Pale Yellow Crystals MS (ESI) m/z 347 $MH^+$.

Example 86

8-Butyl-3-mesityl-2,5-dimethyl-8H-pyrazolo[1,5-a]pyrrolo[3,2 e]pyrimidine hydrochloride Pale Yellow Crystals MS (ESI) m/z 361 $MH^+$.

Example 87

2-[8-(1-Ethylpropyl)-2,5-dimethyl-7,8-dihydro-6H-pyrazolo[1,5-a]pyrrolo[3,2-e]pyrimidin-3-yl]-5-methylphenol White Crystals ¹H NMR (4001 Hz, CDCl₃) δ 0.93 (t, J=7.2 Hz, 6H), 1.56–1.70 (m, 4H), 2.33 (s, 3H), 2.34 (s, 3H), 2.56 (s, 3H), 3.10 (t, J=8.4 Hz, 2H), 3.71 (t, J=8.8 Hz, 2H), 5.61–5.63 (m, 1H), 6.77 (dd, J=1.6, 7.6 Hz, 1H), 6.90 (br s, 1H), 7.28 (d, J=7.6 Hz, 1H).

Example 88

3-Mesityl-2,5,7,8-tetramethyl-8H-pyrazolo[1,5-a]pyrrolo[3,2-e]pyrimidine

White Crystals

¹H NMR (400 MHz, CDCl₃) δ 2.02 (s, 6H), 2.26 (s, 3H), 2.33 (s, 3H), 2.41 (s, 3H), 2.58 (s, 3H), 4.34 (s, 3H), 6.28 (s, 1H), 6.96 (s, 2H).

Example 89

2-(8-(1-Ethylpropyl)-2,5-dimethyl-8H-pyrazolo[1,5-a]pyrrolo[3,2-e]pyrimidin-3-yl)-3,5-dimethylphenyl methyl ether Yellow Amorphous ¹H NMR (400 MHz, CDCl₃) δ 0.85–0.90 (m, 6H), 1.90–2.05 (m, 4H), 2.09 (s, 3H), 2.29 (s, 3H), 2.38 (s, 3H), 2.63 (s, 3H), 3.73 (s, 3H), 5.88–6.03 (m, 1H), 6.57 (d, J=3.2 Hz, 1H), 6.66 (s, 1H), 6.79 (s, 1H), 6.83 (d, J=3.2 Hz, 1H).

Example 90

3-Mesityl-2,5-dimethyl-8-pentyl-8H-pyrazolo[1,5-a]pyrrolo[3,2-e]pyrimidine hydrochloride White Crystals MS (ESI) m/z 375 MH⁺.

Example 91

8-Hexyl-3-mesityl-2,5-dimethyl-8H-pyrazolo[1,5-a]pyrrolo[3,2-e]pyrimidine hydrochloride MS (ESI) m/z 389 MH⁺.

Example 92

8-Heptyl-3-mesityl-2,5-dimethyl-8H-pyrazolo[1,5-a]pyrrolo[3,2-e]pyrimidine hydrochloride MS (ESI) m/z 403 MH⁺.

Example 93

3-(2-Bromo-4,6-dimethylphenyl)-8-(1-ethylpropyl)-2,5-8H-pyrazolo[1,5-a]pyrrolo[3,2-e]pyrimidine ¹H NMR (400 MHz, CDCl₃) δ 0.88 (td, J=4.8 Hz, 2.8 Hz, 6H), 1.82–1.93 (m, 2H), 1.95–2.02 (m, 2H), 2.09 (s, 3H), 2.30 (s, 3H), 2.34 (s, 3H), 2.64 (s, 3H), 5.90–6.02 (m, 1H), 6.60 (d, J=3.6 Hz, 1H), 6.86 (d, J=3.6 Hz, 1H), 7.07 (s, 1H), 7.37 (s, 1H).

MS (ESI) m/z 441 MH⁺.

Example 94

2-Cyclobutyl-8-(1-ethylpropyl)-3-mesityl-5-methyl-7,8-dihydro-6H-pyrazolo[1,5-1,5-a]pyrrolo[3,2-e]pyrimidine White Crystals ¹H NMR (400 MHz, CDCl₃) δ 0.98 (t, J=7.2 Hz, 6H), 1.60–1.70 (m, 4H), 1.82–1.92 (m, 2H), 1.98 (s, 6H), 2.10–2.20 (m, 2H), 2.26 (s, 3H), 2.29–2.40 (m, 2H), 2.30 (s, 3H), 3.08 (t, J=9.2 Hz, 2H), 3.29 (q, J=8.4 Hz, 1H), 3.69 (t, J=9.2 Hz, 2H), 5.70–5.80 (m, 1H), 6.91 (s, 2H).

Example 95

3-Mesityl-2,5-dimethyl-8-phenyl-8H-pyrazolo[1,5-a]pyrrolo[3,2-e]pyrimidine

Yellow Crystals

¹H NMR (400 MHz, CDCl₃) δ 2.00 (s, 6H), 2.11 (s, 3H), 2.33 (s, 3H), 2.69 (s, 3H), 6.71 (d, J=3.2 Hz, 1H), 6.95 (d, J=3.2 Hz, 1H), 6.91 (s, 2H), 7.49–7.56 (m, 3H), 7.60–7.66 (m, 2H).

Example 96

8-(2-Ethylphenyl)-mesityl-2,5-dimethyl-8H-pyrazolo[1,5-a]pyrrolo[3,2-e]pyrimidine Yellow Amorphous ¹H NMR (400 MHz, CDCl₃) δ 1.03 (t, J=7.6 Hz, 3H), 1.98 (s, 3H), 1.99 (s, 3H), 2.01 (s, 3H), 2.32 (s, 3H), 2.30–2.44 (m, 2H), 2.70 (s, 3H), 6.69 (d, J=3.2 Hz, 1H), 6.80 (d, J=3.6 Hz, 1H), 6.95 (s, 2H), 7.36 (dd, J=7.6, 7.6 Hz, 1H), 7.40–7.46 (m, 2H), 7.50 (dd, J=7.2, 7.6 Hz, 1H).

Example 97

8-(2,6-Dimethylphenyl)-3-mesityl-2,5-dimethyl-8H-pyrazolo[1,5-a]pyrrolo[3,2-e]pyrimidine Red Crystals ¹H NMR (400 MHz, CDCl₃) δ 2.00 (s, 6H), 2.01 (s, 3H), 2.03 (s, 3H), 2.32 (s, 3H), 2.70 (s, 3H), 6.70 (d, J=3.2 Hz, 1H), 6.73 (d, J=3.6 Hz, 1H), 6.95 (s, 2H), 7.21 (d, J=7.6 Hz, 2H), 7.34 (dd, J=7.6, 7.6 Hz, 1H).

Example 98

3-Mesityl-2,5-dimethyl-8-(1-propylbutyl)-8H-pyrazolo[1,5-a]pyrrolo[3,2-e]pyrimidine Brown Oil ¹H NMR (400 MHz, CDCl₃) δ 0.90 (t, J=7.2 Hz, 6H), 1.05–1.20 (m, 4H), 1.80–1.94 (m, 4H), 2.03 (s, 6H), 2.23 (s, 3H), 2.33 (s, 3H), 2.62 (s, 3H), 6.12–6.20 (m, 1H), 6.58 (d, J=3.6 Hz, 1H), 6.86 (d, J=3.6 Hz, 1H), 6.97 (s, 2H).

Example 99

2-Cyclopropyl-8-(1-ethylpropyl)-3-mesityl-5-methyl-8H-pyrazolo[1,5-a]pyrrolo[3,2-e]pyrimidine Brown Oil ¹H NMR (400 MHz, CDCl₃) δ 0.84–0.92 (m, 8H), 1.01–1.03 (m, 2H), 1.65–1.75 (m, 1H), 1.90–2.00 (m, 4H), 2.11 (s, 6H), 2.34 (s, 3H), 2.61 (s, 3H), 5.75–5.90 (m, 1H), 6.57 (d, J=3.6 Hz, 1H), 6.83 (d, J=3.6 Hz, 1H), 6.98 (s, 2H).

Example 100

8-(1-Ethylpropyl)-3-mesityl-5-methyl-8H-pyrazolo[1,5-a]pyrrolo[3,2-e]pyrimidine

Brown Oil

¹H NMR (400 MHz, CDCl₃) δ 0.88 (t, J=7.2 Hz, 6H), 1.80–2.10 (m, 4H), 2.14 (s, 6H), 2.33 (s, 3H), 2.67 (s, 3H), 5.88–6.00 (m, 1H), 6.64 (d, J=3.2 Hz, 1H), 6.92 (d, J=3.6 Hz, 1H), 6.98 (s, 2H), 7.87 (s, 1H).

Example 101

2-Ethyl-8-(1-ethylpropyl)-3-mesityl-5-methyl-8H-pyrazolo[1,5-a]pyrrolo[3,2-e]pyrimidine Brown Oil ¹H NMR (400 MHz, CDCl₃) δ 0.89 (t, J=7.2 Hz, 6H), 1.19 (t, J=7.6 Hz, 3H), 1.80–2.01 (m, 4H), 2.03 (s, 6H), 2.33 (s, 3H), 2.59 (q, J=7.6 Hz, 2H), 2.62 (s, 3H), 5.90–6.10 (m, 1H), 6.59 (d, J=3.6 Hz, 1H), 6.85 (d, J=3.2 Hz, 1H), 6.97 (s, 2H).

Example 102

8-(2,3-Dihydro-1H-2-idenyl)-3-mesityl-2,5-dimethyl-8H-pyrazolo[1,5-a]pyrrolo[3,2-e]pyrimidine White Crystals
$^1$H NMR (400 MHz, CDCl$_3$) δ 2.04 (s, 6H), 2.26 (s, 3H), 2.34 (s, 3H), 2.61 (s, 3H), 3.33 (dd, J=4.8, 16.4 Hz, 2H), 3.72 (dd, J=8.0, 16.4 Hz, 2H), 6.47 (d, J=3.2 Hz, 1H), 6.69 (d, J=3.6 Hz, 1H), 6.96–7.00 (m, 3H), 7.25–7.33 (m, 4H).

Example 103

N-5-[8-(1-Ethylpropyl)-2,5-dimethyl-8H-pyrazolo[1,5-a]pyrrolo[3,2-pyrimidin-3-yl)-4-methyl-2-pyridyl-N,N-dimethylamine White Crystals
$^1$H NMR (400 MHz, CDCl$_3$) δ 0.87 (t, J=7.6 Hz, 6H), 1.80–2.02 (m, 4H), 2.19 (s, 3H), 2.38 (s, 3H), 2.65 (s, 3H), 3.12 (s, 6H), 5.90–6.02 (m, 1H), 6.51 (s, 1H), 6.60 (d, J=3.6 Hz, 1H), 6.85 (d, J=3.2 Hz, 1H), 8.07 (s, 1H).

Example 104

3-(4-Bromo-2,6-dimethylphenyl)-8-(1-ethylpropyl)-2,5-dimethyl-7,8-dihydro-6H-pyrazolo[1,5-a]pyrrolo[3,2-e]pyrimidine White Crystals
$^1$H NMR (400 MHz, CDCl$_3$) δ 0.95 (t, J=7.4 Hz, 6H), 1.53–1.74 (m, 4H), 2.03 (s, 6H), 2.13 (s, 3H), 2.27 (s, 3H), 3.09 (t, J=9.2 Hz, 2H), 3.68 (t, J=9.2 Hz, 2H), 5.56–5.70 (m, 1H), 7.25 (s, 2H).

Example 105

3-(4-Bromo-2,6-dimethylphenyl)-8-(1-ethylpropyl)-2,5-dimethyl-8H-pyrazolo[1,5-a]pyrrolo[3,2-e]pyrimidine White Crystals
$^1$H NMR (400 MHz, CDCl$_3$) δ 0.88 (t, J=7.3 Hz, 6H), 1.70–2.10 (m, 4H), 2.05 (s, 6H), 2.22 (s, 3H), 2.64 (s, 3H), 5.82–6.04 (m, 1H), 6.61 (d, J=3.2 Hz, 1H), 6.87 (d, J=3.5 Hz, 1H), 7.95 (s, 2H).

Example 106

4-[8-(1-Ethylpropyl)-2,5-dimethyl-7,8-dihydro-6H-pyrazolo[1,5-a]pyrrolo[3,2-e]pyrimidin-3-yl]-3,5-dimethylbenzaldehyde Yellow Amorphous
$^1$H NMR (400 MHz, CDCl$_3$) δ 0.96 (t, J=7.3 Hz, 6H), 1.52–1.74 (m, 4H), 2.15 (s, 3H), 2.16 (s, 6H), 2.28 (s, 3H), 3.10 (t, J=9.2 Hz, 2H), 3.70 (t, J=9.1 Hz, 2H), 5.56–5.71 (m, 1H), 7.62 (s, 2H), 9.98 (s, 1H).

Example 107

1-4-[8-(1-Ethylpropyl)-2,5 dimethyl-7,8-dihydro-6H-pyrazolo[1,5-a]pyrrolo[3,2-e]pyrimidin-3-yl]-3,5-dimethylphenyl-1-ethanone Pale Yellow Crystals
$^1$H NMR (400 MHz, CDCl$_3$) δ 0.96 (t, J=7.4 Hz, 6H), 1.50–1.74 (m, 4H), 2.13 (s, 6H), 2.14 (s, 3H), 2.27 (s, 3H), 2.60 (s, 3H), 3.09 (t, J=9.2 Hz, 2H), 3.69 (t, J=9.2 Hz, 2H), 5.55–5.72 (m, 1H), 7.71 (s, 2H).

Example 108

1-4-[8-(Ethylpropyl)-2,5-dimethyl-8H-pyrazolo[1,5-a]pyrrolo[3,2-e]pyrimidin-3-yl]-3,5-dimethylphenyl-1-ethanone White Crystals
$^1$H NMR (400 MHz, CDCl$_3$) δ 0.89 (t, J=7.3 Hz, 6H), 1.80–2.08 (m, 4H), 2.14 (s, 6H), 2.23 (s, 3H), 2.62 (s, 3H), 2.64 (s, 3H), 5.88–6.02 (m, 1H), 6.61 (d, J=3.5 Hz, 1H), 6.88 (d, J=3.5 Hz, 1H), 7.74 (s, 2H).

Example 109

8-(1-Ethylpropyl)-3-(4-isopropenyl-2,5-dimethylphenyl)-2,5-dimethyl-8H-pyrazolo[1,5-a]pyrrolo[3,2-e]pyrimidine White Crystals
$^1$H NMR (400 MHz, CDCl$_3$) δ 0.89 (t, J=7.4 Hz, 6H), 1.80–2.09 (m, 4H), 2.10 (s, 6H), 2.19 (s, 3H), 2.26 (s, 3H), 2.64 (s, 3H), 5.07 (s, 1H), 5.41 (s, 1H), 5.86–6.06 (m, 1H), 6.61 (d, J=3.5 Hz, 1H), 6.87 (d, J=3.5 Hz, 1H), 7.27 (s, 2H).

Example 110

2-[8-(1-Ethylpropyl)-2,5-dimethyl-8H-pyrazolo[1,5-a]pyrrolo[1,3-e]pyrimidin-3-yl]-3,5-dimethylphenol Yellowish White Amorphous
$^1$H NMR (400 MHz, CDCl$_3$) δ 0.85–0.90 (m, 6H), 1.80–1.92 (m, 2H), 1.92–2.05 (m, 2H), 2.12 (s, 3H), 2.33 (s, 3H), 2.34 (s, 3H), 2.67 (s, 3H), 5.93 (br s, 1H), 6.63 (d, J=3.6 Hz, 1H), 6.75 (s, 2H), 6.89 (d, J=3.2 Hz, 1H).

Example 111

2-(3-Mesityl-2,5,7-trimethyl-8H-pyrazolo[1,5-a]pyrrolo[3,2-e]pyrimidin-8-yl)ethyl methyl ether Yellowish Brown Crystals
$^1$H NMR (400 MHz, CDCl$_3$) δ 2.02 (s, 3H), 2.22 (s, 3H), 2.30 (s, 3H), 2.46 (s, 3H), 2.61 (s, 3H), 3.36 (s, 3H), 3.89 (t, J=5.66 Hz, 2H), 4.87 (t, J=5.6 Hz, 2H), 6.27 (s, 1H), 6.92 (s, 2H).

Example 112

2-(8-(1-Ethylpropyl)-2,5-dimethyl-8H-pyrazolo[1,5-a]pyrrolo[3,2-e]pyrimidin-3-yl)-3,5-dimethylphenyl methanesulfonate Yellow Oil
$^1$H NMR (400 MHz, CDCl$_3$) δ 0.81–0.91 (m, 6H), 1.80–1.94 (m, 2H), 1.94–2.04 (m, 2H), 2.16 (s, 3H), 2.32 (s, 3H), 2.39 (s, 3H), 2.40 (s, 3H), 2.64 (s, 3H), 5.95 (br s, 1H), 6.61 (d, J=3.6 Hz, 1H), 6.89 (d, J=3.6 Hz, 1H), 7.12 (d, J=4.0 Hz, 1H), 7.19 (d, J=4.0 Hz, 1H).

Example 113

8-Benzyl-3-mesityl-2,5-dimethyl-8H-pyrazolo[1,5-a]pyrrolo[3,2-e]pyrimidine hydrochloride Grayish White Crystals
MS (ESI) m/z 395 MH$^+$.

Example 114

3-(2-Bromo-4,6-dimethylphenyl)-8-(2-methoxyethyl)-2,5-dimethyl-8H-pyrazolo[1,5-a]pyrrolo[1,2-e]pyrimidine hydrochloride White Crystals
MS (ESI) m/z 427, 429 MH$^+$.

Example 115

3-Mesityl-2,5-dimethyl-8-(2-pyridlymethyl)-8H-pyrazolo[1,5-e]pyrimidine hydrochloride Brown Crystals $^1$H NMR (400 MHz, CDCl$_3$) δ 1.92 (s, 6H), 2.11 (s, 3H), 2.30 (s, 3H), 2.66 (s, 3H), 6.23 (s, 2H), 6.89 (d, J=3.6 Hz, 1H), 6.98 (s, 2H), 7.32 (d, J=3.6 Hz, 1H), 7.35 (d, J=7.2 Hz, 1H), 7.45 (dd, J=7.2 Hz, 4.8 Hz, 1H), 7.94 (dd, J=7.2 Hz, 7.2 Hz, 1H), 8.59 (d, J=4.8 Hz, 1H).

MS (ESI) m/z 396 MH$^+$.

Example 116

3-Mesityl-2,5-dimethyl-8-(3-pyridylmethyl)-8H-pyrazolo[1,5-a]pyrrolo[2,5-d]pyrimidine hydrochloride Pale Yellow Crystals MS (ESI) m/z 396 MH$^+$.

Example 117

3-Mesityl-2,5-dimethyl-8-(4-pyridylmethyl)-8H-pyrazolo[1,5-a]pyrrolo[3,2-e]pyrimidine hydrochloride Pale Yellow Crystals MS (ESI) m/z 396 MH$^+$.

Example 118

Ethyl 2-(2-(8-(1-ethylpropyl)-2,5-dimethyl-8H-pyrazolo[1,5-a]pyrrolo[3,2-e]pyrimidin-3-yl)-3,5-dimethylphenoxy)acetate Yellowish White Crystals $^1$H NMR (400 MHz, CDCl$_3$) δ 0.85–0.91 (m, 6H), 1.21 (t, J=7.2 Hz, 3H), 1.79–1.93 (m, 2H), 1.93–2.03 (m, 2H), 2.11 (s, 3H), 2.35 (s, 3H), 2.36 (s, 3H), 2.63 (s, 3H), 4.16 (q, J=7.2 Hz, 2H), 4.45 (d, J=16.4 Hz, 1H), 4.51 (d, J=16.0 Hz, 1H), 5.98 (br s, 1H), 6.55 (s, 1H), 6.58 (d, J=3.2 Hz, 1H), 6.82–6.86 (m, 1H), 6.84 (s, 1H).

Example 119

1-(2-(8-(1-Ethylpropyl)-2,5-dimethyl-8H-pyrazolo[1,5-a]pyrrolo[3,2-e]pyrimidin-3-yl)-3,5-dimethylphenoxy)-2-methyl-2-propanol Yellow Amorphous $^1$H NMR (400 MHz, CDCl$_3$) δ 0.78 (t, J=7.2 Hz, 3H), 0.84 (s, 3H), 0.91 (t, J=7.6 Hz, 3H), 1.02 (s, 3H), 1.70–1.85 (m, 2H), 1.85–2.03 (m, 2H), 2.12 (s, 3H), 2.29 (s, 3H), 2.36 (s, 3H), 2.64 (s, 3H), 3.68 (d, J=8.8 Hz, 1H), 3.80 (d, J=9.2 Hz, 1H), 5.98 (br s, 1H), 6.60 (d, J=3.6 Hz, 1H), 6.63 (s, 1H), 6.79 (s, 1H), 6.85 (d, J=3.6 Hz, 1H).

Example 120

(2-(8-(1-Ethylpropyl)-2,5-dimethyl-8H-pyrazolo[1,5-a]pyrrolo[3,2-e]pyrimidin-3-yl)-3,5-dimethylphenoxy)methylcyanide Pale Orange Crystals $^1$H NMR (400 MHz, CDCl$_3$) δ 0.88 (t, J=7.2 Hz, 6H), 1.79–1.92 (m, 2H), 1.92–2.03 (m, 2H), 2.11 (s, 3H), 2.29 (s, 3H), 2.39 (s, 3H), 2.64 (s, 3H), 4.57 (s, 2H), 5.94 (br s, 1H), 6.60 (d, J=3.6 Hz, 1H), 6.79 (s, 1H), 6.60 (d, J=3.6 Hz, 1H), 6.94 (s, 1H).

Example 121

2-(2-(8-(1-Ethylpropyl)-2,5-dimethyl-8H-pyrazolo[1,5-a]pyrrolo[3,2-e]pyrimidin-3-yl)-3,5-dimethylphenoxy)acetamide Yellow Amorphous $^1$H NMR (400 MHz, CDCl$_3$) δ 0.876 (t, J=7.2 Hz, 3H), 0.880 (t, J=7.2 Hz, 3H), 1.80–1.92 (m, 2H), 1.92–2.06 (m, 2H), 2.13 (s, 3H), 2.33 (s, 3H), 2.37 (s, 3H), 2.57 (s, 3H), 4.39 (d, J=16.0 Hz, 1H), 4.56 (d, J=16.4 Hz, 1H), 5.46 (br s, 1H), 5.96 (br s, 1H), 6.61 (d, J=3.6 Hz, 1H), 6.63 (s, 1H), 6.84 (s, 1H), 6.88 (d, J=3.2 Hz, 1H), 8.32 (br s, 1H).

Example 122

(2,4-Dimethoxy-6-methylphenyl)-8-(1-ethylpropyl)-2,5-dimethyl-8H-pyrazolo[1,5-a]pyrrolo[3,2-e]pyrimidine Pale Yellow Crystals $^1$H NMR (400 MHz, CDCl$_3$) δ 0.87 (t, J=7.2 Hz, 3H), 0.88 (t, J=7.2 Hz, 3H), 1.80–2.02 (m, 4H), 2.11 (s, 3H), 2.27 (s, 3H), 2.63 (s, 3H), 3.72 (s, 3H), 3.85 (s, 3H), 5.90–6.02 (m, 1H), 6.43 (d, J=2.8 Hz, 1H), 6.51 (d, J=2.4 Hz, 1H), 6.57 (d, J=3.6 Hz, 1H), 6.83 (d, J=3.6 Hz, 1H).

Example 123

3-(2-Bromo-4,6-dimethylphenyl)-8-[1-(methoxymethylpropyl]-2,5-dimethyl-8H-pyrazolo[1,5-a]pyrrolo[3,2-e]pyrimidine hydrochloride MS (ESI) m/z 455, 457 MH$^+$.

Example 124

3-(2-Bromo-4,6-dimethylphenyl)-2,5-dimethyl-8-(1 propylbutyl)-8H-pyrazolo[1,5-a]pyrrolo[3,2-e]pyrimidine hydrochloride MS (ESI) m/z 469 MH$^+$.

Example 125

3-Mesityl-2,5-dimethyl-8-neopentyl-8H-pyrazolo[1,5-a]pyrrolo[3,2-e]pyrimidine

Brown Oil $^1$H NMR (400 MHz, CDCl$_3$) δ 1.04 (s, 9H), 2.02 (s, 6H), 2.25 (s, 3H), 2.33 (s, 3H), 2.63 (s, 3H), 4.72 (s, 2H), 6.53 (d, J=3.6 Hz, 1H), 6.76 (d, J=3.6 Hz, 1H), 6.97 (s, 2H).

Example 126

8-(1-Ethylbutyl)-3-mesityl-2,5-dimethyl-8H-pyrazolo[1,5-a]pyrrolo[3,2-e]pyrimidine Brown Oil $^1$H NMR (400 MHz, CDCl$_3$) δ 0.87 (t, J=7.6 Hz, 3H), 0.91 (t, J=7.2 Hz, 3H), 1.13–1.40 (m, 2H), 1.80–2.00 (m, 4H), 2.03 (s, 6H), 2.24 (s, 3H), 2.33 (s, 3H), 2.62 (s, 3H), 6.00–6.13 (m, 1H), 6.59 (d, J=3.6 Hz, 1H), 6.85 (d, J=3.6 Hz, 1H), 6.97 (s, 2H).

Example 127

8-(1,3-Dimethylbutyl)-3-Mesityl-2,5-dimethyl-8H-pyrazolo[1,5-a]pyrrolo[3,2-e]pyrimidine Brown Oil $^1$H NMR (400 MHz, CDCl$_3$) δ 0.95 (d, J=6.8 Hz, 3H), 0.96 (d, J=6.4 Hz, 3H), 1.44–1.52 (m, 1H), 1.56 (d, J=6.8 Hz, 3H), 1.60–1.68 (m, 2H), 1.85–1.93 (m, 1H), 2.03 (s, 3H), 2.03 (s, 3H), 6.20–6.30 (m, 1H), 6.57 (d, J=3.6 Hz, 1H), 6.90 (d, J=3.6 Hz, 1H), 6.97 (s, 2H).

Example 128

3-Mesityl-2,5-dimethyl-8-(1-methylbutyl)-8H-pyrazolo[1,5-a]pyrrolo[3,2-e]pyrimidine Brown Oil $^1$H NMR (400 MHz, CDCl$_3$) δ 0.93 (t, J=7.6 Hz, 3H), 1.20–1.43 (m, 2H), 1.58 (d, J=7.2 Hz, 3H), 1.80–1.97 (m, 2H), 2.04 (s, 3H), 2.04 (s, 3H), 2.25 (s, 3H), 2.33 (s, 3H), 2.61 (s, 3H), 6.12–6.20 (m, 1H), 6.57 (d, J=3.6 Hz, 1H), 6.90 (d, J=3.6 Hz, 1H), 6.97 (s, 2H).

Example 129

3-Mesityl-2,5-dimethyl-8-(2-methylbutyl)-8H-pyrazolo[1,5-a]pyrrolo[3,2-e]pyrimidine Brown Oil $^1$H NMR (400 MHz, CDCl$_3$) δ 0.95 (d, J=6.8 Hz, 3H), 1.00 (t, J=7.2 Hz, 3H), 1.25–1.37 (m, 1H), 1.43–1.58 (m, 1H), 2.03 (s, 3H), 2.03 (s, 3H), 2.05–2.20 (m, 1H), 2.24 (s, 3H), 2.33 (s, 3H), 2.62 (s, 3H), 4.48 (dd, J=8.0, 13.6 Hz, 1H), 4.74 (dd, J=6.8, 13.6 Hz, 1H), 6.52 (d, J=3.2 Hz, 1H), 6.74 (d, J=3.2 Hz, 1H), 6.97 (s, 2H).

Example 130

2-(3-Mesityl-2,5-dimethyl-7-propyl-8H-pyrazolo[1,5-a]pyrrolo[3,2-e]pyrimidin-8-yl)ethyl methyl ether Yellowish Brown Oil $^1$H NMR (400 MHz, CDCl$_3$) δ 1.09 (t, J=7.2 Hz, 3H), 1.75–1.82 (m, 2H), 2.03 (s, 6H), 2.24 (s, 3H), 2.33 (s, 3H), 2.60 (s, 3H), 2.77 (t, J=7.2 Hz, 2H), 3.36 (s, 3H), 3.88 (t, J=5.6 Hz, 2H), 4.89 (t, J=5.6 Hz, 2H), 6.26 (s, 1H), 6.97 (s, 2H).

Example 131

8-(1-Ethylpropyl)-3-(2-isopropenyl-4,6-dimethylphenyl)-2,5-dimethyl-8H-pyrazolo[1,5-a]pyrrolo[3,2-e]pyrimidine $^1$H NMR (400 MHz, CDCl$_3$) δ 0.86 (t, J=7.3 Hz, 3H), 0.88 (t, J=7.3 Hz, 3H), 1.62 (s, 3H), 1.80–2.03 (m, 4H), 2.05 (s, 3H), 2.21 (s, 3H), 2.36 (s, 3H), 2.62 (s, 3H), 4.79 (s, 1H), 4.80 (s, 1H), 5.86–6.04 (m, 1H), 6.59 (d, J=3.5 Hz, 1H), 6.85 (d, J=3.5 Hz, 1H), 6.98 (s, 1H), 7.05 (s, 1H).

Example 132

3-Mesityl-8-]1-(methoxymethyl)propyl]-2,5-dimethyl-8H-pyrazolo[1,5-a]pyrrolo[3,2-e]pyrimidine White Crystals.

MS (ESI) m/z 391 MH$^+$.

Example 133

8-Isopentyl-3-mesityl-2,5-dimethyl-8H-pyrazolo[1,5-a]pyrrolo[3,2-e]pyrimidine

Brown Oil $^1$H NMR (400 MHz, CDCl$_3$) δ 1.04 (d, J=6.8 Hz, 6H), 1.65–1.80 (m, 1H), 1.84–1.90 (m, 2H), 2.03 (s, 6H), 2.25 (s, 3H), 2.34 (s, 3H), 2.62 (s, 3H), 4.79–4.83 (m, 2H), 6.53 (d, J=3.2 Hz, 1H), 6.78 (d, J=3.2 Hz, 1H), 6.98 (s, 2H).

Example 134

3-(2,6-Dimethoxy-4-methylphenyl)-8-(1-ethylpropyl)-2,5-dimethyl-8H-pyrazolo[1,5-a]pyrrolo[3,2-e]pyrimidine Pale Brown Crystals $^1$H NMR (400 MHz, CDCl$_3$) δ 0.87 (t, J=7.2 Hz, 6H), 1.80–2.00 (m, 4H), 2.32 (s, 3H), 2.42 (s, 3H), 2.62 (s, 3H), 3.75 (s, 6H), 6.52 (s, 2H), 6.55 (d, J=3.2 Hz, 1H), 6.81 (d, J=3.2 Hz, 1H).

Example 135

2-(3-Mesityl-2,5-dimethyl-8H-pyrazolo[1,5-a]pyrrolo[3,2-e]pyrimidin-8-yl)propyl methyl ether White Crystals $^1$H NMR (400 MHz, CDCl$_3$) δ 1.63 (d, J=7.2 Hz, 3H), 2.02 (s, 6H), 2.24 (s, 3H), 2.33 (s, 3H), 2.62 (s, 3H), 3.39 (s, 3H), 3.70–3.82 (m, 2H), 6.30–6.40 (m, 1H), 6.56 (d, J=3.6 Hz, 1H), 6.97 (s, 2H), 7.01 (d, J=3.6 Hz, 1H).

Example 136

3-(2-Bromo-4,6-dimethylphenyl-8-(1-ethylbutyl)-2,5-dimethyl-8H-pyrazolo[1,5-a]pyrrolo[3,2-e]pyrimidine Brown Oil $^1$H NMR (400 MHz, CDCl$_3$) δ 0.83–0.93 (m, 6H), 1.10–1.40 (m, 2H), 1.80–2.00 (m, 4H), 2.09 (s, 3H), 2.29 (s, 3H), 2.34 (s, 3H), 2.64 (s, 3H), 6.00–6.10 (m, 1H), 6.59 (d, J=3.2 Hz, 1H), 6.86 (d, J=3.6 Hz, 1H), 7.07 (br s, 1H), 7.37 (br s, 1H).

Example 137

8-(1,2-Dimethylpropyl)-3-mesityl-2,5-dimethyl-8H-pyrazolo[1,5-a]pyrrolo[3,2-e]pyrimidine White Crystals $^1$H NMR (400 MHz, CDCl$_3$) δ 0.85 (d, J=6.8 Hz, 3H), 1.06 (d, J=6.8 Hz, 3H), 1.58 (d, J=6.8 Hz, 3H), 2.02 (s, 3H), 2.04 (s, 3H), 2.05–2.20 (m, 1H), 2.25 (s, 3H), 2.33 (s, 3H), 2.62 (s, 3H), 5.85–5.96 (m, 1H), 6.57 (d, J=3.2 Hz, 1H), 6.89 (d, J=3.6 Hz, 1H), 6.97 (s, 2H).

Example 138

2-(7-Ethyl-3-mesityl-2,5-dimethyl-8H-pyrazolo[1,5-a]pyrrolo[3,2-e]pyrimidin-8-yl)ethyl methyl ether Reddish White Crystals $^1$H NMR (400 MHz, CDCl$_3$) δ 1.38 (t, J=7.6 Hz, 3H), 2.03 (s, 6H), 2.24 (s, 3H), 2.33 (s, 3H), 2.60 (s, 3H), 2.82 (q, J=7.6 Hz, 2H), 3.36 (s, 3H), 3.88 (t, J=6.0 Hz, 2H), 4.88 (t, J=5.6 Hz, 2H), 6.27 (s, 1H), 6.97 (s, 2H).

Example 139

8-Butyl-3-mesityl-2,5-dimethyl-7-propyl-8H-pyrazolo[1,5-a]pyrrolo[3,2-e]pyrimidine Yellow Oil $^1$H NMR (400 1Hz, CDCl$_3$) δ 1.02 (t, J=7.2 Hz, 3H), 1.09 (t, J=7.6 Hz, 3H), 1.43–1.53 (m, 2H), 1.75–1.83 (m, 2H), 1.83–1.92 (m, 2H), 2.03 (s, 3H), 2.25 (s, 3H), 2.33 (s, 3H), 2.59. (s, 3H), 2.70 (t, J=7.6 Hz, 2H), 4.72 (t, J=7.6 Hz, 2H), 6.26 (s, 1H), 6.97 (s, 2H).

Example 140

3-Mesityl-2,5,8-trimethyl-7-propyl-8H-pyrazolo[1,5-a]pyrrolo[3,2-e]pyrimidine

White Amorphous $^1$H NMR (400 MHz, CDCl$_3$) δ 1.08 (t, J=7.2 Hz, 3H), 1.74–1.80 (m, 2H), 2.02 (s, 6H), 2.27 (s, 3H), 2.33 (s, 3H), 2.59 (s, 3H), 2.68 (t, J=7.6 Hz, 2H), 4.35 (s, 3H), 6.27 (s, 1H), 6.97 (s, 2H).

Example 141

8-(1-Ethylpropyl)-3-(2-isopropenyl-4,6-dimethylphenyl)-2,5-dimethyl-8H-pyrazolo[1,5-a]pyrrolo[3,2-e]pyrimidine $^1$H NMR (400 MHz, CDCl$_3$) δ 0.88 (t, J=7.4 Hz, 3H), 0.93 (t, J=7.4 Hz, 3H), 1.07 (d, J=6.8 Hz, 3H), 1.10 (d, J=6.9 Hz, 3H), 1.80–2.08 (m, 4H), 1.99 (s, 3H), 2.24 (s, 3H), 2.38 (s, 3H), 2.61 (s, 3H), 2.65–2.80 (m, 1H), 5.84–6.07 (m, 1H), 6.59 (dd, J=3.3, 1.0 Hz, 1H), 6.86 (dd, J=3.3, 1.0 Hz, 1H), 6.98 (s, 1H), 7.06 (s, 1H).

Example 142

2-(3-Mesityl-2,5-dimethyl-8H-pyrazolo[1,5-a]pyrrolo[3,2-e]pyrimidin-8-yl)-1-butanol Brown Amorphous $^1$H NMR (400 MHz, CDCl$_3$) δ 1.03 (t, J=7.2 Hz, 3H), 1.90–2.10 (m, 2H), 2.04 (s, 6H), 2.24 (s, 3H), 2.33 (s, 3H), 2.63 (s, 3H), 3.60 (br s, 1H), 3.80–3.85 (m, 1H), 4.10–4.17 (m, 1H), 5.80–5.90 (m, 1H), 6.63 (d, J=3.6 Hz, 1H), 6.95 (d, J=3.6 Hz, 1H), 6.97 (s, 2H).

Example 143

2-(3-Mesityl-2,5-dimethyl-8H-pyrazolo[1,5-a]pyrrolo[3,2-e]pyrimidin-8-yl)-1-pentanol Brown Amorphous $^1$H NMR (400 MHz, CDCl$_3$) δ 0.97 (t, J=7.2 Hz, 3H), 1.33–1.45 (m, 2H), 1.90–2.10 (m, 2H), 1.99 (s, 3H), 2.05 (s, 3H), 2.24 (s, 3H), 2.33 (s, 3H), 2.63 (s, 3H), 3.82 (dd, J=8.8, 11.2 Hz, 1H), 4.04–4.14 (m, 1H), 5.95–6.05 (m, 1H), 6.63 (d, J=3.6 Hz, 1H), 6.95 (d, J=3.6 Hz, 1H), 6.97 (s, 2H).

Example 144

8-(1-Ethylpropyl)-3-(2-isopropyl-4,6-dimethylphenyl)-2,5-dimethyl-8H-pyrazolo[1,5-a]pyrrolo[3,2-e]pyrimidine White Crystals $^1$H NMR (400 MHz, CDCl$_3$) δ 0.88 (t, J=7.4 Hz, 6H), 1.27 (d, J=7.0 Hz, 6H), 1.80–2.04 (m, 4H), 2.05 (s, 6H), 2.24 (s, 3H), 2.63 (s, 3H), 2.81–2.93 (m, 1H), 5.88–6.04 (m, 1H), 6.59 (d, J=3.5 Hz, 1H), 6.85 (d, J=3.5 Hz, 1H), 6.98 (s, 2H).

Example 145

1-2-[8-(1-Ethylpropyl)-2,5-dimethyl-8H-pyrazolo[1,5-a]pyrrolo[3,2-e]pyrimidin-3-yl]-3,5-dimethylphenylethyl methyl ether Yellow Crystals $^1$H NMR (400 MHz, CDCl$_3$) δ 0.88 (t, J=7.3 Hz, 3H), 0.92 (t, J=7.3 Hz, 3H), 1.14 (d, J=6.4 Hz, 2H), 1.30 (d, J=6.4 Hz, 1H), 1.80–2.04 (m, 4H), 2.02 (s, 2H), 2.05 (s, 1H), 2.22 (s, 2H), 2.24 (s, 1H), 2.40 (s, 3H), 2.59 (s, 3H), 3.11 (s, 1H), 3.22 (s, 2H), 4.10–4.18 (m, 1H), 5.87–6.02 (m, 1H), 6.60 (d, J=3.3 Hz, 1H), 6.88 (d, J=3.3 Hz, 1H), 7.06 (s, 1H), 7.25 (s, 1H).

Example 146

1-2-[8-(1-Ethylpropyl)-2,5-dimethyl-7,8-dihydro-6H-pyrazolo[1,5-a]pyrrolo[3,2-e]pyrimidin-3-yl]-3,5-dimethylphenylethyl methyl ether Yellow Oil $^1$H NMR (400 MHz, CDCl$_3$) δ 0.90–1.02 (m, 6H), 1.13 (d, J=6.4 Hz, 2H), 1.30 (d, J=6.4 Hz, 1H), 1.52–1.78 (m, 4H), 2.00 (s, 2H), 2.05 (s, 1H), 2.14 (s, 2H), 2.16 (s, 1H), 2.23 (s, 3H), 2.37 (s, 3H), 3.10 (s, 1H), 3.21 (s, 2H), 3.09 (t, J=8.8 Hz, 2H), 3.69 (t, J=8.8 Hz, 2H), 4.08–4.18 (m, 1H), 5.57–5.69 (m, 1H), 7.02 (s, 1H), 7.18 (s, 0.34H), 7.20 (s, 0.66H).

Example 147

8-(sec-Butyl)-3-mesityl-2,5-dimethyl-8H-pyrazolo[1,5-a]pyrrolo[3,2-e]pyrimidine

Pale Yellow Crystals $^1$H NMR (400 MHz, CDCl$_3$) δ 0.92 (t, J=7.6 Hz, 3H), 1.59 (d, J=6.4 Hz, 3H), 1.90–2.00 (m, 1H), 2.02 (s, 3H), 2.04 (s, 3H), 2.25 (s, 3H), 2.33 (s, 3H), 2.62 (s, 3H), 6.02–6.08 (m, 1H), 6.58 (d, J=3.6 Hz, 1H), 6.90 (d, J=3.6 Hz, 1H), 6.97 (s, 2H).

Example 148

2-(3-Mesityl-2,5-dimethyl-8H-pyrazolo[1,5-a]pyrrolo[3,2-e]pyrimidin-8-yl)-1-hexanol Pale Brown Crystals $^1$H NMR (400 MHz, CDCl$_3$) δ 0.89 (t, J=7.2 Hz, 3H), 1.25–1.42 (m, 4H), 1.90–2.00 (m, 2H), 1.99 (s, 3H), 2.04 (s, 3H), 2.24 (s, 3H), 2.33 (s, 3H), 2.63 (s, 3H), 3.60 (br s, 1H), 3.74–3.84 (m, 1H), 4.12 (dd, J=3.2, 11.2 Hz, 1H), 5.90–6.00 (m, 1H), 6.62 (d, J=3.2 Hz, 1H), 6.95 (d, J=3.6 Hz, 1H), 6.97 (s, 2H).

Example 149

3-(2-Bromo-4,6-dimethylphenyl)-2,5-dimethyl-8-(1-methylbutyl)-7,8-dihydro)-6H-pyrazolo[1,5-a]pyrrolo[3,2-e]pyrimidine White Amorphous $^1$H NMR (400 MHz, CDCl$_3$) δ 0.95 (dt, J=7.4, 4.4 Hz, 3H), 1.27 (dd, J=4.4, 2.2 Hz, 3H), 1.30–1.59 (m, 4H), 2.08 (s, 3H), 2.21 (s, 3H), 2.27 (s, 3H), 2.31 (s, 3H), 3.05 (t, J=9.2 Hz, 2H), 3.74 (t, J=9.2 Hz, 2H), 5.80–5.93 (m, 1H), 7.03 (s, 1H), 7.33 (s, 1H).

Example 150

3-(2-Bromo-4,6-dimethylphenyl)-2,5-dimethyl-8-(1-methylbutyl)-8H-pyrazolo[1,5-a]pyrrolo[3,2-e]pyrimidine White Amorphous $^1$H NMR (400 MHz, CDCl$_3$) δ 0.93 (dt, J=7.3, 2.0 Hz, 3H), 1.18–1.48 (m, 2H), 1.57 (dd, J=6.8, 2.4 Hz, 3H), 1.77–1.98 (m, 2H), 2.08 (d, J=8.4 Hz, 3H), 2.30 (s, 3H), 2.34 (s, 3H), 2.63 (s, 3H), 6.10–6.22 (m, 1H), 6.58 (d, J=3.5 Hz, 1H), 6.91 (d, J=3.5 Hz, 1H), 7.07 (s, 1H), 7.37 (s, 1H).

Example 151

3-(2-Bromo-4,6-dimethylphenyl-4,6-dimethylbutyl)-2,5-dimethyl-7,8-dihydro-6H-pyrazolo[1,5-a]pyrrolo[3,2-e]pyrimidine Pale Yellow Amorphous $^1$H NMR (400 MHz, CDCl$_3$) δ 0.96 (d, J=2.2 Hz, 3H), 0.98 (d, J=6.0 Hz, 3H), 1.26 (dd, J=5.3, 1.3 Hz, 3H), 1.31–1.42 (m, 1H), 1.53–1.70 (m, 2H), 2.08 (s, 3H), 2.20 (s, 3H), 2.27 (s, 3H), 2.31 (s, 3H), 3.05 (t, J=9.5 Hz, 2H), 3.62–3.80 (m, 2H), 5.93–6.05 (m, 1H), 7.03 (s, 1H), 7.33 (s, 1H).

Example 152

3-(2-Bromo-4,6-dimethylphenyl)-8-(1,3-dimethylbutyl)-2,5-dimethyl-8H-pyrazolo[1,5-a]pyrrolo[3,2-e]pyrimidine Pale Brown Amorphous $^1$H NMR (400 MHz, CDCl$_3$) δ 0.91–1.00 (m, 6H), 1.40–1.70 (m, 2H), 1, 55 (dd, J=6.6, 2.9 Hz, 3H), 1.83–1.94 (m, 1H), 2.08 (s, 3H), 2.29 (s, 3H), 2.34 (s, 3H), 2.63 (s, 3H), 6.20–6.32 (m, 1H), 6.58 (d, J=3.5 Hz, 1H), 6.91 (d, J=3.5 Hz, 1H), 7.07 (s, 1H), 7.37 (s, 1H).

Example 153

3-(2-Bromo-4,6-dimethylphenyl-8-(1,2-dimethylpropyl)-2,5-dimethyl-7,8-dihydro-6H-pyrazolo[1,5-a]pyrrolo[3,2-e]pyrimidine Pale Yellow Amorphous $^1$H NMR (400 MHz, CDCl$_3$) δ 0.97 (t, J=6.1 Hz, 3H), 1.04 (d, J=6.8 Hz, 3H), 1.30 (dd, J=5.0, 1.7 Hz, 3H), 1.79–1.92 (m, 1H), 2.08 (s, 3H), 2.21 (s, 3H), 2.72 (s, 3H), 2.31 (s, 3H), 3.06 (t, J=9.2 Hz, 2H), 3.64–3.84 (m, 2H), 5.48–5.62 (m, 1H), 7.03 (s, 1H), 7.33 (s, 1H).

Example 154

3-(2-Bromo-4,6-dimethylphenyl)-8-(1,2-dimethylpropyl)-2,5-dimethyl-8H-pyrazolo[1,5-a]pyrrolo[3,2-e]pyrimidine Pale Yellow Amorphous $^1$H NMR (400 MHz, CDCl$_3$) δ 0.86 (t, J=6.5 Hz, 3H), 1.05 (d, J=6.8 Hz, 3H), 1,57 (dd, J=4.2, 2.7 Hz, 3H), 2.07 (s, 3H), 2.00–2.20 (m, 1H), 2.30 (s, 3H), 2.34 (s, 3H), 2.64 (s, 3H), 5.84–5.98 (m, 1H), 6.57 (dd, J=3.5, 1.1 Hz, 1H), 6.89 (d, J=3.3 Hz, 1H), 7.07 (s, 1H), 7.37 (s, 1H).

Example 155

2-[3-(2-Bromo-4-dimethylphenyl)-2,5-dimethyl-7,8-dihydro-6H-pyrazolo[1,5-a]pyrrolo[3,2-e]pyrimidin-8-propyl methyl ether Yellow Amorphous $^1$H NMR (400 MHz, CDCl$_3$) δ 1.30 (t, J=6.9 Hz, 3H), 2.06 (d, J=6.0 Hz, 3H), 2.21 (s, 3H), 2.28 (s, 3H), 2.31 (s, 3H), 3.00–3.12 (m, 2H), 3.37 (d, J=7.3 Hz, 3H), 3.47–3.55 (m, 1H), 3.58–3.67 (m, 1H), 3.76–3.86 (m, 2H), 6.05–6.18 (m, 1H), 7.03 (s, 1H), 7.33 (s, 1H).

Example 156

2-[3-(2-Bromo-4,6-dimethylphenyl)-2-dimethyl-8H-pyrazolo[1,5-a]pyrrolo[3,2-e]pyrimidin-8-yl]propyl methyl ether Pale Yellow Amorphous $^1$H NMR (400 MHz, CDCl$_3$) δ 1.63 (dd, J=7.1, 4.1 Hz, 3H), 2.08 (s, 3H), 2.30 (s, 3H), 2.34 (s, 3H), 2.64 (s, 3H), 3.70–3.84 (m, 2H), 6.29–6.42 (m, 1H), 6.57 (d, J=3.5 Hz, 1H), 7.02 (dd, J=4.8, 3.5 Hz, 1H), 7.07 (s, 1H), 7.37 (s, 1H).

Example 157

3-(2-Bromo-4,6-dimethylphenyl)-8-isopentyl-2,5-dimethyl-7,8-dihydro-6H-pyrazolo[1,2-a]pyrrolo[3,2-a]pyrimidine Pale Yellow Amorphous $^1$H NMR (400 MHz, CDCl$_3$) δ 1.01 (d, J=6.6 Hz, 6H), 1.58–1.67 (m, 2H), 1.67–1.79 (m, 1H), 2.08 (s, 3H), 2.22 (s, 3H), 2.28 (s, 3H), 2.31 (s, 3H), 3.07 (dd, J=10.0, 8.2 Hz, 2H), 3.68–3.84 (m, 2H), 4.10–4.23 (m, 1H), 4.24–4.38 (m, 1H), 7.03 (s, 1H), 7.33 (s, 1H).

Example 158

3-(2-Bromo-4,6-dimethylphenyl)-8-isopentyl-2,5-dimethyl-8H-pyrazolo[1,5-e]pyrrolo[3,2-e]pyrimidine White Amorphous $^1$H NMR (400 MHz, CDCl$_3$) δ 1.03 (d, J=5.5 Hz, 6H), 1.67–1.79 (m, 1H), 1.82–1.91 (m, 2H), 2.09 (s, 3H), 2.31 (s, 3H), 2.34 (s, 3H), 2.63 (s, 3H), 4.71–4.90 (m, 2H), 6.53 (d, J=3.3 Hz, 1H), 6.78 (d, J=3.5 Hz, 1H), 7.07 (s, 1H), 7.37 (s, 1H).

Example 159

3-(2-Bromo-4,6-dimethylphenyl)-8-(sec-butyl)-2,5-dimethyl-7,8-dihydro-6H-pyrazolo[1,5-a]pyrrolo[3,2e]pyrimidine Yellow Crystals $^1$H NMR (400 MHz, CDCl$_3$) δ 0.98 (td, J=7.3, 5.3 Hz, 3H), 1.28 (dd, J=6.6, 4.0 Hz, 3H), 1.54–1.74 (m, 2H), 2.08 (s, 3H), 2.22 (s, 3H), 2.28 (s, 3H), 2.31 (s, 3H), 3.06 (t, J=9.2 Hz, 2H), 3.63–3.80 (m, 2H), 5.68–5.82 (m, 1H), 7.03 (s, 1H), 7.33 (s, 1H).

Example 160

3-(2-Bromo-4,6-dimethylphenyl)-8-(sec-butyl)-2,5-dimethyl-8H-pyrazolo[1,5-a]pyrrolo[3,2-e]pyrimidine Yellow Crystals $^1$H NMR (400 MHz, CDCl$_3$) δ 0.92 (td, J=7.3, 3.1 Hz, 3H), 1.58 (dd, J=6.8, 1.7 Hz, 3H), 1.87–2.00 (m, 2H), 2.08 (d, J=7.5 Hz, 3H), 2.31 (s, 3H), 2.34 (s, 3H), 2.64 (s, 3H), 5.95–6.12 (m, 1H), 6.58 (d, J=3.5 Hz, 1H), 6.91 (d, J=3.5 Hz, 1H), 7.07 (s, 1H), 7.37 (s, 1H).

Example 161

3-Mesityl-2,5-dimethyl-8-(1-phenylethyl)-8H-pyrazolo[1,5-a]pyrrolo[3,2-e]pyrimidine hydrochloride Brown Amorphous MS (ESI) m/z 409 MH$^+$.

Example 162

2-(7-Isopropyl-3-mesityl-2,5-dimethyl-8H-pyrazolo[1,5-a]pyrrolo[3,2-e]pyrimidin-8-yl)ethyl methyl ether White Crystals $^1$H NMR (400 MHz, CDCl$_3$) δ 1.35 (d, J=6.8 Hz, 6H), 2.02 (s, 6H), 2.24 (s, 3H), 2.33 (s, 3H), 2.60 (s, 3H), 3.15–3.27 (m, 1H), 3.35 (s, 3H), 3.86 (t, J=5.6 Hz, 2H), 4.94 (t, J=5.6 Hz, 2H), 6.29 (s, 1H), 6.97 (s, 2H).

Example 163

8-Isopentyl-3-mesityl-2,5-dimethyl-7-propyl-8H-pyrazolo[1,5-a]pyrrolo[3,2-e]pyrimidine Yellow Crystals $^1$H NMR (400 MHz, CDCl$_3$) δ 1.07 (d, J=6.4 Hz, 6H), 1.09 (t, J=7.2 Hz, 3H), 1.72–1.86 (m, 5H), 2.03 (s, 6H), 2.24 (s, 3H), 2.33 (s, 3H), 2.59 (s, 3H), 2.70 (t, J=8.0 Hz, 2H), 4.73 (t, J=6.4 Hz, 2H), 6.26 (s, 1H), 6.96 (s, 2H).

Example 164

8-(1-Benzylpropyl)-3-mesityl-2,5-dimethyl-8H-pyrazolo[1,5-a]pyrrolo[3,2-e]pyrimidine White Crystals $^1$H NMR (400 MHz, CDCl$_3$) δ 0.94 (t, J=7.2 Hz, 3H), 1.90–2.07 (m, 2H), 2.00 (s, 3H), 2.03 (s, 3H), 2.24 (s, 3H), 2.33 (s, 3H), 2.60 (s, 3H), 3.08–3.23 (m, 2H), 6.20–6.38 (m, 1H), 6.57 (d, J=3.6 Hz, 1H), 6.86 (br s, 1H), 6.96 (s, 2H), 7.01–7.15 (m, 5H).

Example 165

N-5-[2-5-Dimethyl-8-(1-propylbutyl)-8H-pyrazolo[1,5-a]pyrrolo[3,2-e]pyrimidin-3-yl]-4-methyl-2-pyridyl-N,N-dimethylamine Brown Oil $^1$H NMR (400 MHz, CDCl$_3$) δ 0.90 (t, J=7.2 Hz, 6H), 1.05–1.40 (m, 4H), 1.78–1.86 (m, 4H), 2.19 (s, 3H), 2.38 (s, 3H), 2.64 (s, 3H), 3.12 (s, 6H), 6.13–6.20 (m, 1H), 6.51 (s, 1H), 6.59 (d, J=3.6 Hz, 1H), 6.86 (d, J=3.6 Hz, 1H), 8.08 (s, 1H).

Example 166

2-(3-Mesityl-2,5-dimethyl-8H-pyrazolo[1,5-a]pyrrolo[3,2-e]pyrimidin-8-yl)hexyl methyl ether Yellow Oil $^1$H NMR (400 MHz, CDCl$_3$) δ 0.85 (t, J=7.2 Hz, 3H), 1.15–1.42 (m, 4H), 1.90–2.02 (m, 2H), 2.02 (s, 3H), 2.03 (s, 3H), 2.23 (s, 3H), 2.33 (s, 3H), 2.61 (s, 3H), 3.37 (s, 3H), 3.73–3.83 (m, 2H), 6.20–6.36 (m, 1H), 6.57 (d, J=3.6 Hz, 1H), 6.97 (s, 2H), 7.00 (d, J=3.6 Hz, 1H).

Example 167

8-(Cyclopropylmethyl)-3-mesityl-2,5-dimethyl-7-propyl-8H-pyrazolo[1,5-a]pyrrolo[3,2-e]pyrimidine Yellow Oil $^1$H NMR (400 MHz, CDCl$_3$) δ 0.49–0.54 (m, 2H), 0.60–0.64 (m, 2H), 1.10 (t, J=7.2 Hz, 3H), 1.29–1.40 (m, 1H), 1.77–1.87 (m, 2H), 2.02 (s, 6H), 2.24 (s, 3H), 2.33 (s, 3H), 2.61 (s, 3H), 2.75 (t, J=7.6 Hz, 2H), 4.73 (d, J=6.8 Hz, 2H), 6.31 (s, 1H), 6.97 (s, 2H).

Example 168

3-(3-Mesityl-2,5-dimethyl-7-propyl-8H-pyrazolo[1,5-a]pyrrolo[3,2-e]pyrimidin-8-yl)propyl methyl ether Yellow Oil $^1$H NMR (400 MHz, CDCl$_3$) δ 1.09 (t, J=7.2 Hz, 3H), 1.74–1.84 (m, 2H), 2.02 (s, 3H), 2.16–2.24 (m, 2H), 2.33 (s, 3H), 2.60 (s, 3H), 2.73 (t, J=7.2 Hz, 2H), 3.35 (s, 3H), 3.47 (t, J=6.0 Hz, 2H), 4.80 (t, J=6.8 Hz, 2H), 6.27 (s, 1H), 6.97 (s, 2H).

Example 169

2-(3-Mesityl-2,5-dimethyl-7-propyl-8H-pyrazolo[1,5-a]pyrrolo[3,2-e]pyrimidin-8-yl)ethyl cyanide Yellow Oil $^1$H NMR (400 MHz, CDCl$_3$) δ 1.11 (t, J=7.2 Hz, 3H), 1.76–1.88 (m, 2H), 2.02 (s, 6H), 2.23 (s, 3H), 2.33 (s, 3H), 2.60 (s, 3H), 2.80 (t, J=7.6 Hz, 2H), 3.19 (t, J=6.8 Hz, 2H), 4.93 (t, J=6.4 Hz, 2H), 6.32 (s, 1H), 6.97 (s, 2H).

Example 170

3-Mesityl-2,5-dimethyl-8-[2-(3-pyridyl)ethyl]-8H-pyrazolo[1,5-a]pyrrolo[3,2-e]pyrimidine MS (ESI) m/z 410 MH$^+$.

Example 171

8-(Dicyclopropylmethyl)-3-mesityl-2,5-dimethyl-8H-pyrazolo[1,5-a]pyrrolo[3,2-e]pyrimidine MS (ESI) m/z 399 MH$^+$.

Example 172

3-Mesityl-2,5-dimethyl-8-phenethyl-8H-pyrazolo[1,5-a]pyrrolo[3,2-e]pyrimidine

White crystals

MS (ESI) m/z 409 MH$^+$.

Example 173

3-Mesityl-2,5-dimethyl-8-(2-phenylpropyl)-8H-pyrazolo[1,5-a]pyrrolo[3,2-e]pyrimidine hydrochloride MS (ESI) m/z 423 MH$^+$.

Example 174

2-(3-Mesityl-2,5-dimethyl-8H-pyrazolo[1,5-a]pyrrolo[3,2-e]pyrimidin-8H-yl)ethyl methyl ether White Crystals $^1$H NMR (400 MHz, CDCl$_3$) δ 2.02 (s, 6H), 2.24 (s, 3H), 2.33 (s, 3H), 2.62 (s, 3H), 3.39 (s, 3H), 3.90 (t, J=5.2 Hz, 2H), 5.00 (t, J=5.2 Hz, 2H), 6.52 (d, J=3.4 Hz, 1H), 6.89 (d, J=3.4 Hz, 1H), 6.97 (s, 2H).

Example 175

3-(3-Mesityl-2,5-dimethyl-8H-pyrazolo[1,5-a]pyrrolo[3,2-e]pyrimidin-8-yl)propyl methyl ether hydrochloride White Crystals $^1$H NMR (400 MHz, DMSO-d$_6$) δ 1.94 (s, 6H), 2.11–2.20 (m, 2H), 2.19 (s, 3H), 2.32 (s, 3H), 2.69 (s, 3H), 3.19 (s, 3H), 3.39 (t, J=6.0 Hz, 2H), 4.82 (t, J=7.0 Hz, 2H), 6.92 (d, J=3.3 Hz, 1H), 7.01 (s, 2H), 7.35 (d, J=3.3 Hz, 1H).

Example 176 (Diastereomer Mixture)

3-Mesityl-2,5-dimethyl-8-(2-methylcyclohexyl)-8H-pyrazolo[1,5-a]pyrrolo[3,2-e]pyrimidine hydrochloride Pale Yellow Oil $^1$H NMR (400 MHz, DMSO-d$_6$) δ 0.66–0.82 (d×2, J=6.6, 6.9 Hz, 3H), 1.16–2.12 (m, 9H), 1.90–1.95 (s×2, 6H), 2.16–2.20 (s×2, 3H), 2.31 (s, 3H), 2.65 (s, 3H), 5.50–5.75 (m, 1H), 6.84–6.98 (br d×2, J=3.0, 3.0 Hz, 1H), 6.99 (s, 2H), 7.37–7.55 (br d×2, J=3.0, 3.0 Hz, 1H).

Example 177

8-(1-Ethyl-1H-5-pyrazoly)-3-mesityl-2,5-dimethyl-8H-pyrazolo[1,5-a]pyrrolo[3,2-e]pyrimidine Brown Oil $^1$H NMR (400 MHz, CDCl$_3$) δ 1.35 (t, J=7.2 Hz, 3H), 1.98 (s, 6H), 2.09 (s, 3H), 2.32 (s, 3H), 2.69 (s, 3H), 3.92 (q, J=7.2 Hz, 2H), 6.48 (d, J=1.2 Hz, 1H), 6.73 (d, J=3.6 Hz, 1H), 6.82 (d, J=3.6 Hz, 1H), 6.95 (s, 2H), 7.69 (d, J=1.2 Hz, 1H).

Example 178

8-Isobutyl-3-mesityl-2,5-dimethyl-7-propyl-8H-pyrazolo[1,5-a]pyrrolo[3,2-e]pyrimidine Yellow Oil $^1$H-NMR (400 MHz, CDCl$_3$) δ 0.97 (t, J=6.8 Hz, 6H), 1.08 (t, J=7.2 Hz, 3H), 1.76–1.81 (m, 2H), 2.03 (s, 6H), 2.24 (s, 3H), 2.30–2.35 (m, 1H), 2.33 (s, 3H), 2.60 (s, 3H), 2.69 (t, J=8.0 Hz, 2H), 4.45–4.58 (m, 2H), 6.27 (s, 1H), 6.96 (s, 2H).

Example 179

8-(2-Ethylbutyl)-3-mesityl-2,5-dimethyl-7-propyl-8H-pyrazolo[1,5-a]pyrrolo[3,2-e]pyrimidine Brown Oil $^1$H-NMR (400 MHz, CDCl$_3$) δ 0.94 (t, J=7.6 Hz, 6H), 1.08 (t, J=7.2 Hz, 3H), 1.24–1.36 (m, 2H), 1.38–1.52 (m, 2H), 1.74–1.84 (m, 2H), 1.96–2.04 (m, 1H), 2.03 (s, 6H), 2.24 (s, 3H), 2.33 (s, 3H), 2.60 (s, 3H), 2.69 (t, J=7.6 Hz, 2H), 4.59–4.62 (m, 2H), 6.28 (s, 1H), 6.97 (s, 2H).

Example 180

3-Mesityl-2,5-dimethyl-8-(1-methylbutyl)-7-propyl-8H-pyrazolo[1,5-a]pyrrolo[3,2-e]pyrimidine Brown Crystals $^1$H-NMR (400 MHz, CDCl$_3$) δ 0.92 (t, J=7.6 Hz, 3H), 1.12 (t, J=7.2 Hz, 3H), 1.11–1.22 (m, 2H), 1.23–1.44 (m, 2H), 1.65 (d, J=6.8 Hz, 3H), 1.81–1.87 (m, 2H), 2.02 (s, 3H), 2.03 (s, 3H), 2.24 (s, 3H), 2.33 (s, 3H), 2.58 (s, 3H), 2.80–2.90 (m, 2H), 6.32 (s, 1H), 6.84–6.92 (m, 1H), 6.97 (s, 2H).

Example 181

8-(1-Benzylbutyl)-3-mesityl-2,5-dimethyl-8H-pyrazolo[1,5-a]pyrrolo[3,2-e]pyrimidine hydrochloride Brown Amorphous MS (ESI) m/z 451 MH$^+$.

Example 182

3-Mesityl-8-[2-methoxy-1-(methoxymethyl)ethyl]-2,9-dimethyl 8H-pyrazolo[1,5-a]pyrrolo[3,2-e]pyrimidine White Crystals MS (ESI) m/z 407 MH$^+$.

Example 183

4-[8-(1-Ethylpropyl)-2,5-dimethyl-8H-pyrazolo[1,5-a]pyrrolo[3,2-pyrimidine-3-yl]-3,5-dimethylphenyl methyl ether White Crystals $^1$H NMR (400 MHz, CDCl$_3$) δ 0.89 (t, J=7.2 Hz, 6H), 1.82–2.04 (m, 4H), 2.05 (s, 6H), 2.24 (s, 3H), 2.63 (s, 3H), 3.83 (s, 3H), 5.97 (br s, 1H), 6.59 (d, J=3.6 Hz, 1H), 6.71 (s, 2H), 6.86 (d, J=3.6 Hz, 1H).

Example 184

8-(1-Ethyl-3-methylbutyl)-3-mesityl-2,5-dimethyl-8H-pyrazolo[1,5-a]pyrrolo[3,2-e]pyrimidine Brown Oil $^1$H NMR (400 MHz, CDCl$_3$) δ 0.83 (t, J=7.2 Hz, 3H), 0.90 (d, J=6.8 Hz, 3H), 0.95 (d, J=6.4 Hz, 3H), 1.32–1.40 (m, 1H), 1.70–2.00 (m, 4H), 2.03 (s, 3H), 2.04 (s, 3H), 2.23 (s, 3H), 2.33 (s, 3H), 2.62 (s, 3H), 6.10–6.20 (m, 1H), 6.59 (d, J=3.2 Hz, 1H), 6.85 (d, J=3.6 Hz, 1H), 6.97 (s, 2H).

Example 185

8-(2-Ethoxyethyl)-3-mesityl-2,5-dimethyl-7-propyl-8H-pyrazolo[1,5-a]pyrrolo[3,2-e]pyrimidine Yellow Oil $^1$H NMR (400 MHz, CDCl$_3$) δ 1.08 (t, J=7.2 Hz, 3H), 1.14 (t, J=6.8 Hz, 3H), 1.74–1.83 (m, 2H), 2.02 (s, 6H), 2.23 (s, 3H), 2.33 (s, 3H), 2.60 (s, 3H), 2.78 (t, J=7.6 Hz, 2H), 3.51 (q, J=6.8 Hz, 2H), 3.90 (t, J=6.0 Hz, 2H), 4.89 (t, J=5.6 Hz, 2H), 6.26 (s, 1H), 6.97 (s, 2H).

Example 186

8-Cycloheptyl-3-mesityl-2,5-dimethyl-8H-pyrazolo[1,5-a]pyrrolo[3,2-e]pyrimidine hydrochloride White Crystals $^1$H NMR (400 MHz, DMSO-d$_6$) δ 1.57–1.88 (m, 8H), 1.94 (s, 6H), 2.00–2.20 (m, 4H), 2.19 (s, 3H), 2.32 (s, 3H), 2.66 (s, 3H), 5.90 (br s, 1H), 6.93 (br d, J=3.2 Hz, 1H), 7.00 (s, 2H), 7.52 (br d, J=3.2 Hz, 1H).

Example 187

4-[8-(1-Ethylpropyl)-2,5-dimethyl-8H-pyrazolo[1,5-a]pyrrolo[3,2-e]pyrimidine-3-yl]3,5-dimethylphenyl isopropyl ether White Crystals $^1$H NMR (400 MHz, CDCl$_3$) δ 0.89 (t, J=7.0 Hz, 6H), 1.36 (d, J=6.0 Hz, 6H), 1.80–2.05 (m, 4H), 2.03 (s, 6H), 2.23 (s, 3H), 2.64 (s, 3H), 4.50–4.62 (m, 1H), 6.59 (d, J=3.4 Hz, 1H), 6.69 (s, 2H), 6.86 (d, J=3.4 Hz, 1H).

Example 188

8-(1-Ethylpropyl)-2,5-dimethyl-3-(pyridyl)-8H-pyrazolo[1,5-a]pyrrolo[3,2-e]pyrimidine dihydrochloride White Crystals $^1$H NMR (400 MHz, DMSO-d$_6$) δ 0.71 (t, J=7.4 Hz, 6H), 1.90–2.00 (m, 4H), 2.71 (s, 3H), 2.75 (s, 3H), 5.80 (br s, 1H), 6.96 (d, J=3.5 Hz, 1H), 7.49 (d, J=3.5 Hz, 1H), 8.14 (dd, J=8.4, 5.5 Hz, 1H), 8.77 (d, J=5.5 Hz, 1H), 9.01 (dd, J=8.4, 2.0 Hz, 1H), 9.40 (d, J=2.0 Hz, 1H).

Example 189

8-Isobutyl-3-mesityl-2,5-dimethyl-8H-pyrazolo[1,5-a]pyrrolo[3,2-e]pyrimidine hydrochloride White Crystals $^1$H NMR (400 MHz, DMSO-d$_6$) δ 0.93 (d, J=6.8 Hz, 6H), 1.93 (s, 6H), 2.17 (s, 3H), 2.22–2.32 (m, 1H), 2.31 (s, 3H), 2.64 (s, 3H), 4.58 (d, J=7.3 Hz, 2H), 6.85 (br d, J=3.0 Hz, 1H), 6.99 (s, 2H), 7.32 (br d, J=3.0 Hz, 1H).

Example 190

3-Mesityl-8-(4-methoxybutyl)-2,5-dimethyl-7-propyl-8H-pyrazolo[1,5-a]pyrrolo[3,2-e]pyrimidine Yellow Oil $^1$H NMR (400 MHz, CDCl$_3$) δ 1.09 (t, J=7.6 Hz, 3H), 1.69–1.83 (m, 4H), 1.91–2.00 (m, 2H), 2.03 (s, 6H), 2.25 (s, 3H), 2.33 (s, 3H), 2.59 (s, 3H), 2.71 (t, J=7.6 Hz, 2H), 3.35 (s, 3H), 3.48 (t, J=6.4 Hz, 2H), 4.76 (t, J=8.0 Hz, 2H), 6.26 (s, 1H), 6.97 (s, 2H).

Example 191

8-Benzyl-3-mesityl-2,5-dimethyl-7-propyl-8H-pyrazolo[1,5-a]pyrrolo[3,2-e]pyrimidine White Amorphous $^1$H NMR (400 MHz, CDCl$_3$) δ 0.98 (t, J=7.6 Hz, 3H), 1.64–1.72 (m, 2H), 2.03 (s, 6H), 2.19 (s, 3H), 2.33 (s, 3H), 2.53 (t, J=8.0 Hz, 2H), 2.63 (s, 3H), 6.21 (s, 2H), 6.33 (s, 1H), 6.97 (s, 2H), 7.11 (d, J=6.8 Hz, 2H), 7.24–7.33 (m, 3H).

Example 192

8-(2-Furylmethyl)-3-mesityl-2,5-dimethyl-7-propyl-8H-pyrazolo[1,5-a]pyrrolo[3,2-e]pyrimidine White Amorphous $^1$H NMR (400 MHz, CDCl$_3$) δ 1.08 (t, J=7.2 Hz, 3H), 1.72–1.82 (m, 2H), 2.03 (s, 6H), 2.27 (s, 3H), 2.33 (s, 3H), 2.59 (s, 3H), 2.81 (t, J=7.6 Hz, 2H), 6.09 (s, 2H), 6.28 (s, 1H), 6.30 (dd, J=2.8, 3.2 Hz, 1H), 6.40 (dd, J=0.4, 2.8 Hz, 1H), 6.97 (s, 2H), 7.35 (dd, J=0.8, 5.6 Hz, 1H).

Example 193

4-(3-Mesityl-2,5-dimethyl-7-propyl-8H-pyrazolo[1,5-a]pyrrolo[3,2-e]pyrimidin-8-yl)-1-butanol Pale Yellow Oil $^1$H NMR (400 MHz, CDCl$_3$) δ 1.10 (t, J=7.6 Hz, 3H), 1.72–1.86 (m, 4H), 2.02 (s, 6H), 2.04–2.12 (m, 2H), 2.27 (s, 3H), 2.33 (s, 3H), 2.60 (s, 3H), 2.71 (s, 3H), 3.90 (dd, J=6.4, 12.0 Hz, 2H), 4.47 (t, J=6.8 Hz, 1H), 4.67 (t, J=8.0 Hz, 2H), 6.29 (s, 1H), 6.97 (s, 2H).

Example 194

3-Mesityl-2,5-dimethyl-7-propyl-8H-pyrazolo[1,5-a]pyrrolo[3,2-e]pyrimidine

Brown Oil $^1$H NMR (400 MHz, CDCl$_3$) δ 0.89 (t, J=7.6 Hz, 3H), 1.58–1.68 (m, 2H), 2.06 (s, 6H), 2.31 (s, 3H), 2.34 (s, 3H), 2.62 (t, J=7.6 Hz, 2H), 2.66 (s, 3H), 6.27 (s, 1H), 6.98 (s, 2H), 11.58 (s, 1H).

Example 195

3-(4-Bromo-2-methylphenyl)-8-(1-ethylpropyl)-2,5-dimethyl-8H-pyrazolo[1,5-a]pyrrolo[3,2-e]pyrimidine White Crystals $^1$H NMR (400 MHz, CDCl$_3$) δ 0.82–0.94 (m, 6H), 1.80–2.05 (m, 4H), 2.23 (s, 3H), 2.36 (s, 3H), 2.67 (s, 3H), 5.96 (br s, 1H), 6.62 (d, J=3.5 Hz, 1H), 6.88 (d, J=3.5 Hz, 1H), 7.18 (d, J=8.1 Hz, 1H), 7.38 (dd, J=8.1, 2.11 Hz, 1H), 7.48 (d, J=2.1 Hz, 1H).

Example 196

3-[8-(1-Ethylpropyl)-2,5-dimethyl-8H-pyrazolo[1,5-a]pyrrolo[3,2-e]pyrimidin-3-yl]-6-methyl-2-pyridylmethyl ether White Crystals $^1$H NMR (400 MHz, CDCl$_3$) δ 0.85 (t, J=7.3 Hz, 6H), 1.78–2.03 (m, 4H), 2.41 (s, 3H), 2.51 (s, 3H), 2.66 (s, 3H), 3.97 (s, 3H), 5.97 (br s, 1H), 6.59 (d, J=3.5 Hz, 1H), 6.85 (d, J=3.5 Hz, 1H), 6.86 (d, J=7.3 Hz, 1H), 7.71 (d, J=7.3 Hz, 1H).

Example 197

3-mesityl-2,5-dimethyl-8H-(1-phenylpropyl)-8H-pyrazolo[1,5-a]pyrrolo[3,2-e]pyrimidine MS (ESI) m/z 423 MH$^+$.

Example 198

8-Benzhydryl-3-mesityl-2,5-dimethyl-8-pyrazolo[1,5-a]pyrrolo[3,2-e]pyrimidine

White Crystals

MS (ESI) m/z 471 MH$^+$.

Example 199

8-(1,2-diphenylethyl)-3-mesityl-2,5-dimethyl-8H-pyrazolo[1,5-a]pyrrolo[3,2-e]pyrimidine hydrochloride Yellow Amorphous MS (ESI) m/z 485 MH$^+$.

Example 200

8-(2-Isopropoxyethyl)-3-mesityl-2,5-dimethyl-7-propyl-8H-pyrazolo[1,5-a]pyrrolo[3,2-e]pyrimidine Yellow Oil $^1$H NMR (400 MHz, CDCl$_3$) δ 1.06 (m, 3H), 1.10 (d, J=6.0 Hz, 6H), 1.74–1.82 (m, 2H), 2.03 (s, 6H), 2.24 (s, 3H), 2.33 (s, 3H), 2.60 (s, 3H), 2.79 (t, J=7.6 Hz, 2H), 3.57–3.63 (m, 1H), 3.89 (t, J=6.0 Hz, 2H), 4.86 (t, J=6.0 Hz, 2H), 6.25 (s, 1H), 6.97 (s, 2H).

Example 201

2-(3-Mesityl-2,5-dimethyl-7-propyl-8H-pyrazolo[1,5-a]pyrrolo[3,2-e]pyrimidin-8-yl)ethylpropyl ether Yellow Oil $^1$H NMR (400 MHz, CDCl$_3$) δ 0.86 (t, J=7.6 Hz, 3H), 1.08 (t, J=7.6 Hz, 3H), 1.48–1.58 (m, 2H), 1.74–1.83 (m, 2H), 2.03 (s, 6H), 2.23 (s, 3H), 2.33 (s, 3H), 2.60 (s, 3H), 2.78 (t, J=7.6 Hz, 2H), 3.40 (t, J=6.4 Hz, 2H), 3.89 (t, J=6.4 Hz, 2H), 4.90 (t, J=5.6 Hz, 2H), 6.26 (s, 1H), 6.97 (s, 2H).

Example 202

5-8-(1-Ethylpropyl)-2,5-dimethyl-8H-pyrazolo[1,5-a]pyrrolo[3,2-e]pyrimidin-8-yl]-6-methyl2-pyridyl methyl ether White Crystals $^1$H NMR (400 MHz, CDCl$_3$) δ 0.82–0.94 (m, 6H), 1.80–2.05 (m, 4H), 2.35 (s, 3H), 2.38 (s, 3H), 2.67 (s, 3H), 3.97 (s, 3H), 5.96 (br s, 1H), 6.61 (d, J=3.5 Hz, 1H), 6.66 (d, J=8.3 Hz, 1H), 6.87 (d, J=3.5 Hz, 1H), 7.51 (d, J=8.3 Hz, 1H).

Example 203

3-(7-Ethyl-1-mesityl-2,5-dimethyl-8H-pyrazolo[1,5-a]pyrrolo[3,2-e]pyrimidin-8-yl)propyl methyl ether White Crystals.

$^1$H NMR (400 MHz, CDCl$_3$) δ 1.39 (t, J=7.6 Hz, 3H), 2.02 (s, 6H), 2.16–2.24 (m, 2H), 2.33 (s, 3H), 2.60 (s, 3H), 2.78 (q, J=7.2 Hz, 2H), 3.34 (s, 3H), 3.47 (t, J=6.4 Hz, 2H), 4.78 (t, J=6.8 Hz, 2H), 6.27 (s, 1H), 6.96 (s, 2H).

Example 204

3-Mesityl-8-[(1R)-3-methoxy-1-(methoxymethyl)propyl]2,5-dimethyl-8H-pyrazolo[1,5-a]pyrrolo[3,2-e]pyrimidine Yellow Oil $^1$H NMR (400 MHz, CDCl$_3$) δ 2.02 (s, 6H), 2.20–2.30 (m, 2H), 2.24 (s, 3H), 2.33 (s, 3H), 2.63 (s, 3H), 3.17 (s, 3H), 3.23–3.42 (m, 2H), 3.89 (s, 3H), 3.76–3.96 (m, 2H), 6.38–6.58 (m, 1H), 6.57 (d, J=3.6 Hz, 1H), 6.97 (s, 2H), 7.03 (br s, 1H).

Example 205

3-Mesityl-2,5-dimethyl-8-phenethyl-7-propyl-8H-cyclopenta[e]pyrazolo[1,5-a]pyrimidine Yellow Oil $^1$H NMR (400 MHz, CDCl$_3$) δ 1.05 (t, J=7.6 Hz, 3H), 1.70–1.80 (m, 2H), 2.05 (s, 6H), 2.30 (s, 3H), 2.34 (s, 3H), 2.56 (t, J=7.2 Hz, 2H), 2.61 (s, 3H), 3.21 (t, J=7.6 Hz, 2H), 4.91 (t, J=7.6 Hz, 2H), 6.26 (s, 1H), 6.98 (s, 2H), 7.21–7.27 (m, 1H), 7.28–7.34 (m, 4H).

Example 206

N-(2-(3-Mesityl-2,5-dimethyl-7-propyl-8H-pyrazolo[1,5-a]pyrrolo[3,2-e]pyrimidin-8-yl)ethyl)-N,N-dimethylamine Yellow Oil $^1$H NMR (400 MHz, CDCl$_3$) δ 1.09 (t, J=7.2 Hz, 3H), 1.74–1.84 (m, 2H), 2.03 (s, 6H), 2.24 (s, 3H), 2.33 (s, 3H), 2.45 (s, 6H), 2.59 (s, 3H), 2.73 (t, J=7.2 Hz, 2H), 2.81 (t, J=7.6 Hz, 2H), 4.86 (t, J=7.6 Hz, 2H), 6.27 (s, 1H), 6.97 (s, 2H).

Example 207

3-Mesityl-8-(2-methoxyethyl)-7-(3-methyoxypropyl)-2,5-dimethyl-8H-pyrazolo[1,5-a]pyrrolo[3,2-e]pyrimidine Yellow Oil $^1$H NMR (400 MHz, CDCl$_3$) δ 1.95–2.06 (m, 2H), 2.03 (s, 6H), 2.23 (s, 3H), 2.33 (s, 3H), 2.60 (s, 3H), 2.89 (t, J=8.0 Hz, 2H), 3.35 (s, 3H), 3.39 (s, 3H), 3.52 (t, J=6.0 Hz, 2H), 3.88 (t, J=6.0 Hz, 2H), 4.90 (t, J=5.6 Hz, 2H), 6.27 (s, 1H), 6.97 (s, 2H).

Example 208

7-(3-(Benzyloxy)propyl)-3-mesityl-8-(2-methoxyethyl)-2,5-dimethyl-8H-pyrazolo[1,5-a]pyrrolo[3,2-e]pyrimidine Yellow Oil $^1$H NMR (400 MHz, CDCl$_3$) δ 1.72–2.20 (m, 2H), 1.95 (s, 6H), 2.16 (s, 3H), 2.26 (s, 3H), 2.54 (s, 3H), 2.85 (t, J=7.2 Hz, 2H), 3.27 (s, 3H), 3.55 (t, J=6.0 Hz, 2H), 3.80 (t, J=5.6 Hz, 2H), 4.49 (s, 2H), 4.82 (t, J=6.0 Hz, 2H), 6.17 (s, 1H), 6.90 (s, 2H), 7.19–7.23 (m, 1H), 7.25–7.31 (m, 4H).

Example 209

7-Benzyl-8-butyl-3-mesityl-2,5-dimethyl-8H-pyrazolo[1,5-a]pyrrolo[3,2-e]pyrimidine MS (ESI) m/z 451 MH$^+$.

Example 210

7-Benzyl-3-mesityl-2,5,8-trimethyl-8H-pyrazolo[1,5-a]pyrrolo[3,2-e]pyrimidine

Pale Yellow Amorphous $^1$H NMR (400 MHz, CDCl$_3$) δ 2.02 (s, 6H), 2.25 (s, 3H), 2.33 (s, 3H), 2.59 (s, 3H), 4.12 (s, 2H), 4.23 (s, 3H), 6.31 (s, 1H), 6.97 (s, 2H), 7.21–7.36 (m, 5H).

MS (ESI) m/z 409 MH$^+$.

Example 211

7-Ethyl-8-(2-isopropoxeythyl)-3-mesityl-2,5-dimethyl-8H-pyrazolo[1,5-a]pyrrolo[3,2-e]pyrimidine $^1$H NMR (400 MHz, CDCl$_3$) δ 1.10 (d. J=6.0 Hz, 6H), 1.38 (t, J=7.6 Hz, 3H), 2.03 (s, 6H), 2.23 (s, 3H), 2.33 (s, 3H), 2.60 (s, 3H), 2.84 (q, J=7.6 Hz, 2H), 3.59 (hept., J=6.0 Hz, 1H), 3.89 (t, J=6.0 Hz, 2H), 4.86 (t, J=6.0 Hz, 2H), 6.26 (s, 1H), 6.97 (s, 2H).

MS (ESI) m/z 419 MH$^+$.

Example 212

3-Mesityl-8-(2-(2-methoxyethoxy)ethyl)-2,5-dimethyl-7-propyl-8H-pyrazolo[1,5-a]pyrrolo[3,2-e]pyrimidine Reddish Brown Oil $^1$H NMR (400 MHz, CDCl$_3$) δ 1.08 (t, J=7.2 Hz, 3H), 1.74–1.82 (m, 2H), 2.02 (s, 6H), 2.23 (s, 3H), 2.33 (s, 3H), 2.60 (s, 3H), 2.77 (t, J=6.8 Hz, 2H), 3.34 (s, 3H), 3.46–3.48 (m, 2H), 3.63–3.65 (m, 2H), 3.97 (t, J=6.0 Hz, 2H), 4.91 (t, J=5.6 Hz, 2H), 6.26 (s, 1H), 6.96 (s, 2H).

Example 213

2-Bromoethyl(2-(3-mesityl-2,5-dimethyl-7-propyl-8H-pyrazolo[1,5-a]pyrrolo[3,2-e]pyrimidin-8-yl)ethyl)ether Yellow Oil $^1$H NMR (400 MHz, CDCl$_3$) δ 1.09 (t, J=7.2 Hz, 3H), 1.74–1.83 (m, 2H), 2.03 (s, 6H), 2.23 (s, 3H), 2.33 (s, 3H), 2.60 (s, 3H), 2.79 (t, J=7.2 Hz, 2H), 3.40 (t, J=6.0 Hz, 2H), 3.80 (t, J=6.0 Hz, 2H), 4.00 (t, J=5.6 Hz, 2H), 4.91 (t, J 5.6 Hz, 2H), 6.27 (s, 1H), 6.97 (s, 2H).

Example 214

(3-Mesityl-2,5-dimethyl-8H-pyrazolo[1,5-a]pyrrolo[3,2-e]pyrimidin-8-yl)methyl methyl ether Pale Yellow Oil $^1$H NMR (400 MHz, CDCl$_3$) δ 2.02 (s, 6H), 2.27 (s, 3H), 2.33 (s, 3H), 2.65 (s, 3H), 3.46 (s, 3H), 6.17 (s, 2H), 6.61 (d, J=3.6 Hz, 1H), 6.94 (d, J=3.2 Hz, 1H), 6.97 (s, 2H).

Example 215

8-(1-Ethylpropyl)-2,5-dimethyl-3-(2,4,6-trimethyl-3-pyridyl)-8H-pyrazolo[1,5-a]pyrrolo[3,2-e]pyrimidine White Crystals $^1$H NMR (400 MHz, CDCl$_3$) δ 0.85–0.92 (m, 6H), 1.83–2.05 (m, 4H), 2.06 (s, 3H), 2.24 (s, 3H), 2.31 (s, 3H), 2.55 (s, 3H), 2.64 (s, 3H), 5.95 (br s, 1H), 6.62 (d, J=3.5 Hz, 1H), 6.88 (d, J=3.5 Hz, 1H), 6.97 (s, 1H).

Example 216

4-[8-(1-Ethylbutyl)-2-methyl-8H-pyrazolo[1,5-a]pyrrolo[3,2-e]pyrimidin-3-yl]-3,5-dimethylphenyl methyl ether White Crystals $^1$H NMR (400 MHz, CDCl$_3$) δ 0.87 (t, J=7.6 Hz, 3H), 0.91 (t, J=7.4 Hz, 3H), 1.13–1.40 (m, 2H), 1.82–2.03 (m, 4H), 2.05 (s, 6H), 2.23 (s, 3H), 2.63 (s, 3H), 3.83 (s, 3H), 6.06 (br s, 1H), 6.59 (d, J=3.6 Hz, 1H), 6.71 (s, 2H), 6.86 (d, J=3.6 Hz, 1H).

Example 217

3-(4-Methoxy-2,6-dimethylphenyl)-8-[1-(methoxymethyl)propyl]-2,5-dimethyl-8H-pyrazolo[1,5-a]pyrrolo[3,2-e]-pyrimidine White Crystals $^1$H NMR (400 MHz, CDCl$_3$) δ 0.95 (t, J=7.4 Hz, 3H), 1.95–2.10 (m, 2H), 2.03 (s, 3H), 2.05 (s, 3H), 2.23 (s, 3H), 2.63 (s, 3H), 3.38 (s, 3H), 3.74–3.79 (m, 1H), 3.80–3.90 (m, 1H), 3.82 (s, 3H) 6.19 (br s, 1H), 6.57 (d, 1=3.6 Hz, 1H), 6.71 (s, 2H), 7.00 (d, J=3.6 Hz, 1H).

Example 218

3-(4-Ethoxy-2,6-dimethylphenyl)-8-(1-ethylpropyl)-2,5-dimethyl-8H-pyrazolo[1,5-a]pyrrolo[3,2-e]pyrimidine Pale Yellow Crystals $^1$H NMR (400 MHz, CDCl$_3$) δ 0.88 (t, J=7.3 Hz, 6H), 1.43 (t, J=7.0 Hz, 3H), 1.82–2.05 (m, 4H), 2.04 (s, 6H), 2.23 (s, 3H), 2.63 (s, 3H), 4.05 (q, J=7.0 Hz, 2H), 5.96 (br s, 1H), 6.59 (d, J=3.5 Hz, 1H), 6.70 (s, 2H), 6.85 (d, J=3.5 Hz, 1H).

Example 219

3-(Mesityl-2,5-dimethyl-8-[(1S)-1-phenylethyl]-8H-pyrazolo[1,5-a]pyrrolo[3,2-e]pyrimidine MS (FAB) m/z 409 MH$^+$.

Example 220

3-Mesityl-8-(3-methoxybeznyl)-2,5-dimethyl-8H-pyrazolo[1,5-a]pyrrolo[3,2-e]pyrimidine MS (FAB) m/z 425 MH$^+$.

Example 221

3-Mesityl-8-(4-methoxybenzyl)-2,5-dimethyl-8H-pyrazolo[1,5-a]pyrrolo[3,2-e]pyrimidine MS (FAB) m/z 425 MH$^+$.

Example 222

3-Mesityl-2,5-dimethyl-8-(2-methylbenzyl)-8H-pyrazolo[1,5-a]pyrrolo[3,2-e]pyrimidine MS (FAB) m/z 409 MH$^+$.

Example 223

3-Mesityl-2,5-dimethyl-8-(3-methylbenzyl)-8H-pyrazolo[1,5-a]pyrrolo[3,2-e]pyrimidine MS (FAB) m/z 409 MH$^+$.

Example 224

3-Mesityl-2,5-dimethyl-8-[(1R)-1-phenylethyl]-8H-pyrazolo[1,5-a]pyrrolo[3,2-e]pyrimidine MS (FAB) m/z 409 MH$^+$.

Example 225

Ethyl 4-(3-mesityl-2,5-dimethyl-8H-pyrazolo[1,5-a]pyrrolo[3,2-e]pyrimidin-8-yl)butanone MS (FAB) m/z 419 MH$^+$.

Example 226

3-Mesityl-2,5-dimethyl-8-[2-(methylsulfanil)ethyl]-8H-pyrazolo[1,5-a]pyrrolo[3,2-e]pyrimidine MS (ESI) m/z 379 MH$^+$.

Example 227

3-Mesityl-2,5-dimethyl-8-(1,2,2-trimethylpropyl)-8H-pyrazolo[1,5-a]pyrrolo[3,2-e]pyrimidine MS (FAB) m/z 389 MH$^+$.

Example 228

(3-Mesityl-2,5-dimethyl-7-propyl-8H-pyrazolo[1,5-a]pyrrolo[3,2-e]pyrimidin-8-yl)methyl methyl ether Yellow Oil $^1$H NMR (400 MHz, CDCl$_3$) δ 1.08 (t, J=7.2 Hz, 3H), 1.75–1.84 (m, 2H), 2.02 (s, 6H), 2.26 (s, 3H), 2.33 (s, 3H), 2.62 (s, 3H), 2.79 (t, J=7.2 Hz, 2H), 3.43 (s, 3H), 6.27 (s, 2H), 6.34 (s, 1H), 6.97 (s, 2H).

Example 229

3-Mesityl-2,5-dimethyl-8-pentyl-7-propyl-8H-pyrazolo[1,5-a]pyrrolo[3,2-e]pyrimidine MS (ESI) m/z 417 MH$^+$.

Example 230

3-(8-Ethyl-3-mesityl-2,5-dimethyl-8H-pyrazolo[1,5-a]pyrrolo[3,2-e]pyrimidin-7-yl)propyl methyl ether Yellow Oil $^1$H NMR (400 MHz, CDCl$_3$) δ 1.51 (t, J=7.2 Hz, 3H), 2.00–2.08 (m, 2H), 2.03 (s, 6H), 2.26 (s, 3H), 2.33 (s, 3H), 2.60 (s, 3H), 2.84 (t, J=7.6 Hz, 2H), 3.40 (s, 3H), 3.52 (t, J=6.0 Hz, 2H), 4.82 (dd, J=7.2, 7.2 Hz, 2H), 6.28 (s, 1H), 6.97 (s, 2H).

Example 231

3-(6-Bromo-1,3-benzodioxol-5-yl)-8-(1-ethylpropyl)-2,5-dimethyl-8H-pyrazolo[1,5-a]pyrrolo[3,2-e]pyrimidine White Crystals $^1$H NMR (400 MHz, CDCl$_3$) δ 0.85 (t, J=7.3 Hz, 3H), 0.88 (t, J=7.3 Hz, 3H), 1.80–2.03 (m, 4H), 2.39 (s, 3H), 2.68 (s, 3H), 5.95 (br s, 1H), 6.02 (d, J=7.6 Hz, 1H), 6.02 (d, J=7.6 Hz, 1H), 6.61 (d, J=3.5 Hz, 1H), 6.86 (d, J=3.5 Hz, 1H), 6.89 (s, 1H), 7.16 (s, 1H).

Example 232

8-Butyl-3-mesityl-7-(methoxymethyl)-2,5-dimethyl-8H-pyrazolo[1,5-a]pyrrolo[3,2-e]pyrimidine $^1$H NMR (400 MHz, CDCl$_3$) δ 1.03 (t, J=7.2 Hz, 3H), 1.51 (qt. J=7.2 Hz, 7.6 Hz, 2H), 1.88–1.98 (m, 2H), 2.03 (s, 6H), 2.25 (s, 3H), 2.33 (s, 3H), 2.60 (s, 3H), 3.36 (s, 3H), 4.58 (s, 2H), 4.78 (t, J=7.2 Hz, 2H), 6.52 (s, 1H), 6.97 (s, 2H).

MS (ESI) m/z 405 MH$^+$.

Example 233

7,8-Dibutyl-3-mesityl-2,5-dimethyl-8H-pyrazolo[1,5-a]pyrrolo[3,2-e]pyrimidine

Pale Yellow Crystals

MS (ESI) m/z 417 MH$^+$.

Example 234

3-Mesityl-2,5-dimethyl-8-propyl-7-(1-propynyl)-8H-pyrazolo[1,5-a]pyrrolo[3,2-e]pyrimidine MS (ESI) m/z 385 MH$^+$.

Example 235

8-Butyl-3-mesityl-2,5-dimethyl-7-(1-propynyl)-8H-pyrazolo[1,5-a]pyrrolo[3,2-e]pyrimidine MS (ESI) m/z 399 MH$^+$.

Example 236

3-Mesityl-2,5-dimethyl-8-pentyl-7-(1-propynyl)-8H-pyrazolo[1,5-a]pyrrolo[3,2-e]pyrimidine MS (ESI) m/z 413 MH$^+$.

Example 237

8-(1-Ethylpropyl)-3-mesityl-2,5-dimethyl-7-(1-propynyl)-8H-pyrazolo[1,5-a]pyrrolo[3,2-e]pyrimidine MS (ESI) m/z 413 MH$^+$.

Example 238

8-(2-Ethylbutyl)-3-mesityl-2,5-dimethyl-7-(1-propynyl)-8H-pyrazolo[1,5-a]pyrrolo[3,2-e]pyrimidine MS (ESI) m/z 427 MH$^+$.

Example 239

8-Isopentyl-3-mesityl-2,5-dimethyl-7-(1-propynyl)-8H-pyrazolo[1,5-a]pyrrolo[3,2-e]pyrimidine MS (ESI) m/z 413 MH$^+$.

Example 240

8-Allyl-3-mesityl-2,5-dimethyl-7-(1-propynyl)-8H-pyrazolo[1,5-a]pyrrolo[3,2-e]pyrimidine MS (ESI) m/z 383 MH$^+$.

Example 241

8-(2-Ethoxyethyl)-3-mesityl-2,5-dimethyl-7-(1-propynyl)-8H-pyrazolo[1,5-a]pyrrol[3,2-e]pyrimidine MS (ESI) m/z 415 MH$^+$.

Example 242

2-[3-Mesityl-2,5-dimethyl-7-(1-propynyl)-8H-pyrazolo[1,5-a]pyrrolo[3,2-e]pyrimidin-8-yl] ethylpropyl ether MS (ESI) m/z 429 MH$^+$.

Example 243

8-(2-Isopropoxyethyl)-3-mesityl-2,5-dimethyl-7-(1-propynyl)-8H-pyrazolo[1,5-a]pyrrolo[3,2-e]pyrimidine MS (ESI) m/z 429 MH$^+$.

Example 244

3-[3-Mesityl-2,5-dimethyl-7-(1-propynyl)-8H-pyrazolo[1,5-a]pyrrolo[3,2-e]pyrimidin-8-yl]propyl methyl ether MS (ESI) m/z 415 MH$^+$.

Example 245

2-[(3-Mesityl-2,5-dimethyl-7-propyl-8H-pyrazolo[1,5-a]pyrrolo[3,2-e]pyrimidin-8-yl)methyl]phenyl methyl ether MS (ESI) m/z 467 MH$^+$.

Example 246

3-[(3-Mesityl-2,5-dimethyl-7-propyl-8H-pyrazolo[1,5-a]pyrrolo[3,2-e]pyrimidin-8-yl)methyl]phenyl methyl ether MS (ESI) m/z 467 MH$^+$.

Example 247

3-Mesityl-8-(4-methoxybenzyl)-2,5-dimethyl-7-propyl-8H-pyrazolo[1,5-a]pyrrolo[3,2-e]pyrimidine MS (ESI) m/z 467 MH$^+$.

Example 248

8-(1,3-Benzodioxol-5-ylmethyl)-3-mesityl-2,5-dimethyl-7-propyl-8H-pyrazolo[1,5-a]pyrrolo[3,2-e]pyrimidine MS (ESI) m/z 481 MH$^+$.

Example 249

8-(3-Ethoxypropyl)-3-mesityl-2,5-dimethyl-8H-pyrazolo[1,5-a]pyrrolo[3,2-e]pyrimidine MS (ESI) m/z 433 MH$^+$.

Example 250

8-(3-Isopropoxypropyl)-3-mesityl-2,5-dimethyl-7-propyl-8H-pyrazolo[1,5-a]pyrrolo[3,2-e]pyrimidine MS (ESI) m/z 447 MH$^+$.

Example 251

3-Mesityl-2,5-dimethyl-7,8-dipropyl-8H-pyrazolo[1,5-a]pyrrolo[3,2-e]pyrimidine

MS (ESI) m/z 389 MH$^+$.

Example 252

2-[3-Mesityl-2,5-dimethyl-7-(1-propynyl)-8H-pyrazolo[1,5-a]pyrrolo[3,2-e]pyrimidin-8-yl]ethyl methyl ether MS (ESI) m/z 401 MH$^+$.

Example 253

7-Butyl-8-(2-isopropoxyethyl)-3-mesityl-2,5-dimethyl-8H-pyrazolo[1,5-a]pyrrolo[3,2-e]pyrimidine MS (FAB) m/z 447 MH$^+$.

Example 254

8-Benzyl-7-butyl-mesityl-2,5-dimethyl-8H-pyrazolo[1,5-a]pyrrolo[3,2-e]pyrimidine MS (FAB) m/z 451 MH$^+$.

Example 255

7-butyl-8-(1-ethylpropyl)-3-mesityl-2,5-dimethyl-8H-pyrazolo[1,5-a]pyrrolo[3,2-e]pyrimidine MS (FAB) m/z 431 MH$^+$.

Example 256

7-Butyl-3-mesityl-2,5-dimethyl-8-[(1S)-1-phenylethyl]-8H-pyrazolo[1,5-a]pyrrolo[3,2-e]pyrimidine MS (FAB) m/z 465 MH$^+$.

Example 257

7-Butyl-3-mesityl-8-(3-methoxypropyl)-2,5-dimethyl-8H-pyrazolo[1,5-a]pyrrolo[3,2-e]pyrimidine MS (FAB) m/z 433 MH$^+$.

Example 258

8-(2-Isopropoxyethyl)-3-mesityl-7-(methoxymethyl)-2,5-dimethyl-8H-pyrazolo[1,5-a]pyrrolo[3,2-e]pyrimidine MS (FAB) m/z 435 MH$^+$.

Example 259

8-Benzyl-3-mesityl-7-(methoxymethyl)-2,5-dimethyl-8H-pyrazolo[1,5-a]pyrrolo[3,2-e]pyrimidine MS (FAB) m/z 439 MH$^+$.

Example 260

3-Mesityl-7-(methoxymethyl)-2,5-dimethyl-8-[(1S)-1-phenylethyl]-8H-pyrazolo[1,5-a]pyrrolo[3,2-e]pyrimidine MS (FAB) m/z 453 MH$^+$.

Example 261

7-Butyl-3-mesityl-8-(methoxymethyl)-2,5-dimethyl-8H-pyrazolo[1,5-a]pyrrolo[3,2-e]pyrimidine MS (FAB) m/z 419 MH$^+$.

Example 262

8-(2-Ethoxymethyl)-3-mesityl-2,5,7-trimethyl-8H-pyrazolo[1,5-a]pyrrolo[3,2-pyrimidine MS (ESI) m/z 391 MH$^+$.

Example 263

2-(3-Mesityl-2,5,7-trimethyl-8H-pyrazolo[1,5-a]pyrrolo[3,2-e]pyrimidin-8-yl)ethylpropyl ether MS (ESI) m/z 405 MH$^+$.

Example 264

8-(2-Isopropoxyethyl)-mesityl-2,5,7-trimethyl-8H-pyrazolo[1,5-a]pyrrolo[3,2-e]pyrimidine MS (ESI) m/z 405 MH$^+$.

Example 265

3-(3-Mesityl-2,5,7-trimethyl-8H-pyrazolo[1,5-a]pyrrolo[3,2-e]pyrimidin-8-yl)propyl methyl ether MS (ESI) m/z 391 MH$^+$.

Example 266

8-(3-Ethoxypropyl)-3-mesityl-2,5,7-trimethyl-8H-pyrazolo[1,5-a]pyrrolo[3,2-e]pyrimidine MS (ESI) m/z 405 MH$^+$.

Example 267

3-(3-Mesityl-2,5,7-trimethyl-8H-pyrazolo[1,5-a]pyrrolo[3,2-e]pyrimidin-8-yl)propyl propyl ether MS (ESI) m/z 419 MH$^+$.

Example 268

8-(3-Isopropoxypropyl)-3-mesityl-2,5,7-trimethyl-8H-pyrazolo[1,5-a]pyrrolo[3,2-e]pyrimidine MS (ESI) m/z 419 MH$^+$.

Example 269

8-Benzyl-3-mesityl-2,5,7-trimethyl-8H-pyrazolo[1,5-a]pyrrolo[3,2-e]pyrimidine

MS (ESI) m/z 409 MH$^+$.

Example 270

3-Mesityl-2,5-dimethyl-8-(3-propoxypropyl)-7-propyl-8H-pyrazolo[1,5-a]pyrrolo[3,2-e]pyrimidine MS (ESI) m/z 447 MH$^+$.

Example 271

4-((7-Allyl-3-mesityl-2,5-dimethyl-8H-pyrazolo[1,5-a]pyrrolo[3,2-e]pyrimidin-8-yl)methyl)phenyl methyl ether Yellow Oil
$^1$H NMR (400 MHz, CDCl$_3$) δ 2.04 (s, 6H), 2.21 (s, 3H), 2.33 (s, 3H), 2.62 (s, 3H), 3.34 (d, J=6.0 Hz, 2H), 3.78 (s, 3H), 5.11 (dd, J=1.2, 18.8 Hz, 1H), 5.18 (dd, J=1.2, 10.4 Hz, 1H), 5.38–6.00 (m, 1H), 6.13 (s, 2H), 6.34 (s, 1H), 6.85 (d, J=8.4 Hz, 2H), 6.97 (s, 2H), 7.07 (d, J=8.8 Hz, 2H).

Example 272

8-Benzyl-3-mesityl-2,5-dimethyl-7-(1-propynyl)-8H-pyrazolo[1,5-a]pyrrolo[3,2-e]pyrimidine MS (ESI) m/z 433 MH$^+$.

Example 273

3-Mesityl-8-(4-methoxybenzyl)-2,5-dimethyl-7-(1-propynyl)-8H-pyrazolo[1,5-a]pyrrolo[3,2-e]pyrimidine MS (ESI) m/z 463 MH$^+$.

Example 274

8-(1,3-Benzodioxol-5-ylmethyl)-3-mesityl-2,5-dimethyl-7-(1-propynyl)-8H-pyrazolo[1,5-a]pyrrolo[3,2-e]pyrimidine MS (ESI) m/z 477 MH$^+$.

Example 275

8-Benzyl-3-mesityl-2,5,7-trimethyl-8H-pyrazolo[1,5-a]pyrrolo[3,2-e]pyrimidine

MS (ESI) m/z 409 MH$^+$.

Example 276

3-Mesityl-8-(4-methoxybenzyl)-2,5,7-trimethyl-8H-pyrazolo[1,5-a]pyrrolo[3,2-e]pyrimidine MS (ESI) m/z 439 MH$^+$.

Example 277

8-(1,3-Benzodioxol-5-ylmethyl)-3-mesityl-2,5,7-trimethyl-8H-pyrazolo[1,5-a]pyrrolo[3,2-e]pyrimidine MS (ESI) m/z 453 MH$^+$.

Example 278

8-Butyl-7-isopropyl-3-mesityl-2,5-dimethyl-8H-pyrazolo[1,5-a]pyrrolo[3,5-e]pyrimidine MS (ESI) m/z 403 MH$^+$.

Example 279

8-Allyl-7-isopropyl-3-mesityl-2,5-dimethyl-8H-pyrazolo[125-a]pyrrolo[3,2-e]pyrimidine MS (ESI) m/z 387 MH$^+$.

Example 280

8-(2-Ethoxyethyl)-7-isopropyl-3-mesityl-2,5-dimethyl-8H-pyrazolo[1,5-a]pyrrolo[3,2]pyrimidine MS (ESI) in/z 419 MH$^+$.

Example 281

8-(2-Isopropoxyethyl)-7-isopropyl-3-mesityl-2,5-dimethyl-8H-pyrazolo[1,5-a]pyrrolo[3,2-e]pyrimidine MS (ESI) m/z 433 MH$^+$.

Example 282

3-(7-Isopropyl-3-mesityl-2,5-dimethyl-8H-pyrazolo[1,5-a]pyrrolo[3,2-e]pyrimidin-8-yl)propyl methyl ether MS (ESI) m/z 419 MH$^+$.

Example 283

8-Benzyl-7-isopropyl-3-mesityl-2,5-dimethyl-8H-pyrazolo[1,5-a]pyrrolo[3,2]pyrimidine MS (ESI) m/z 437 MH$^+$.

Example 284

4-((7-Isopropyl-3-mesityl-2,5-dimethyl-8H-pyrazolo[1,5-a]pyrrolo[3,2-e]pyrimidin-8-yl)methyl)phenyl methyl ether MS (ESI) m/z 467 MH$^+$.

Example 285

8-(1,3-Benzodioxol-5-ylmethyl)-7-isopropyl-3-mesityl-2,5-dimethyl-8H-pyrazolo[1,5-a]pyrrolo[3,2-e]pyrimidine MS (ESI) m/z 481 MH$^+$.

Example 286

7-Allyl-8-butyl-3-mesityl-2,5-dimethyl-8H-pyrazolo[1,5-a]pyrrolo[3,2-e]pyrimidine MS (ESI) m/z 401 MH$^+$.

Example 287

7,8-Diallyl-3-mesityl-2,5-dimethyl-8H-pyrazolo[1,5-a]pyrrolo[3,2-e]pyrimidine

MS (ESI) m/z 385 MH$^+$.

Example 288

2-(7-Allyl-3-mesityl-2,5-dimethyl-8H-pyrazolo[1,5-a]pyrrolo[3,2-e]pyrimidin-8-yl)ethyl methyl ether MS (ESI) m/z 403 MH$^+$.

Example 289

2-(7-Allyl-3-mesityl-2,5-dimethyl-8H-pyrazolo[1,5-a]pyrrolo[3,2-e]pyrimidin-8-yl)ethyl ethyl ether MS (ESI) m/z 417 MH$^+$.

Example 290

2-(7-Allyl-3-mesityl-2,5-dimethyl-8H-pyrazolo[1,5-a]pyrrolo[3,2-e]pyrimidin-8-yl)ethyl isopropyl ether MS (ESI) m/z 431 MH$^+$.

Example 291

3-(7-Allyl-mesityl-2,5-dimethyl-8H-pyrazolo[1,5-a]pyrrolo[3,2-e]pyrimidin-8-yl)propyl methyl ether MS (ESI) m/z 417 MH$^+$.

Example 292

7-Allyl-8-benzyl-3-mesityl-2,5-dimethyl-8H-pyrazolo[1,5-a]pyrrolo[3,2-e]pyrimidine MS (ESI) m/z 435 MH$^+$.

Example 293

7-Allyl-8-(1,3-benzodioxol-5-ylmethyl)-3-mesityl-2,5-dimethyl-8H-pyrazolo[1,5-a]pyrrolo[3,2-e]pyrimidine MS (ESI) m/z 479 MH$^+$.

Example 294

8-(3-Isopropoxypropyl)-3-mesityl-2,5-dimethyl-8H-pyrazolo[1,5-a]pyrrolo[3,2-e]pyrimidine
Yellow Oil
MS (ESI) m/z 405 MH$^+$.

Example 295

6,7-Dibromo-8-(3-isopropoxypropyl)-3-mesityl 2,5-dimethyl-8H-pyrazolo[1,5-a]pyrrolo[3,2-e]pyrimidine
MS (ESI) m/z 563 MH$^+$.

Example 296

7-Bromo-8-(3-isopropoxypropyl)-3-mesityl-2,5-dimethyl-8H-pyrazolo[1,5-a]pyrrolo[3,2-e]pyrimidine
MS (ESI) m/z 483 MH$^+$.

Example 297

8-(2-Isopropoxyethyl)-3-mesityl-2,5-dimethyl-8H-pyrazolo[1,5-a]pyrrolo[3,2-e]pyrimidine
Pale Brown Crystals
MS (ESI) m/z 391 MH$^+$.

Example 298

6-Bromo-8-(2-isopropoxyethyl)-3-mesityl-7-(methoxymethyl)-2,5-dimethyl-8H-pyrazolo[1,5-a]pyrrolo[3,2-e]pyrimidine
$^1$H NMR (400 MHz, CDCl$_3$) δ 1.09 (d, J=6.0 Hz, 6H), 2.02 (s, 6H), 2.23 (s, 3H), 2.34 (s, 3H), 2.85 (s, 3H), 3.36 (s, 3H), 3.58 (hept., J=6.4 Hz, 1H), 3.90 (t, J=5.6 Hz, 2H), 4.79 (s, 2H), 5.06 (t, J=5.6 Hz, 2H), 6.70 (s, 2H).

Example 299

3-Mesityl-7-(methoxymethyl)-2,5-dimethyl-8-propyl-8H-pyrazolo[1,5-a]pyrrolo[3,2-e]pyrimidine
MS (FAB) m/z 391 MH$^+$.

Example 300

3-Mesityl-7-(methoxymethyl)-2,5-dimethyl-8-pentyl-8H-pyrazolo[1,5-a]pyrrolo[3,2-e]pyrimidine
MS (FAB) m/z 419 MH$^+$.

Example 301

8-(Cyclopropylmethyl)-3-mesityl-7-(methoxymethyl)-2,5-dimethyl-8H-pyrazolo[1,5-a]pyrrolo[3,2-e]pyrimidine
MS (FAB) m/z 403 MH$^+$.

Example 302

3-Mesityl-8-(2-methoxyethyl)-7-(methoxymethyl)-2,5-dimethyl-8H-pyrazolo[1,5-a]pyrrolo[3,2-e]pyrimidine
MS (FAB) in/z 407 MH$^+$.

Example 303

8-(2-Ethoxyethyl)-3-mesityl-7-(methoxymethyl)-2,5-dimethyl-8H-pyrazolo[1,5-a]pyrrolo[3,2-e]pyrimidine
MS (FAB) m/z 421 MH$^+$.

Example 304

3-mesityl-7-(methoxymethyl)-2,5-dimethyl-8-(2-propoxyethyl)-8H-pyrazolo[1,5-a]pyrrolo[3,2-e]pyrimidine
MS (FAB) m/z 435 MH$^+$.

Example 305

3-Mesityl-7-(methoxymethyl)-8-(3-methoxypropyl)-2,5-dimethyl-8H-pyrazolo[1,5-a]pyrrolo[3,2-e]pyrimidine
MS (FAB) m/z 421 MH$^+$.

Example 306

8-(3-Ethoxypropyl)-3-mesityl-7-(methoxymethyl)-2,5-dimethyl-8H-pyrazolo[1,5-a]pyrrolo[3,2-e]pyrimidine
MS (FAB) m/z 435 MH$^+$.

Example 307

(3-Isopropxypropyl)-3-mesityl-7-(methoxymethyl)-2,5-dimethyl-8H-pyrazolo[1,5-a]pyrrolo[3,2-e]pyrimidine
MS (FAB) m/z 449 MH$^+$.

Example 308

3-Mesityl-8-(2-methoxybenzyl)-7-(methoxymethyl)-2,5-dimethyl-8H-pyrazolo[1,5-a]pyrrolo[3,2-e]pyrimidine
MS (FAB) in/z 469 MH$^+$.

Example 309

3-Mesityl-8-(3-methoxybenzyl)-7-(methoxymethyl)-2,5-dimethyl-8H-pyrazolo[1,5-a]pyrrolo[3,2-e]pyrimidin
MS (FAB) m/z 469 MH$^+$.

Example 310

3-Mesityl-8-(4-methoxybenzyl)-7-(methoxymethyl)-2,5-dimethyl-8H-pyrazolo[1,5-a]pyrrolo[3,2e]pyrimidine
MS (FAB) m/z 469 MH$^+$.

Example 311

8-(1,3-Benzodioxol-5-ylmethyl)-3-mesityl-7-(methoxymethyl)-2,5-dimethyl-8H-pyrazolo[1,5-a]pyrrolo[3,2-e]pyrimidine
MS (FAB) m/z 483 MH$^+$.

Example 312

7-Butyl-8-(2-ethoxyethyl)-3-mesityl-2,5-dimethyl-8H-pyrazolo[1,5-a]pyrrolo[3,2-e]pyrimidine
MS (FAB) m/z 433 MH$^+$.

Example 313

7-Butyl-3-mesityl-8-(4-methoxybenzyl)-2,5-dimethyl-8H-pyrazolo[1,5-a]pyrrolo[3,2-e]pyrimidine
MS (FAB) m/z 481 MH$^+$.

Example 314

4-[(3-Mesityl-2,5-dimethyl-8H-pyrazolo[1,5-a]pyrrolo[3,2-e]pyrimidin-8-yl)methyl phenol
White Crystals
MS (ESI) m/z 411 MH$^+$.

Example 315

8-(4-Ispropoxybenzyl)-3-mesityl-2,5-dimethyl-8H-pyrazolo[1,5-a]pyrrolo[3,2-e]pyrimidine hydrochloride
MS (ESI) m/z 453 MH$^+$.

Example 316

4-(8-Butyl-2,5-dimethyl-7-propyl-8H-8H-pyrazolo[1,5-a]pyrrolo[3,2-e]pyrimidin-3-yl)-3,5-dimethylphenyl methyl ether
MS (ESI) m/z 419 MH$^+$.

Example 317

8-(2-Ethoxyethyl)-3-(4-methoxy-2,6-dimethylphenyl)-2,5-dimethyl-7-propyl-8H-pyrazolo[1,5-a]pyrrolo[3,2-e]pyrimidine
MS (ESI) m/z 435 MH$^+$.

Example 318

8-(2-Isopropoxyethyl)-3-(4-methoxy-2,6-dimethylphenyl)-2,5-dimethyl-7-propyl-8H-pyrazolo[1,5-a]pyrrolo[3,2-e]pyrimidine
MS (ESI) m/z 449 NH$^+$.

Example 319

3-(4-Methoxy-2-6-dimethylphenyl)-8-(3-methoxypropyl)-2,5-dimethyl-7-propyl-8H-pyrazolo[1,5-a]pyrrolo[3,2-e]pyrimidine
MS (ESI) m/z 434 MH$^+$.

Example 320

3-(4-Methoxybenzyl)-3-(4-methoxy-2,6-dimethylphenyl)-2,5-dimethyl-7-propyl-8H-pyrazolo[1,5-a]pyrrolo[3,2-e]pyrimidine
MS (ESI) m/z 483 NH$^+$.

Example 321

3-(2-Bromo-4,6-dimethylphenyl)-8-butyl-2,5-dimethyl-7-propyl-8H-pyrazolo[1,5-a]pyrrolo[3,2-e]pyrimidine
MS (ESI) m/z 467 MH$^+$.

Example 322

2-(3-(2-Bromo-4,6-dimethylphenyl)-2,5-dimethyl-7-propyl-8H-pyrazolo[1,5-a]pyrrolo[3,2-e]pyrimidin-8-yl)ethyl methyl ether
MS (ESI) m/z 469 MH$^+$.

Example 323

2-(3-(2-Bromo-4,6-dimethylphenyl)-2,5-dimethyl-7-propyl-8H-pyrazolo[1,5-a]pyrrolo[3,2-e]pyrimidin-8-yl)ethyl ethyl ether
MS (ESI) m/z 483 MH$^+$.

Example 324

2-(3-(2-Bromo-4,6-dimethylphenyl)-2,5-dimethyl-7-propyl-8H-pyrazolo[1,5-a]pyrrolo[3,2-e]pyrimidin-8-yl)ethyl isopropyl ether
MS (ESI) m/z 497 MH$^+$.

Example 325

3-(2-Bromo-4,6-dimethylphenyl)-8-(3-methoxypropyl)-2,5-dimethyl-7-propyl-8H-pyrazolo[1,5-a]pyrrolo[3,2-e]pyrimidine
MS (ESI) m/z 483 MH$^+$.

Example 326

3-(2-Bromo-4,6-dimethylphenyl)-8-(4-methoxybenzyl)-2,5-dimethyl-7-propyl-8H-pyrazolo[1,5-a]pyrrolo[3,2-a]pyrimidine
MS (ESI) o/z 531 MH$^+$.

Example 327

8-(Cyclohexylmethyl)-3-mesityl-2,5-dimethyl-7-propyl-8H-pyrazolo[1,5-a]pyrrolo[3,2-e]pyrimidine
MS (ESI) m/z 443 MH$^+$.

Example 328

8-Cyclohexyl-3-mesityl-2,5-dimethyl-7-propyl-8H-pyrazolo[1,5-a]pyrrolo[3,2-e]pyrimidine
MS (ESI) m/z 429 MH$^+$.

Example 329

8-(Dicyclopropylmethyl)-3-mesityl-2,5-dimethyl-7-propyl-8H-pyrazolo[1,5-a]pyrrolo[3,2-e]pyrimidine
MS (ESI) m/z 441 MH$^+$.

Example 330

4-((3-Mesityl-2,5-dimethyl-7-propyl-8H-pyrazolo[1,5-a]pyrrolo[3,2-e]pyrimidine-8-yl)methyl)-1-benzensulfonamide
MS (ESI) m/z 516 MH$^+$.

Example 331

3-Mesityl-2,5-dimethyl-7-propyl-8-(2-pyridylmethyl)-8H-pyrazolo[1,5-a]pyrrolo[3,2-e]pyrimidine
MS (ESI) m/z 438 MH$^+$.

Example 332

3-Mesityl-2,5-dimethyl-7-propyl-8-(3-pyridylmethyl)-8H-pyrazolo[1,5-a]pyrrolo[3,2-e]pyrimidine
MS (ESI) m/z 438 MH$^+$.

Example 333

3-Mesityl-2,5-dimethyl-7-propyl-8-(4-pyridylmethyl)-8H-pyrazolo[1,5-a]pyrrolo[3,2-e]pyrimidine
MS (ESI) m/z 438 MH$^+$.

Example 334

7-Ethyl-8-(3-isopropoxypropyl)-3-mesityl-2,5-dimethyl-8H-pyrazolo[1,5-a]pyrrolo[3,2-e]pyrimidine (FAB) m/z 433 MH+.

Example 335

7-Ethyl-3-mesityl-8-(4-methoxybenzyl)-2,5-dimethyl-8H-pyrazolo[1,5-a]pyrrolo[3,2-e]pyrimidine MS (ESI) m/z 453 MH+.

Example 336

8-(2-Ethoxyethyl-7-ethyl-3-mesityl-2,5-dimethyl-8H-pyrazolo[1,5-a]pyrrolo[3,2-e]pyrimidine
Pale Yellow Crystals
MS (ESI) m/z 405 MH+.

Example 337

7-Ethyl-3-mesityl-2,5-dimethyl-8-(2-propoxyethyl)-8H-pyrazolo[1,5-a]pyrrolo[3,2-e]pyrimidine MS (ESI) m/z 419 MH+.

Example 338

8-(4-Chlorobenzyl)-3-mesityl-2,5-dimethyl-7-propyl)-8H-pyrazolo[1,5-a]pyrrolo[3,2-e]pyrimidine MS (ESI) m/z 471 MH+.

Example 339

8-(4-Fulorobenzyl)-3-mesityl-2,5-dimethyl-7-propyl-8-pyrazolo[1,5-a]pyrrolo[3,2-e]pyrimidine MS (ESI) m/z 455 MH+.

Example 340

3-Mesityl-2,5-dimethyl-7-propyl-8-(4-(trifuluoromethyl)benzyl)-8H-[1,5-a]pyrrolo[3,2-e]pyrimidine MS (ESI) m/z 505 MH+.

Example 341

3-Mesityl-2,5-dimethyl-7-propyl-8-(4-(trifuluoromethyl)benzyl)-8H-[1,5-a]pyrrolo[3,2-e]pyrimidine MS (ESI) m/z 521 MH+.

Example 342

N-(4-((3-Mesityl-2,5-dimethyl-7-propyl-8H-pyrazolo[1,5-a]pyrrolo[3,2-e]pyrimidine MS (ESI) m/z 480 MH+.

Example 343

3-Mesityl-2,5-dimethyl-8-(4-methylbenzyl)-7-propyl-8H-pyrazolo[1,5-a]pyrrolo[3,2-e]pyrimidine MS (ESI) m/z 451 MH+.

Example 344

3-(4-Methoxy-2,6-dimethylphenyl)-8-(2-methoxyethyl)-2,5-dimethyl-7-propyl-8H-pyrazolo[1,5-a]pyrrolo[3,2-e]pyrimidine MS (ESI) ma/z 421 MH+.

Example 345

7-Ethyl-3-mesityl-8-[(6-methoxy-3-pyridyl)methyl]-2,5-dimethyl-8H-pyrazolo[1,5-a]pyrrolo[3,2-e]pyrimidine
Yellow Amorphous
MS (ESI) m/z 454 MH+.

Example 346

5-[(7-Ethyl-3-mesityl-2,5-dimethyl-8H-pyrazolo[1,5-a]pyrrolo[3,2-e]pyrimidine-8-yl)methyl]-1,2-dihydro-2-pyridone
White Crystals
MS (ESI) m/z 440 MH+.

Example 347

5-[(7-Ethyl-3-mesityl-2,5-dimethyl-8H-pyrazolo[1,5-a]pyrrolo[3,2-e]pyrimidin-8-yl)methyl]-1-methyl-1,2-dihydro-2-pyridinone
White Crystals
MS (ESI) m/z 454 MH+.

Example 348

2-(3-(4-Bromo-2,6-dimethylphenyl)-2,5-dimethyl-7-propyl-8H-pyrazolo[1,5-a]pyrazolo[3,2-e]pyrimidine-8-yl)ethyl methyl ether
Yellow Oil
$^1$H-NMR (400 MHz, CDCl$_3$) δ 1.08 (t, J=7.2 Hz, 3H), 1.75–1.82 (m, 2H), 2.03 (s, 6H), 2.21 (s, 3H), 2.60 (s, 3H), 2.77 (t, J=8.0 Hz, 2H), 3.36 (s, 3H), 3.87 (t, J=5.6 Hz, 2H), 4.88 (t, J=5.6 Hz, 2H), 6.27 (s, 1H), 7.29 (s, 2H).

Example 349

2-(3-(4-Bromo)-2,6-dimethylphenyl)-2,5-dimethyl-7-propyl-8H-pyrazolo[1,5-a]pyrrolo[3,2-e]pyrimidin-8-yl)ethyl isopropyl ether
Yellow Oil
$^1$H-NMR (400 MHz, CDCl$_3$) δ 1.01–1.03 (m, 3H), 1.03 (d, J=6.4 Hz, 6H), 1.69–1.75 (m, 2H), 1.97 (s, 6H), 2.14 (s, 3H), 2.54 (s, 3H), 2.72 (s, 2H), 3.50–3.55 (m, 1H), 3.81 (t, J=6.0 Hz, 2H), 4.78 (t, J=6.0 Hz, 2H), 6.20 (s, 1H), 7.22 (s, 2H).

Example 350

3-(4-Bromo-2,6-dimethylphenyl)-8-(4-methoxybenzyl)-2,5-dimethyl-7-propyl-8H-pyrazolo[1,5-a]pyrrolo[3,2-e]pyrimidine MS (ESI) m/z 533 MH+.

Example 351

3-Benzo[b]furan-2-yl-8-(1-ethylpropyl)-2,5-dimethyl-7,8-dihydro-6H-pyrazolo[1,5-a]pyrrolo[3,2-e]pyrimidine A solution of 3-bromo-8-(1-ethylpropyl)-2,5-dimethyl-7,8-dihydro-6H-pyrazolo[1,5-a]pyrrolo[3,2-e]pyrimidine (300 mg, 0.89 mmol), benzo[b]furan-2-yl(tributyl)tin (0.72 g, 1.78 mmol) and Pd(PPh$_3$)$_4$ (103 mg, 0.90 mmol) in N,N-dimethylformamide (15 mL) was stirred at 120° C. for one day. Ethyl acetate and water were added thereto, followed by filtering through Celite. The organic layer of the filtrate was washed with brine, dried over anhydrous magnesium sulfate and evaporated. The residue was purified by silica gel column chromatography (0–5% ethyl acetate/hexane), to give the title compound (111 mg) as white crystals.

$^1$H-NMR (400 MHz, CDCl$_3$) δ 0.92 (t, J=7.2 Hz, 6H), 1.54–1.72 (m, 4H), 2.43 (s, 3H), 2.76 (s, 3H), 3.13 (t, J=9.2 Hz, 2H), 3.69 (t, J=9.2 Hz, 2H), 5.58–5.68 (m, 1H), 7.14–7.20 (m, 2H), 7.27 (d, J=0.8 Hz, 1H), 7.46–7.50 (m, 1H), 7.53–7.56 (m, 1H).

Example 352

3-(3-Bromobenzo[b]furan-2-yl)-8-(1-ethylpropyl)-2,5-dimethyl-7,8-dihydro-6H-1,5-a]pyrrolo[3,2-e]pyrimidine Bromine (1.0 M solution in carbon tetrachloride 0.3 mL, 0.30 mmol) was added to a solution of 3-benzo[b]furan-2-yl-8-(1-ethylpropyl)-2,5-dimethyl-7,8-dihydro-6H-pyrazolo[1,5-a]pyrrolo[3,2-e]pyrimidine (50 mg, 0.13 mmol) in N,N-dimethylformamide (0.3 mL) at 0° C., followed by stirring for one hour. Hypo water was added thereto, and the mixture was diluted with ethyl acetate, washed with an aqueous saturated solution of ammonium chloride and brine, dried over anhydrous magnesium sulfate and evaporated. The residue was purified by silica gel column chromatography (10% ethyl acetate/hexane), to give the title compound (57 mg) as white crystals.

$^1$H-NMR (400 MHz, CDCl$_3$) δ 0.94 (t, J=7.2 Hz, 6H), 1.54–1.72 (m, 4H), 2.36 (s, 3H), 2.49 (s, 3H), 3.12 (t, J=9.2 Hz, 2H), 3.70 (t, J=9.2 Hz, 2H), 5.60–5.66 (m, 1H), 7.27–7.31 (m, 2H), 7.48–7.54 (m, 2H).

Example 353

3-(3-Bromobenzo[b]furan-2-yl)-8-(1-ethylpropyl)-2,5-dimethyl-8H-pyrazolo[1,5-a]pyrrolo[3,2-e]pyrimidine DDQ (33 mg, 0.15 mmol) was added to a solution of 3-(3-bromobenzo[b]furan-2-yl)-8-(1-ethylpropyl)-2,5-dimethyl-7,8-dihydro-6H-pyrazolo[1,5-a]pyrrolo[3,2-e]pyrimidine (60 mg, 0.13 mmol) in methylene chloride (10 mL) at room temperature, followed by stirring for one hour. After overnight, the residue was purified by silica gel column chromatography (10% ethyl acetate/hexane), to give the title compound (40 mg) as a reddish brown oil.

$^1$H-NMR (400 MHz, CDCl$_3$) δ 0.85 (t, J=7.2 Hz, 6H), 1.78–2.04 (m, 4H), 2.59 (s, 3H), 2.74 (s, 3H), 5.90–6.00 (m, 1H), 6.65 (d, J=3.2 Hz, 1H), 6.91 (d, J=3.2 Hz, 1H), 7.27–7.36 (m, 2H), 7.50–7.59 (m, 2H).

Example 354

8-(1-Ethylpropyl)-3-(1H-2-indolyl)-2,5-dimethyl-7,8-dihydro-6H-pyrazolo[1,5-a]pyrrolo[3,2-e]pyrimidine A solution of 2-2-[8-(1-ethynylpropyl)-2,5-dimethyl-7,8-dihydro-6H-pyrazolo[1,5-a]pyrrolo[3,2-e]pyrimidin-3-yl]-1-ethynylaniline (540 mg, 1.45 mmol) and copper iodide (551 mg, 2.89 mmol) in N,N-dimethylformamide (10 mL) was stirred at 120° C. for one day. After filtering through Celite, the filtrate was evaporated. The residue was purified by dry pack silica gel column chromatography (30% ethyl acetate/hexane), to give the title compound (15 mg) as pale yellow crystals.

$^1$H-NMR (400 MHz, CDCl$_3$) δ 0.93 (t, J=7.6 Hz, 6H), 1.55–1.70 (m, 4H), 2.44 (s, 3H), 2.68 (s, 3H), 3.13 (t, J=9.2 Hz, 2H), 3.70 (t, J=9.2 Hz, 2H), 5.58–5.70 (m, 1H), 6.55 (s, 1H), 7.06 (t, J=7.6 Hz, 1H), 7.11 (t, J=7.6 Hz, 1H), 7.45 (d, J=7.6 Hz, 1H), 7.59 (d, J=7.6 Hz, 1H), 11.04 (s, 1H).

Example 355

3-(1H-Benzo[d]imidazol-2-yl)-8-(1-ethylpropyl)-2,5-dimethyl-7,8-dihydro-6H-pyrazolo[1,5-pyrrolo[3,2-e]pyrimidine DDQ (79 mg, 0.35 mmol) was added to a solution of 8-(1-ethylpropyl)-2,5-dimethyl-7,8-dihydro-6H-pyrazolo[1,5-a]pyrrolo[3,2-e]pyrimidin-3-carbaldehyde (100 mg, 0.35 mmol) and 1,2-phenylenediamine (40 mg, 0.37 mmol) in acetonitrile (1 mL) at room temperature and the mixture was stirred for one day. Further, a 0.5N aqueous solution of sodium hydroxide was added thereto, followed by stirring for five hours. The mixture was extracted with ethyl acetate, dried over anhydrous magnesium sulfate and evaporated. The residue was purified by dry pack silica gel column chromatography (50% ethyl acetate/hexane) to give the title compound (23 mg) as pale yellow crystals.

$^1$H-NMR (400 MHz, CDCl$_3$) δ 0.94 (t, J=7.6 Hz, 6H), 1.54–1.74 (m, 4H), 2.45 (s, 3H), 2.93 (s, 3H), 3.15 (t, J=9.2 Hz, 2H), 3.73 (t, J=9.2 Hz, 2H), 5.59–5.67 (m, 1H), 7.15–7.22 (m, 2H), 7.49 (dd, J=7.2 Hz, 3.0 Hz, 1H), 7.78 (d, J=7.2 Hz, 1H), 11.68 (s, 1H).

Example 356

8-(1-Ethylpropyl)-2,5-dimethyl-3-(1-methyl-1H-benzo[d]imidazol-2-yl)-7,8-dihydro-6H-pyrazolo[1,5-a]pyrrolo[3,2-e]pyrimidine According to the method described in the above Example 354, the title compound (65 mg) was obtained as pale yellowish brown crystals from 8-(1-ethylpropyl)-2,5-dimethyl-7,8-dihydro-6H-pyrazolo[1,5-a]pyrrolo[3,2-e]pyrimidin-3-carbaldehyde (100 mg, 0.35 mmol).

$^1$H-NMR (400 MHz, CDCl$_3$) δ 0.94 (t, J=7.6 Hz, 6H), 1.54–1.72 (m, 4H), 2.32 (s, 3H), 2.59 (s, 3H), 3.12 (t, J=9.2 Hz, 2H), 3.71 (t, J=9.2 Hz, 2H), 3.84 (s, 3H), 5.62–5.71 (m, 1H), 7.21–7.28 (m, 2H), 7.35–7.40 (m, 1H), 7.74–7.79 (m, 1H).

Example 357

8-(1-Ethylpropyl)-2,5-dimethyl-3-(4-methyl-1H-benzo[d]imidazol-2-yl)-7,8-dihydro-6H-pyrazolo[1,5-a]pyrrolo[3,2-e]pyrimidine According to the method described in the above Example 354, the title compound (50 mg) was obtained as pale yellowish brown crystals from 8-(1-ethylpropyl)-2,5-dimethyl-7,8-dihydro-6H-pyrazolo[1,5-a]pyrrolo[3,2-e]pyrimidin-3-carbaldehyde (200 mg, 0.70 mmol).

$^1$H-NMR (400 MHz, CDCl$_3$) δ 0.93 (t, J=7.6 Hz, 6H×1/2), 0.94 (t, J=7.6 Hz, 6H×1/2), 1.54–1.75 (m, 4H), 2.44 (s, 3H), 2.60 (s, 3H×1/2), 2.72 (s, 3H×1/2), 2.93 (s, 3H×1/2), 2.96 (s, 3H×1/2), 3.14 (t, J=9.2 Hz, 2H×1/2), 3.15 (t, J=9.2 Hz, 2H×1/2), 3.72 (t, J=9.2 Hz, 2H×1/2), 3.73 (t, J=9.2 Hz, 2H×1/2), 5.58–5.67 (m, 1H), 6.96–7.15 (m, 2H), 7.32 (d,

J=8.0 Hz, 1H×1/2), 7.63 (d, J=8.0 Hz, 1H×1/2), 11.50 (s, 1H×1/2), 11.78 (s, 1H×1/2).

Example 358

2-[8-(1-Ethylpropyl)-2,5-dimethyl-7,8-dihydro 6H-pyrazolo[1,5-a]pyrrolo[3,2-e]pyrimidin-3-yl]-1H-benzo[d]imidazol-1-yl methyl sulfone Methanesulfonyl chloride (12 mL, 0.16 mmol) was added to a solution of 3-(1H-benzo[d]imidazol-2-yl)-8-(1-ethylpropyl)-2,5-dimethyl-7,8-dihydro-6H-pyrazolo[1,5-a]pyrrolo[3,2-e]pyrimidine (50 mg, 0.13 mmol) in pyridine (0.5 mL) at room temperature and the mixture was stirred for one hour. Water was added thereto, and the mixture was extracted with ethyl acetate, washed with brine, dried over anhydrous magnesium sulfate and evaporated. The residue was purified by silica gel column chromatography (50% ethyl acetate/hexane), to give the title compound (48 mg) as pale yellow crystals.

$^1$H-NMR (400 MHz, CDCl$_3$) δ 0.93 (t, J=7.6 Hz, 6H), 1.54–1.72 (m, 4H), 2.24 (s, 3H), 2.49 (s, 3H), 3.09 (t, J=9.2 Hz, 2H), 3.69 (t, J=9.2 Hz, 2H), 3.77 (s, 3H), 5.60–5.68 (m, 1H), 7.36–7.41 (m, 2H), 7.77–7.82 (m, 1H), 7.89–7.94 (m, 1H).

Example 359

6-Mesityl-1,3,4,7-tetramethyl-2,3-dihydro-1H-pyrazolo[5,1-b]purin-2-one

Hydrazine monohydrate (5 mL) was added to a solution of ethyl 7-amino-3-mesityl-2,5-dimethylpyrazolo[1,5-a]pyrimidin-6-carboxylate (809 mg, 2.30 mmol) in ethanol (30 mL), followed by heating under reflux for eight hours. The reaction mixture was evaporated as it was, to give a crude compound. A 10% aqueous solution of hydrogen chloride was added to a solution of the crude compound in ethanol (25 mL) under ice-cooling, and a solution of sodium nitrite (177 mg, 2.53 mmol) in water (10 mL) was gradually added dropwise. After one hour, a temperature was raised to room temperature and the mixture was stirred for 1five hours. The reaction mixture was evaporated as it was, water was added, and the resulting solid was dried, to give a crude compound (571 mg). Sodium hydride (27 mg, 0.66 mmol) was added to a solution of the crude compound (107 mg, 0.33 mmol) in N,N-dimethylformamide (5 mL) at room temperature. After 30 minutes, methyl iodide (0.052 mL, 0.83 mmol) was added, followed by stirring at the same temperature for one hour. Water was added under ice-cooling, followed by extracting with ether. The organic layer was washed with brine, dried over anhydrous magnesium sulfate and evaporated. The residue was purified by silica gel column chromatography (25% ethyl acetate/hexane), to obtain the title compound (65 mg) as brown crystals.

$^1$H NMR (400 MHz, CDCl$_3$) δ 2.00 (s, 6H), 2.25 (s, 3H), 2.33 (s, 3H), 2.72 (s, 3H), 3.68 (s, 3H), 4.08 (s, 3H), 6.97 (s, 2H).

Example 360

Ethyl 7-[(1-ethylpropyl)amino]-3-mesityl-2,5-dimethylpyrazolo[1,5-a]pyrimidine-6-carboxylate 3-Aminopentane (5 mL) was added to a solution of ethyl 7-chloro-3-mesityl-2,5-dimethylpyrazolo[1,5-a]pyrimidin-6-carboxylate (1.94 g, 5.22 mmol) in acetonitrile (20 mL), followed by heating under reflux for eight hours. The mixture was extracted with ethyl acetate, and the organic layer was washed with brine, dried over anhydrous magnesium sulfate and evaporated. The residue was purified by silica gel column chromatography (20% ethyl acetate/hexane), to give the title compound (1.70 g).

$^1$H NMR (400 Hz, CDCl$_3$) δ 0.83 (t, J=7.4 Hz, 6H), 1.43 (t, J=7.1 Hz, 3H), 1.35–1.60 (m, 4H), 2.05 (s, 6H), 2.17 (s, 3H), 2.34 (s, 3H), 3.02 (s, 3H), 3.92–4.12 (m, 1H), 4.41 (q, J=7.1 Hz, 2H), 6.94 (s, 2H), 7.39 (d, J=8.1 Hz, 1H).

Example 361

1-(1-Ethylpropyl)-6-mesityl-4,7-dimethyl-2,3-dihydro-1H-pyrazolo[1,5-b]purin-2-one Hydrazine monohydrate (10 mL) was added to a solution of ethyl 7-[(1-ethylpropyl)amino]-3-mesityl-2,5-dimethylpyrazolo[1,5-a]pyrimidine-6-carboxylate (1.25 g, 2.97 mmol) in ethanol (30 mL), followed by heating under reflux for five hours. The reaction mixture was evaporated as it was, to give a crude compound. A 10% solution of hydrogen chloride (20 mL) was added to a solution of the crude compound in ethanol (40 mL) under ice-cooling, and a solution of sodium nitrile (229 mg, 3.27 mmol) in water (10 mL) was gradually added dropwise. After one hour, the mixture was stirred at room temperature for 13 hours. The reaction mixture was evaporated as it was, and a 2N aqueous solution of sodium hydroxide was added to the residue. The mixture was extracted with ethyl acetate, and the organic layer was washed with brine, dried over anhydrous magnesium sulfate and evaporated. The residue was purified by silica gel column chromatography (50% ethyl acetate/hexane) to obtain the title compound (393 mg) as yellow crystals.

Yellow Crystals $^1$H NMR (400 MHz, CDCl$_3$) δ 0.83 (t, J=7.4 Hz, 6H), 1.68–1.84 (m, 2H), 2.02 (s, 6H), 2.08–2.24 (m, 2H), 2.25 (s, 3H), 2.36 (s, 3H), 2.82 (s, 3H), 4.20–4.31 (m, 1H), 6.98 (s, 2H), 9.67 (s, 1H).

Example 362

1-(1-Ethylpropyl)-6-mesityl-3,4,7-trimethyl-2,3-dihydro-1H-pyrazolo[1,5-a]purin-2-one (CRFA-343)

Sodium hydride (11.2 mg, 0.28 mmol) was added to a solution of 1-(1-ethylpropyl)-6-mesityl-4,7-dimethyl-2,3-dihydro-1H-pyrazolo[1,5-b]purin-2-one (100 mg, 0.26 mmol) in N,N-dimethylformamide (5 mL) at room temperature. After 30 minutes, methyl iodide (0.018 mL, 0.28 mmol) was added, followed by stirring at the same temperature for one hour. Water was added under ice-cooling, and the mixture was extracted with ether. The organic layer was washed with brine, dried over anhydrous magnesium sulfate and evaporated. The residue was purified by silica gel column chromatography (20–50% ethyl acetate/hexane), to give the title compound (85 mg) and the compound (13 mg) of Example 363 as white crystals.

$^1$H NMR (400 MHz, CDCl$_3$) δ 0.78 (t, J=7.4 Hz, 6H), 1.65–1.80 (m, 2H), 2.01 (s, 6H), 2.07–2.20 (m, 2H), 2.24 (s, 3H), 2.36 (s, 3H), 3.01 (s, 3H), 3.61 (s, 3H), 4.19–4.32 (m, 1H), 6.97 (s, 2H).

Example 363

4-Ethyl-1-(1-ethylpropyl)-6-mesityl-3,7-dimethyl-2, 3-dihydro-1H-pyrazolo[5,1-b]purin-2-one (CRFA-344)

Yellow Crystals
$^1$H NMR (400 MHz, CDCl$_3$) δ 0.79 (t, J=7.4 Hz, 6H), 1.56 (t, J=7.4 Hz, 3H), 1.66–1.80 (m, 2H), 2.02 (s, 6H), 2.04–2.18 (m, 2H), 2.23 (s, 3H), 2.36 (s, 3H), 3.46 (q, J=7.4 Hz, 2H), 3.60 (s, 3H), 4.16–4.32 (m, 1H), 6.97 (s, 2H).

Example 364

3-Benzyl-1-(1-ethylpropyl)-6-mesityl-4,7-dimethyl-2,3-dihydro-1H-pyrazolo[5,1-b]purin-2-one Sodium hydride (28 mg, 0.71 mmol) was added to a solution of 1-(1-ethylpropyl)-6-mesityl-4,7-dimethyl-2,3-dihydro-1H-pyrazolo[5,1-b]purin-2-one (230 mg, 0.59 mmol) in N,N-dimethylformamide (5 mL) at room temperature. After 30 minutes, benzyl bromide (0.079 mL, 0.65 mmol) was added, followed by stirring at 70' for one hour. Water was added under ice-cooling, followed by extracting with ethyl acetate. The organic layer was washed with brine, dried over anhydrous magnesium sulfate and evaporated. The residue was purified by silica gel column chromatography (15–20% ethylacetate/hexane), to give the title compound (259 mg) as brown crystals.
$^1$H NMR (400 MHz, CDCl$_3$) δ 0.83 (t, J=7.3 Hz, 6H), 1.66–1.90 (m, 2H), 2.02 (s, 6H), 1.95–2.20 (m, 2H), 2.21 (s, 3H), 2.36 (s, 3H), 2.69 (s, 3H), 4.26–4.46 (m, 1H), 5.26 (s, 2H), 6.98 (s, 2H), 7.14–7.46 (m, 5H).

Example 365

6-Mesityl-4,7-dimethyl-2,3-dihydro-1H-dipyrazolo[1,5-a:4,3-e]pyrimidin-3-one

Hydrazine monohydrate (5 mL) was added to a solution of ethyl 7-chloro-3-mesityl-2,5-dimethylpyrazolo[1,5-a]pyrimidin-6-carboxylate (343 mg, 0.922 mmol) in ethanol (10 mL), followed by stirring at room temperature for one hour. The reaction mixture was evaporated as it was, and extracted with ethyl acetate. The organic layer was washed with brine, dried over anhydrous magnesium sulfate and evaporated. The residue was purified by silica gel column chromatography (ethyl acetate), to give the title compound (298 mg) as brown crystals.
$^1$H NMR (400 MHz, CDCl$_3$) δ 2.03 (s, 6H), 2.22 (s, 3H), 2.50 (s, 3H), 3.09 (s, 3H), 7.13 (s, 2H).

Example 366

6-Mesityl-4,7-dimethyl-1H-dipyrazolo[1,5-a: 4,3-e]pyrimidine

One droplet of N,N-dimethylaniline was added to a solution of 6-mesityl-4,7-dimethyl-2,3-dihydro-1H-dipyrazolo[1,5-a:4,3-e]pyrimidin-3-one (60 mg, 0.187 mmol) in phosphorus oxychloride (3 mL), followed by heating under reflux for two hours. The reaction mixture was added to ice, stirred for a while, and then extracted with ethyl acetate. The organic layer was washed with an aqueous saturated solution of sodium bicarbonate and brine, dried over anhydrous magnesium sulfate and evaporated. Ammonium formate (70 mg, 1.12 mmol) and 10% Pd—C (60 mg) were added to a solution of the resulting crude compound in methanol (3 mL), followed by heating under reflux for one hour. The reaction mixture was filtered using Celite, and the resulting filtrate was evaporated. The residue was purified by silica gel column chromatography (50% ethyl acetate/hexane), to give the title compound (5.5 mg) as yellow crystals.
MS (ESI) m/z 306 MH$^+$.

Example 367

6-Mesityl-2,4,7-trimethyl)-2H-dipyrazolo[1,5-a:4,3-e]pyrimidine

Ammonium formate (15 mg, 0.237 mmol) and 10% Pd—C (14 mg) were added to a solution of 3-chloro-6-mesityl-2,4,7-trimethyl-2H-dipyrazolo[1,5-a:4,3-e]pyrimidine (14 mg, 0.14 mmol) in methanol (5 mL), followed by heating under reflux for one hour. The reaction mixture was filtered using Celite, and the resulting filtrate was evaporated. The residue was purified by silica gel column chromatography (35% ethyl acetate/hexane), to give the title compound (9 mg) as a yellow amorphous.
$^1$H NMR (400 MHz, CDCl$_3$) δ 2.04 (s, 6H), 2.34 (s, 3H), 2.35 (s, 3H), 3.12 (s, 3H), 3.93 (s, 3H), 7.01 (s, 2H), 8.09 (s, 1H).

Example 368

1,2-Di(1-ethylpropyl)-6-mesityl-4,7-dimethyl-2,3-dihydro-1H-dipyrazolo[1,5-a:4,3-e]pyrimidine-3-one (CRFA-395)

3-Bromopentane (0.152 mL, 1.184 mmol), potassium carbonate (744 mg, 5.38 mmol) and a catalytic amount of lithium iodide were added to a solution of 6-mesityl-4,7-dimethyl-2,3-dihydro-1H-dipyrazolo[1,5-a:4,3-e]pyrimidin-3-one (346 mg, 1.076 mmol) in N,N-dimethylformamide (10 mL), followed by stirring at 100° C. for three hours. The mixture was extracted with ethyl acetate, and the organic layer was washed with brine, dried over anhydrous magnesium sulfate and evaporated. The residue was purified by silica gel column chromatography (10–15% ethyl acetate/hexane), to give the title compound (107 mg) and the compound (49 mg) of Example 369 as brown crystals.
$^1$H NMR (400 MHz, CDCl$_3$) δ 0.70 (t, J=7.3 Hz, 6H), 1.00 (t, J=7.5 Hz, 6H), 1.62–1.90 (m, 8H), 2.04 (s, 6H), 2.29 (s, 3H), 2.36 (s, 3H), 3.12 (s, 3H), 4.40–4.52 (m, 1H), 4.84–4.95 (m, 1H), 6.99 (s, 2H).

Example 369

2-(1-Ethylpropyl)-6-mesityl-4,7-dimethyl-2,3-dihydro-1H-dipyrazolo[1,5-a:4,3-e]pyrimidin-3-one (CRFA-396)

Brown Crystals
$^1$H-NMR (400 MHz, CDCl$_3$) δ 1.01 (t, J=7.5 Hz, 6H), 1.75–1.90 (m, 4H), 2.00 (s, 6H), 2.32 (s, 3H), 2.33 (s, 3H), 3.15 (s, 3H), 4.81–4.89 (m, 1H), 6.98 (s, 2H), 8.69 (s, 1H).

Example 370

4-Ethyl-2-(1-ethylpropyl-6-mesityl-3-methoxy-7-methyl-2H-dipyrazolo[1,5-a:4,3-e]pyrimidine (CRFA-502)

Sodium hydride (31 mg, 0.766 mmol) was added to a solution of 2-(1-ethylpropyl)-6-mesityl-4,7-dimethyl-2,3-dihydro-1H-dipyrazolo[1,5-a:4,3-e]pyrimidin-3-one (250 mg, 0.639 mmol) in N,N-dimethylformamide (10 mL) at room temperature. After 30 minutes, methyl iodide (0.048 mL, 0.766 mmol) was added, followed by stirring at the same temperature for three hours. Water was added under ice-cooling, and the mixture was extracted with ethyl acetate. The organic layer was washed with brine, dried over anhydrous magnesium sulfate and evaporated. The residue was purified by silica gel column chromatography (10–15% ethyl acetate/hexane), to give the title compound (19 mg) and the compound (30 mg) of Example 371.

$^1$H NMR (400 MHz, CDCl$_3$) δ 0.71 (t, J=7.3 Hz, 6H), 1.56 (t, J=7.5 Hz, 3H), 1.62–1.94 (m, 4H), 2.05 (s, 6H), 2.29 (s, 3H), 2.36 (s, 3H), 3.58 (q, J=7.5 Hz, 2H), 4.09 (s, 3H), 4.41–4.52 (m, 1H), 6.99 (s, 2H).

Example 371

2-(1-Ethylpropyl)-4-isopropyl-6-mesityl-1,7-dimethyl-2,3-dihydro-1H-dipyrazolo[1,5-a:4,3-e]pyrimidin-3-one (CRFA-503)

$^1$H-NMR (400 MHz, CDCl$_3$) δ 0.91 (t, J=7.3 Hz, 6H), 1.70 (d, J=7.1 Hz, 6H), 1.68–1.97 (m, 4H), 2.05 (s, 6H), 2.27 (s, 3H), 2.35 (s, 3H), 3.34 (s, 3H), 4.05–4.19 (m, 1H), 4.65–4.78 (m, 1H), 6.98 (s, 2H).

Example 372

6-Mesityl-4,7-dimethyl-1-propyl-1H-dipyrazolo[1,5-a:4,3-e]pyrimidin-3-yl propyl ether 3-Bromopropane (0.109 mL, 1.20 mmol), potassium carbonate (753 mg, 5.45 mmol) and a catalytic amount of lithium iodide were added to a solution of 6-mesityl-4,7-dimethyl-2,3-dihydro-1H-dipyrazolo[1,5-a:4,3-e]pyrimidin-3-one (350 mg, 1.09 mmol) in N,N-dimethylformamide (10 mL), followed by stirring at 100° C. for three hours. After extracting with ethyl acetate, the organic layer was washed with brine, dried over anhydrous magnesium sulfate and evaporated. The residue was purified by silica gel column chromatography (10% ethyl acetate/hexane), to give the title compound (48 mg).

$^1$H NMR (400 MHz, CDCl$_3$) δ 1.01 (t, J=7.4 Hz, 3H), 1.08 (t, J=7.4 Hz, 3H), 1.80–1.93 (m, 2H), 1.94–2.10 (m, 2H), 2.01 (s, 6H), 2.24 (s, 3H), 2.33 (s, 3H), 2.65 (s, 3H), 4.32 (t, J=6.4 Hz, 2H), 4.72 (t, J=6.9 Hz, 2H), 6.97 (s, 2H).

Example 373

2-(1-Ethylpropyl)-6-mesityl-4,7-dimethyl-2H-dipyrazolo[1,5-a:4,3-e]pyrimidine

Phosphorus oxycloride (1.06 mL, 11.34 mmol), N,N-dimethylaniline (0.018 mL, 0.142 mmol) and methyltriethylammonium chloride (172 mg, 1.134 mmol) were added to a solution of 2-(1-ethylpropyl)-6-mesityl-4,7-dimethyl-2,3-dihydro-1H-dipyrazolo[1,5-a:4,3-e]pyrimidin-3-one (222 mg, 0.567 mmol) in acetonitrile (10 mL) followed by heating under reflux for six hours. The reaction mixture was added to ice, stirred for a while, and then extracted with ethyl acetate. The organic layer was washed with an aqueous saturated solution of sodium bicarbonate and brine, dried over anhydrous magnesium sulfate and evaporated. Ammonium formate (215 mg, 3.40 mmol) and 10% Pd—C (200 mg) were added to a solution of the resulting crude compound in methanol (5 mL), followed by heating under reflux for one hour. The reaction mixture was filtered through Celite, and the resulting filtrate was evapoarated. The residue was purified by silica gel column chromatography (20% ethyl acetate/hexane), to give the title compound (6.6 mg).

$^1$H NMR (400 MHz, CDCl$_3$) δ 0.62 (t, J=7.3 Hz, 6H), 1.66–1.95 (m, 4H), 1.97 (s, 6H), 2.27 (s, 3H), 2.30 (s, 3H), 3.06 (s, 3H), 4.53–4.64 (m, 1H), 6.94 (s, 2H), 8.07 (s, 1H).

Example 374

7-(1-Ethylpropyl)-3-mesityl-2,5-dimethyl-7,8-dihydro-6H-pyrazolo[1,5-a]pyrimidin-6,8-dione 3-Aminopentane (0.283 mL, 2.43 mmol) was added to a solution of 3-mesityl-2,5-dimethylpyrazolo[1,5-a]pyrimidin-6,7-dicarboxylic acid (780 mg, 2.21 mmol) in acetic acid (10 mL), followed by stirring at 100° C. for two hours. Water was added thereto, followed by extracting with ether. The organic layer was washed with brine, dried over anhydrous magnesium sulfate and evaporated. The residue was purified by silica gel column chromatography (15% ethyl acetate/hexane), to give the title compound (480 mg).

$^1$H NMR (400 MHz, CDCl$_3$) δ 0.89 (t, J=7.4 Hz, 6H), 1.74–1.87 (m, 2H), 1.96 (s, 6H), 1.98–2.14 (m, 2H), 2.33 (s, 3H), 2.34 (s, 3H), 3.20 (s, 3H), 4.08–4.18 (m, 1H), 6.96 (s, 2H).

Example 375

2-Chloro-1-(1-ethylpropyl)-6-mesityl-4,7-dimethyl-1H-pyrazolo[1,5-b]purine

Two droplets of N,N-dimethylaniline was added to a solution of 1-(1-ethylpropyl)-6-mesityl-4,7-dimethyl-2,3-dihydro-1H-pyrazolo[5,1-b]purin-2-one (100 mg, 0.225 mmol), followed by heating under reflux for seven hours. The reaction mixture was added to ice, stirred for a while, and then extracted with ethyl acetate. The organic layer was washed with an aqueous saturated solution of sodium bicarbonate and brine, dried over anhydrous magnesium sulfate and evaporated. The residue was purified by silica gel column chromatography (15% ethyl acetate/hexane) to give the title compound (76 mg) as brown crystals.

$^1$H NMR (400 MHz, CDCl$_3$) δ 0.76 (t, J=7.4 Hz, 6H), 1.75–1.89 (m, 2H), 2.02 (s, 6H), 2.20–2.40 (m, 2H), 2.32 (s, 3H), 2.37 (s, 3H), 3.09 (s, 3H), 4.27–4.50 (m, 1H), 6.99 (s, 2H).

Example 376

1-(1-Ethylpropyl)-6-mesityl-4,7-dimethyl-1H-pyrazolo[1,5-b]purine

Ammonium formate (70 mg, 1.11 mmol) and 10% Pd—C (76 mg) were added to a solution of 2-chloro-1-(1-ethylpropyl)-6-mesityl-4,7-dimethyl-1H-pyrazolo[5,1-b]purine (76 mg, 0.185 mmol) in methanol (5 ml), followed by heating under reflux for one hour. The reaction mixture was filtered through Celite, and the resulting filtrate was evaporated. The residue was purified by silica gel column chromatography (65% ethyl acetate/hexane), to give the title compound (67 mg).

$^1$H NMR (400 MHz, CDCl$_3$) δ 0.79 (t, J=7.4 Hz, 6H), 1.82–1.93 (m, 4H), 2.03 (s, 6H), 2.33 (s, 3H), 2.37 (s, 3H), 3.15 (s, 3H), 4.36–4.45 (m, 1H), 7.00 (s, 2H), 7.95 (s, 1H).

Example 377

3-Mesityl-2,5-dimethyl-6,7-dihydrofuro[3,2-e]pyrazolo[1,5-a]pyrimidine

A solution of 6-(2-hydroxyethyl)-3-mesityl-2,5-dimethylpyrazolo[1,5-a]pyrimidin-7-ol (500 mg, 1.54 mmol) and thionyl chloride (0.26 mL) in benzene (30 mL) was heated under reflux for two hours. After cooling to room temperature, the resulting crystals were collected by filtration. A suspension of the resulting crystals in 2% sodium carbonate was stirred at room temperature for two hours. The crystals were collected by filtration and purified by silica gel column chromatography (50–70% ethyl acetate/hexane), to give the title compound (310 mg) as pale brown crystals.

$^1$H NMR (400 MHz, CDCl$_3$) δ 1.97 (s, 6H), 2.13 (s, 3H), 2.67 (s, 3H), 2.39 (s, 3H), 2.98 (t, J=6.4 Hz, 2H), 3.73 (t, J=6.4 Hz, 2H), 6.89 (s, 2H).

Example 378

3-Mesityl-2,5,7-trimethyl-6,7-dihydrofuro[3,2-e]pyrazolo[1,5-a]pyrimidine

According to the method of Example 377, the title compound (66 mg) was obtained as pale yellowish brown crystals from 6-(2-hydroxypropyl)-3-mesityl-2,5-dimethylpyrazolo[1,5-a]pyrimidin-7-ol (300 mg, 0.88 mmol).

$^1$H-NMR (400 MHz, CDCl$_3$) δ 1.58 (s, 3H), 1.95 (s, 3H), 1.99 (s, 3H), 2.17 (s, 3H), 2.30 (s, 3H), 2.37 (s, 3H), 2.75–2.80 (m, 1H), 3.00–3.05 (m, 1H), 4.00–4.05 (m, 1H), 6.93 (s, 2H).

Example 379

3-Mesityl-2,5-dimethyl-7-propyl-6,7-dihydrofuro[3,2-e]pyrazolo[1,5-a]pyrimidine

According to the method of Example 377, the title compound (90 mg) was obtained as pale grayish brown crystals from 6-(2-hydroxypentyl)-3-mesityl-2,5-dimethylpyrazolo[1,5-a]pyrimidin-7-ol (1.00 g, 2.72 mmol).

$^1$H-NMR (400 MHz, DMSO-d$_6$) δ 0.88 (t, J=5.4 Hz, 3H), 1.32–1.46 (m, 1H), 1.50–1.61 (m, 1H), 1.63–1.84 (m, 2H), 1.93 (s, 3H), 1.94 (s, 3H), 1.97 (s, 3H), 2.27 (s, 3H), 2.29 (s, 3H), 2.75–2.85 (m, 1H), 2.90–3.00 (m, 1H), 4.29–4.38 (m, 1H), 6.96 (s, 2H).

Example 380

3-mesityl-2,5-dimethyl-6,7-dihydropyrazolo[1,5-a]thieno[3,2-e]pyrimidine

A solution of 7-chloro-6-(2-chloroethyl)-3-mesityl-2,5-dimethylpyrazolo[1,5-a]pyrimidine (500 mg, 1.38 mmol), thiourea (105 mg, 1.38 mmol) and sodium carbonate (180 mg, 1.73 mmol) in ethanol (10 mL) was heated under reflux for one hour. After overnight, water was added and the resulting crystals were collected by filtration. The crystals were washed with water, to give the title compound (436 mg) as white crystals.

$^1$H NMR (400 MHz, CDCl$_3$) δ 2.00 (s, 6H), 2.27 (s, 3H), 2.32 (s, 3H), 2.43 (s, 3H), 3.44 (t, J=8.0 Hz, 2H), 3.68 (t, J=8.0 Hz, 2H), 6.96 (s, 2H).

Example 381

3-Mesityl-2,5-dimethyl-7,8-dihydro-6H-cyclopenta[e]pyrazolo[1,5-a]pyrimidine

A solution of 4-mesityl-3-methyl-1H-5-pyrazoloamine (200 mg, 0.93 mmol) and 2-acetylcyclopentanone (0.12 mL, 0.10 mmol) in toluene (2 mL) was heated under reflux for seven hours. The reaction mixture was evaporated, and the resulting crystals were washed with a mixed solvent of ethyl acetate/hexane, to give the title compound (88 mg) as grayish white crystals.

$^1$H NMR (400 MHz, CDCl$_3$) δ 2.00 (s, 6H), 2.28 (s, 3H), 2.33 (s, 3H), 2.34 (tt, J=7.2 Hz, 8.0 Hz, 2H), 3.01 (t, J=7.2 Hz, 2H), 3.42 (t, J=8.0 Hz, 2H), 6.97 (s, 2H).

MS (ESI) m/z 306 MH$^+$.

Example 382

2-(3-mesityl-2,5-dimethyl-8-propyl-6,7,8,9-tetrahydropyrazolo[1,5-a]pyrido[3,2-e]pyrimidin-9-yl)ethyl methyl ether 7-Chloro-6-(3-chlorohexyl)-3-mesityl-2,5-dimethylpyrazolo[1,5-a]pyrimidine (170 mg, 0.406 mmol) was dissolved in 2-methoxyethylamine (2 mL), followed by heating under reflux for one hour. Water was added to the reaction mixture, followed by extracting with ethyl acetate. The organic layer was washed with water and brine, dried over anhydrous magnesium sulfate and evaporated, to give a pale yellow oil. The oil was dissolved in N,N-dimethylformamide (10 mL), and sodium iodide (62 mg, 0.416 mmol) and potassium carbonate (172 mg, 1.25 mmol) were added thereto. The mixture was stirred at 150° C. for two days. After cooling, water was added to the reaction mixture and extracted with ethyl acetate. The organic layer was washed with water and brine, dried over anhydrous magnesium sulfate, and then evaporated. The residue was purified by silica gel column chromatography (5–10% ethyl acetate/hexane), to give the title compound (60 mg, 0.143 mmol) as a pale yellow oil.

$^1$H NMR (400 MHz, CDCl$_3$) δ 0.93 (t, J=7.6 Hz, 3H), 1.30–1.65 (m, 4H), 1.90–1.96 (m, 2H), 2.02 (s, 3H), 2.03 (s, 3H), 2.19 (s, 3H), 2.32 (s, 3H), 2.36 (s, 3H), 2.50–2.68 (m, 2H), 3.37 (s, 3H), 3.45–3.55 (m, 1H), 3.65–3.85 (m, 2H), 3.92–4.01 (m, 1H), 4.35–4.45 (m, 1H), 6.95 (s, 2H).

MS (ESI) m/z 421 MH$^+$.

According to the method of Example 382, the title compounds of Examples 383 to 458 were synthesized.

Example 383

3-Mesityl-2,5-dimethyl-9-propyl-6,7,8,9-tetrahydropyrazolo[1,5-a]pyrido[3,2-e]pyrimidine $^1$H NMR (400 MHz, CDCl$_3$) δ 0.96 (t, J=7.2 Hz, 3H), 1.76–1.86 (m, 2H) 1.95–2.03 (m, 2H), 2.01 (s, 6H), 2.20 (s, 3H), 2.32 (s, 3H), 2.34 (s, 3H), 2.66 (t, J=6.2 Hz, 2H), 3.38–3.42 (m, 2H), 4.00–4.05 (m, 2H), 6.94 (s, 2H).

Example 384

9-Butyl-3-mesityl-2,5-dimethyl-6,7,8,9-tetrahydropyrazolo[1,5-a]pyrido[3,2-e]pyrimidine $^1$H NMR (400 MHz, CDCl$_3$) δ 0.97 (t, J=7.2 Hz, 3H), 1.33–1.42 (m, 2H), 1.72–1.80 (m, 2H), 1.95–2.03 (m, 2H), 2.01 (s, 6H), 2.19 (s, 3H), 2.32 (s, 3H), 2.34 (s, 3H), 2.66 (t, J=6.2 Hz, 2H), 3.38–3.42 (m, 2H), 4.00–4.05 (m, 2H), 6.94 (s, 2H).

Example 385

2-(3-Mesityl-2,5-dimethyl-6,7,8,9-tetrahydropyrazolo[1,5-a]pyrido[3,2-e]pyrimidin-9-yl)ethyl methyl ether $^1$H NMR (400 MHz, CDCl$_3$) δ 1.95–2.02 (m, 2H), 2.00 (s, 6H), 2.19 (s, 3H), 2.32 (s, 3H), 2.35 (s, 3H), 2.66 (t, J=6.2 Hz, 2H), 3.38 (s, 3H), 3.48–3.52 (m, 2H), 3.81 (t, J=6.2 Hz, 2H), 4.21 (t, J=6.2 Hz, 2H), 6.95 (s, 2H).

Example 386

9-(sec-Butyl)-3-mesityl-2,5-dimethyl-6,7,8,9-tetrahydropyrazolo[1,5-a]pyrido[3,2-e]pyrimidine ¹H-NMR (400 Hz, CDCl₃) δ 0.96 (t, J=7.2 Hz, 3H), 1.28 (d, J=6.8 Hz, 3H), 1.56–1.84 (m, 2H), 1.90–2.06 (m, 2H), 2.02 (s, 6H), 2.19 (s, 3H), 2.32 (s, 3H), 2.33 (s, 3H), 2.63–2.69 (m, 2H), 3.26–3.40 (m, 2H), 5.86–5.94 (m, 1H), 6.95 (s, 2H).

Example 387

9-Ethyl-mesityl-2,5-dimethyl-6,7,8,9-tetrahydropyrazolo[1,5-a]pyrido[3,2-e]pyrimidine ¹H NMR (400 MHz, CDCl₃) δ 1.34 (t, J=6.8 Hz, 3H), 1.95–2.02 (m, 2H), 2.00 (s, 6H), 2.20 (s, 3H), 2.31 (s, 3H), 2.34 (s, 3H), 2.66 (t, J=6.4 Hz, 2H), 3.36–3.40 (m, 2H), 4.03 (q, J=6.8 Hz, 2H), 6.94 (s, 2H).

Example 388

9-Isopropyl-3-mesityl-2,5-dimethyl-6,7,8,9-tetrahydropyrazolo[1,5-a]pyrido[3,2-e]pyrimidine ¹H-NMR (400 MHz, CDCl₃) δ 1.31 (d, J=6.8 Hz, 6H), 1.94–2.02 (m, 2H), 2.03 (s, 6H), 2.20 (s, 3H), 2.32 (s, 3H), 2.35 (s, 3H), 2.66 (t, J=6.2 Hz, 2H), 3.33–3.37 (m, 2H), 5.89–5.96 (m, 1H), 6.94 (s, 2H).

Example 389

3-Mesityl-2,5-dimethyl-8,9-dipropyl-6,7,8,9-tetrahydropyrazolo[1,5-a]pyrido[3,2-e]pyrimidine ¹H NMR (400 MHz, CDCl₃) δ 0.93 (t, J=6.8 Hz, 3H), 0.95 (t, J=7.2 Hz, 3H), 1.35–1.50 (m, 2H), 1.53–1.72 (m, 3H), 1.82–2.00 (m, 3H), 2.03 (s, 6H), 2.20 (s, 3H), 2.31 (s, 3H), 2.36 (s, 3H), 2.52–2.68 (m, 2H), 3.34–3.40 (m, 1H), 3.78–3.86 (m, 1H), 3.98–4.04 (m, 1H), 6.94 (s, 2H).

Example 390

9-Benzyl-3-mesityl-2,5-dimethyl-8-propyl-6,7,8,9-tetrahydropyrazolo[1,5-a]pyrido[3,2-e]pyrimidine ¹H NMR (400 MHz, CDCl₃) δ 0.78 (t, J=6.8 Hz, 3H), 1.18–1.34 (m, 4H), 1.47–1.54 (m, 1H), 1.60–1.72 (m, 2H), 1.77–1.85 (m, 1H), 2.05 (s, 3H), 2.07 (s, 3H), 2.23 (s, 3H), 2.33 (s, 3H), 2.39 (s, 3H), 2.54–2.60 (m, 2H), 3.34–3.40 (m, 1H), 5.15–5.20 (m, 1H), 5.34–5.44 (m, 1H), 6.94 (s, 2H), 7.28–7.38 (m, 3H), 7.43–7.47 (m, 2H).

Example 391

9-Ethyl-3-mesityl-2,5-dimethyl-8-propyl-6,7,8,9-tetrahydropyrazolo[1,5-a]pyrido[3,2-e]pyrimidine ¹H NMR (400 MHz, CDCl₃) δ 0.94 (t, J=7.2 Hz, 3H), 1.35 (t, J=7.2 Hz, 3H), 1.35–1.50 (m, 2H), 1.55–1.70 (m, 2H), 1.80–2.00 (m, 2H), 2.03 (s, 6H), 2.22 (s, 3H), 2.33 (s, 3H), 2.38 (s, 3H), 2.52–2.68 (m, 2H), 3.32–3.40 (m, 1H), 3.90–4.10 (m, 2H), 6.94 (s, 2H).

Example 392

9-(Cyclopropylmethyl)-3-mesityl-2,5-dimethyl-6,7,8,9-tetrahydropyrazolo[1,5-a]pyrido[3,2-e]pyrimidine ¹H-NMR (400 MHz, CDCl₃) δ 0.25–0.30 (m, 1H), 0.47–0.52 (m, 1H), 0.85–0.90 (m, 2H), 1.15–1.30 (m, 2H), 2.01 (s, 6H), 2.01–2.08 (m, 2H), 2.20 (s, 3H), 2.31 (s, 3H), 2.36 (s, 3H), 2.67 (t, J=6.0 Hz, 2H), 3.48–3.53 (m, 2H), 3.97–4.03 (m, 2H), 6.94 (s, 2H).

Example 393

3-Mesityl-2,5,9-trimethyl-6,7,8,9-tetrahydropyrazolo[1,5-a]pyrido[3,2-pyrimidine ¹H-NMR (400 MHz, CDCl₃) δ 1.98–2.05 (m, 2H), 2.02 (s, 6H), 2.22 (s, 3H), 2.33 (s, 3H), 2.36 (s, 3H), 2.67 (t, J=6.0 Hz, 2H), 3.35–3.39 (m, 2H), 3.62 (s, 3H), 6.96 (s, 2H).

Example 394

2-(8-Ethyl-3-mesityl-2,5-methyl-6,7,8,9-tetrahydropyrazolo[1,5-a]pyrido[3,2-e]pyrimidin-9-yl)ethyl methyl ether ¹H-NMR (400 MHz, CDCl₃) δ 1.00 (t, J=7.6 Hz, 3H), 1.37–1.45 (m, 1H), 1.60–1.70 (m, 1H), 1.90–2.05 (In, 2H), 2.03 (s, 6H), 2.20 (s, 3H), 2.33 (s, 3H), 2.36 (s, 3H), 2.50–2.68 (m, 2H), 3.38 (s, 3H), 3.38–3.50 (m, 1H), 3.70–3.85 (m, 2H), 3.90–4.03 (m, 1H), 4.40–4.50 (m, 1H), 6.96 (s, 2H).

Example 395

8-Ethyl-3-mesityl-2,5-dimethyl-9-propyl-6,7,8,9-tetrahydropyrazolo[1,5-a]pyrido[3,2-e]pyrimidine ¹H-NMR (400 MHz, CDCl₃) δ 0.96 (t, J=7.2 Hz, 3H), 1.01 (t, J=7.2 Hz, 3H), 1.40–1.50 (m, 1H), 1.60–1.70 (m, 2H), 1.80–2.05 (m, 3H), 2.03 (s, 3H), 2.04 (s, 3H), 2.21 (s, 3H), 2.33 (s, 3H), 2.36 (s, 3H), 2.50–2.68 (m, 2H), 3.25–3.32 (m, 1H), 3.80–3.88 (m, 1H), 4.00–4.12 (m, 1H), 6.96 (s, 2H).

Example 396

8,9-Diethyl-3-mesityl-2,5-dimethyl-6,7,8,9-tetrahydropyrazolo[1,5-a]pyrido[3,2-e]pyrimidine ¹H-NMR (400 MHz, CDCl₃) δ 1.00 (t, J=7.2 Hz, 3H), 1.34 (t, J=7.2 Hz, 3H), 1.38–1.48 (m, 1H), 1.58–1.70 (m, 1H), 1.80–1.90 (m, 1H), 1.95–2.02 (m, 1H1H), 2.02 (s, 3H), 2.03 (s, 3H), 2.21 (s, 3H), 2.32 (s, 3H), 2.35 (s, 3H), 2.50–2.68 (m, 2H), 3.25–3.30 (m, 1H), 3.90–4.08 (m, 2H), 6.95 (s, 2H).

Example 397

9-(Cyclopropylmethyl)-8-ethyl-3-mesityl-2,5-dimethyl-6,7,8,9-tetrahydropyrazolo[1,5-a]pyrido[3,2-e]pyrimidine ¹H-NMR (400 MHz, CDCl₃) δ 0.12–0.15 (m, 1H), 0.38–0.46 (m, 2H), 0.48–0.56 (m, 1H), 1.02 (t, J=7.2 Hz, 3H), 1.14–1.23 (m, 1H), 1.23–1.28 (m, 1H), 1.38–1.48 (m, 1H), 1.63–1.73 (m, 1H), 1.96–2.03 (m, 1H), 2.02 (s, 6H), 2.20 (s, 3H), 2.32 (s, 3H), 2.37 (s, 3H), 2.52–2.70 (m, 2H), 3.41–3.48 (m, 1H), 3.83 (dd, J=6.2, 14.4 Hz, 1H), 4.22 (dd, J=7.7, 14.4 Hz, 1H), 6.95 (s, 2H).

Example 398

3-Mesityl-9-(2-methoxyethyl)-8-(methoxymethyl)-2,5-dimethyl-6,7,8,9-tetrahydropyrazolo[1,5-a]pyrido[3,2-e]pyrimidine ¹H-NMR (400 MHz, CDCl₃) δ 1.88–2.00 (m, 1H), 2.01 (s, 3H), 2.02 (s, 3H), 2.12–2.22 (m, 1H), 2.19 (s, 3H), 2.32

(s, 3H), 2.36 (s, 3H), 2.50–2.73 (m, 2H), 3.28–3.38 (m, 1H), 3.36 (s, 3H), 3.37 (s, 3H), 3.50–3.55 (m, 1H), 3.68–3.76 (m, 1H), 3.77–3.86 (m, 2H), 4.06–4.13 (m, 1H), 4.38–4.46 (m, 1H), 6.95 (s, 2H).

Example 399

3-Mesityl-2,5,8-trimethyl-9-propyl-6,7,8,9-tetrahydropyrazolo[1,5-a]pyrido[3,2-a]pyrido[3,2-e]pyrimidine MS (ESI) m/z 377 MH$^+$.

Example 400

9-Butyl-3-mesityl-2,5,8-trimethyl-6,7,8,9-tetrahydropyrazolo[1,5-a]pyrido[3,2-e]pyrimidine MS (ESI) m/z 391 MH$^+$.

Example 401

2-(3-Mesityl-2,5,8-trimethyl-6,7,8,9-tetrahydropyrazolo[1,5-a]pyrido[3,2-e]pyrimidin-9-yl)ethyl methyl ether MS (ESI) m/z 393 MH$^+$.

Example 402

3-(3-Mesityl-2,5,8-trimethyl-6,7,8,9-tetrahydropyrazolo[1,5-a]pyrido[3,2-e]pyrimidin-9-yl)propyl methyl ether MS (ESI) in/z 407 MH$^+$.

Example 403

9-(2-Isopropoxyethyl)-3-mesityl-2,5,8-trimethyl-6,7,8,9-tetrahydropyrazolo[1,5-a]pyrido[3,2-e]pyrimidine MS (ESI) m/z 421 MH$^+$.

Example 404

9-Isopentyl-3-mesityl-2,5,8-trimethyl-6, 7, 8, 9-tetrahydropyrazolo[1,5-a]pyrido[3,2-e]pyrimidine MS (ESI) m/z 405 MH$^+$.

Example 405

3-Mesityl-2,5,8-trimethyl-9-(1-phenylethyl)-6,7,8,9-tetrahydropyrazolo[1,5-a]pyrido[3,2-e]pyrimidine MS (ESI) m/z 439 MH$^+$.

Example 406

3-(8-Ethyl-3-mesityl-2,5-dimethyl-6,7,8,9-tetrahydropyrazolo[1,5-a]pyrido[3,2-e]pyrimidin-9-yl)propyl methyl ether MS (ESI) m/z 421 MH$^+$.

Example 407

2-(8-Ethyl-3-mesityl-2,5-dimethyl-6,7,8,9-tetrahydropyrazolo[1,5-a]pyrid[3,2-e]pyrimidin-9-yl)ethyl isopropyl ether MS (ESI) m/z 435 MH$^+$.

Example 408

8-Ethyl-9-isopentyl-3-mesityl-2,5-dimethyl-6,7,8,9-tetrahydropyrazolo[1,5-a]pyrido[3,2-e]pyrimidine MS (ESI) m/z 419 MH$^+$.

Example 409

8-Ethyl-3-Mesityl-2,5-dimethyl-6,7,8,9-tetrahydropyrazolo[1,5-a]pyrido[3,2-e]pyrimidine MS (ESI) m/z 453 MH$^+$.

Example 410

9-(1-Benzylpropyl)-8-ethyl-3-mesityl-2,5-dimethyl-6,7,8,9-tetrahydropyrazolo[1,5-a]pyrido[3,2-e]pyrimidine MS (ESI) m/z 481 MH$^+$.

Example 411

3-Mesityl-8-(methoxymethyl)-9-(3-methoxypropyl)-2,5-dimethyl-6,7,8,9-tetrahydropyrazolo[1,5-a]pyrido[3,2-e]pyrimidine MS (ESI) m/z 437 MH$^+$.

Example 412

9-(2-Isopropoxyethyl)-3-mesityl-8-(methoxymethyl)-2,9-dimethyl-6,7,8,9tetrahydropyrazolo[1,5-a]pyrido[3,2-e]pyrimidine MS (ESI) m/z 451 MH$^+$.

Example 413

(9-Isopentyl-3-mesityl-2,5-dimethyl-6,7,8,9-tetrahydropyrazolo[1,5-a]pyrido[3,2-e]pyrimidin-8-yl)methyl methyl ether MS (ESI) m/z 435 MH$^+$.

Example 414

9-Ethyl-3-mesityl-2,5,8-trimethyl-6,7,8,9-tetrahydropyrazolo[1,5-a]pyrido[3,2-e]pyrimidine MS (ESI) m/z 363 MH$^+$.

Example 415

(3-Mesityl-2,5-dimethyl-9-propyl-6,7,8,9-tetrahydropyrazolo[1,5-a]pyrido[3,2-e]pyrimidin-8-yl methyl methyl ether MS (ESI) m/z 407 MH$^+$.

Example 416

(9-Ethyl-3-mesityl-2,5-dimethyl-6,7,8,9-tetrahydropyrazolo[1,5-a]pyrido[3,2-e]pyrimidin-8-yl)methyl methyl ether MS (ESI) in/z 393 MH$^+$.

Example 417

9-Butyl-8-ethyl-3-mesityl-2,5-dimethyl-6,7,8,9-tetrahydropyrazolo[1,5-a]pyrido[3,2-e]pyrimidine MS (ESI) m/z 405 MH$^+$.

Example 418

8-Ethyl-3-mesityl-2,5-dimethyl-6,7,8,9-tetrahydropyrazolo[1,5-a]pyrido[3,2-e]pyrimidine MS (ESI) M/z 419 MH$^+$.

Example 419

8-Ethyl-9-(1-ethylpropyl)-3-mesityl-2,5-dimethyl-6,7,8,9-tetrahydropyrazolo[1,5-a]pyrid[3,2-e]pyrimidine MS (ESI) m/z 419 MH$^+$.

Example 420

2-(8-Ethyl-3-mesityl-2,5-dimethyl-6,7,8,9-tetrahydropyrazolo[1,5-a]pyrido[3,2-e]pyrimidin-9-yl)ethyl propyl ether MS (ESI) m/z 435 MH$^+$.

Example 421

9-(Cyclohexylmethyl)-8-ethyl-3-mesityl-2,5-dimethyl-6,7,8,9-tetrahydropyrazolo[1,5-a]pyrido[3,2-e]pyrimidine MS (ESI) m/z 445 MH$^+$.

Example 422

8-Ethyl-3-mesityl-2,5-dimethyl-9-(2-phenylpropyl)-6,7,8,9-tetrahydropyrazolo[1,5-a]pyrido[3,2-e]pyrimidine MS (ESI) m/z 467 MH$^+$.

Example 423

9-(1-Ethylpropyl)-mesityl-2,5,8-trimethyl-6,7,8,9-tetrahydropyrazolo[1,5-a]pyrido[3,2-e]pyrimidine MS (ESI) m/z 405 MH$^+$.

Example 424

8-Ethyl-9-(2-ethylbutyl)-3-mesityl-2,5-dimethyl-6,7,8,9-tetrahydropyrazolo[1,5-a]pyrido[3,2-e]pyrimidine MS (ESI) m/z 433 MH$^+$.

Example 425

9-(3,3-Dimethylbutyl)-8-ethyl-3-mesityl-2,5-dimethyl-6,7,8,9-tetrahydropyrazolo[1,5-a]pyrido[3,2-e]pyrimidine MS (ESI) m/z 433 MH$^+$.

Example 426

8-Ethyl-3-mesityl-2,5-dimethyl-9-(tetrahydro-2-franylmethyl)-6,7,8,9-tetrahydropyrazolo[1,5-a]pyrido[3,2-e]pyrimidine MS (ESI) m/z 433 MH$^+$.

Example 427

4-[2-(8-Ethyl-3-mesityl-2,5-dimethyl-6,7,8,9-tetrahydropyrazolo[1,5-a]pyrido[3,2-e]pyrimidin-9-yl)ethyl]phenyl methyl ether MS (ESI) m/z 462 MH$^+$.

Example 428

2-[(8-Ethyl-3-mesityl-2,5-dimethyl-6,7,8,9-tetrahydropyrazolo[1,5-a]pyrido[3,2-e]pyrimidin-9-yl)ethyl]phenyl methyl ether MS (ESI) m/z 469 MH$^+$.

Example 429

3-[(8-Ethyl-3-mesityl-2,5-dimethyl-6,7,8,9-tetrahydropyrazolo[1,5-a]pyrido[3,2-e]pyrimidin-9-yl)ethyl]phenyl methyl ether MS (ESI) m/z 469 MH$^+$.

Example 430

4-[(8-Ethyl-3-mesityl-2,5-dimethyl-6,7,8,9-tetrahydropyrazolo[1,5-a]pyrido[3,2-e]pyrimidin-9-yl)methyl]phenyl methyl ether MS (ESI) m/z 469 MH$^+$.

Example 431

8-Ethyl-3-mesityl-2,5-dimethyl 9-(2,2,2-trifiluoroethyl)-6,7,8,9-tetrahydropyrazolo[1,5-a]pyrido[3,2-e]pyrimidine MS (ESI) m/z 431 MH$^+$.

Example 432

9-(2-Ethoxyethyl)-3-mesityl-2,5,8-trimethyl-6,7,8,9-tetrahydropyrazolo[1,5-a]pyrido[3,2-e]pyrimidine MS (ESI) m/z 421 MH$^+$.

Example 433

9-(2-Ethylbutyl)-mesityl-2,5,8-trimethyl-6,7,8,9-tetrahydropyrazolo[1,5-a]pyrid[3,2-e]pyrimidine MS (ESI) m/z 419 MH$^+$.

Example 434

3-Mesityl-2,5,8-trimethyl-9-(tetrahydro-2-furanylmethyl)-6,7,8,9-tetrahydropyrazolo[1,5-a]pyrido[3,2-e]pyrimidine MS (ESI) m/z 419 MH$^+$.

Example 435

9-(2-Ethoxyethyl)-3-mesityl-8-(methoxymethyl)-2,5-dimethyl-6,7,8,9-tetrahydropyrazolo[1,5-a]pyrido[3,2-e]pyrimidine MS (ESI) m/z 451 MH$^+$.

Example 436

[9-(2-Ethylbutyl)-mesityl-2,5-dimethyl-6,7,8,9-tetrahydropyrazolo[1,5-a]pyrido[3,2-e]pyrimidin-8-yl]methyl methyl ether MS (ESI) m/z 449 MH$^+$.

Example 437

[3-Mesityl-2,5-dimethyl-9-(tetrahyro-2-furanylmethyl)-6,7,8,9-tetrahydropyrazolo[1,5-a]pyrido[3,2-e]pyrimidin-8-yl]methyl methyl ether MS (ESI) m/z 449 MH$^+$.

Example 438

9-(Cyclopropylmethyl)-3-mesityl-2,5,8-trimethyl-6,7,8,9-tetrahydropyrazolo[1,5-a]pyrido[3,2-e]pyrimidine MS (ESI) m/z 389 MH$^+$.

Example 439

9-(2-Ethoxyethyl)-3-mesityl-2,5,8-trimethyl-6,7,8,9-tetrahydropyrazolo[1,5-a]pyrido[3,2-e]pyrimidine MS (ESI) m/z 407 MH$^+$.

Example 440

9-(2-Ethoxyethyl)-8-ethyl-3-mesityl-2,5-dimethyl-6,7,8,9-tetrahydropyrazolo[1,5-a]pyrid[3,2-e]pyrimidine MS (ESI) m/z 421 MH$^+$.

Example 441

9-(2-Ethoxyethyl)-3-mesityl-8-(methoxymethyl)-2,5-dimethyl-6,7,8,9-tetrahydropyrazolo[1,5-a]pyrido[3,2-e]pyrimidine MS (ESI) m/z 437 MH$^+$.

Example 442

9-(3-Ethoxypropyl)-3-mesityl-2,5,8-trimethyl-6,7,8,9-tetrahydropyrazolo[1,5-a]pyrido[3,2-e]pyrimidine MS (ESI) m/z 421 MH$^+$.

Example 443

9-(3-Ethoxypropyl)-8-ethyl-3-mesityl-2,5-dimethyl-6,7,8,9-tetrahydropyrazolo[1,5-a]pyrido[3,2-e]pyrimidine MS (ESI) m/z 435 MH$^+$.

Example 444

9-(3-Ethoxypropyl)-3-mesityl-8-(methoxymethyl)-2,5-dimethyl-6,7,8,9-tetrahydropyrazolo[1,5-a]pyrido[3,2-e]pyrimidine MS (ESI) m/z 451 MH$^+$.

Example 445

[9-(Cyclopropylmethyl)-3-mesityl-2,5-dimethyl-6,7,8,9-tetrahydropyrazolo[1,5-a]pyrido[3,2-e]pyrimidin-8-yl]methyl]-1-benzensulfonamide MS (ESI) m/z 419 MH$^+$.

Example 446

4-[(8-Ethyl-3-mesityl-2,5-dimethyl-6,7,8,9-tetrahydropyrazolo[1,5-a]pyrido[3,2-e]pyrimidin-9-yl]methyl]-1-benzenesulfonamide MS (ESI) m/z 518 MH$^+$.

Example 447

8-Ethyl-3-mesityl-2,5-dimethyl-9-[4-(trifluoromethyl)benzyl]-6,78,9-tetrahydropyrazolo[1,5-a]pyrido[3,2-e]pyrimidine MS (ESI) m/z 507 MH$^+$.

Example 448

9-(4-Chlorobenzyl)-8-ethyl-3-mesityl-2,5-dimethyl-6,7,8,9-tetrahydropyrazolo[1,5-a]pyrido[3,2-e]pyrimidine MS (ESI) m/z 473 MH$^+$.

Example 449

8-Ethyl-mesityl-2,5-dimethyl-9-[3-(trifluoromethyl)benzyl]-6,7,8,9-tetrahydropyrazolo[1,5-a]pyrido[3,2-e]pyrimidine MS (ESI) m/z 507 MH$^+$.

Example 450

9-(3-Chlorobenzyl)-8-ethyl-3-mesityl-2,5-dimethyl-6,7,8,9-tetrahydropyrazolo[1,5-a]pyrido[3,2-e]pyrimidine MS (ESI) m/z 473 MH$^+$.

Example 451

8-Ethyl-3-mesityl-2,5-dimethyl-9-(methylbenzyl)-6,7,8,9-tetrahydropyrazolo[1,5-a]pyrido[3,2-e]pyrimidine MS (ESI) m/z 453 MH$^+$.

Example 452

3-[(3-Ethyl-3-mesityl-2,5-dimethyl-6,7,8,9-tetrahydropyrazolo[1,5-a]pyrid[3,2-e]pyrimidin-9-yl)methyl]phenyl trifluoromethyl ether MS (ESI) m/z 523 MH$^+$.

Example 453

1-(2-Bromo-4,6-dimethylphenyl)-8-ethyl-9-(2-methoxyethyl)-2,5-dimethyl-6,7,8,9-tetrahydropyrazolo[1,5-a]pyrido[3,2-e]pyrimidine MS (ESI) m/z 470 M$^+$.

Example 454

3-(2-Bromo-4,6-dimethylphenyl)-9-(cyclopropylmethyl)-8H-ethyl-2,5-dimethyl-6,7,8,9-tetrahydropyrazolo[1,5-a]pyrido[3,2-e]pyrimidine MS (ESI) m/z 466 M$^+$.

Example 455

8-Ethyl-3-(4-methoxy-2,6-dimethylphenyl)-9-(2-methoxyethyl)-2,5-dimethyl-6,7,8,9-tetrahydropyrazolo[1,5-a]pyrido[3,2-e]pyrimidine MS (ESI) m/z 423 MH$^+$.

Example 456

8-Ethyl-3-(4-methoxy-2,6-dimethylphenyl-9-(cyclopropylmethyl)-2,5-dimethyl-6,7,8,9-tetrahydropyrazolo[1,5-a]pyrido[3,2-e]pyrimidine MS (ESI) m/z 419 MH$^+$.

Example 457

2-[8-(Cyclopropylmethyl)-3-mesityl-2,5-dimethyl-6,7,8,9-tetrahydropyrazolo[1,5-a]pyrido[1,3-e]pyrimidin-9-yl]ethyl methyl ether MS (ESI) m/z 433 MH$^+$.

Example 458

8-9-Di(cyclopropylmethyl)-3-mesityl-2,5-dimethyl-6,7,8,9-tetrahydropyrazolo[1,5-a]pyrido[3,2-e]pyrimidine MS (ESI) m/z 429 MH+.

Example 459

10-butyl-mesityl-2,5-dimethyl-7,8,9,10-tetrahydro-6H-pyrazolo[5',1'-:2,3]pyrimido[4,5-b]azepine Sodium iodine (catalytic amount) and potassium carbonate (65 mg, 0.47 mmol) were added to a solution of N-butyl-N-(6-(4-chlorobutyl)-3-mesityl-2,5-dimethylpyrazolo[1,5-a]pyrimidin-6-yl)amine (65 mg, 0.15 mmol) in 1-methyl-2-piperidone (2 mL), followed by stirring at 150° C. for four hours. Then, the mixture was treated with water, extracted with ethyl acetate, dried over anhydrous magnesium sulfate and evaporated. The residue was purified by silica gel chromatography (15% ethyl acetate/hexane), to give the title compound (18 mg) as yellow crystals.

$^1$H NMR (400 MHz, CDCl$_3$) δ 0.89 (t, J=7.2 Hz, 3H), 1.26–1.36 (m, 2H), 1.65–1.74 (m, 2H), 1.76–1.90 (m, 4H), 1.95 (s, 6H), 2.15 (s, 3H), 2.25 (s, 3H), 2.34 (s, 3H), 2.75 (t, J=5.6 Hz, 2H), 3.49 (t, J=6.0 Hz, 2H), 3.69 (t, J=8.0 Hz, 2H), 6.87 (s, 2H).

Example 460

1-(1-Ethylpropyl)-4,8-dimethyl-6-(2,4,6-trichlorophenyl)-1,2,3,6-tetrahydropyrazolo[3,4-b]pyrrolo[2,3,-d]pyridine 4-Chloro-5-(2-chloroethyl)-3,6-dimethyl-1-(2,4,6-trichlorophenyl-1H-pyrazolo[3,4-b]pyridine (185 mg, 0.437 mmol) was dissolved in 3-aminopentane (6 mL), followed by adding p-toluenesulfonic acid (185 mg, 1.074 mmol). The mixture was sealed in a tube at 200° C. for six hours. Water was added to the reaction mixture, followed by extracting with ethyl acetate. The organic layer was washed with water and brine, dried over anhydrous magnesium sulfate, and then evaporated. The residue was purified by silica gel column chromatography (10% ethyl acetate/hexane), to give the title compound (145 mg, 0.331 mmol) as white crystals.

$^1$H NMR (400 Hz, CDCl$_3$) δ 0.96 (t, J=7.6 Hz, 6H), 1.60–1.75 (m, 4H), 2.29 (s, 3H), 2.73 (s, 3H), 3.04 (t, J=8.8 Hz, 2H), 3.60 (t, J=8.8 Hz, 2H), 4.20–4.30 (m, 1H), 7.47 (s, 2H).

Example 461

1-(1-Ethylpropyl)-4,8-dimethyl-6-(2,4,6-trichlorophenyl)-1,6-dihydropyrazolo[3,4-b]pyrrolo[2,3-d]pyridine 1-(1-Ethylpropyl)-4,8-dimethyl-6-(2,4,6-trichlorophenyl)-1,2,3,6-tetrahydropyrazolo[3,4-b]pyrrolo[2,3-d]pyridine (70 mg, 0.160 mmol) was dissolved in toluene (7 mL). Manganese dioxide (700 mg) was added thereto, followed by stirring at 40° C. overnight. The reaction mixture was filtered through Celite and washed with ethyl acetate. The filtrate was evaporated, and the residue was purified by silica gel column chromatography (5% ethyl acetate/hexane), to give the title compound (48 mg, 0.110 mmol) as white crystals.

$^1$H NMR (400 MHz, CDCl$_3$) δ 0.88 (t, J=7.2 Hz, 6H), 1.85–2.05 (m, 4H), 2.73 (s, 3H), 2.92 (s, 3H), 4.88–4.95 (m, 1H), 6.78 (bs, 1H), 7.10 (d, J=5.0 Hz, 1H), 7.52 (s, 2H).

Example 462

1-(1-Ethylpropyl)-6-mesityl-4,8-dimethyl-2,3-dihydro-1H-imidazo[1,5-a]pyrrolo[3,2-e]pyrimidine A solution of 4-chloro-3-(2-chloroethyl)-8-mesityl-2,6-dimethylimidazo[1,5-a]pyrimidine (139 mg, 0.38 mmol) in 3-aminopentane (10 mL) was heated under reflux for five days. After overnight, the residue was purified by dry pack silica gel column chromatography (25–40% ethyl acetate/hexane), to give the title compound (69 mg) as pale yellow crystals.

$^1$H NMR (400 MHz, CDCl$_3$) δ 0.90 (t, J=7.6 Hz, 6H), 1.50–1.68 (m, 4H), 2.10 (s, 6H), 2.29 (s, 3H), 2.30 (s, 3H), 2.95 (s, 3H), 2.95 (t, J=7.2 Hz, 2H), 3.58–3.66 (m, 1H), 3.64 (t, J=7.2 Hz, 2H), 6.90 (s, 2H).

Example 463

1-(1-Ethylpropyl)-6-mesityl-4,6-dimethyl-1H-imidazo[1,5-a]pyrrolo[3,2-e]pyrimidine Manganese dioxide (67 mg, 0.77 mmol) was added to a solution of 1-(1-ethylpropyl)-6-mesityl-4,8-dimethyl-2,3-dihydro-1H-imidazo[1,5-a]pyrrolo[3,2-e]pyrimidine (58 mg, 0.15 mmol) in toluene (10 mL), followed by heating under reflux for three days. After filtering through Celite, the mixture was evaporated. The residue was purified by silica gel column chromatography (30% ethyl acetate/hexane), to give the title compound (22 mg) as pale yellow crystals.

$^1$H NMR (400 MHz, CDCl$_3$) δ 0.83 (t, J=7.6 Hz, 6H), 1.83–2.06 (m, 4H), 2.12 (s, 6H), 2.31 (s, 3H), 2.55 (s, 3H), 3.11 (s, 3H), 4.85–4.94 (m, 1H), 6.64 (d, J=3.6 Hz, 1H), 6.84 (d, J=3.6 Hz, 1H), 6.92 (s, 2H).

Example 464

1-(1-Ethylpropyl)-mesityl-4-methyl-2,3-dihydro-1H-pyrrolo[3,2-c]quinoline 1-(1-Ethylpropyl)-6-iodo-4-methyl-2,3-dihydro-1H-pyrrolo[3,2-c]quinoline (200 mg, 0.526 mmol), mesitylboric acid (95 mg, 0.579 mmol), barium hydroxide octahydrate (249 mg, 0.782 mmol) and tetrakistriphenylphosphine-palladium (12 mg, 0.01 mmol) were suspended into a mixture of dimethoxyethane (6 mL) and water (1 mL), followed by stirring at 80° C. for two days in nitrogen atmosphere. Water was added to the reaction mixture, followed by extracting with ethyl acetate. The organic layer was washed with water and brine, dried over anhydrous magnesium sulfate, and then evaporated. The residue was purified by silica gel column chromatography (ethyl acetate), to give the title compound (28 mg, 0.08 mmol) as a pale yellow oil.

$^1$H NMR (400 MHz, CD$_3$OD) δ 0.98 (t, J=7.6 Hz, 6H), 1.66–1.76 (m, 4H), 1.85 (s, 6H), 2.31 (s, 3H), 2.32 (s, 3H), 3.09 (t, J=9.6 Hz, 3H), 3.75 (t, J=9.6 Hz, 3H), 4.40–4.50 (m, 1H), 6.91 (s, 2H), 7.19 (dd, J=1.2, 6.8 Hz, 1H), 7.33 (dd, J=6.8, 8.4 Hz, 1H), 8.16 (dd, J=1.2, 8.4 Hz, 1H).

Example 465

1-(1-Ethylpropyl)-6-mesityl-4-methyl-1H-pyrrolo[3,2-c]quinoline 1-(1-Ethylpropyl)-6-iodo-4-methyl-1H-pyrrolo[3,2-c]quinoline (170 mg, 0.45 mmol), mesitylboric acid (82 mg, 0.50 mmol), barium hydroxide octahydrate (213 mg, 0.68 mmol) and tetrakistriphenylphosphinepalladium (26 mg, 0.02 mmol) were suspended into a mixture of 1,2-dimethoxyethane (6 mL) and water (1 mL), followed by stirring at 80° C. overnight in nitrogen atmosphere. Water was added to the reaction mixture, followed by extracting with ethyl acetate. The organic layer was washed with water and brine, dried over anhydrous magnesium sulfate, and then evaporated. The residue was purified by silica gel column chromatography (5% ethyl acetate/hexane), to give the title compound (11 mg, 0.03 mmol) as a pale yellow oil.

$^1$H NMR (400 MHz, CDCl$_3$) δ 0.94 (t, J=7.6 Hz, 6H), 1.92 (s, 6H), 2.00–2.13 (m, 4H), 2.39 (s, 3H), 2.71 (br s, 3H), 5.05–5.14 (m, 1H), 6.75 (d, J=2.8 Hz, 1H), 6.99 (s, 2H), 7.28 (d, J=2.8 Hz, 1H), 7.33 (d, J=7.6 Hz, 1H), 7.52 (t, J=7.6 Hz, 1H) 8.34 (d, J=7.6 Hz, 1H).

Example 466

6-(2,4-dichlorophenyl)-1-(1-ethylpropyl)-4-methyl-1H-pyrrolo[3,2]-quinoline $^1$H-NMR (400 MHz, CDCl$_3$) δ 0.85–0.97 (m, 6H), 2.00–2.13 (m, 4H), 2.72 (s, 3H), 5.04–5.12 (m, 1H), 6.75 (d, J=3.2 Hz, 1H), 7.28 (d, J=3.2 Hz, 1H), 7.33 (dd, J=2.0, 8.0 Hz, 1H), 7.40 (d, J=8.0 Hz, 1H), 7.47 (d, J=7.6 Hz, 1H), 7.52 (d, J=2.0 Hz, 1H), 7.53 (t, J=7.6 Hz, 1H), 8.41 (d, J=7.6 Hz, 1H).

Example 467

1-(1-Ethylpropyl)-6-(4-methoxy-2,6-dimethylphenyl-4-methyl-1H-pyrrolo[3,2-c]quinoline $^1$H-NMR (400 MHz, CDCl$_3$) δ 0.94 (t, J=7.6 Hz, 6H), 1.93 (s, 6H), 1.98–2.13 (m, 4H), 2.70 (s, 3H), 3.87 (s, 3H), 5.05–5.14 (m, 1H), 6.73 (s, 2H), 6.74 (d, J=3.2 Hz, 1H), 7.28 (d, J=3.2 Hz, 1H), 7.32 (d, J=8.0 Hz, 1H), 7.51 (t, J=8.0 Hz, 1H), 8.34 (d, J=8.0 Hz, 1H).

Example 468

2-[6-(2,4-Dichlorophenyl)-4-methyl-1H-pyrrolo[3,2-c]quinolin-1-yl]butyl methyl ether $^1$H-NMR (400 MHz, CDCl$_3$) δ 0.92–1.00 (m, 3H), 2.02–2.12 (m, 1H), 2.15–2.26 (m, 1H), 2.72 (s, 3H), 3.37 (br s, 3H), 3.78–3.83 (m, 1H), 3.86–3.93 (m, 1H), 5.20–5.38 (m, 1H), 6.75 (d, J=3.2 Hz, 1H), 7.33 (dd, J=2.0, 8.0 Hz, 1H), 7.36 (d, J=3.2 Hz, 1H), 7.39 (d, J=8.0 Hz, 1H), 7.47 (d, J=7.6 Hz, 1H), 7.52 (d, J=2.0 Hz, 1H), 7.54 (t, J=7.6 Hz, 1H), 8.37 (d, J=7.6 Hz, 1H).

Example 469

6-(4-Methoxy-2,6-dimethylphenyl)-1-[1-(methoxymethyl)propyl]-4-methyl-1H-pyrrolo[3,2-c]quinoline $^1$H-NMR (400 MHz, CDCl$_3$) δ 0.99 (t, J=7.6 Hz, 3H), 1.92 (s, 3H), 1.94 (s, 3H), 2.05–2.15 (m, 1H), 2.17–2.26 (m, 1H), 2.69 (s, 3H), 3.39 (s, 3H), 3.81 (dd, J=4.5, 10.5 Hz, 1H), 3.87 (s, 3H), 3.93 (dd, J=4.5, 10.5 Hz, 1H), 5.22–5.30 (m, 1H), 6.73 (s, 2H), 6.74 (d, J=3.2 Hz, 1H), 7.33 (d, J=8.0 Hz, 1H), 7.36 (d, J=3.2 Hz, 1H), 7.52 (t, J=8.0 Hz, 1H), 8.30 (d, J=8.0 Hz, 1H).

Example 470

2-(6-Mesityl-4-methyl-1H-pyrrolo[3,2-c]quinolin-1-yl)butyl methyl ether $^1$H-NMR (400 MHz, CDCl$_3$) δ 0.99 (t, J=7.2 Hz, 3H), 1.90 (s, 3H), 1.92 (s, 3H), 2.05–2.15 (m, 1H), 2.17–2.26 (m, 1H), 2.39 (s, 3H), 2.69 (s, 3H), 3.39 (s, 3H), 3.81 (dd, J=4.5, 10.5 Hz, 1H), 3.93 (dd, J=4.5, 10.5 Hz, 1H), 5.22–5.30 (m, 1H), 6.74 (d, J=3.2 Hz, 1H), 6.99 (s, 2H), 7.33 (d, J=8.0 Hz, 1H), 7.36 (d, J=3.2 Hz, 1H), 7.52 (t, J=8.0 Hz, 1H), 8.30 (d, J=8.0 Hz, 1H).

Example 471

6-Mesityl-1-[2-methoxy-1-(methoxymethyl)ethyl]-4-methyl-1H-pyrrolo[3,2]-quinoline $^1$H NMR (400 MHz, CDCl$_3$) δ 1.90 (s, 6H), 2.39 (s, 3H), 2.70 (br s, 3H), 3.43 (s, 6H), 3.92–4.02 (m, 4H), 5.45–5.50 (m, 1H), 6.72 (d, J=3.2 Hz, 1H), 7.00 (s, 2H), 7.34 (d, J=8.0 Hz, 1H), 7.46 (d, J=3.2 Hz, 1H), 7.54 (t, J=8.0 Hz, 1H), 8.29 (d, J=8.0 Hz, 1H).

Example 472

1-[2-Ethoxyethyl)-6-mesityl-4-methyl-1H-pyrrolo[3,2-c]quinoline $^1$H NMR (400 MHz, CDCl$_3$) δ 1.19 (t, J=7.2 Hz, 3H), 1.91 (s, 6H), 2.39 (s, 3H), 2.71 (s, 3H), 3.51 (q, J=7.2 Hz, 2H), 3.98 (t, J=6.0 Hz, 2H), 4.77 (t, J=6.0 Hz, 2H), 6.68 (d, J=3.2 Hz, 1H), 7.00 (s, 2H), 7.18 (d, J=3.2 Hz, 1H), 7.35 (dd. J=1.2, 7.2 Hz, 1H), 7.54 (dd, J=7.2, 8.4 Hz, 1H), 8.22 (dd, J=1.2, 8.4 Hz, 1H).

Example 473

6-(4-Methoxy-2,6-dimethylphenyl)-1-[2-methoxy-1-(methoxymethyl)ethyl]-4-methyl-1H-pyrrolo[3,2]-quinoline $^1$H NMR (400 MHz, CDCl$_3$) δ 1.92 (s, 6H), 2.70 (s, 3H), 3.43 (s, 6H), 3.87 (s, 3H), 3.94–4.04 (m, 4H), 5.44–5.50 (m, 1H), 6.72 (d, J=3.2 Hz, 1H), 6.73 (s, 2H), 7.34 (dd, J=1.2, 7.2 Hz, 1H), 7.46 (d, J=3.2 Hz, 1H), 7.53 (dd, J=7.2, 8.4 Hz, 1H), 8.28 (dd, J=1.2, 8.4 Hz, 1H).

Example 474

1-(2-Ethoxyethyl)-6-mesityl-4-methyl-2-propyl-1H-pyrrolo[3,2-c]quinoline $^1$H NMR (400 MHz, CDCl$_3$) δ 1.11 (t, J=7.2 Hz, 3H), 1.20 (t, J=7.2 Hz, 3H), 1.78–1.90 (m, 2H), 1.90 (s, 6H), 2.39 (s, 3H), 2.68 (s, 3H), 2.85 (t, J=7.6 Hz, 2H), 3.51 (q, J=7.2 Hz, 2H), 3.93 (t, J=6.8 Hz, 2H), 4.73 (t, J=6.8 Hz, 2H), 6.47 (s, 1H), 7.00 (s, 2H), 7.31 (dd, J=1.2, 7.2 Hz, 1H), 7.53 (dd, J=7.2, 8.4 Hz, 1H), 8.22 (dd, J=1.2, 8.4 Hz, 1H).

Example 475

3-(6-Mesityl-4-methyl-2-propyl-1H-pyrrolo[3,2-c]quinolin-1-yl)propyl methyl ether $^1$H NMR (400 MHz, CDCl$_3$) δ 1.11 (t, J=7.6 Hz, 3H), 1.78–1.90 (m, 2H), 1.90 (s, 6H), 2.18–2.32 (m, 2H), 2.39 (s, 3H), 2.68–2.76 (m, 2H), 2.82 (t, J=7.6 Hz, 2H), 3.42 (s, 3H), 3.45 (t, J=5.6 Hz, 2H), 4.66 (t, J=7.6 Hz, 2H), 6.50 (s, 1H), 7.00 (s, 2H), 7.32 (d, J=8.0 Hz, 1H), 7.56 (t, J=8.0 Hz, 1H), 8.34 (d, J=8.0 Hz, 1H).

Example 476

1-(2-Isopropoxyethyl)-6-mesityl-4-methyl-2-propyl-1H-pyrrolo[3,2-c]quinoline $^1$H NMR (400 MHz, CDCl$_3$) δ 1.11 (t, J=7.6 Hz, 3H), 1.14 (d, J=4.8 Hz, 6H), 1.80–1.90 (m, 2H), 1.91 (s, 6H), 2.39

(s, 3H), 2.68 (s, 3H), 2.85 (t, J=7.6 Hz, 2H), 3.52–3.60 (m, 1H), 3.91 (t, J=6.8 Hz, 2H), 4.70 (t, J=6.8 Hz, 2H), 6.46 (s, 1H), 7.00 (s, 2H), 7.31 (dd, J=1.6, 7.2 Hz, 1H), 7.53 (dd, J=7.2, 8.4 Hz, 1H), 8.22 (d d, J=1.6, 8.4 Hz, 1H).

Example 477

N-(5-1-[1-(Methoxymethyl)propyl]-4-methyl-1H-pyrrolo[3,2-c]quinolin-6-yl-4-methyl-2-pyridyl)-N,N-dimethylamine $^1$H NMR (400 MHz, CDCl$_3$) δ 0.92–1.02 (m, 3H), 2.00–2.13 (m, 3H), 2.14–2.25 (m, 1H), 2.74 (s, 3H), 3.16 (s, 3H), 3.33–3.40 (m, 3H), 3.76–3.85 (m, 1H), 3.87–3.95 (m, 1H), 5.20–5.30 (m, 1H), 6.51 (s, 1H), 6.74 (d, J=3.2 Hz, 1H), 7.35 (d, J=3.2 Hz, 1H), 7.46 (d, J=8.0 Hz, 1H), 7.52 (t, J=8.0 Hz, 1H), 8.13 (s, 1H), 8.32 (d, J=8.0 Hz, 1H).

Example 478

N-5-[1-(1-ethylpropyl)-4-methyl-1H-pyrrolo[3,2-c]quinolin-6-yl]-4-methyl-2-pyrizyl-N,N-dimethylamine MS (ESI) m/z 386 M$^+$.

Example 479

6-(2,4-Dimethoxyphenyl)-1-(1-ethylpropyl)-4-methyl-1H-pyrrolo[3,2-c]quinoline

MS (ESI) m/z 388 M$^+$.

Example 480

6-(2,6-Dimethoxy-4-methylphenyl)-1-(1-ethylpropyl)-4-methyl-1H-pyrrolo[3,2-c]quinoline MS (ESI) m/z 402 M$^+$.

Example 481

6-(2,4-Dimethoxy-6-methylphenyl)-1-(1-ethylpropyl)-4-methyl-1H-pyrrolo[3,2-c]quinoline MS (ESI) m/z 402 M$^+$.

Example 482

1-(1-Ethylpropyl)-4-methyl-6-(2,4,6-trimethoxyphenyl)-1H-pyrrolo[3,2-c]quinoline MS (ESI) m/z 418 M$^+$.

Example 483

6-[2-Chloro-4-(trifluoromethyl)phenyl]-1-(1-ethylpropyl)-4-methyl-1H-pyrrolo[3,2-c]quinoline MS (ESI) m/z 430 M$^+$.

Example 484

6-(2-Methoxy-4,6-dimethylphenyl)-1-[1-(methoxymethyl)propyl]-4-methyl-1H-pyrrolo[3,2-c]quinoline MS (ESI) m/z 402 M$^+$.

Example 485

6-(2,4-Dimethoxyphenyl)-1-[1-(methoxymethyl)propyl]-4-methyl-1H-pyrrolo[3,2-c]quinoline MS (ESI) m/z 404 M$^+$.

Example 486

2-6-[2-Chloro-4-(trifluoromethyl)phenyl]-4-methyl-1H-pyrrolo[3,2-c]quinolin-1-ylbutyl methyl ether MS (ESI) m/z 446-M$^+$.

Example 487

1-(1-Ethylpropyl)-6-(2-methoxy-4,6-dimethylphenyl)-4-methyl-1H-pyrrolo[3,2-c]quinoline MS (ESI) m/z 387 MH$^+$.

Example 488

6-Mesityl-4-methyl-1-(1-(propylbutyl)-1H-pyrrolo[3,2-c]quinoline

MS (ESI) m/z 399 MH$^+$.

Example 489

6-(2,6-Dimethoxy-4-methylphenyl)-1-[1-(methoxymethyl)propyl]-4-methyl-1H-pyrrolo[3,2]quinoline MS (ESI) m/z 418 M$^+$.

Example 490

6-(2,4-Dimethoxy-6-methylphenyl)-1-[1-(methoxymethyl)propyl]-4-methyl-1-H-pyrrolo[3,2-c]quinoline MS (ESI) m/z 418 M$^+$.

Example 491

1-[1-(Methoxymethyl)propyl]-4-methyl-6-(2,4,6-trimethoxyphenyl)-1H-pyrrolo[3,2]quinoline MS (ESI) m/z 434 M$^+$.

Example 492

1-(1-Ethylbutyl)-6-mesityl-4-methyl-1H-pyrrolo[3,2-c]quinoline

MS (ESI) m/z 384 M$^+$.

Example 493

6-(2-Bromo-4-isopropylphenyl)-1-(1-ethylpropyl)-4-methyl-1H-pyrrolo[3,2-c]quinoline MS (ESI) m/z 448 M$^+$.

Example 494

1-(1-Ethylpropyl)-6-mesityl-4-methyl-2,3-dihydro-1H-pyrrolo[3,2-c][1,7]naphthyridine A solution of 4-chloro-3-(2-chloroethyl)-8-mesityl-2-methyl[1,7]naphthyridine (100 mg, 0.28 mmol) in 3-aminopentane (5.0 mL) was stirred at 200° C. for six hours in a sealed tube. After overnight, the residue was purified by silica gel column chromatography (30–50% ethyl acetate/hexane), to give the title compound (104 mg) as pale brown crystals.

$^1$H-NMR (400 MHz, CDCl$_3$) δ 1.00 (t, J=7.2 Hz, 6H), 1.60–1.80 (m, 4H), 1.91 (s, 6H), 2.35 (s, 3H), 2.38 (s, 3H), 3.09 (t, J=5.6 Hz, 2H), 3.72 (t, J=5.6 Hz, 2H), 4.24–4.32 (m, 1H), 6.94 (s, 2H), 7.80 (d, J=6.0 Hz, 1H), 8.39 (d, J=6.0 Hz, 1H).

Example 495

1-(1-Ethylpropyl)-6-mesityl-4-methyl-1H-pyrrolo[3,2-c][1,7]naphthyridine

An activated manganese dioxide (108 mg, 1.25 mmol) was added to a solution of 1-(1-ethylpropyl)-6-mesityl-4-methyl-2,3-dihydro-1H-pyrrolo[3,2-c][1,7]naphthyridine (93 mg, 0.25 mmol) in toluene (9.0 mL) and methylene chloride (3.0 mL) and the mixture was heated under reflux for three days. After filtering through Celite, the mixture was evaporated. The residue was purified by silica gel column chromatography (10% ethyl acetate/hexane), to give the title compound (55 mg) as pale brown crystals.

$^1$H-NMR (400 MHz, CDCl$_3$) δ 0.93 (t, J=7.6 Hz, 6H), 1.92 (s, 6H), 1.98–2.15 (m, 4H), 2.37 (s, 3H), 2.74 (s, 3H), 5.01–5.10 (m, 1H), 6.81 (d, J=3.2 Hz, 1H), 6.96 (s, 2H), 7.40 (d, J=3.2 Hz, 1H), 8.10 (d, J=6.0 Hz, 1H), 8.64 (d, J=6.0 Hz, 1H).

Example 496

2-(6-Mesityl-4-methyl-2,1-dihydro-1H-pyrrolo [3,2-c][1,7]naphthyridin-yl)butyl methyl ether According to the method of Example 494, the title compound (34 mg) was obtained as white crystals from 4-chloro-3-(2-chloroethy)-8-mesityl-2-methyl[1,7]naphthyridine (100 mg, 0.28 mmol).

$^1$H-NMR (400 MHz, CDCl$_3$) δ 1.04 (t, J=7.6 Hz, 3H), 1.65–1.85 (m, 2H), 1.90 (s, 3H), 1.92 (s, 3H), 2.35 (s, 3H), 2.41 (s, 3H), 3.12 (t, J=9.6 Hz, 2H), 3.36 (s, 3H), 3.57 (dd, J=10.0 Hz, 4.8 Hz, 1H), 3.66 (dd, J=10.0 Hz, 7.2 Hz, 1H), 3.83 (t, J=9.6 Hz, 2H), 4.51–4.60 (m, 1H), 6.94 (s, 2H), 7.83 (d, J=6.0 Hz, 1H), 8.42 (d, J=6.0 Hz, 1H).

Example 497

2-(6-Mesityl-4-methyl-1-pyrrolo[3,2-c][1,7]naphthyridin-yl)butyl methyl ether

According to the method of Example 495, the title compound (~24 mg) was obtained as pale yellow crystals from 2-(6-mesityl-4-methyl-2,3-dihydro-1H-pyrrolo[3,2-c][1,7]naphthyridin-1-yl)butyl methyl ether (30 mg, 0.08 mmol).

$^1$H-NMR (400 MHz, CDCl$_3$) δ 0.99 (t, J=7.6 Hz, 3H), 1.91 (s, 3H), 1.92 (s, 3H), 2.03–2.28 (m, 2H), 2.37 (s, 3H), 2.73 (s, 3H), 3.38 (s, 3H), 3.83 (dd, J=10.0 Hz, 4.8 Hz, 1H), 3.91 (dd, J=10.0 Hz, 6.0 Hz, 1H), 5.18–5.27 (m, 1H), 6.81 (d, J=3.2 Hz, 1H), 6.96 (s, 2H), 7.50 (d, J=3.2 Hz, 1H), 8.10 (d, J=6.0 Hz, 1H), 8.65 (d, J=6.0 Hz, 1H).

Example 498

6-Mesityl-1-[2-methoxy-1-(methoxymethyl)ethyl]-4-methyl-1-H-pyrrolo[3,2-c][1,7]naphthyridine According to the methods of Examples 495 and 495, the title compound (59 mg) was obtained as pale yellow crystals from 4-chloro-3-(2-chloroethyl)-8-mesityl-2-methyl[1,7]naphthyridine (180 mg, 0.50 mmol).

$^1$H-NMR (400 MHz, CDCl$_3$) δ 1.91 (s, 6H), 2.37 (s, 3H), 2.73 (s, 3H), 3.43 (s, 6H), 3.92–4.02 (m, 4H), 5.39–5.45 (m, 1H), 6.80 (d, J=3.2 Hz, 1H), 6.96 (s, 2H), 7.62 (d, J=3.2 Hz, 1H), 8.11 (d, J=6.0 Hz, 1H), 8.66 (d, J=6.0 Hz, 1H).

Example 499

1-(1-ethylpropyl)-6-mesityl-4-methyl-1H-pyrrolo[3,2-c][1,5]naphthyridine

Activated manganese dioxide (47 mg, 0.54 mmol) was added to a solution of 1-(1-ethylpropyl)-6-mesityl-4-methyl-2,3-dihydro-1H-pyrrolo(3,2-c][1,5]naphthyridine (40 mg, 0.11 mmol) in toluene (4.0 mL) and the mixture was heated under reflux for one day. After filtering through Celite, the mixture was evaporated. The residue was purified by silica gel column chromatography (10% ethyl acetate/hexane), to give the title compound (32 mg) as white crystals.

$^1$H-NMR (400 MHz, CDCl$_3$) δ 0.86 (t, J=7.2 Hz, 6H), 1.86–2.10 (m, 4H), 1.93 (s, 6H), 2.39 (s, 3H), 2.74 (s, 3H), 6.71–6.62 (m, 1H), 6.76 (d, J=3.2 Hz, 1H), 7.00 (s, 2H), 7.25 (d, J=4.8 Hz, 1H), 7.36 (d, J=3.2 Hz, 1H), 8.77 (d, J=4.8 Hz, 1H).

Example 500

2-(6-Mesityl-4-mesityl-1H-pyrrolo[3,2-c][1,5]naphthyridin-1-yl)-butyl methyl ether A solution of 4-chloro-3-(2-chloroethyl)-8-mesityl-2-methyl[1,5]naphthyridine (200 mg, 0.557 mmol) in 2-amino-1-methoxybutane (2.0 mL) was stirred at 200° C. for four hours in a sealed tube. After overnight, the residue was purified by silica gel column chromatography (30–50% ethylacetate/hexane) Activated manganese dioxide (290 mg, 3.24 mmol) was added to a solution of the resulting product (130 mg, 0.33 mmol) in toluene (20 mL) and the mixture was heated under reflux for one day. After filtering through Celite, the mixture was evaporated. The residue was purified by silica gel column chromatography-(10% ethyl acetate/hexane), to give the title compound (108 mg) as white crystals.

$^1$H-NMR (400 MHz, CDCl$_3$) δ 0.93 (t, J=7.2 Hz, 3H), 1.91 (s, 3H), 1.94 (s, 3H), 1.96–2.18 (m, 2H), 2.39 (s, 3H), 2.74 (s, 3H), 3.37 (s, 3H), 3.76–3.94 (m, 2H), 6.75 (d, J=2.4 Hz, 1H), 6.75–6.86 (m, 1H), 7.00 (s, 2H), 7.25 (d, J=4.8 Hz, 1H), 7.48 (d, J=2.4 Hz, 1H), 8.77 (d, J=4.8 Hz, 1H).

Example 501

6-Mesityl-1-[2-methoxy-1-(methoxymethyl)ethyl]-4-methyl-1H-pyrrolo[3,2-c][1,5]naphthyridine According to the method of Example 500, the title compound (115 mg) was obtained as pale yellow crystals from 4-chloro-3-(2-chloroethyl)-8-mesityl-2-methyl[1,5]naphthyridine (200 mg, 0.56 mmol).

$^1$H-NMR (400 MHz, CDCl$_3$) δ 1.92 (s, 6H), 2.39 (s, 3H), 2.74 (s, 3H), 3.41 (s, 6H), 3.90–4.06 (m, 4H), 6.73 (d, J=3.6 Hz, 1H), 7.00 (s, 2H), 7.02–7.12 (m, 1H), 7.26 (d, J=4.4 Hz, 1H), 7.57 (d, J=3.6 Hz, 1H), 8.77 (d, J=4.4 Hz, 1H).

Example 502

6-Mesityl-4-methyl-1-(1-methylpropyl)-1H-pyrrolo [3,2-c][1,5]naphthyridine hydrochloride According to the method of Example 500, the title compound (107 mg) was obtained as pale yellow crystals from 4-chloro-3-(2-chloroethyl)-8-mesityl-2-methyl[1,5]naphthyridine (200 mg, 0.56 mmol).

$^1$H-NMR (400 MHz, CDCl$_3$) δ 0.92 (t, J=7.2 Hz, 3H), 1.22–1.44 (m, 2H), 1.60 (d, J=6.8 Hz, 3H), 1.96–2.18 (m, 2H), 1.91 (s, 3H), 1.95 (s, 3H), 2.39 (s, 3H), 2.73 (s, 3H), 6.64–6.76 (m, 1H), 6.74 (d, J=3.2 Hz, 1H), 7.00 (s, 2H), 7.26 (d, J=4.4 Hz, 1H), 7.41 (d, J=3.2 Hz, 1H), 8.79 (d, J=4.4 Hz, 1H).

Example 503

2-(6-Mesityl-4-methyl-1H-pyrrolo[3,2-c][1,5] naphthyridin-1-yl)propyl methyl ether hydrochloride According to the method of Example 500, the title compound (83 mg) was obtained as pale yellow crystals from 4-chloro-3-(2-chloroethyl)-8-mesityl-2-methyl[1,5] naphthyridine (200 mg, 0.56 mmol).

$^1$H-NMR (400 MHz, CDCl$_3$) δ 1.68 (d, J=7.2 Hz, 3H), 1.91 (s, 3H), 1.93 (s, 3H), 2.39 (s, 3H), 2.74 (s, 3H), 3.39 (s, 3H), 3.78 (dd, J=10 Hz, 4.8 Hz, 1H), 3.89 (dd, J=10 Hz, 5.6 Hz, 1H), 6.74 (d, J=3.2 Hz, 1H), 6.78–6.90 (m, 1H), 7.00 (s, 2H), 7.26 (d, J=4.4 Hz, 1H), 7.50 (d, J=3.2 Hz, 1H), 8.78 (d, J=4.4 Hz, 1H).

Example 504

1-(1-Ethylpropyl)-7-mesityl-4,6-dimethyl-1-pyrrolo[3,2-c]quinoline

A solution of 4-chloro-3-(2-chloroethyl)-7-mesityl-2,8-dimethylquinoline (200 mg, 0.54 mmol) in 3-aminopentane (6.0 mL) was stirred in a sealed tube at 200° C. for 8 hr. After evaporating, activated manganese dioxide (101 mg, 1.16 mmol) was added to a solution of the residue in toluene (9.0 mL) and the mixture was stirred for two days. After filtering through Celite, the mixture was evaporated. The residue was purified by silica gel column chromatography (10% ethyl acetate/hexane) to give the title compound (12 mg) as white crystals.

$^1$H-NMR (400 MHz, CDCl$_3$) δ 0.91 (t, J=7.6 Hz, 6H), 1.95 (s, 6H), 1.96–2.12 (m, 4H), 2.37 (s, 3H), 2.55 (s, 3H), 2.90 (s, 3H), 5.06–5.14 (m, 1H), 6.79 (d, J=3.2 Hz, 1H), 6.99 (s, 2H), 7.17 (d, J=8.0 Hz, 1H), 7.28 (d, J=3.2 Hz, 1H), 8.23 (d, J=8.0 Hz, 1H).

Example 505

1-(1-Ethylpropyl)-7-mesityl-4-methyl-1H-pyrrolo[3,2-c]quinoline

A solution of 1-(1-ethylpropyl)-7-iodo-4-mesityl-1H-pyrrolo[3,2-c]quinoline (32 mg, 0.09 mmol), mesitylboric acid (17 mg, 0.10 mmol), Pd(PPh$_3$)$_4$ (5 mg, 4.23×10$^{-3}$ mmol) and barium hydroxide octahydrate (40 mg, 0.13 mmol) in 2,2-dimethoxyethane (6.0 mL) and water (1.0 mL) was stirred at 80 for one day. After filtering through Celite, the filtrate was diluted with ethyl acetate, washed with brine, dried over anhydrous magnesium sulfate and evaporated. The residue was purified by silica gel column chromatography (10% ethyl acetate/hexane), to give the title compound (17 mg) as white crystals.

$^1$H-NMR (400 MHz, CDCl$_3$) δ 0.92 (t, J=7.2 Hz, 6H), 1.96–2.14 (m, 4H), 2.06 (s, 6H), 2.36 (s, 3H), 2.90 (s, 3H), 5.05–5.14 (m, 1H), 6.81 (d, J=3.2 Hz, 1H), 6.97 (s, 2H), 7.28 (d, J=8.0 Hz, 1H), 7.29 (d, J=3.2 Hz, 1H), 7.97 (s, 1H), 8.36 (d, J=8.0 Hz, 1H).

TEST EXAMPLES

The present compounds were evaluated for the ability to bind to a corticotrophin releasing hormone receptor (CRFR) and the adenylate cyclase activity inhibitory ability. Each test procedures and the results are as follows:

Test Example 1

CRFR Binding Experiment (1) Preparation of CRFR expressing cell: As an experiment material for the CRFR binding experiment, a membrane fraction of a cell which expressed highly human CRFR1. CRFR expressing cell was prepared as follows. The full length gene of CRFR$^1$ was obtained by a PCT method using human brain (QuickClone™ Clontech) as cDNA library. The resulting DNA fragment was inserted into a cloning vector to confirm the base sequence. A cDNA having the correct base sequence was ligated to an expression vector (pcDNA3.1™, Invitrogen). A gene was inserted into Hek 283 cell and grown in a cell culturing solution containing G418 (1 mg/ml) to obtain a resistance cell, into which a CRFR$^1$ expression vector was cloned by a limitation diluting method. A clone having the high binding ability of membrane and sauvagine per unit protein was finally selected from cloned cells by a binding experiment shown by the method shown below, which was used for an experiment.

(2) Preparation of a membrane fraction: G418 resistant cells into which a gene for CRFR$^1$ was introduced were collected, and cell rupture was performed by an ultrasound generator with a sonicate buffer (D-PBS-10 mM MgCl$_2$, 2 mM EGTA). A suspension after ultrasound rupture was centrifuged (46,000×g, 10 minutes), the sediment thereof was further resuspended with a sonicate buffer, and the same procedures were related. Finally, the sediment was suspended in a binding buffer (D-PBS-10 mM MgCl$_2$, 2 mM EGTA, 1.5% BSA, 0.15 mM bacitracin, 1× protease inhibitor cocktail (COMPLETE™, Boehringer), to adjust the protein concentration at 1.6 mg/ml, which was used as a membrane fraction.

(3) Binding experiment: Binding experiment with sauvagine was performed using a 96-well plate and SP™ (Amersham pharmacia) An experiment was according to the specification of SPA beads. 40 mg of a membrane fraction protein, 0.5 mg of beads and 40 pM $^{125}$I-sauvaging (Amersham pharmacia) were allowed to stand at room temperature for two hours in the presence a test compound, centrifuged (1,000×g, 5 minutes), and then the radioactivity of each well was measured with TopCount™ (Packard).

(4) Calculation of the binding ability: The radioactivity as the non-specific binding when 1,000-fold excessive amount of non-radioactive sauvagine was added was substacted from each value, the radioactivity where no test material is added is regarded as 100% (control), and each value is shown by % (% of control). The concentration showing 50% in % (% of control) was obtained from a graph where the concentration test material is plotted on an abscissa axis and % (% of control) is plotted on a coordinate axis and IC$_{50}$ value was calculated (Table 1)

Test Example 2

Experiment for Measuring Adenyrate Cyclase the Activity Using AtT-20 Cell (1) Test procedures: AtT-20 cell is a cell strain derived from mouse pytuitari gland tumor, it is known that the intracellular adenyrate cyclase system is activated in response to corticotrophin release hormone (CRF), to produce cyclic AMP (cAMP), releasing adrenocortical hormone (ACTH) (Biochem. Piophys. Res. Com. 106. 1364–1371, 1982). In this experiment, the cell $1\times10^5$) suspended in D-MEM medium (0.1% FPS), seeded on a 96-well plate, a phosphodiesterase inhibitor (IBMX, Calbiochem) was added to the final concentration of 1 mM, which was cultured at 37° C. for 30 minutes. A diluted test compound solution and CRF (30 nM) were added, which was further cultured at 37° C. for 10 minutes, cells were collected by centrifugation (500×g, 5 minutes), cells were lysed with a lysis buffer (Amersham Pharmacia), and an amount of intracellular cAMP produced was quantitated using the ELISA method. For ELISA, cAMP EIA system (BIOTRAK™ Amersham Pharmacia) was used.

(2) Calculation of adenyrate cyclase activity inhibitory ability: Treatment of the resulting data was carried out as follows. An amount of cAMP produced by a cell to which 30 nM CRF was added is regarded as 100% (control) and a value of each sample is expressed as % (% of control). The concentration showing 50% in % (% of control) was obtained from a graph where the concentration of a test material is plotted on an abscissa axis and % (% of control) is plotted on a coordinate and $IC_{50}$ value was calculated (Table 2).

TABLE 1

| Ex. No. | CRF1 receptor binding ability $IC_{50}$ (nM) |
|---|---|
| 1 | 100 |
| 2 | 500 |
| 3 | 600 |
| 6 | 1000 |
| 12 | 1500 |
| 13 | 2500 |
| 23 | 1500 |
| 33 | 1000 |
| 38 | 3000 |
| 44 | 400 |
| 45 | 1500 |
| 67 | 200 |
| 74 | 1400 |

TABLE 2

| Ex. No. | adenylate cyclase ability $IC_{50}$ (nM) |
|---|---|
| 1 | 900 |
| 13 | 1500 |
| 67 | 2000 |

The present compound has an excellent binding ability to CRFR and significantly inhibited the adenylate cyclase activity By CRF.

According to the present invention, novel compounds having the CRF receptor antagonism, a pharmacologically acceptable salt thereof and hydrates thereof can be provided. The compound of the present invention, a pharmacologically acceptable salt thereof or hydrates thereof have an excellent antagonism to a CRF receptor, are low toxic, highly safe and highly useful as a drug. Therefore, the compounds of the present invention are useful as an agent for treating or preventing diseases to which CRF and/or its receptor relate. In particular, they are useful as an agent for treating or preventing depression, depressive symptom (great depression, monostotic depression, recurrent depression, infant tyrannism by depression, postpartum depression etc.), mania, anxiety, generalized anxiety disorder, panic disorder, phobia, compulsive disorder, post-traumatic stress disorder, Tourette syndrome, autism, emotional disorder, sentimental disorder, bipolar disorder, cyclothymia, schizophrenia, peptic ulcer, irritable bowel syndrome, ulcerative colitis, Crohn's disease, diarrhea, coprostasis, postoperational ileus, gastrointestinal function abnormality associated with stress, neural vomiting etc.

What is claimed is:

1. A compound represented by the formula:

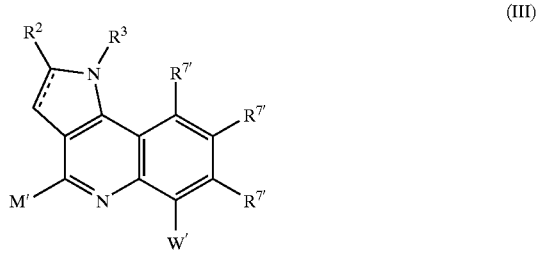

(III)

wherein
$R^2$ is a hydrogen atom, a $C_{1-6}$ alkyl group, a $C_{2-6}$ alkenyl group, a $C_{2-6}$ alkynyl group, a $C_{1-6}$ alkoxy group, a $C_{3-8}$ cycloalkyl group, a $C_{1-6}$ alkoxy $C_{1-6}$ alkyl group, a $C_{3-8}$ cycloalkyl $C_{1-6}$ alkyl group or a $C_{1-6}$ alkyl-aryl group;
$R^3$ is
(i) a hydrogen atom;
(ii) formula —$COR^4$ (wherein $R^4$ represents a $C_{1-6}$ alkyl group, an optionally substituted aryl $C_{1-4}$ alkyl group, an optionally substituted aryl group, an optionally substituted heteroaryl $C_{1-4}$ alkyl group or an optionally substituted heteroaryl group);
(iii) —$S(O)_nR^5$ (wherein $R^5$ represents a $C_{1-6}$ alkyl group, an optionally substituted aryl $C_{1-4}$ alkyl group, an optionally substituted aryl group, an optionally substituted heteroaryl $C_{1-4}$ alkyl group or an optionally substituted heteroaryl group; and n is an integer of 0, 1 or 2);
(iv) a $C_{1-10}$ alkyl group optionally substituted with any of one or more groups defined in the following A group;
(v) a $C_{2-10}$ alkenyl group optionally substituted with any of one or more groups defined in the following A group;
(vi) a $C_{2-10}$ alkynyl group optionally substituted with any of one or more groups defined in the following A group;
(vii) an optionally substituted aryl group; or
(viii) a $C_{3-8}$ cycloalkyl group optionally fused with optionally substituted benzene ring and optionally substituted with a $C_{1-4}$ alkyl group;
the partial structure - - - represents a single or double bond, and
the A group defined above is selected from at least one of the group consisting of:
(1) halogen atom,
(2) hydroxy group,
(3) nitro group,
(4) cyano group,
(5) carboxy group,
(6) a $C_{1-6}$ alkyloxycarbonyl group, and
(7) a group represented by the formula —$S(O)_rR^{15}$ (wherein r is an integer of 0, 1 or 2; and $R^{15}$ represents:
(i) hydrogen atom;
(ii) a $C_{1-6}$ alkyl group;
(iii) a group represented by the formula —$NR^{16}R^{17}$ (wherein $R^{16}$ and $R^{17}$ are the same as or different from each other and each represents hydrogen atom, a $C_{1-6}$ alkyl group optionally substituted with an optionally substituted aryl group, a $C_{1-4}$ alkylacyl group, an optionally substituted aryl $C_{1-4}$ alkyl group, an optionally substituted heteroaryl $C_{1-4}$ alkyl group, an optionally substituted aryl group or an optionally substituted heteroaryl group);

(iv) an optionally substituted aryl $C_{1-4}$ alkyl group;
(v) an optionally substituted aryl group;
(vi) an optionally substituted heteroaryl $C_{1-4}$ alkyl group; or
(vii) an optionally substituted heteroaryl group);

M' represents a hydrogen atom, a halogen atom or a $C_{1-6}$ alkyl group;

$R^7$, represents a hydrogen atom or a $C_{1-6}$ alkyl group; and

W' represents a phenyl group, pyridyl group, thienyl group, or furyl group, each being optionally substituted; and a pharmacologically acceptable salt thereof or hydrates thereof.

2. The compound of claim 1, a pharmacologically acceptable salt thereof or hydrates thereof, wherein at least one selected from $R^2$ and $R^3$ are the same as or different from each other and each represents hydrogen atom, a $C_{1-6}$ alkyl group, a $C_{2-6}$ alkynyl group, a $C_{1-6}$ alkoxy $C_{1-6}$ alkyl group or a $C_{1-6}$ alkyl-aryl group.

3. A medicament which comprises the compound of claim 1, a pharmacologically acceptable salt thereof or hydrates thereof, and a pharmacologically acceptable carrier.

4. A method for treating a disease to which at least one of CRF and CRF receptor relate, by administering a pharmaceutically effective dose of the compound of claim 1, a pharmacologically acceptable salt thereof or hydrates thereof to a patient.

5. A method for treating a disease against which CRF receptor antagonism is efficacious, by administering a pharmaceutically effective dose of the compound of claim 1, a pharmacologically acceptable salt thereof or hydrates thereof to a patient.

* * * * *